United States Patent
Gaul et al.

(10) Patent No.: US 8,420,657 B2
(45) Date of Patent: Apr. 16, 2013

(54) PYRROLO[2,3-D]PYRIMIDINES AND USE THEREOF AS TYROSINE KINASE INHIBITORS

(75) Inventors: Christoph Gaul, Basel (CH); Marc Gerspacher, Basel (CH); Philipp Holzer, Basel (CH); Carole Pissot Soldermann, Basel (CH)

(73) Assignee: Novartis AG, Basel (CH)

( * ) Notice: Subject to any disclaimer, the term of this patent is extended or adjusted under 35 U.S.C. 154(b) by 919 days.

(21) Appl. No.: 12/366,218

(22) Filed: Feb. 5, 2009

(65) Prior Publication Data

US 2009/0203688 A1  Aug. 13, 2009

(30) Foreign Application Priority Data

Feb. 6, 2008  (EP) .................................... 08151137

(51) Int. Cl.
  *C07D 487/04*  (2006.01)
  *A61K 31/519*  (2006.01)
  *A61P 35/02*  (2006.01)
  *A61P 37/06*  (2006.01)
  *A61P 35/04*  (2006.01)
  *A61P 25/28*  (2006.01)

(52) U.S. Cl. ..................................... 514/265.1; 544/280

(58) Field of Classification Search .................. 544/280; 514/265.1
See application file for complete search history.

(56) References Cited

U.S. PATENT DOCUMENTS

| | | | |
|---|---|---|---|
| 7,319,102 B1 | 1/2008 | Clark et al. | |
| 7,968,557 B2 * | 6/2011 | Choi et al. | 514/265.1 |
| 2008/0096903 A1 | 4/2008 | Chen et al. | |
| 2008/0139588 A1 | 6/2008 | Clark et al. | |
| 2009/0163468 A1 | 6/2009 | Chen et al. | |
| 2009/0181959 A1 | 7/2009 | Rodgers et al. | |
| 2009/0192176 A1 | 7/2009 | Zask et al. | |

FOREIGN PATENT DOCUMENTS

| | | |
|---|---|---|
| EP | 1382339 A1 | 1/2004 |
| JP | 2006/241089 A1 | 9/2006 |
| WO | 9965908 A1 | 12/1999 |
| WO | WO 02/076985 A1 | 10/2002 |
| WO | 03/074530 A1 | 9/2003 |
| WO | 2005/085253 A1 | 9/2005 |
| WO | WO 2005/080393 A1 | 9/2005 |
| WO | 2005/107760 A1 | 11/2005 |
| WO | WO 2006/045828 A1 | 5/2006 |
| WO | 2006/074985 A1 | 7/2006 |
| WO | WO 2006/096270 A1 | 9/2006 |
| WO | 2006/122003 A2 | 11/2006 |
| WO | 2006127406 A2 | 11/2006 |
| WO | 2007/042299 A1 | 4/2007 |
| WO | WO 2007/109362 A2 | 9/2007 |
| WO | 2007140222 A2 | 12/2007 |
| WO | WO 2007/140222 A2 | 12/2007 |
| WO | 2008/049105 A2 | 4/2008 |
| WO | 2008157207 A2 | 12/2008 |
| WO | 2009070524 A1 | 6/2009 |
| WO | 2009/085185 A1 | 7/2009 |

OTHER PUBLICATIONS

Choi, et al., Bioorganic & Medicinal Chemistry Letters, 16: 2173-2176, (2006), Part 1.
Choi, et al., Bioorganic & Medicinal Chemistry Letters, 16: 2689-2692, (2006), Part 2.
Hong, et al., ACS Chemical Biology 2(3); 171-175 (2007).
Koretskaya et al., Khimiko-Farmatsevticheskii Zhurnal, 6: 5-12 (Jun. 1968).
Moriarty et al., Bioorganic & Medicinal Chemistry Letters, 16: 5778-5783 (2006).
Siddiqi et al., J. Med. Chem., 38: 1174-1188, 1995.
Choi et al, "Design and synthesis of 7H-pyrrolo[2,3-d]pyrimidines as focal adhesion kinase inhibitors. Part 2", Bioorganic & Medicinal Chemistry Letters, 2006 vol. 16 No. 10 pp. 2689-2692.

\* cited by examiner

*Primary Examiner* — Susanna Moore
(74) *Attorney, Agent, or Firm* — Laura K. Madden

(57) ABSTRACT

The invention relates to compounds of formula I and salts thereof (I)

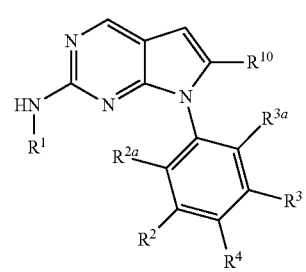

wherein the substituens are as defined in the specification, processes for the preparation thereof; to pharmaceuticals containing such compounds, in particular for the use in one or more Protein tyrosine kinase mediated diseases.

8 Claims, No Drawings

PYRROLO[2,3-D]PYRIMIDINES AND USE THEREOF AS TYROSINE KINASE INHIBITORS

This application claims priority to European Serial No. 08151137.0 filed 6 Feb. 2008, the contents of which are incorporated herein by reference in their entirety.

The invention relates to 7-phenyl-7H-pyrrolo[2,3d]pyrimidin-2yl-amino derivatives of the formula I given below, as well as salts thereof; processes for the preparation thereof; pharmaceutical compositions comprising a compound of the formula (I), optionally in the presence of a combination partner; the application of a compound of formula (I) in a process for the treatment of the human or animal body, (in particular with regard to a proliferative disease); the use of a compound of formula (I) for manufacturing a medicament for the treatment of such diseases.

Janus kinases (JAKs) form a family of intracellular protein tyrosine kinases with four members, JAK1, JAK2, JAK3 and TYK2. These kinases are important in the mediation of cytokine receptor signaling which induces various biological responses including cell proliferation, differentiation and apoptosis. Knock-out experiments in mice have shown that JAKs are inter alia important in hematopoiesis. In addition, JAK2 was shown to be implicated in myeloproliferative diseases and cancers. JAK2 activation by chromosome re-arrangements and/or loss of negative JAK/STAT (STAT=signal transducing and activating factor(s)) pathway regulators has been observed in hematological malignancies as well as in certain solid tumors.

WO 2005/080393 discloses inter alia 7H-pyrrolo[2,3d]pyrimidin-2yl-amino derivatives which are useful in the treatment of disorders associated with abnormal or deregulated kinase activity.

Bioorganic & Medical Chemistry Letters 16 (2006), 2689 discloses design and synthesis of certain 7H-pyrrolo[2,3d] pyrimidines as focal adhesion kinase inhibitors.

It has now been found that the 7-phenyl-7H-pyrrolo[2,3d] pyrimidin-2yl-amino derivatives of the formula I given below, have advantageous pharmacological properties and inhibit, for example, the tyrosine kinase activity of Janus kinases, such as JAK2 kinase and/or JAK3- (but also JAK-1-) kinase. Hence, the compounds of formula I are suitable, for example, to be used in the treatment of diseases depending on the tyrosine kinase activity of JAK2 (and/or JAK3) kinase, especially proliferative diseases such as tumor diseases, leukaemias, polycythemia vera, essential thrombocythemia, and myelofibrosis with myeloid metaplasia. Through the inhibition of JAK-3 kinase, compounds of the invention also have utility as immunosuppressive agents, for example for the treatment of diseases such as organ transplant rejection, lupus erythematodes, multiple sclerosis, rheumatoid arthritis, psoriasis, dermatitis, Crohn's disease, type-1 diabetes and complications from type-1 diabetes.

In a first aspect, the invention relates to compounds of the formula I,

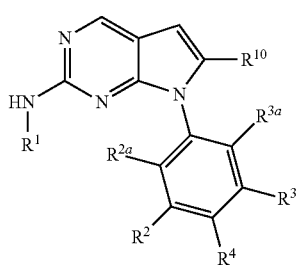

(I)

wherein
$R^1$ represents unsubstituted or substituted heterocyclyl, unsubstituted or substituted aryl, unsubstituted or substituted cycloalkyl;
$R^2$ represents hydrogen, halogen, lower alkyl, lower alkyloxy, lower haloalkyl, cycloalkyl, cycloalkyloxy, halocycloalkyl, cycloalkyloxy, halocycloalkyloxy;
$R^3$ represents hydrogen, halogen, lower alkyl, lower alkyloxy, lower haloalkyl, cycloalkyl, cycloalkyloxy, halocycloalkyl, cycloalkyloxy, halocycloalkyloxy;
or $R^2$ and/or $R^3$ are connected to $R^5$ or $R^7$ to form a cyclic moiety fused to the phenyl ring to which $R^2/R^3$ are attached;
$R^{2a}$ represents hydrogen, halogen, lower alkyl, lower alkyloxy, lower haloalkyl, cycloalkyl, cycloalkyloxy, halocycloalkyl, cycloalkyloxy, halocycloalkyloxy;
$R^{3a}$ represents hydrogen, halogen, lower alkyl, lower alkyloxy, lower haloalkyl, cycloalkyl, cycloalkyloxy, halocycloalkyl, cycloalkyloxy, halocycloalkyloxy;
$R^4$ represents a group:

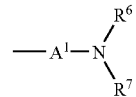

wherein $A^1$ represents one of the following groups:

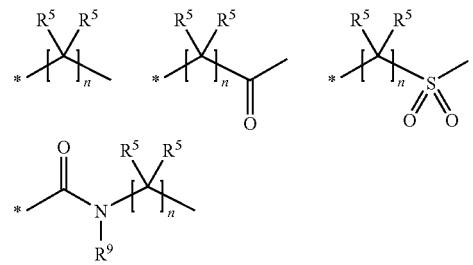

in which the atom marked * is bond to the phenyl ring;
or
$R^4$ represents one of the following groups:

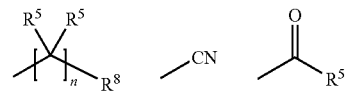

$R^5$ represents independent from each other hydrogen, lower alkyl, lower haloalkyl, cycloalkyl, halocycloalkyl or form, together with the carbon to which they are attached a cycloalkyl;
$R^6$ and $R^7$ represent together with the nitrogen to which they are attached an optionally substituted heterocycle
or
$R^6$ represents hydrogen or optionally substituted alkyl and $R^7$ represents optionally substituted alkyl;
$R^8$ represents alkyl, hydroxy, lower alkyloxy, lower haloalkyloxy, cycloalkyloxy, halocycloalkyloxy, lower alkyl-sulfonyl, lower-haloalkyl-sulfonyl, cycloalkyl-sulfonyl, halocycloalkyl-sulfonyl, lower alkyl-sulfinyl, lower haloalkyl-sulfinyl, cycloalkyl-sulfinyl, halocycloalkyl-sulfinyl;
$R^9$ represents H or lower alkyl;
$R^{10}$ represents hydrogen, lower alkyl, lower haloalkyl, cycloalkyl, halocycloalkyl;

n represents 0, 1 or 2;
or salts thereof.

The invention may be more fully appreciated by reference to the following description, including the following glossary of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula I, such a compound may exist in optically active form or in the form of a mixture of optical isomers, e. g. in the form of a racemic mixture. All optical isomers and their mixtures, including the racemic mixtures, are part of the present invention. Thus, any given formula given herein is intended to represent a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2H$, $^3H$, $^{11}C$, $^{13}C$, $^{14}C$, $^{15}N$, $^{18}F$ $^{31}P$, $^{32}P$, $^{35}S$, $^{36}Cl$, $^{125}I$ respectively. Various isotopically labeled compounds of the present invention, for example those into which radioactive isotopes such as $^3H$, $^{13}C$, and $^{14}C$ are incorporated. Such isotopically labelled compounds are useful in metabolic studies (preferably with $^{14}C$), reaction kinetic studies (with, for example $^2H$ or $^3H$), detection or imaging techniques [such as positron emission tomography (PET) or single-photon emission computed tomography (SPECT) including drug or substrate tissue distribution assays, or in radioactive treatment of patients. In particular, an $^{18}F$ or labeled compound may be particularly preferred for PET or SPECT studies. Further, substitution with heavier isotopes such as deuterium (i.e., $^2H$) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula (where one or more up to all more general expressions in embodiments characterized as preferred above or below can be replaced with a more specific definition, thus leading to a more preferred embodiment of the invention, respectively).

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present.

The acid addition salt of compounds of formula I are preferably pharmaceutically acceptable salts. Such salts are known in the field.

The following general definitions shall apply in this specification, unless otherwise specified:

Halogen (or halo) denotes fluorine, bromine, chlorine or iodine, in particular fluorine, chlorine. Halogen-substituted groups and moieties, such as alkyl substituted by halogen (halogenalkyl) can be mono-, poly- or per-halogenated.

Hetero atoms are atoms other than Carbon and Hydrogen, preferably nitrogen (N), oxygen (O) or sulfur (S).

Carbon containing groups, moieties or molecules contain 1 to 8, preferably 1 to 6, more preferably 1 to 4, most preferably 1 or 2, carbon atoms. Any non-cyclic carbon containing group or moiety with more than 1 carbon atom is straight-chain or branched.

The prefix "lower" or "$C_1$-$C_7$" denotes a radical having up to and including a maximum of 7, especially up to and including a maximum of 4 carbon atoms, the radicals in question being either linear or branched with single or multiple branching.

"Alkyl" refers to a straight-chain or branched-chain alkyl group, preferably represents a straight-chain or branched-chain $C_{1-12}$alkyl, particularly preferably represents a straight-chain or branched-chain $C_{1-7}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to hydroxyl, alkoxy, oxo (i.e. =O), halogen and amino. An example of a substituted alkyl is trifluoromethyl. Cycloalkyl may also be a substituent to alkyl. An example of such a case is the moiety (alkyl)-cyclopropyl or alkandiyl-cyclopropyl, e.g. —$CH_2$-cyclopropyl. $C_1$-$C_7$-alkyl is preferably alkyl with from and including 1 up to and including 7, preferably from and including 1 up to and including 4, and is linear or branched; preferably, lower alkyl is butyl, such as n-butyl, sec-butyl, isobutyl, tert-butyl, propyl, such as n-propyl or isopropyl, ethyl or preferably methyl.

Each alkyl part of other groups like "alkoxy", "alkoxyalkyl", "alkoxycarbonyl", "alkoxycarbonylalkyl", "alkylsulfonyl", "alkylsulfinyl", "alkylamino", "halogenalkyl" shall have the same meaning as described in the above-mentioned definition of "alkyl".

"Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—$CH(CH_3)$—), 1,1-, 1,2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

"Alkendiyl" refers to a straight-chain or branched-chain alkendiyl group bound by two different Carbon atoms to the molecule, it preferably represents a straight-chain or branched-chain $C_{2-6}$alkandiyl; for example, —CH=CH—, —CH=C($CH_3$)—, —CH=CH—$CH_2$—, —C($CH_3$)

=CH—CH$_2$—, —CH=C(CH$_3$)—CH$_2$—, —CH=CH—C(CH$_3$)H—, —CH=CH—CH=CH—, —C(CH$_3$)=CH—CH=CH—, —CH=C(CH$_3$)—CH=CH—, with particular preference given to —CH=CH—CH$_2$—, —CH=CH—CH=CH—. Alkendiyl may be substituted or unsubstituted "Cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cyclchexyl. Cycloalkyl may be unsubstituted or substituted; exemplary substituents are provided in the definition for alkyl.

"Aryl" refers to an aromatic homocyclic ring system with 6 or more carbon atoms; aryl is preferably an aromatic moiety with 6 to 14 ring carbon atoms, more preferably with 6 to 10 ring carbon atoms, such as phenyl or naphthyl, preferably phenyl. Aryl may be unsubstituted or substituted by one or more, preferably up to three, more preferably up to two substituents independently selected from the group consisting of unsubstituted or substituted heterocyclyl as described below, especially pyrrolidinyl, such as pyrrolidino, oxopyrrolidinyl, such as oxo-pyrrolidino, C$_1$-C$_7$-alkyl-pyrrolidinyl, 2,5-di-(C$_1$-C$_7$alkyl)pyrrolidinyl, such as 2,5-di-(C$_1$-C$_7$alkyl)-pyrrolidino, tetrahydrofuranyl, thiophenyl, C$_1$-C$_7$-alkylpyrazolidinyl, pyridinyl, C$_1$-C$_7$-alkylpiperidinyl, piperidino, piperidino substituted by amino or N-mono- or N,N-di-[lower alkyl, phenyl, C$_1$-C$_7$-alkanoyl and/or phenyl-lower alkyl)-amino, unsubstituted or N-lower alkyl substituted piperidinyl bound via a ring carbon atom, piperazino, lower alkylpiperazino, morpholino, thiomorpholino, S-oxo-thiomorpholino or S,S-dioxothiomorpholino; C$_1$-C$_7$-alkyl, amino-C$_1$-C$_7$-alkyl, N—C$_1$-C$_7$-alkanoylamino-C$_1$-C$_7$-alkyl, N—C$_1$-C$_7$-alkanesulfonyl-amino-C$_1$-C$_7$-alkyl, carbamoyl-C$_1$-C$_7$-alkyl, [N-mono- or N,N-di-(C$_1$-C$_7$-alkyl)-carbamoyl]-C$_1$-C$_7$-alkyl, C$_1$-C$_7$-alkanesulfinyl-C$_1$-C$_7$-alkyl, C$_1$-C$_7$-alkanesulfonyl-C$_1$-C$_7$-alkyl, phenyl, naphthyl, mono- to tri-[C$_1$-C$_7$-alkyl, halo and/or cyano]-phenyl or mono- to tri-[C$_1$-C$_7$-alkyl, halo and/or cyano]-naphthyl; C$_3$-C$_8$-cycloalkyl, mono- to tri-[C$_1$-C$_7$-alkyl and/or hydroxy]-C$_3$-C$_8$-cycloalkyl; halo, hydroxy, lower alkoxy, lower-alkoxy-lower alkoxy, (lower-alkoxy)-lower alkoxy-lower alkoxy, halo-C$_1$-C$_7$-alkoxy, phenoxy, naphthyloxy, phenyl- or naphthyl-lower alkoxy; amino-C$_1$-C$_7$-alkoxy, lower-alkanoyloxy, benzoyloxy, naphthoyloxy, formyl (CHO), amino, N-mono- or N,N-di-(C$_1$-C$_7$-alkyl)-amino, C$_1$-C$_7$-alkanoylamino, C$_1$-C$_7$-alkanesulfonylamino, carboxy, lower alkoxy carbonyl, e.g.; phenyl- or naphthyl-lower alkoxycarbonyl, such as benzyloxycarbonyl; C$_1$-C$_7$-alkanoyl, such as acetyl, benzoyl, naphthoyl, carbamoyl, N-mono- or N,N-disubstituted carbamoyl, such as N-mono- or N,N-di-substituted carbamoyl wherein the substituents are selected from lower alkyl, (lower-alkoxy)-lower alkyl and hydroxy-lower alkyl; amidino, guanidino, ureido, mercapto, lower alkylthio, phenyl- or naphthylthio, phenyl- or naphthyl-lower alkylthio, lower alkyl-phenylthio, lower alkyl-naphthylthio, halogen-lower alkylmercapto, sulfo (—SO$_3$H), lower alkanesulfonyl, phenyl- or naphthyl-sulfonyl, phenyl- or naphthyl-lower alkylsulfonyl, alkylphenylsulfonyl, halogen-lower alkylsulfonyl, such as trifluorome-thanesulfonyl; sulfonamido, benzosulfonamido, azido, azido-C$_1$-C$_7$-alkyl, especially azido-methyl, C$_1$-C$_7$-alkanesulfonyl, sulfamoyl, N-mono- or N,N-di-(C$_1$-C$_7$-alkyl)-sulfamoyl, morpholinosulfonyl, thiomorpholinosulfonyl, cyano and nitro; where each phenyl or naphthyl (also in phenoxy or naphthoxy) mentioned above as substituent or part of a substituent of substituted alkyl (or also of substituted aryl, heterocyclyl etc. mentioned herein) is itself unsubstituted or substituted by one or more, e.g. up to three, preferably 1 or 2, substituents independently selected from halo, halo-lower alkyl, such as trifluoromethyl, hydroxy, lower alkoxy, azido, amino, N-mono- or N,N-di-(lower alkyl and/or C$_1$-C$_7$-alkanoyl)-amino, nitro, carboxy, lower-alkoxycarbonyl, carbamoyl, cyano and/or sulfamoyl.

"Heterocyclyl" refers to a heterocyclic radical that is unsaturated (=carrying the highest possible number of conjugated double bonds in the ring(s) i.e. heteroaryl), saturated or partially saturated and is preferably a monocyclic or in a broader aspect of the invention bicyclic, tricyclic or spirocyclic ring; and has 3 to 24, more preferably 4 to 16, most preferably 5 to 10 and most preferably 5 or 6 ring atoms; wherein one or more, preferably one to four, especially one or two carbon ring atoms are replaced by a heteroatom, the bonding ring preferably having 4 to 12, especially 5 to 7 ring atoms. The heterocyclic radical (heterocyclyl) may be unsubstituted or substituted by one or more, especially 1 to 3, substituents independently selected from the group consisting of the substituents defined above for substituted alkyl and/or from one or more of the following substituents: oxo (=O), thiocarbonyl (=S), imino(=NH), imino-lower alkyl. Further, heterocyclyl is especially a heterocyclyl radical selected from the group consisting of oxiranyl, azirinyl, aziridinyl, 1,2-oxathiolanyl, thienyl (=thiophenyl), furanyl, tetrahydrofuryl, pyranyl, thiopyranyl, thianthrenyl, isobenzofuranyl, benzofuranyl, chromenyl, 2H-pyrrolyl, pyrrolyl, pyrrolinyl, pyrrolidinyl, imidazolyl, imidazolidinyl, benzimidazolyl, pyrazolyl, pyrazinyl, pyrazolidinyl, thiazolyl, isothiazolyl, dithiazolyl, oxazolyl, isoxazolyl, pyridyl, pyrazinyl, pyrimidinyl, piperidinyl, piperazinyl, pyridazinyl, morpholinyl, thiomorpholinyl, (S-oxo or S,S-dioxo)-thiomorpholinyl, indolizinyl, azepanyl, diazepanyl, especially 1,4-diazepanyl, isoindolyl, 3H-indolyl, indolyl, benzimidazolyl, cumaryl, indazolyl, triazolyl, tetrazolyl, purinyl, 4H-quinolizinyl, isoquinolyl, quinolyl, tetrahydroquinolyl, tetrahydroisoquinolyl, decahydroquinolyl, octahydroisoquinolyl, benzofuranyl, dibenzofuranyl, benzothiophenyl, dibenzothiophenyl, phthalazinyl, naphthyridinyl, quinoxalyl, quinazolinyl, quinazolinyl, cinnolinyl, pteridinyl, carbazolyl, beta-carbolinyl, phenanthridinyl, acridinyl, perimidinyl, phenanthrolinyl, furazanyl, phenazinyl, phenothiazinyl, phenoxazinyl, chromenyl, isochromanyl, chromanyl, benzo[1,3]dioxol-5-yl and 2,3-dihydro-benzo[1,4]dioxin-6-yl, each of these radicals being unsubstituted or substituted by one or more, preferably up to three, substituents selected from those mentioned above for substituted aryl and/or from one or more of the following substituents: oxo (=O), thiocarbonyl (=S), imino(=NH), imino-lower alkyl.

"Arylalkyl" refers to an aryl group bound to the molecule via an alkyl group, such as a methyl or ethyl group, preferably phenethyl or benzyl, in particular benzyl. Similarly, cycloalkylalkyl and heterocyclylalkyl represents a cycloalkyl group bound to the molecule via an alkyl group or a heterocyclyl group bound to the molecule via an alkyl group. In each instance, aryl, heterocyclyl, cycloalkyl and alkyl may be substituted as defined above.

"Treatment" includes prophylactic (preventive) and therapeutic treatment as well as the delay of progression of a disease or disorter.

"Protein tyrosine kinase mediated diseases" (especially JAK2 and/or JAK3 kinase mediated diseases) are especially such disorders that respond in a beneficial way (e.g. amelioration of one or more symptoms, delay of the onset of a disease, up to temporary or complete cure from a disease) to the inhibition of a protein tyrosine kinase, especially inhibition of a JAK (preferably JAK2 and/or JAK3) kinase or TYK2, more especially inhibition of JAK2 kinase (where among the diseases to be treated, especially proliferative diseases such as tumor diseases, leukaemias, polycythemia vera, essential thrombocythemia, and myelofibrosis with myeloid metaplasia may be mentioned) and/or of JAK3 kinase (where preferably the treatment (e.g. by immunosuppression) of diseases such as organ transplant rejection, lupus erythematodes, multiple sclerosis, rheumatoid arthritis, psoriasis, dermatitis, Crohn's disease, type-1 diabetes and complications from type-1 diabetes are to be mentioned as preferred.

"Salts" (which, what is meant by "or salts thereof" or "or a salt thereof", can be present alone or in mixture with free compound of the formula I) are preferably pharmaceutically acceptable salts. Such salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, e.g., carboxylic acids or sulfonic acids, such as fumaric acid or methansulfonic acid. For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred. In view of the close relationship between the novel compounds in free form and those in the form of their salts, including those salts that can be used as intermediates, for example in the purification or identification of the novel compounds, any reference to the free compounds hereinbefore and hereinafter is to be understood as referring also to the corresponding salts, as appropriate and expedient.

Combination refers to either a fixed combination in one dosage unit form, or a kit of parts for the combined administration where a compound of the formula I and a combination partner (e.g. an other drug as explained below, also referred to as "therapeutic agent" or "co-agent") may be administered independently at the same time or separately within time intervals, especially where these time intervals allow that the combination partners show a cooperative, e.g. synergistic effect. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a combination partner, are both administered to a patient simultaneously in the form of a single entity or dosage. The term "non-fixed combination" means that the active ingredients, e.g. a compound of formula I and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more active ingredients.

In preferred embodiments, which are preferred independently, collectively or in any combination or sub-combination, the invention relates to a compound of the formula I, in free base form or in acid addition salt form, wherein the substituents are as defined herein.

In an embodiment, the invention relates to a compound of formula IA

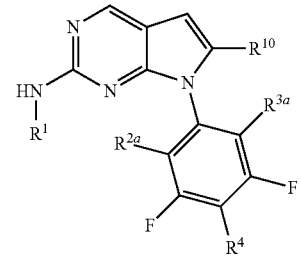

IA wherein the substituents are as defined for a compound of formula I.

In a further embodiment, the invention relates to a compound of formula IB

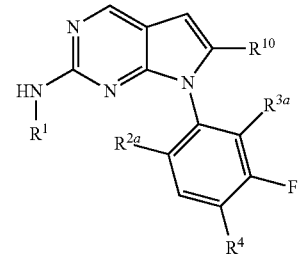

IB wherein the substituents are as defined for a compound of formula I.

In a further embodiment, the invention relates to a compound of formula IC

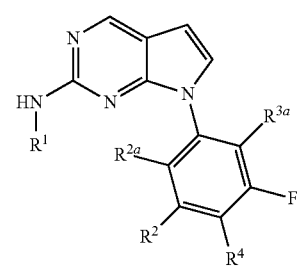

IC wherein the substituents are as defined for a compound of formula I.

In a further embodiment, the invention relates to a compound of formula ID

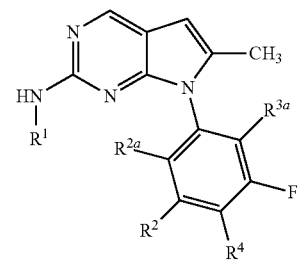

ID wherein the substituents are as defined for a compound of formula I.

In a further embodiment, the invention relates to a compound of formula IE

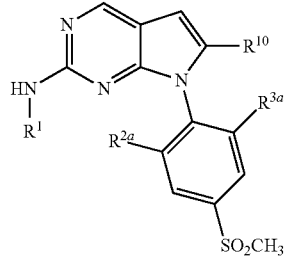

IE wherein the substituents are as defined for a compound of formula I.

In a further embodiment, the invention relates to compounds of the formula (I) wherein $R^{2a}$ and $R^{3a}$ are both H, that is, this embodiment relates to compounds of the formula I':

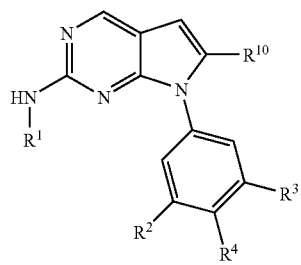

(I')

wherein $R^1$ represents unsubstituted or substituted heterocyclyl, unsubstituted or substituted aryl, unsubstituted or substituted cycloalkyl;

$R^2$ represents hydrogen, halogen, lower alkyl, lower alkyloxy, lower haloalkyl, cycloalkyl, cycloalkyloxy, halocycloalkyl, cycloalkyloxy, halocycloalkyloxy;

$R^3$ represents hydrogen, halogen, lower alkyl, lower alkyloxy, lower haloalkyl, cycloalkyl, cycloalkyloxy, halocycloalkyl, cycloalkyloxy, halocycloalkyloxy;

$R^4$ represents a group:

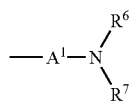

wherein $A^1$ represents one of the following groups:

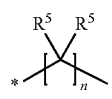 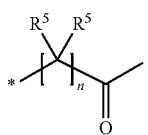 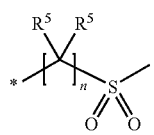

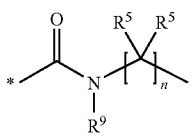

in which the atom marked * is bond to the phenyl ring; or $R^4$ represents one of the following groups:

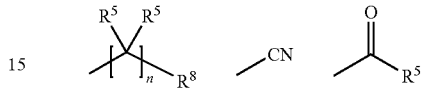

$R^5$ represents independent from each other hydrogen, lower alkyl, lower haloalkyl, cycloalkyl, halocycloalkyl or form, together with the carbon to which they are attached a cycloalkyl;

$R^6$ and $R^7$ represent together with the nitrogen to which they are attached an optionally substituted heterocycle or $R^6$ represents hydrogen or optionally substituted alkyl and $R^7$ represents optionally substituted alkyl;

$R^8$ represents hydroxy, lower alkyloxy, lower haloalkyloxy, cycloalkyloxy, halocycloalkyloxy, lower alkyl-sulfonyl, lower-haloalkyl-sulfonyl, cycloalkyl-sulfonyl, halocycloalkyl-sulfonyl, lower alkyl-sulfinyl, lower haloalkyl-sulfinyl, cycloalkyl-sulfinyl, halocycloalkyl-sulfinyl;

$R^9$ represents H or lower alkyl;

$R^{10}$ represents hydrogen, lower alkyl, lower haloalkyl, cycloalkyl, halocycloalkyl;

n represents 0, 1 or 2;

or salts thereof.

In a further embodiment, the invention relates to a compound of formula I'A

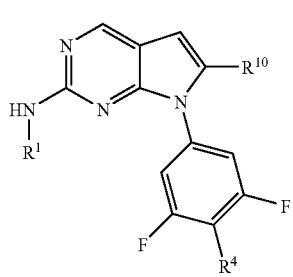

I'A wherein the substituents are as defined for a compound of formula I.

In a further embodiment, the invention relates to a compound of formula I'B

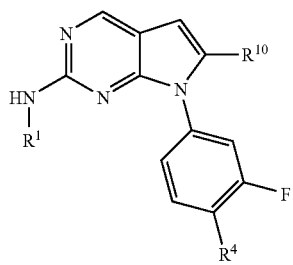

I'B wherein the substituents are as defined for a compound of formula I.

In a further embodiment, the invention relates to a compound of formula I'C

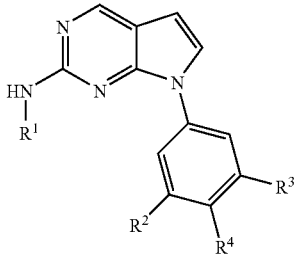

I'C wherein the substituents are as defined for a compound of formula I.

In a further embodiment, the invention relates to a compound of formula I'D

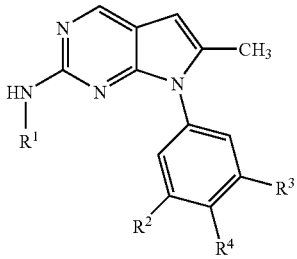

I'D wherein the substituents are as defined for a compound of formula I.

In a further embodiment, the invention relates to a compound of formula I'E

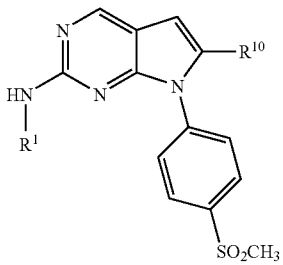

I'E wherein the substituents are as defined for a compound of formula I.

$A^1$ preferably represents a direct bond, carbonyl (—C(=O)—) or methandiyl (—CH$_2$—).

The following definitions apply to any of the formulae described herein.

$R^1$ preferably represents unsubstituted or substituted heterocyclyl or unsubstituted or substituted aryl
wherein said heterocyclyl is selected from unsaturated, saturated or partially saturated heterocycles which are monocyclic, bicyclic, tricyclic or spirocyclic and have 4 to 16, ring atoms wherein one to four heteroatoms are present;

wherein said aryl is selected from aromatic moieties with 6 to 14 ring carbon atoms;

wherein said substiutents are independently selected from one or more, preferably one to four of the following moieties: $C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-di-oxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, cyano and nitro.

$R^1$ particular preferably represents unsubstituted or substituted heterocyclyl or unsubstituted or substituted aryl
wherein said heterocyclyl or aryl is selected from the group consisting of phenyl, naphthyl, indanyl, pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline and wherein said heterocyclyl or aryl is substituted by one or more, preferably one to three moieties independently selected from the group consisting of $C_1$-$C_7$-alkyl, (amino, $C_1$-$C_7$-alkyl-amino, $C_1$-$C_7$-dialkyl-amino)-$C_1$-$C_7$-alkyl, (amino, $C_1$-$C_7$-alkyl-amino, $C_1$-$C_7$-dialkyl-amino)-$C_1$-$C_7$-alkyloxy, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxo-pyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$C_7$-alkyl, morpholino-$C_1$-$C_7$-alkyl, thiomorpholino-$C_1$-$C_7$-alkyl, S-mono- or S,S-di-oxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl 1,4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, cyano and nitro.

$R^1$ very particular preferably represents heterocyclyl, heteroaryl or aryl in each case unsubstituted or substituted by one or more (preferably 0, 1 or 2 substituents), wherein said heterocyclyl, heteroaryl or aryl is selected from the group consisting of phenyl, 2-, 3-, 4-pyridyl, 2-, 4-, 5-pyrimidinyl, pyrazinyl, 3-, 4-pyridanzinyl, 3-, 4-, 5-pyrazolyl, 2-, 4-, 5-imidazolyl, 2-, 4-, 5-thiazolyl, 3-, 4-, 5-isothiazolyl and wherein said substituent is selected from the group consisting of fluoro, chloro, cyano, $C_1$-$C_4$-alkyl (in particular methyl, ethyl), $C_1$-$C_4$-alkyloxy (in particular methoxy), hydroxyl-$C_1$-$C_4$-alkyl (in particular 2-hydroxyethyl), halo-$C_1$-$C_4$-alkyl (in particular $CF_3$), $C_1$-$C_4$-alkyloxy-$C_1$-$C_4$-alkyl (in particular methoxymethyl), cyclopropyl, cyclopentyl, cyclopropyloxy, cyclopentyloxy or a group

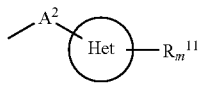

in which
$A^2$ represents a single bond, carbonyl, methandiyl, 1,1-ethandiyl, 1,2-ethandiyl
Het represents a saturated heteroycycle with 5 or 6 ring atoms (in particular piperidinyl, piperazinyl, morpholinyl
m represents 0, 1 or 2
$R^{11}$ represents $C_1$-$C_4$-alkyl (in particular methyl, ethyl), $C_1$-$C_4$-alkyloxy (in particular methoxy), $C_1$-$C_4$-alkyloxycarbonyl (in particular tert-Butoxycarbonyl), hydroxyl-$C_1$-$C_4$-alkyl (in particular 2-hydroxyethyl), halo-$C_1$-$C_4$-alkyl (in particular $CF_3$), $C_1$-$C_4$-alkyloxy-$C_1$-$C_4$-alkyl (in particular methoxymethyl), cyclopropyl, cyclopropyloxy.

In any of the formulae herein, $R^1$ is preferably aryl or heteroaryl, each being unsubstituted or substituted as defined herein.

$R^2$ preferably represents hydrogen, halogen, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy.

$R^2$ particular preferably represents hydrogen, fluoro, chloro, $C_1$-$C_4$-alkyl, $C_1$-$C_4$-alkyloxy, cyclopropyl, cyclopentyl, cyclopropyloxy or cyclopentyloxy in each case optionally substituted by one or more substituents selected from the group consisting of fluoro and chloro.

$R^2$ very particular preferably represents hydrogen, fluoro, chloro, methyl.

$R^3$ preferably represents hydrogen, halogen, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy.

$R^3$ particular preferably represents hydrogen, fluoro, chloro, $C_1$-$C_4$-alkyl, $C_1$-$C_4$-alkyloxy, cyclopropyl, cyclopentyl, cyclopropyloxy or cyclopentyloxy in each case optionally substituted by one or more substituents selected from the group consisting of fluoro and chloro.

$R^3$ very particular preferably represents hydrogen, fluoro, chloro, methyl.

When $R^2$ and/or $R^3$ are connected to $R^5$ or $R^7$ to form a cyclic moiety fused to the phenyl ring to which $R^2$/$R^3$ are attached, the resultant fused ring system is preferably a 1,3-dihydro-indol-2-one, optionally substituted in the 1-position with lower alkyl such as methyl, or a 3,4-dihydro-1H-quinolin-2-one.

$R^{2a}$ preferably represents hydrogen, halogen, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy.

$R^{2a}$ particular preferably represents hydrogen, fluoro, chloro, $C_1$-$C_4$-alkyl, $C_1$-$C_4$-alkyloxy, cyclopropyl, cyclopentyl, cyclopropyloxy or cyclopentyloxy in each case optionally substituted by one or more substituents selected from the group consisting of fluoro and chloro.

$R^{2a}$ very particular preferably represents hydrogen, fluoro, chloro, methyl.

$R^{2a}$ more preferably represents hydrogen or methyl, even more preferably hydrogen.

$R^{3a}$ preferably represents hydrogen, halogen, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy.

$R^{3a}$ particular preferably represents hydrogen, fluoro, chloro, $C_1$-$C_4$-alkyl, $C_1$-$C_4$-alkyloxy, cyclopropyl, cyclopentyl, cyclopropyloxy or cyclopentyloxy in each case optionally substituted by one or more substituents selected from the group consisting of fluoro and chloro.

$R^{3a}$ very particular preferably represents hydrogen, fluoro, chloro, methyl.

$R^{3a}$ more preferably represents hydrogen or methyl, even more preferably hydrogen.

$R^5$ preferably represents hydrogen, $C_1$-$C_7$-alkyl, $C_1$-$C_7$-haloalkyl, $C_3$-$C_6$-cycloalkyl, $C_3$-$C_6$-halocycloalkyl or both R5 form together with the carbon to which they are attached a cyclopropyl.

$R^5$ particular preferably represents hydrogen, $C_1$-$C_4$-alkyl, $C_1$-$C_2$-haloalkyl, cyclopropyl.

$R^5$ very particular preferably represents hydrogen, methyl or cyclopropyl.

$R^6$ and $R^7$ preferably represent together with the nitrogen to which they are attached an optionally substituted heterocycle substituted by one or more substituents, wherein said heterocycle is saturated, contains 5 or 6 ring atoms, and 1, 2 or 3 heteroatoms selected from the group of N, O and S, and wherein said substituents are selected from the group consisting of oxo (e.g. in C=O or SO2), hydroxy, halo, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-C6-halocycloalkyl, $C_3$-$C_6$-halocycloalkyloxy hydroxy-$C_1$-$C_7$-alkyl, $C_1$-$C_7$-alkylamino, di-$C_1$-$C_7$-alkylamino.

$R^6$ and $R^7$ very preferably represent together with the nitrogen to which they are attached an optionally substituted heterocycle optionally substituted by one to three substituents, wherein said heterocycle is selected from the group of morpholinyl, piperazinyl, thiazidinyl, pyrrolidinyl and wherein said substituents are selected from the group consisting of oxo (e.g. in C=O or SO$_2$), fluoro, chloro, $C_1$-$C_4$-alkyl, $C_1$-$C_4$-alkyloxy, cyclopropyl, cyclopropyloxy, hydroxy-$C_1$-$C_4$-alkyl, $C_1$-$C_4$-alkylamino, di-$C_1$-$C_4$-alkylamino.

$R^6$ preferably represents hydrogen, optionally substituted $C_1$-$C_7$-alkyl, and $R^7$ represents hydrogen, optionally substituted $C_1$-$C_7$-alkyl, wherein said substituents are selected from the group consisting of oxo (e.g. in C=O or SO$_2$), hydroxy, halo, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy hydroxy-$C_1$-$C_7$-alkyl, $C_1$-$C_7$-alkylamino, di-$C_1$-$C_7$-alkylamino.

$R^6$ very preferably represents hydrogen and $R^7$ very preferably represents n-butyl, sec-butyl, iso-butyl, tert-butyl, n-propyl, iso-propyl, ethyl or methyl in particular tert.-butyl each being optionally substituted, wherein said substituents are selected from the group consisting of oxo (e.g. in C=O or SO$_2$), hydroxy, halo, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxyhydroxy-$C_1$-$C_7$-alkyl, $C_1$-$C_7$-alkylamino, di-$C_1$-$C_7$-alkylamino.

$R^8$ preferably represents hydroxy, $C_1$-$C_7$-alkyloxy, $C_1$-$C_7$-haloalkyloxy, $C_3$-$C_6$-cycloalkyloxy, $C_3$-$C_6$-halocycloalkyloxy, $C_1$-$C_7$-alkyl-sulfonyl, $C_1$-$C_7$-haloalkyl-sulfonyl, $C_3$-$C_6$-cycloalkyl-sulfonyl, $C_3$-$C_6$-halocycloalkyl-sulfonyl, $C_1$-$C_7$-alkyl-sulfinyl, $C_1$-$C_7$-haloalkyl-sulfinyl, $C_3$-$C_6$-cycloalkyl-sulfinyl, $C_3$-$C_6$-halocycloalkyl-sulfinyl.

$R^8$ particular preferably represents hydroxy, methoxy, ethoxy, iso-propoxy, halomethoxy, methylcarbonyl, methylsulfonyl (H$_3$CSO$_2$—), cyclopropylsulfonyl.

$R^8$ very particular preferably represents hydroxy, methoxy or methylsulfonyl.

$R^9$ preferably represents hydrogen, $C_1$-$C_7$-alkyl.

$R^9$ particular preferably represents hydrogen, $C_1$-$C_4$-alkyl.

$R^9$ very particular preferably represents hydrogen.

$R^{10}$ preferably represents hydrogen, $C_1$-$C_7$-alkyl, $C_1$-$C_7$-haloalkyl, $C_3$-$C_6$-cycloalkyl, $C_3$-$C_6$-halocycloalkyl.

$R^{10}$ particular preferably represents hydrogen, $C_1$-$C_4$-alkyl, $C_1$-$C_2$-haloalkyl, cyclopropyl.

$R^{10}$ very particular preferably represents hydrogen or methyl.

n preferably represents 0 or 1.

n particular preferably represents 0.

n further particular preferably represents 1.

In a further advantageous embodiment, n represents 0 and $R^8$ represents —SO$_2$CH$_3$.

In a yet further advantageous embodiment, n represents 0 or 1 and R4 represents the group:

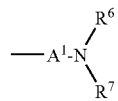

as defined above, more preferably wherein the group is as defined above and $R^6$ and $R^7$ together with the nitrogen atom to which they are attached form a morpholinyl, piperazinyl, thiazidinyl or pyrrolidinyl group, each being optionally substituted, most preferably $R^6$ and $R^7$ together with the nitrogen atom to which they are attached form an optionally substituted morpholinyl group, wherein said substituents are selected from the group consisting of oxo (e.g. in C=O or SO$_2$), hydroxy, halo, $C_1$-$C_7$-alkyl, $C_1$-$C_7$-alkyloxy, $C_1$-$C_7$-haloalkyl, $C_1$-$C_7$-haloalkyloxy, $C_3$-$C_6$-cycloalkyl, $C_3$-$C_6$-cycloalkyloxy, $C_3$-$C_6$-halocycloalkyl, $C_3$-$C_6$-halocycloalkyloxy hydroxy-$C_1$-$C_7$-alkyl, $C_1$-$C_7$-alkylamino, di-$C_1$-$C_7$-alkylamino In a further advantageous embodiment, at least one of $R^2$ and $R^3$ does not represent hydrogen.

In a further advantageous embodiment, $R^1$ is optionally substituted aryl selected from the group consisting of phenyl, naphthyl, each of which is unsubstituted or substituted by one to three moieties independently selected from the group consisting of $C_1$-$C_7$-alkyl, amino-$C_1$-$C_7$-alkyl, halo-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, pyrrolidino-$C_1$-$C_7$-alkyl, oxopyrrolidino-$C_1$-$C_7$-alkyl, piperidino-$C_1$-$C_7$-alkyl, piperazin-1-yl-$C_1$-$C_7$-alkyl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl-$C_1$-$C_7$-alkyl, 4-(amino-$C_1$-$C_7$-alkyl)-piperazin-1-yl-$C_1$-$C_7$-alkyl, 4-[N-mono- or N,N-di-($C_1$-$C_7$-alkylamino)-$C_1$-$C_7$-alkyl]-piperazin-1-yl-$C_1$-$_7$-alkyl, morpholino-$C_1$-$C_7$-alkyl, thiomorpholino-$C_1$-$C_7$-alkyl, S-mono- or S,S-dioxo-thiomorpholino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, pyrrolidino, oxo-pyrrolidino, piperidino, piperazin-1-yl, 4-($C_1$-$C_7$-alkyl, $C_1$-$C_7$-alkoxy-$C_1$-$C_7$-alkyl, halo-$C_1$-$C_7$-alkyl or $C_3$-$C_{10}$-cycloalkyl)-piperazin-1-yl, 4-(amino-$C_1$-$C_7$-alkyl)-piperazin-1-yl, 4-[N-mono- or N,N-di-($C_1$-$C_7$-alkylamino)-$C_1$-$C_7$-alkyl]-piperazin-1-yl, morpholino, thiomorpholino, S-oxo- or S,S-dioxothiomorpholino, $C_1$-$C_7$-alkanesulfonylamino, carbamoyl, N-mono- or N,N-di-($C_1$-$C_7$-alkyl, $C_1$-$C_7$-alkoxy-$C_1$-$C_7$-alkyl, amino-$C_1$-$C_7$-alkyl and/or (N'-mono- or N',N'-di-($C_1$-$C_7$-alkyl)-amino-$C_1$-$C_7$-alkyl)-carbamoyl, pyrrolidin-1-carbonyl, piperidin-1-carbonyl, piperazin-1-carbonyl, 4-($C_1$-$C_7$-alkyl)piperazin-1-carbonyl, morpholin-1-carbonyl, thiomorpholin-1-carbonyl, S-oxo- or S,S-dioxothiomorpholin-1-carbonyl, sulfo, $C_1$-$C_7$-alkanesulfonyl, $C_1$-$C_7$-alkanesulfinyl, sulfamoyl, N-mono- or N,N-di-($C_1$-$C_7$-alkyl)-sulfamoyl, morpholinosulfonyl, thiomorpholinosulfonyl, cyano and nitro; for example, it can preferably be phenyl or naphthyl that is substituted by one or more, especially one to four substituents independently selected from the group consisting of $C_1$-$C_7$-alkoxy, carbamoyl, N-mono- or N,N-di-($C_1$-$C_7$-alkyl and/or $C_1$-$C_7$-alkyloxy-$C_1$-$C_7$-alkyl)-carbamoyl, N-mono- or N,N-di-{[unsubstituted, N'-mono- or N',N'-di-($C_1$-$C_7$-alkyl)-substituted]-carbamoyl, sulfamoyl, N-mono- or N,N-di-($C_1$-$C_7$-alkyl)-sulfamoyl, piperidino, piperazino, N—$C_1$-$C_7$-alkylpiperazino, morpholino, thiomorpholino, S-oxothiomorpholino and S,S-dioxothiomorpholino, in the case of $R^2$, unsubstituted or substituted aryl is preferably phenyl or naphthyl that is unsubstituted or substituted by one or more, especially up to three, more especially up to two, substituents, preferably not in ortho-position, more preferably with not more than one substituent in meta-position, most preferably with one substituent in meta- and/or one substituent in para position, most preferably with one substituent in meta-position or especially one in para-position, where the substituents are independently selected from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkanesulfonylamino, carbamoyl, N-mono- or N,N-di-($C_1$-$C_7$-alkyl)-carbamoyl, $C_1$-$C_7$-alkanesulfonyl, sulf-amoyl, N-mono- or N,N-di-($C_1$-$C_7$-alkyl)-sulfamoyl, morpholino-sulfonyl, thiomorpholino-sulfonyl, cyano and nitro.

In a further advantageous embodiment, $R^1$ is optionally substituted aryl selected from the group consisting of phenyl, (especially 3,4,5-)trimethoxyphenyl*, (especially 3,4- or 3,5-)dimethoxyphenyl*, (especially 4-)morpholinophenyl, (especially 4-)N-(2-methoxyethyl)-carbamoylphenyl*, or (especially 4-)N,N-(2-dimethylamino-ethyl)-carbamoylphenyl*, (especially 4-)dimethylaminocarbonyl-(especially 3-)methyl-phenyl*, (especially 4-)-(preferably 4-)-(2-methoxy-ethyl-piperazin-(especially 1-)yl-(especially 3-)-methyl-phenyl, (especially 4-)pyrrolidin-1-carbonyl-(especially 3-)methyl-phenyl*, (especially 3-)methyl-(especially 4-)-4-methylpiperazin-1-carbonyl-phenyl, (especially 3- or 4-)4-methyl-piperazin-1-yl-phenyl*, (especially 4-)-4-ethyl-piperazin-1-yl-(especially 3-) methyl-phenyl*, (especially 4-)-4-methylpiperazin-1-yl-(especially 3-)cyano-phenyl, (especially 4-)-piperazin-1-yl-phenyl, (especially 4-)-4-cyclopropyl-piperazin-1-yl-phenyl, (especially 4-)-4-(2-dimethylaminoethyl)-piperazin-1-yl-(especially 3-)methyl-phenyl*, (especially 4-)4-isopropyl-piperazin-1-yl)-(especially 3-)methyl-phenyl*, (especially 4-)N,N-diethylaminocarbonyl-(especially 3-)methyl-phenyl*, (especially 4-)4-ethylpiperazin-1-carbonyl-(especially 3-)methyl-phenyl, (especially 4-)-(4-ethylpiperazin-1-ylmethyl)-(especially 3-)methyl-phenyl, (especially 4-)N-methylaminocarbonyl-(especially 3-)methylphenyl, (especially 4-)-4-(3,3,3-trifluoropropyl)-piperazin-1-yl-(especially 3-)methyl-phenyl, (especially 4-)-4-(2-(N',N'-dimethylamino)ethyl-aminocarbonyl-(especially 3-)methyl-phenyl, (especially 4-)-methanesufonyl-phenyl*, (especially 4-)[(especially 2-)-oxo-pyrrolidin-1-yl]-phenyl, (especially 4-)N,N-diethylaminocarbonyl-(especially 3-)methoxyphenyl, (especially 3-)-4-methylpiperazin-1-yl-(especially 4-)methyl-phenyl, (especially 3-)-4-methylpiperazin-1-yl-(especially 4-)methoxy-phenyl*, (especially 3- or 4-)-morpholinomethyl-(especially 4- or 3-)methyl-phenyl, (especially 2-)acetylamino-indan-(especially 5-)yl, (especially 2-)oxo-2,3-dihydroindol-(especially 5-)yl, (especially 4-)methylsulfinylphenyl, (especially 4-)methoxyphenyl, (especially 4-)methyl-(especially 3-)methoxyphenyl, (especially 4-)-N-(2-methoxyethyl)-aminocarbonyl-phenyl, (especially 4-)N,N-dimethylcarbamoyl-phenyl, (especially 3-)methanesulfonylamino-phenyl, (especially 4-)methoxycarbonyl-(especially 3-)methoxy-phenyl, (especially 4-)N,N-dimethylcarbamoyl-(especially 3-)methoxy-phenyl, (especially 4-)-(4-cyclopropyl-piperazin-1-yl)-(especially 3-)methyl-phenyl*, (especially 4-)-N-(2-(N',N'-dimethylaminoethyl)-N-methylcarbamoyl-(especially 3-)methyl-phenyl*, 1,3-dimethyl-oxo-1 H-pyridine-5-yl, (especially 3- or 4-)morpholino-(especially 4- or 3-)methyl-phenyl*, (especially 4-)morpholinomethyl-(especially 3-)methyl-phenyl, (especially 4-)morpholin-1-carbonyl-(especially 3-)methyl-phenyl, (especially 4-)-N-2-(methoxyethyl)aminocarbonyl-(especially 3-)methyl-phenyl, (especially 4-)-N-(3-N'.N'-dimethylaminopropyl)amino-carbonyl-(especially 3-)methyl-phenyl, (especially 5-)-methyl-(especially 6-)methoxy-pyridin-3-yl, (especially 4-)dimethylcarbamoyl-(especially 3,5-)dimethyl-phenyl, (especially 4-)dimethylcarbamoyl-(especially 3-)ethyl-phenyl, (especially 4-(4-)N, N-dimethylcarbamoyl-(especially 3-)methyl-phenyl or (especially 4-)morpholino-(especially 3-)cyano-phenyl; where the moieties marked with an asterisk (*) are especially preferred, as are the moieties where the position after "especially" is given).

In a further advantageous embodiment, $R^1$ is optionally substituted heterocyclyl selected from the group consisting of preferably pyridyl, pyrimidyl, pyrazolyl, thiophenyl, pyrrolyl imidazolyl, or 1H-benzoimidazolyl, each of which is unsubstituted or substituted by one to three moieties independently selected from those mentioned above as substituents for aryl $R^1$, or especially from the group consisting of $C_1$-$C_7$-alkyl, amino-$C_1$-$C_7$-alkyl, N—$C_1$-$C_7$-alkanoylamino-$C_1$-$C_7$-alkyl, N—$C_1$-$C_7$-alkanesulfonyl-amino-$C_1$-$C_7$-alkyl, carbamoyl-$C_1$-$C_7$-alkyl, [N-mono- or N,N-di-($C_1$-$C_7$-alkyl)-carbamoyl]-$C_1$-$C_7$-alkyl, $C_1$-$C_7$-alkanesulfinyl-$C_1$-$C_7$-alkyl, $C_1$-$C_7$-alkanesulfonyl-$C_1$-$C_7$-alkyl, halo, hydroxyl, $C_1$-$C_7$-alkoxy, amino, N-mono- or N,N-di-($C_1$-$C_7$-alkyl)-amino, $C_1$-$C_7$-alkanoylamino, $C_1$-$C_7$-alkanesulfonylamino, carbamoyl, N-mono- or N,N-di-($C_1$-$C_7$-alkyl)-carbamoyl, $C_1$-$C_7$-alkanesulfonyl, sulfamoyl, N-mono- or N,N-di-($C_1$-$C_7$-alkyl)-sulfamoyl, morpholinosulfonyl, thiomorpholinosulfonyl, thiomorpholinosulfinyl, cyano and nitro.

In a further advantageous embodiment, $R^1$ represents phenyl or pyridiyl in each case optionally substituted by one or two substituents, the substituents being selected from the group consisting of $C_1$-$C_4$-alkyl (in particular methyl), $C_1$-$C_4$-alkoxy (in particular methoxy), halo (in particular fluoro), N-methyl-N-piperazinyl-methyl, N-methyl-N-piperazinyl-carbonyl, 3,5-dimethyl-N-piperazinyl.

The invention further relates to pharmaceutically acceptable prodrugs of a compound of formula (I).

The invention further relates to pharmaceutically acceptable metabolites of a compound of formula (I).

The invention relates especially to the compounds of the formula I given in the Examples, as well as the methods of manufacture described therein.

The compounds of formula I thereof have valuable pharmacological properties, as described hereinbefore and hereinafter. They inhibit various protein tyrosine kinases, and especially JAK2 and/or JAK3-receptor tyrosine kinase. Preferably, the compounds of formula I exhibit selectivity for JAK2 and JAK3 over JAK1 and TYK2 kinases. Most preferably, the compounds of formula I exhibit selectivity for JAK2 over the other JAK family kinases, i.e. preferably, selectivity is exhibited for JAK2 over JAK1, JAK3 and TYK2 kinases.

Preferably, the compounds of formula I exhibit selectively for JAK2 inhibition when compared to other kinases, for example cMet, cKit, ALK and/or PDGFRa.

The compounds of formula I typically show IC50 values for JAK2 inhibition in the range <0.003 to 2 umol l−1, preferably <0.003 to 1 umol l−1, more preferably <0.003 to 0.100 umol l−1, even more preferably <0.003 to 0.050 umol l−1.

The efficacy of the compounds of the invention as inhibitors of JAK/TYK kinase activity can be demonstrated as follows (Results are given at the end of the specification):

All four kinases of the JAK/TYK-kinase family were used as purified recombinant GST-fusion proteins, containing the active kinase domains. GST-JAK1 (866-1154), GST-JAK3 (811-1124), and GST-TYK2(888-1187) were expressed and purified by affinity chromatography at the EPK biology unit. GST-JAK2(808-1132) was purchased from Invitrogen (Carlsbad, USA, #4288).

The kinase assays were based on the Caliper mobility shift assay using the LabChip 3000 systems. This technology is similar to capillary electrophoresis and uses charge driven separation of substrate and product in a microfluidic chip.

All kinase reactions were performed in 384 well microtiter plates in a total reaction volume of 18 µl. The assay plates were prepared with 0.1 µl per well of test compound in the appropriate test concentration, as described under the section "preparation of compound dilutions". The reactions were started by combining 9 µl of substrate mix (consisting of peptide and ATP) with 9 µl of kinase dilution. The reactions were incubated for 60 minutes at 30° C. and stopped by adding 70 µl of stop buffer (100 mM Hepes, 5% DMSO, 0.1% Coating reagent, 10 mM EDTA, 0.015% Brij 35).

Fluorescently labeled synthetic peptides were used as substrates in all reactions. A peptide derived from the sequence of IRS-1(IRS-1 peptide, SEQ ID NO: 1 FITC-Ahx-KKSRGDYMTMQIG-NH2) was used for JAK1 and TYK2 and a peptide named JAK3tide SEQ ID NO: 2 (FITC-GGEEEEYFELVKKKK-NH2) for JAK2 and JAK3. Specific assay conditions are described in Table1:

Pre-dilution plates: 96 polypropylene well plates were used as pre-dilution plates. A total of 4 pre-dilution plates were prepared including 10 test compounds each on the plate positions A1-A10, one standard compound at A11 and one DMSO control at A12. All dilution steps were done on a HamiltonSTAR robot.

Master plates: 100 µL of individual compound dilutions including standard compound and controls of the 4 "pre-dilution plates" were transferred into a 384 "master plate" including the following concentrations 1,820, 564, 182, 54.6, 18.2, 5.46, 1.82 and 0.546 µM, respectively in 90% of DMSO.

Assay plates: Identical assay plates were then prepared by pipetting 100 nL each of compound dilutions of the master plates into 384-well "assay plates". In the following the compounds were mixed with 9 µL of assays components plus 9 µL enzyme corresponding to a 1:181 dilution steps enabling the final concentration of 10, 3.0, 1.0, 0.3, 0.1, 0.03, 0.01 and 0.003 µM, respectively. The preparation of the master plates were handled by the Matrix PlateMate Plus robot and replication of assay plates by the HummingBird robot.

On the basis of these studies, a compound of the invention shows therapeutic efficacy especially against disorders dependent on protein kinase, especially proliferative diseases mediated by JAK/TYK kinase activity.

STAT Nuclear Translocation Assays:

Alternatively, the activity of the compounds of the invention as inhibitors of the JAK/STAT pathway can be demonstrated as follows (Results are given at the end of the specification):

The medium-throughput (96-well format) cellular automated fluorescence microscopy Cellomics assay can be routinely used to assess the functional activation of Janus Kinases (JAKs), based on the nuclear translocation of their

TABLE1

Assay conditions of individual kinase assays

| Kinase | JAK1 | JAK2 | JAK3 | TYK2 |
|---|---|---|---|---|
| Buffer | 50 mM Hepes pH 7.5, 0.02% Tween 20, 1 mM DTT, 0.02% BSA, 12 mM MgCl2 | 50 mM Hepes pH 7.5, 0.02% Tween 20, 1 mM DTT, 0.02% BSA, 9 mM MgCl2 | 50 mM Hepes pH 7.5, 0.02% Tween 20, 1 mM DTT, 0.02% BSA, 1.5 mM MgCl$_2$ | 50 mM Hepes pH 7.5, 0.02% Tween 20, 1 mM DTT, 0.02% BSA, 9 mM MgCl2 |
| DMSO | 0.6% | 0.6% | 0.6% | 0.6% |
| Kinase conc. | 50 nM | 1.8 nM | 6 nM | 40 nM |
| Substrate peptide conc. | 5 µM | 2 µM | 2 µM | 5 µM |
| ATP conc. | 40 µM | 20 µM | 80 or 18 µM | 30 µM |

The terminated reactions were transferred to the Caliper LabChip 3000 reader and the turnover of each reaction was measured by determining the substrate/product ratio.

Preparation of Compound Dilutions

Test compounds were dissolved in DMSO (10 mM) and transferred into 1.4 mL flat bottom or V-shaped Matrix tubes carrying a unique 2D matrix chip by individual compound hubs. The numbers of these chips were distinctively linked to the individual compound identification numbers. The stock solutions were stored at −20° C. if not used immediately. For the test procedure the vials were defrosted and identified by a scanner whereby a working sheet was generated that guided the subsequent working steps. Compound dilutions were made in 96 well plates. This format enabled the assay of maximally 40 individual test compounds at 8 concentrations (single points) including 4 reference compounds. The dilution protocol included the production of pre-dilution plates, master plates and assay plates:

substrate, Signal Transducer and Activator of Transcription (STAT). Nuclear translocation can be monitored either in HT1080 fibrosarcoma cells stably transfected with STAT1 fused to Green Fluorescence Protein (GFP) or in U-2 OS osteosarcoma cells stably transfected with STAT5 fused to Green Fluorescence Protein (GFP). Stimulation of HT1080 cells with interferon-γ (IFN-γ) results in JAK1/JAK2-dependent nuclear translocation of STAT1-GFP, whereas stimulation of U-2 OS cells with recombinant human erythropoietin (rhEpo) results in JAK2-dependent nuclear translocation of STAT5-GFP, both of which can be quantified using the Cellomics Cyto/NucTrans software package. This assay may be used to provide an assessment of the nuclear-cytoplasmic differential (NCD) of STAT-GFP using Hoechst dye to define the boundaries of the nucleus.

Generation of HT1080 Fibrosarcoma Cells Stably Expressing GFP-STAT1:

HT1080 fibrosarcoma cells may be obtained from ATCC and can be cultured in alpha Modified Eagle Medium with 10% FCS. Cells can be transfected with pEGFP-N2 STAT1 using Fugene 6 Transfection Reagent following the manufacturers' protocol. 24 hours after transfection the medium can be replaced and selected in 1 mg/ml Geneticin.

Generation of U2OS Cells Stably Expressing STAT5a-GFP and EpoR:

U-2 OS osteosarcoma cells may be obtained from ATCC and can be cultured in standard RPMI medium supplemented with 10% FCS and 2 mM L-glutamine. Cells can be stably transfected with STAT5a-GFP using Lipofectamine following the manufacturers' protocol. 24 hours after transfection the medium can be replaced and selected in 400 µg/ml Geneticin. Subsequently, cells can be stably transfected with EpoR using Lipofectamine following the manufacturers' protocol. 24 hours after transfection the medium can be replaced and cells selected in 100 µg/ml Hygromycin B.

Preparation of Compound Stocks:

Compounds can be dissolved in DMSO to a final stock concentration of 10 mM and stored as aliquots at 4° C. Compounds may be pre-diluted in 100% DMSO at 10 mM, 3 mM 1 mM, 0.3 mM, 0.1 mM, 0.03 mM, 0.01 mM and 0.003 mM. Subsequently, compounds may be diluted in medium and added in 50 µl to the cells. The final compound concentrations tested may be 10 µM, 3 µM 1 µM, 0.3 µM, 0.1 µM, 0.03 µM, 0.01 µM and 0.003 µM and the final DMSO concentration can be 0.1%.

Cellomics Nuclear STAT-GFP Translocation Assays:

HT1080 STAT1-GFP cells may be seeded at a density of 10,000 cells per well in clear-bottom black 96-well Packard View-Plates™. 16-24 hours later, the cells can be treated for 2 hours with 100 ng/ml IFN-γ, washed twice in pre-warmed PBS and fixed in 200 µl of pre-warmed fixation solution (PBS, 3.7% Formaldehyde) for 10 minutes. The plates may be washed twice in 200 µl PBS and incubated, protected from light, in 100 µl of DNA-staining solution (PBS, 0.5 µg/ml Hoechst-33342) for 1 minute. The plates may then be washed once in PBS, and 200 µl PBS finally added per well. The plates, being finally covered with a black adhesive, may be either read directly or stored at 4° C. for later imaging. Where appropriate, the compounds may be added 30 min before stimulation with IFN-γ.

U-2 OS may be seeded at a cell density of 12,000 cells per well in clear-bottom black 96-well Packard View-Plates™. The following day, medium can be removed and replaced with medium containing either the vehicle (DMSO) or increasing concentrations of test compounds for 30 minutes at 37° C. Cells can then be stimulated for 1 hour by adding 10 µl per well of 50 U/ml rhEpo to obtain 5 U/ml of rhEpo as the final concentration. Following treatments, cells can fixed and processed as described above.

STAT-GFP Nuclear Translocation Measurement by Cellomics Automated Fluorescence Microcopy Imaging and Analysis:

The plates can be read on a Cellomics® ArrayscanII automated fluorescence microscope plate reader equipped with a Mercury-Xenon white light illumination source and a Zeiss Axiovert inverted microscope, using the XF100 dichroic/emission filter cube and matching excitation filters, 10× magnification, and a 0.3 numerical aperture objective. Image acquisition and analysis can be performed using a customized protocol based on the 'NuclearTranslocation' Bioapplication. For each well, multiple images (fields) can be acquired until a minimum of 1000 cells are counted using two 2 channels: Channel 1 (Hoechst)=focus+nuclear mask, Channel 2 (GFP)= ignal quantification in mask areas as outlined below. Nuclei may be first identified based on the Hoechst staining and a mask generated for each nucleus that then serves as a template to generate a circle (eroded inwards by 1 pixel) and a 3 pixel-wide collar-like ring (off-set outwards by 1 pixel), in which the nuclear and cytoplasmic intensity of GFP, respectively, are quantified in the corresponding channel. High content analysis yields numerous measurements per cell and the GFP intensity differential between the nuclear and the cytoplasmic masks may be chosen as a measure of sub-cellular STAT-GFP relocation. The resulting values may be averaged for all cells in the well to return a single measurement plus standard deviation.

To generate $IC_{50}$ values, the nuclear-cytoplasmic STAT-GFP differential of untreated cells may be used as a baseline and the following equation used to determine the percentage increase in nuclear translocation: Percentage=100*(NCD Compound pre-treated and stimulated−NCD Untreated)/(NCD DMSO-pretreated and stimulated−NCD Untreated). In these assays, compounds of formula (I) generally inhibit JAK2 kinases in the range of 1-10 000 nM.

The activity of the compounds of the formula I can also be determined in vivo:

JAK-2 in vivo

The assay can be performed as described by G. Wernig, T. Mercher, R. Okabe, R. L. Levine, B. H. Lee, D. G. Gilliland, Blood First Edition paper, published online Feb. 14, 2006; DOI 10, 1182/blood-2005-12-4824.

On the basis of these studies, a compound of formula I according to the invention shows therapeutic efficacy especially against disorders dependent on protein kinase, especially proliferative diseases mediated JAK2 kinase activity.

In addition, further protein kinases can be inhibited by compounds of this invention, such as Tyk2, c-src, Flt-3, KDR and others, for each of which test systems are known in the art.

A compound of formula I can be administered alone or in combination with one or more other therapeutic agents, possible combination therapy taking the form of fixed combinations or the administration of a compound of the invention and one or more other therapeutic agents being staggered or given independently of one another, or the combined administration of fixed combinations and one or more other therapeutic agents. A compound of formula I can besides or in addition be administered especially for tumor therapy in combination with chemotherapy, radiotherapy, immunotherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Thus, a compound of the formula I may be used to advantage in combination with other anti-proliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TEMODAL®); kinesin spindle protein inhibitors, such as SB715992 or SB743921 from GlaxoSmithKline, or pentamidine/chlorpromazine from CombinatoRx; MEK inhibitors such as ARRY142886 from Array PioPharma, AZD6244 from AstraZeneca, PD181461 from Pfizer, leucovorin, EDG binders, antileukemia compounds, ribonucleotide reductase inhibitors, S-adenosylmethionine decarboxylase inhibitors, antiproliferative antibodies or other chemotherapeutic compounds. Further, alternatively or in addition they may be used in combination with other tumor treatment approaches, including surgery, ionizing radiation, photodynamic therapy, implants, e.g. with corticosteroids, hormones, or they may be used as radiosensitizers. Also, in anti-inflammatory and/or antiproliferative treatment, combination with anti-inflammatory drugs is included. Combination is also possible with antihistamine drug substances, bronchodilatatory drugs, NSAID or antagonists of chemokine receptors.

The term "aromatase inhibitor" as used herein relates to a compound which inhibits the estrogen production, i.e. the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane can be administered, e.g., in the form as it is marketed, e.g. under the trademark AROMASIN. Formestane can be administered, e.g., in the form as it is marketed, e.g. under the trademark LENTARON. Fadrozole can be administered, e.g., in the form as it is marketed, e.g. under the trademark AFEMA. Anastrozole can be administered, e.g., in the form as it is marketed, e.g. under the trademark ARIMIDEX. Letrozole can be administered, e.g., in the form as it is marketed, e.g. under the trademark FEMARA or FEMAR. Aminoglutethimide can be administered, e.g., in the form as it is marketed, e.g. under the trademark ORIMETEN. A combination of the invention comprising a chemotherapeutic agent which is an aromatase inhibitor is particularly useful for the treatment of hormone receptor positive tumors, e.g. breast tumors.

The term "antiestrogen" as used herein relates to a compound which antagonizes the effect of estrogens at the estrogen receptor level. The term includes, but is not limited to tam-oxifen, fulvestrant, raloxifene and raloxifene hydrochloride. Tamoxifen can be administered, e.g., in the form as it is marketed, e.g. under the trademark NOLVADEX. Raloxifene hydro-chloride can be administered, e.g., in the form as it is marketed, e.g. under the trademark EVISTA. Fulvestrant can be formulated as disclosed in U.S. Pat. No. 4,659,516 or it can be administered, e.g., in the form as it is marketed, e.g. under the trademark FASLODEX. A combination of the invention comprising a chemotherapeutic agent which is an antiestrogen is particularly useful for the treatment of estrogen receptor positive tumors, e.g. breast tumors.

The term "anti-androgen" as used herein relates to any substance which is capable of inhibiting the biological effects of androgenic hormones and includes, but is not limited to, bicalutamide (CASODEX), which can be formulated, e.g. as disclosed in U.S. Pat. No. 4,636,505. The term "gonadorelin agonist" as used herein includes, but is not limited to abarelix, goserelin and goserelin acetate. Goserelin is disclosed in U.S. Pat. No. 4,100,274 and can be administered, e.g., in the form as it is marketed, e.g. under the trademark ZOLADEX. Abarelix can be formulated, e.g. as disclosed in U.S. Pat. No. 5,843,901.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148 (compound A1 in WO99/17804). Irinotecan can be administered, e.g. in the form as it is marketed, e.g. under the trademark CAMPTOSAR. Topotecan can be administered, e.g., in the form as it is marketed, e.g. under the trademark HYCAMTIN.

The term "topoisomerase II inhibitor" as used herein includes, but is not limited to the anthracyclines such as doxorubicin (including liposomal formulation, e.g. CAELYX), daunorubicin, epirubicin, idarubicin and nemorubicin, the anthraquinones mitoxantrone and losoxantrone, and the podophillotoxines etoposide and teniposide. Etoposide can be administered, e.g. in the form as it is marketed, e.g. under the trademark ETOPOPHOS. Teniposide can be administered, e.g. in the form as it is marketed, e.g. under the trademark VM 26-BRISTOL. Doxorubicin can be administered, e.g. in the form as it is marketed, e.g. under the trademark ADRIBLASTIN or ADRIAMYCIN. Epirubicin can be administered, e.g. in the form as it is marketed, e.g. under the trademark FARMORUBICIN. Idarubicin can be administered, e.g. in the form as it is marketed, e.g. under the trademark ZAVEDOS. Mitoxantrone can be administered, e.g. in the form as it is marketed, e.g. under the trademark NOVANTRON.

The term "microtubule active compound" relates to microtubule stabilizing, microtubule destabilizing compounds and microtublin polymerization inhibitors including, but not limited to taxanes, e.g. paclitaxel and docetaxel, vinca alkaloids, e.g., vinblastine, especially vinblastine sulfate, vincristine especially vincristine sulfate, and vinorelbine, discodermolides, cochicine and epothilones and derivatives thereof, e.g. epothilone B or D or derivatives thereof. Paclitaxel may be administered e.g. in the form as it is marketed, e.g. TAXOL.

Docetaxel can be administered, e.g., in the form as it is marketed, e.g. under the trademark TAXOTERE. Vinblastine sulfate can be administered, e.g., in the form as it is marketed, e.g. under the trademark VINBLASTIN R.P. Vincristine sulfate can be administered, e.g., in the form as it is marketed, e.g. under the trademark FARMISTIN. Discodermolide can be obtained, e.g., as disclosed in U.S. Pat. No. 5,010,099. Also included are Epothilone derivatives which are disclosed in WO 98/10121, U.S. Pat. No. 6,194,181, WO 98/25929, WO 98/08849, WO 99/43653, WO 98/22461 and WO 00/31247. Especially preferred are Epothilone A and/or B.

The term "alkylating compound" as used herein includes, but is not limited to, cyclophosphamide, ifosfamide, melphalan or nitrosourea (BCNU or Gliadel). Cyclophosphamide can be administered, e.g. in the form as it is marketed, e.g. under the trademark CYCLOSTIN. Ifosfamide can be administered, e.g., in the form as it is marketed, e.g. under the trademark HOLOXAN.

The term "histone deacetylase inhibitors" or "HDAC inhibitors" relates to compounds which inhibit the histone deacetylase and which possess antiproliferative activity. This includes compounds disclosed in WO 02/22577, especially N-hydroxy-3-[4-[[(2-hydroxyethyl)[2-(1H-indol-3-yl) ethyl]-amino]methyl]phenyl]-2E -2-propenamide, N-hydroxy-3-[4-[[[2-(2-methyl-1H-indol-3-yl)-ethyl]-amino]

methyl]phenyl]-2E-2-propenamide and pharmaceutically acceptable salts thereof. It further especially includes Suberoylanilide hydroxamic acid (SAHA).

The term "antineoplastic antimetabolite" includes, but is not limited to, 5-Fluorouracil or 5-FU, capecitabine, gemcitabine, DNA demethylating compounds, such as 5-azacytidine and decitabine, methotrexate and edatrexate, and folic acid antagonists such as pemetrexed. Capecitabine can be administered, e.g., in the form as it is marketed, e.g. under the trademark XELODA. Gemcitabine can be administered, e.g., in the form as it is marketed, e.g. under the trademark GEMZAR.

The term "platin compound" as used herein includes, but is not limited to, carboplatin, cisplatin, cisplatinum and oxaliplatin. Carboplatin can be administered, e.g., in the form as it is marketed, e.g. under the trademark CARBOPLAT. Oxaliplatin can be administered, e.g., in the form as it is marketed, e.g. under the trademark ELOXATIN.

The term "compounds targeting/decreasing a protein or lipid kinase activity"; or a "protein or lipid phosphatase activity"; or "further anti-angiogenic compounds" as used herein includes, but is not limited to, protein tyrosine kinase and/or serine and/or threonine kinase inhibitors or lipid kinase inhibitors, e.g., a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, e.g. a N-phenyl-2-pyrimidine-amine derivative, e.g. imatinib, SU101, SU6668 and GFB-111;
b) compounds targeting, decreasing or inhibiting the activity of the fibroblast growth factor-receptors (FGFR);
c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, such as those compounds disclosed in WO 02/092599, or antibodies that target the extracellular domain of IGF-I receptor or its growth factors;
d) compounds targeting, decreasing or inhibiting the activity of the Trk receptor tyrosine kinase family, or ephrin B4 inhibitors;
e) compounds targeting, decreasing or inhibiting the activity of the Axl receptor tyrosine kinase family;
f) compounds targeting, decreasing or inhibiting the activity of the Ret receptor tyrosine kinase;
g) compounds targeting, decreasing or inhibiting the activity of the Kit/SCFR receptor tyrosine kinase, e.g. imatinib;
h) compounds targeting, decreasing or inhibiting the activity of the C-kit receptor tyrosine kinases—(part of the PDGFR family), such as compounds which target, decrease or inhibit the activity of the c-Kit receptor tyrosine kinase family, especially compounds which inhibit the c-Kit receptor, e.g. imatinib;
i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, e.g. a N-phenyl-2-pyrimidine-amine derivative, e.g. imatinib or nilotinib (AMN107); PD180970; AG957; NSC 680410; PD173955 from ParkeDavis; or dasatinib (BMS-354825)
j) compounds targeting, decreasing or inhibiting the activity of members of the protein kinase C (PKC) and Raf family of serine/threonine kinases, members of the MEK, SRC, JAK, FAK, PDK1, PKB/Akt, and Ras/MAPK family members, and/or members of the cyclin-dependent kinase family (CDK) and are especially those staurosporine derivatives disclosed in U.S. Pat. No. 5,093,330, e.g. midostaurin; examples of further compounds include e.g. UCN-01, safingol, BAY 43-9006, Bryostatin 1, Perifosine; Ilmofosine; RO 318220 and RO 320432; GO 6976; Isis 3521; LY333531/LY379196; isochinoline compounds such as those disclosed in WO 00/09495; FTIs; PD184352 or QAN697 (a P13K inhibitor) or AT7519 (CDK inhibitor);
k) compounds targeting, decreasing or inhibiting the activity of protein-tyrosine kinase inhibitors, such as compounds which target, decrease or inhibit the activity of protein-tyrosine kinase inhibitors include imatinib mesylate (GLEEVEC) or tyrphostin. A tyrphostin is preferably a low molecular weight (Mr<1500) compound, or a pharmaceutically acceptable salt thereof, especially a compound selected from the benzylidenemalonitrile class or the S-arylbenzenemalonirile or bisubstrate quinoline class of compounds, more especially any compound selected from the group consisting of Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin);
l) compounds targeting, decreasing or inhibiting the activity of the epidermal growth factor family of receptor tyrosine kinases (EGFR, ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, e.g. EGF receptor, ErbB2, ErbB3 and ErbB4 or bind to EGF or EGF related ligands, and are in particular those compounds, proteins or monoclonal antibodies generically and specifically disclosed in WO 97/02266, e.g. the compound of ex. 39, or in EP 0 564 409, WO 99/03854, EP 0520722, EP 0 566 226, EP 0 787 722, EP 0 837 063, U.S. Pat. No. 5,747,498, WO 98/10767, WO 97/30034, WO 97/49688, WO 97/38983 and, especially, WO 96/30347 (e.g. compound known as CP 358774), WO 96/33980 (e.g. compound ZD 1839) and WO 95/03283 (e.g. compound ZM105180); e.g. trastuzumab (Herceptin™), cetuximab (Erbitux™), Iressa, Tarceva, OSI-774, CI-1033, EKB-569, GW-2016, E1.1, E2.4, E2.5, E6.2, E6.4, E2.11, E6.3 or E7.6.3, and 7H-pyrrolo-[2,3-d] pyrimidine derivatives which are disclosed in WO 03/013541; and
m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF.

Further anti-angiogenic compounds include compounds having another mechanism for their activity, e.g. unrelated to protein or lipid kinase inhibition e.g. thalidomide (THALOMID) and TNP-470.

The term "Compounds which target, decrease or inhibit the activity of a protein or lipid phosphatase" includes, but is not limited to inhibitors of phosphatase 1, phosphatase 2A, or CDC25, e.g. okadaic acid or a derivative thereof.

The term "Compounds which induce cell differentiation processes" includes, but is not limited to e.g. retinoic acid, α- γ- or ε-tocopherol or α- γ- or δ-tocotrienol.

The term "cyclooxygenase inhibitor" as used herein includes, but is not limited to, e.g. Cox-2 inhibitors, 5-alkyl substituted 2-arylaminophenylacetic acid and derivatives, such as celecoxib (CELEBREX), rofecoxib (VIOXX), etoricoxib, valdecoxib or a 5-alkyl-2-arylaminophenylacetic acid, e.g. 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. "Etridonic acid" can be administered, e.g., in the form as it is marketed, e.g. under the trademark DIDRONEL. "Clodronic acid" can be administered, e.g., in the form as it is marketed, e.g. under the trademark BONEFOS. "Tiludronic acid" can be administered, e.g., in the form as it is marketed, e.g. under the trademark SKELID. "Pamidronic acid" can be administered, e.g. in the form as it is marketed, e.g. under the trademark AREDIA™. "Alendronic acid" can be administered, e.g., in the form as it is marketed, e.g. under the trademark FOSAMAX. "Ibandronic acid" can be administered, e.g., in the form as it is marketed, e.g. under the trademark BONDRANAT. "Risedronic acid" can be administered, e.g., in the form as it is marketed, e.g. under the trademark ACTONEL. "Zoledronic acid" can be administered, e.g. in the form as it is marketed, e.g. under the trademark ZOMETA.

The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons, e.g. interferon γ.

The term "inhibitor of Ras oncogenic isoforms", e.g. H-Ras, K-Ras, or N-Ras, as used herein refers to compounds which target, decrease or inhibit the oncogenic activity of Ras e.g. a "farnesyl transferase inhibitor" e.g. L-744832, DK8G557 or R115777 (Zarnestra). The term "telomerase inhibitor" as used herein refers to compounds which target, decrease or inhibit the activity of telomerase. Compounds which target, decrease or inhibit the activity of telomerase are especially compounds which inhibit the telomerase receptor, e.g. telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase are e.g. bengamide or a derivative thereof.

The term "proteasome inhibitor" as used herein refers to compounds which target, decrease or inhibit the activity of the proteasome. Compounds which target, decrease or inhibit the activity of the proteasome include e.g. Bortezomid (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors e.g. compounds targeting, decreasing or inhibiting the activity of FMS-like tyrosine kinase receptors (Flt-3R); interferon, 1-b-D-arabinofuransylcytosine (ara-c) and bisulfan; and ALK inhibitors e.g. compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, e.g. PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90 e.g., 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DCM1,erbitux, bevacizumab (Avastin™), rituximab (Rituxan®), PRO64553 (anti-CD40) and 2C4 Antibody. By antibodies is meant e.g. intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of formula (I) can be used in combination with standard leukemia therapies, especially in combination with therapies used for the treatment of AML. In particular, compounds of formula (I) can be administered in combination with, e.g., farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

The term "antileukemic compounds" includes, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065, in particular, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl) ethyl]-amino]methyl]phenyl]-2E-2-propeneamide, or a pharmaceutically acceptable salt thereof, especially the lactate salt.

"Somatostatin receptor antagonists" as used herein refers to compounds which target, treat or inhibit the somatostatin receptor such as octreotide, and SOM230.

"Tumor cell damaging approaches" refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in *Principles and Practice of Oncology*, Devita et al., Eds., 4th Edition, Vol. 1, pp. 248-275 (1993).

The term "EDG binders" as used herein refers a class of immunosuppressants that modulates lymphocyte recirculation, such as FTY720.

The term "ribonucleotide reductase inhibitors" includes, but is not limited to to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives, such as PL-1, PL-2, PL-3, PL-4, PL-5, PL-6, PL-7 or PL-8 mentioned in Nandy et al., *Acta Oncologica*, Vol. 33, No. 8, pp. 953-961 (1994).

The term "S-adenosylmethionine decarboxylase inhibitors" as used herein includes, but is not limited to the compounds disclosed in U.S. Pat. No. 5,461,076.

Also included are in particular those compounds, proteins or monoclonal antibodies of VEGF disclosed in WO 98/35958, e.g. 1-(4-chloroanilino)-4-(4-pyridylmethyl)phthalazine or a pharmaceutically acceptable salt thereof, e.g. the succinate, or in WO 00/09495, WO 00/27820, WO 00/59509, WO 98/11223, WO 00/27819 and EP 0 769 947; those as described by Prewett et al, *Cancer Res*, Vol. 59, pp. 5209-5218 (1999); Yuan et al., *Proc Natl Acad Sci USA*, Vol. 93, pp. 14765-14770 (1996); Zhu et al., *Cancer Res*, Vol. 58, pp. 3209-3214 (1998); and Mordenti et al., *Toxicol Pathol*, Vol. 27, No. 1, pp. 14-21 (1999); in WO 00/37502 and WO 94/10202; ANGIOSTATIN, described by O'Reilly et al., *Cell*, Vol. 79, pp. 315-328 (1994); ENDOSTATIN, described by O'Reilly et al., *Cell*, Vol. 88, pp. 277-285 (1997); anthranilic acid amides; ZD4190; ZD6474; SU5416; SU6668; bevacizumab; or anti-VEGF antibodies or anti-VEGF receptor antibodies, e.g. rhuMAb and RHUFab, VEGF aptamer e.g. Macugon; FLT-4 inhibitors, FLT-3 inhibitors, VEGFR-2 IgG1 antibody, Angiozyme (RPI 4610) and Bevacizumab (Avastin™).

"Photodynamic therapy" as used herein refers to therapy which uses certain chemicals known as photosensitizing compounds to treat or prevent cancers. Examples of photodynamic therapy includes treatment with compounds, such as e.g. VISUDYNE and porfimer sodium.

"Angiostatic steroids" as used herein refers to compounds which block or inhibit angiogenesis, such as, e.g., anecortave, triamcinolone. hydrocortisone, 11-α-epihydrocotisol, cortexolone, 17α-hydroxyprogesterone, corticosterone, desoxycorticosterone, testosterone, estrone and dexamethasone.

"Implants containing corticosteroids" as used herein includes, but is not limited to compounds, such as e.g. fluocinolone, dexamethasone.

"Other chemotherapeutic compounds" include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of inflammatory diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammator or antihistamine drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate, or steroids described in WO 02/88167, WO 02/12266, WO 02/100879, WO 02/00679 (especially those of Examples 3, 11, 14, 17, 19, 26, 34, 37, 39, 51, 60, 67, 72, 73, 90, 99 and 101), WO 03/035668, WO 03/048181, WO 03/062259, WO 03/064445, WO 03/072592, non-steroidal glucocorticoid receptor agonists such as those described in WO 00/00531, WO 02/10143, WO 03/082280, WO 03/082787, WO 03/104195, WO 04/005229; LTB4 antagonists such LY293111, CGSO$_{25019}$C, CP-195543, SC-53228, BIIL 284, ONO 4057, SB 209247 and those described in U.S. Pat. No. 5,451,700; LTD4 antagonists such as montelukast and zafirlukast; PDE4 inhibitors such cilomilast (Ariflo® GlaxoSmithKline), Roflumilast (Byk Gulden),V-11294A (Napp), BAY19-8004 (Bayer), SCH-351591 (Schering-Plough), Arofylline (Almirall Prodesfarma), PD189659/ PD168787 (Parke-Davis), AWD-12-281 (Asta Medica), CDC-801 (Celgene), SeICID™ CC-10004 (Celgene), VM554/UM565 (Vernalis), T-440 (Tanabe), KW-4490 (Kyowa Hakko Kogyo), and those disclosed in WO 92/19594, WO 93/19749, WO 93/19750, WO 93/19751, WO 98/18796, WO 99/16766, WO 01/13953, WO 03/104204, WO 03/104205, WO 03/39544, WO 04/000814, WO 04/000839, WO 04/005258, WO 04/018450, WO 04/018451, WO 04/018457, WO 04/018465, WO 04/018431, WO 04/018449, WO 04/018450, WO 04/018451, WO 04/018457, WO 04/018465, WO 04/019944, WO 04/019945, WO 04/045607 and WO 04/037805; A2a agonists such as those disclosed in EP 409595A2, EP 1052264, EP 1241176, WO 94/17090, WO 96/02543, WO 96/02553, WO 98/28319, WO 99/24449, WO 99/24450, WO 99/24451, WO 99/38877, WO 99/41267, WO 99/67263, WO 99/67264, WO 99/67265, WO 99/67266, WO 00/23457, WO 00/77018, WO 00/78774, WO 01/23399, WO 01/27130, WO 01/27131, WO 01/60835, WO 01/94368, WO 02/00676, WO 02/22630, WO 02/96462, WO 03/086408, WO 04/ 039762, WO 04/039766, WO 04/045618 and WO 04/046083; A2b antagonists such as those described in WO 02/42298; and beta-2 adrenoceptor agonists such as albuterol (salbutamol), metaproterenol, terbutaline, salmeterol fenoterol, procaterol, and especially, formoterol and pharmaceutically acceptable salts thereof, and compounds (in free or salt or solvate form) of formula I of WO 0075114, which document is incorporated herein by reference, preferably compounds of the Examples thereof, especially a compound of formula

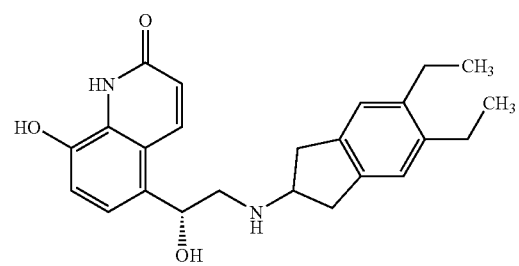 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula I of WO 04/16601, and also compounds of WO 04/033412. Suitable bronchodilatory drugs include anticholinergic or antimuscarinic compounds, in particular ipratropium bromide, oxitropium bromide, tiotropium salts and CHF 4226 (Chiesi), and glycopyrrolate, but also those described in WO 01/04118, WO 02/51841, WO 02/53564, WO 03/00840, WO 03/87094, WO 04/05285, WO 02/00652, WO 03/53966, EP 424021, U.S. Pat. Nos. 5,171,744, 3,714,357, WO 03/33495 and WO 04/018422.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine as well as those disclosed in WO 03/099807, WO 04/026841 and JP 2004107299.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, Takeda antagonists such as N-[[4-[[[6,7-dihydro-2-(4-methylphenyl)-5H-benzocyclohepten-8-yl]carbonyl]amino]phenyl]-methyl]tetrahydro-N,N-dimethyl-2H-pyran-4-amin-ium chloride (TAK-770), and CCR-5 antagonists described in U.S. Pat. No. 6,166,037 (particularly claims 18 and 19), WO 00/66558 (particularly claim 8), WO 00/66559 (particularly claim 9), WO 04/018425 and WO 04/026873.

Therapeutic agents for possible combination are especially one or more antiproliferative, cytostatic or cytotoxic compounds, for example one or several agents selected from the group which includes, but is not limited to, an inhibitor of polyamine biosynthesis, an inhibitor of a protein kinase, especially of a serine/threonine protein kinase, such as protein kinase C, or of a tyrosine protein kinase, such as the EGF receptor tyrosine kinase, e.g. Iressa®, the VEGF receptor tyrosine kinase, e.g. PTK787 or Avastin®, or the PDGF receptor tyrosine kinase, e.g. STI571 (Glivec®), a cytokine, a negative growth regulator, such as TGF-β or IFN-β, an aromatase inhibitor, e.g. letrozole (Femara®) or anastrozole, an inhibitor of the interaction of an SH2 domain with a phosphorylated protein, antiestrogens, topoisomerase I inhibitors, such as irinotecan, topoisomerase II inhibitors, microtubule active agents, e.g. paclitaxel or an epothilone, alkylating agents, antiproliferative antimetabolites, such as gemcitabine or capecitabine, platin compounds, such as carboplatin or cis-platin, bisphosphonates, e.g. AREDIA® or ZOMETA®, and monoclonal antibodies, e.g. against HER2, such as trastuzumab.

The structure of the active agents identified by code nos., generic or trade names may be taken from the actual edition of the standard compendium "The Merck Index" or from databases, e.g. Patents International (e.g. IMS World Publications). The corresponding content thereof is hereby incorporated by reference.

The above-mentioned compounds, which can be used in combination with a compound of the formula I, can be prepared and administered as described in the art, such as in the documents cited above.

Thus, the invention relates in a further aspect to a combination comprising a therapeutically effective amount of a compound of formula I in free form or in pharmaceutically acceptable salt form and a second drug substance, for simultaneous or sequential administration.

The invention also provides, in a further aspect, a pharmaceutical preparation (composition), comprising a compound of formula I as defined herein, or a pharmaceutically acceptable salt of such a compound, or a hydrate or solvate thereof, and at least one pharmaceutically acceptable carrier and/or diluents and optionally one or more further drug substances.

The compounds of the invention may be administered by any conventional route, in particular parenterally, for example in the form of injectable solutions or suspensions, enterally, e.g. orally, for example in the form of tablets or capsules, topically, e.g. in the form of lotions, gels, ointments or creams, or in a nasal or a suppository form. Topical administration is e.g. to the skin. A further form of topical administration is to the eye. Pharmaceutical compositions comprising a compound of the invention in association with at least one pharmaceutical acceptable carrier or diluent may be manufactured in conventional manner by mixing with a pharmaceutically acceptable carrier or diluent.

The invention relates also to pharmaceutical compositions comprising an effective amount, especially an amount effective in the treatment of one of the above-mentioned diseases (=disorders), of a compound of formula I or a pharmaceutically acceptable salt thereof together with one or more pharmaceutically acceptable carriers that are suitable for topical, enteral, for example oral or rectal, or parenteral administration and that may be inorganic or organic, solid or liquid. There can be used for oral administration especially tablets or gelatin capsules that comprise the active ingredient together with diluents, for example lactose, dextrose, mannitol, and/or glycerol, and/or lubricants and/or polyethylene glycol. Tablets may also comprise binders, for example magnesium aluminum silicate, starches, such as corn, wheat or rice starch, gelatin, methylcellulose, sodium carboxymethylcellulose and/or polyvinylpyrrolidone, and, if desired, disintegrators, for example starches, agar, alginic acid or a salt thereof, such as sodium alginate, and/or effervescent mixtures, or adsorbents, dyes, flavorings and sweeteners. It is also possible to use the pharmacologically active compounds of the present invention in the form of parenterally administrable compositions or in the form of infusion solutions. The pharmaceutical compositions may be sterilized and/or may comprise excipients, for example preservatives, stabilisers, wetting compounds and/or emulsifiers, solubilisers, salts for regulating the osmotic pressure and/or buffers. The present pharmaceutical compositions, which may, if desired, comprise other pharmacologically active substances are prepared in a manner known per se, for example by means of conventional mixing, granulating, confectionning, dissolving or lyophilising processes, and comprise approximately from 1% to 99%, especially from approx. 1% to approx. 20%, active ingredient(s).

The dosage of the active ingredient to be applied to a warm-blooded animal depends upon a variety of factors including type, species, age, weight, sex and medical condition of the patient; the severity of the condition to be treated; the route of administration; the renal and hepatic function of the patient; and the particular compound employed. A physician, clinician or veterinarian of ordinary skill can readily determine and prescribe the effective amount of the drug required to prevent, counter or arrest the progress of the condition. Optimal precision in achieving concentration of drug within the range that yields efficacy without toxicity requires a regimen based on the kinetics of the drug's availability to target sites. This involves a consideration of the distribution, equilibrium, and elimination of a drug. The dose of a compound of the formula I or a pharmaceutically acceptable salt thereof to be administered to warm-blooded animals, for example humans of approximately 70 kg body weight, is preferably from approximately 3 mg to approximately 5 g, more preferably from approximately 10 mg to approximately 1.5 g per person per day, divided preferably into 1 to 3 single doses which may, for example, be of the same size. Usually, children receive half of the adult dose.

In a further aspect, the invention relates to a compound of formula I or a pharmaceutically acceptable salt, as a medicament/for use as a medicament, in particular for the treatment of one or more Protein tyrosine kinase mediated diseases.

In a further aspect, the invention relates to the use of a compound of formula I or a pharmaceutically acceptable salt, as active ingredient in a medicament, in particular for the treatment of one or more Protein tyrosine kinase mediated diseases.

In a further aspect, the invention relates to the use of a compound of formula I or a pharmaceutically acceptable salt, as medicament, in particular for the treatment of one or more Protein tyrosine kinase mediated diseases.

In a further aspect, the invention relates to the use of a compound of formula I or a pharmaceutically acceptable salt, for the manufacture of a medicament for the treatment of one or more Protein tyrosine kinase mediated diseases.

In a further aspect, the invention relates to a compound of formula I or a pharmaceutically acceptable salt of such a compound, for use in a method for the treatment of a subject in need thereof, especially for the treatment of a Protein tyrosine kinase mediated disease, most especially in a patient requiring such treatment.

In a further aspect, the invention relates to a method for the treatment of a disease which responds to an inhibition of JAK-2 and/or Jak-3 kinase, which comprises administering a compound of formula I or a pharmaceutically acceptable salt thereof, wherein the radicals and symbols have the meanings as defined above, especially in a quantity effective against said disease, to a warm-blooded animal requiring such treatment.

In a further aspect, the invention relates to a pharmaceutical composition comprising a compound of formula I as active ingredient in association with at least one pharmaceutical carrier or diluent. Such compositions may be manufactured in conventional manner. In a further aspect, the invention relates to a method of treatment of one or more Protein tyrosine kinase mediated diseases, in a subject in need of such treatment, which comprises administering to such subject a therapeutically effective amount of compound of formula I.

In a further aspect, the invention relates to pharmaceutical compositions comprising: (a) an effective amount of compound of formula I and pharmaceutically acceptable salts, pharmaceutically acceptable prodrugs, and pharmaceutically active metabolites thereof; and (b) one or more pharmaceutically acceptable excipients and/or diluents.

In a further aspect, the invention relates to a pharmaceutical composition for treatment of a disease, e.g. of solid or liquid tumours in warm-blooded animals, including humans, comprising a dose effective in the treatment of said disease of a compound of the formula I as described above or a pharmaceutically acceptable salt of such a compound together with a pharmaceutically acceptable carrier (=carrier material).

A compound of the formula I or I' may be prepared by processes that, though not applied hitherto for the new compounds of the present invention where they thus form new processes, are known per se, the following scheme illustrates methods for such preparation.

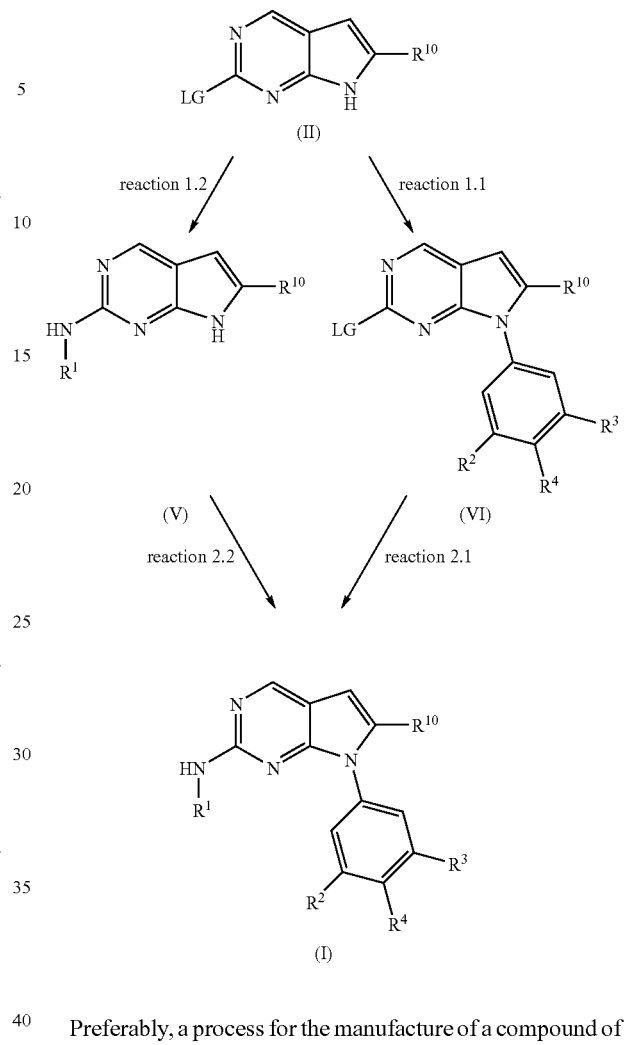

Preferably, a process for the manufacture of a compound of the formula I comprises either Method a) reacting in a first step a compound of the formula II,

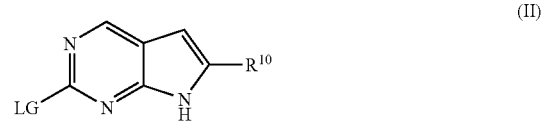

wherein the substituents are as defined for a compound of the formula I and LG represents a leaving group (such as tosylate, mesylate or halo, in particular chloride) with a compound of the formula IV or IV',

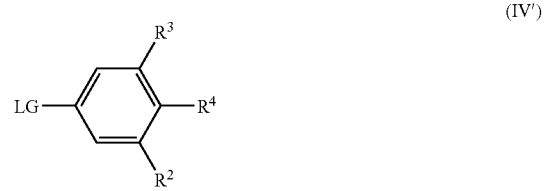

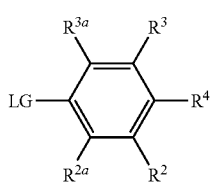
(IV)

wherein the substituents are as defined for a compound of the formula I and LG represents a leaving group (such as tosylate, mesylate or halo, in particular bromide) in a Cu-catalyzed Buchwald reaction to obtain a compound of formula (VI) or (VI')

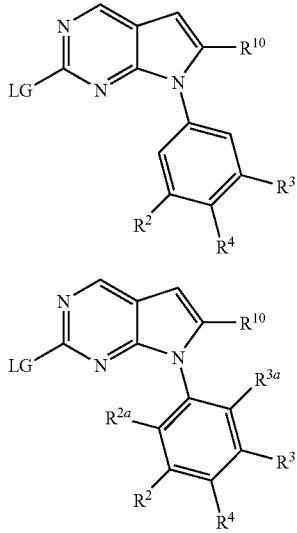
(VI')

(VI)

wherein the substituents are as defined above with a compound of formula I and reacting in a second step the obtained compound of formula VI with a compound of formula (III)

NH₂—R¹ (III)

wherein R1 is as defined in formula I to obtain a compound of formula I;
or
method B) reacting in a first step a compound of the formula II,

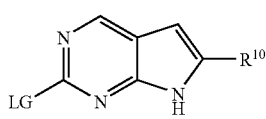
(II)

wherein the substituents are as defined for a compound of the formula I and LG represents a leaving group (such as tosylate, mesylate or halo, in particular chloride) with a compound of the formula III,

NH₂—R¹ (III)

wherein R¹ is as defined in formula I either in a Pd-catalyzed Buchwald reaction or under acidic conditions to obtain a compound of formula (V)

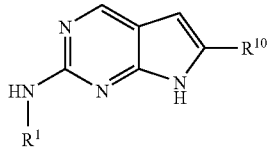
(V)

wherein the substituents are as defined above for a compound of formula I and reacting in a second step the obtained compound of formula V with a compound of formula IV

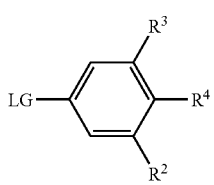
(IV')

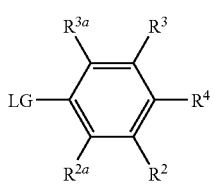
(IV)

wherein the substituents are as defined for a compound of the formula I and LG represents a leaving group (such as tosylate, mesylate or halo, in particular bromide) to obtain a compound of formula I;

and, if desired, converting a compound of the formula I obtained according to method A) or method B) into a different compound of the formula I, and/or converting an obtainable salt of a compound of the formula I into a different salt thereof, and/or converting an obtainable free compound of the formula I into a salt thereof, and/or separating an obtainable isomer of a compound of the formula I from one or more different obtainable isomers of the formula I.

Reaction Conditions

Where temperatures are given hereinbefore or hereinafter, "about" has to be added, as minor deviations from the numeric values given, e.g. variations of ±10%, are tolerable. All reactions may take place in the presence of one or more diluents and/or solvents. The starting materials may be used in equimolar amounts; alternatively, a compound may be used in excess, e.g. to function as a solvent or to shift equilibrium or to generally accelerate reaction rates. Reaction aids, such as acids, bases or catalysts may be added in suitable amounts, as known in the field, required by a reaction and in line with generally known procedures.

Buchwald Reaction

This reaction, also known as Buchwald amination or Buchwald-Hartwig reaction is generally known in the field. This reaction is catalyzed by transition metals, in particular Cu or Pd complexes or salts; takes place in the presence of one or more basic compounds (such as an amine or an alkalialkoxide) and one or more diluents (such as polar aprotic diluents). Further details may be found in the examples.

Protecting Groups

If one or more other functional groups, for example carboxy, hydroxy, amino, sulfhydryl or the like are or need to be protected in a starting material as described herein or any other precursor, because they should not take part in the reaction or disturb the reaction, these are such groups as are usually used in the synthesis of peptide compounds, and also of cephalosporins and penicillins, as well as nucleic acid derivatives and sugars. Protecting groups are such groups that are no longer present in the final compounds once they are removed, while groups that remain as substituents are not protecting groups in the sense used here which are groups that are added at a starting material or intermediate stage and removed to obtain a final compound. Also in the case of conversions of a compound of the formula I into a different compound of the formula I, protecting groups may be introduced and removed, if useful or required.

The protecting groups may already be present in precursors and should protect the functional groups concerned against unwanted secondary reactions, such as acylations, etherifications, esterifications, oxidations, solvolysis, and similar reactions. It is a characteristic of protecting groups that they lend themselves readily, i.e. without undesired secondary reactions, to removal, typically by acetolysis, protonolysis, solvolysis, reduction, photolysis or also by enzyme activity, for example under conditions analogous to physiological conditions, and that they are not present in the end-products. The specialist knows, or can easily establish, which protecting groups are suitable with the reactions mentioned above and below.

The protection of such functional groups by such protecting groups, the protecting groups themselves, and their removal reactions are described for example in standard reference works, such as J. F. W. McOmie, "Protective Groups in Organic Chemistry", Plenum Press, London and New York 1973, in T. W. Greene, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie" (*Methods of organic chemistry*), Houben Weyl, 4th edition, Volume 15/I, Georg Thieme Verlag, Stuttgart 1974, in H.-D. Jakubke and H. Jescheit, "Aminosäuren, Peptide, Proteine" (*Amino acids, peptides, proteins*), Verlag Chemie, Weinheim, Deerfield Beach, and Basel 1982, and in Jochen Lehmann, "Chemie der Kohlenhydrate: Monosaccharide und Derivate" (*Chemistry of carbohydrates: monosaccharides and derivatives*), Georg Thieme Verlag, Stuttgart 1974.

Optional Reactions and Conversions

A compound of the formula I may be converted into a different compound of the formula I.

For example, in a compound of the formula I wherein $R^1$ or especially $R^4$ carries an amino or amino-$C_1$-$C_7$-alkyl substituent, the amino can be converted into acylamino, e.g. $C_1$-$C_7$-alkanoylamino or $C_1$-$C_7$-alkanesulfonylamino, by reaction with a corresponding $C_1$-$C_7$-alkanoylhalogenide or $C_1$-$C_7$-alkanesulfonylhalogenide, e.g. a corresponding chloride, in the presence of a tertiary nitrogen base, such as triethylamine or pyridine, in the absence or presence of an appropriate solvent, such a methylene chloride, for example at temperatures in the range from −20 to 50° C., e.g. at about room temperature.

In a compound of the formula I wherein $R^1$ or especially $R^4$ carries a cyano substituent, the cyano may be converted to an aminomethyl group, e.g. by hydrogenation in the presence of an appropriate metal catalyst, such as Raney Nickel or Raney Cobalt, in an appropriate solvent, e.g. a lower alkanol, such as methanol and/or ethanol, for example at temperatures in the range from −20 to 50° C., e.g. at about room temperature.

In a compound of the formula I wherein $R^1$ or especially $R^4$ carries a carboxyl (COOH) substituent, the latter can be converted into an amide group, e.g. an N—$C_1$-$C_7$-alkyl-carbamoyl group, by reaction with the corresponding amine, e.g. in the presence of a coupling agent, that forms a preferred reactive derivative of the carboxyl group in situ, for example dicyclohexylcarbodiimide/1-hydroxybenzotriazole (DCC/HOBT); bis(2-oxo-3-oxazolidinyl)phosphinic chloride (BOPCl); O-(1,2-dihydro-2-oxo-1-pyridyl)-N,N,N',N'-tetramethyluronium tetrafluoroborate (TPTU); O-benzotriazol-1-yl)-N,N,N',N'-tetramethyluronium tetrafluoroborate (TBTU); (benzotriazol-1-yloxy)-tripyrrolidinophosphonium-hexafluorophosphate (PyBOP), O-(1H-6-chlorobenzotriazole-1-yl)-1,1,3,3-tetramethyluronium hexafluorophosphate, 1-(3-dimethylaminopropyl)-3-ethylcarbodiimidehydrochloride/hydroxybenzotriazole or/1-hydroxy-7-azabenzotriazole (EDC/HOBT or EDC/HOAt) or HOAt alone, or with (1-chloro-2-methyl-propenyl)-dimethylamine. For review of some other possible coupling agents, see e.g. Klauser; Bodansky, *Synthesis* (1972), 453-463. The reaction mixture is preferably stirred at a temperature of between approximately −20 and 50° C., especially between 0° C. and 30° C., e.g. at room temperature.

In a compound of the formula I wherein $R^1$ or especially $R^4$ carries two vicinal amino groups, the two nitrogen atoms of the two amino groups can be bridged by a —CH═ group (thus forming, together with the two carbon atoms that bind the original amino groups and the bond between them, an 1H-imidazolo ring annelated to $R^1$ or $R^4$; for example, (vicinal diamino)-phenyl can be converted into benzoimidazolyl according to this method. The reaction preferably takes place by first reacting the compound of the formula I carrying the two vicinal amino groups with formic acid, e.g. in the presence of a coupling agent as mentioned in the preceding paragraph, such as EDC hydrochloride, a base, such as N,N-dimethylaminopyridine (DMAP) and preferably an appropriate solvent, such as methylene chloride, e.g. at temperatures in the range from −20 to 50° C., e.g. at about room temperature, thus converting one (especially a para-positioned) of the vicinal amino groups into a formylamino group. In a second step, the amino and formylamino group are then reacted to —N═C—N— by heating in the presence of an acid, especially acetic acid, e.g. at temperatures in the range from 50 to 110° C., for example at about 100° C.

Salts of a compound of formula I with a salt-forming group may be prepared in a manner known per se. Acid addition salts of compounds of formula I may thus be obtained by treatment with an acid or with a suitable anion exchange reagent. A salt with two acid molecules (for example a dihalogenide of a compound of formula I) may also be converted into a salt with one acid molecule per compound (for example a monohalogenide); this may be done by heating to a melt, or for example by heating as a solid under a high vacuum at elevated temperature, for example from 130 to 170° C., one molecule of the acid being expelled per molecule of a compound of formula I. Salts can usually be converted to free compounds, e.g. by treating with suitable basic compounds, for example with alkali metal carbonates, alkali metal hydrogencarbonates, or alkali metal hydroxides, typically potassium carbonate or sodium hydroxide.

Stereoisomeric mixtures, e.g. mixtures of diastereomers, can be separated into their corresponding isomers in a manner known per se by means of suitable separation methods. Diastereomeric mixtures for example may be separated into their individual diastereomers by means of fractionated crystallization, chromatography, solvent distribution, and similar procedures. This separation may take place either at the level of a starting compound or in a compound of formula I itself. Enantiomers may be separated through the formation of diastereomeric salts, for example by salt formation with an enantiomer-pure chiral acid, or by means of chromatography, for example by HPLC, using chromatographic substrates with chiral ligands.

It should be emphasized that reactions analogous to the conversions mentioned in this chapter may also take place at the level of appropriate intermediates (and are thus useful in the preparation of corresponding starting materials).

Starting Materials:

The starting materials of the formulae II, III and IV, as well as other starting materials mentioned herein, e.g. below, can be prepared according to or in analogy to methods that are known in the art, are known in the art and/or are commercially available. Novel starting materials, as well as processes for the preparation thereof, are likewise an embodiment of the present invention. In the preferred embodiments, such starting materials are used and the reaction chosen are selected so as to enable the preferred compounds to be obtained.

In the starting materials (including intermediates), which may also be used and/or obtained as salts where appropriate and expedient, the substituents are preferably as defined for a compound of the formula I.

The following examples illustrate the invention without limiting the scope thereof.

Temperatures are measured in degrees Celsius. Unless otherwise indicated, the reactions take place at rt.

The $R_f$ values in TLC indicate the ratio of the distance moved by each substance to the distance moved by the eluent front. $R_f$ values for TLC are measured on 5×10 cm TLC plates, silica gel $F_{254}$, Merck, Darmstadt, Germany; the solvent systems are marked in the examples as follows:

* 10% methanol/190% methylene chloride ($CH_2Cl_2$)

** 5% methanol/195% methylene chloride

*** 2% methanol/98% methylene chloride

‡ 50% hexane/50% ethyl acetate

† 66% hexane/33% ethyl acetate

If not indicated otherwise, the analytical HPLC conditions are as follows:

| Method A | |
|---|---|
| Column | SunFire C18 20 × 4.6 mm, 3.5 μm |
| Column Temperature | 40° C. |
| Eluents | A: H₂O, B: acetonitrile, both containing 0.1% TFA |
| Flow Rate | 3.0 mL/min |
| Gradient | 5-100% B in 4.0 min |
| Method B | |
| Column | Column Engineering, Inc., Matrix, 3 μm C18 150 × 4.6 mm (Lot # 205). Detection by UV absorption at 215 and 254 nm. |
| Column Temperature | 35° C. |
| Eluents | A: H₂O, B: acetonitrile, both containing 0.1% TFA |
| Flow Rate | 1 mL/min |
| Gradient | water (0.1% TFA)/acetonitrile (0.1% TFA) = 98/2 for 1 min. To 100% acetonitrile (0.1% TFA) in 10 min. Stay at 100% for 2 min (total run time: 13 min.) |
| Method C | |
| Column | Macherey-Nagel CC125/4 Nucleosil 100-3 C18 HD |
| Column Temperature | 30° C. |
| Eluents | A: H₂O, B: acetonitrile, both containing 0.1% TFA |
| Flow Rate | 1.0 mL/min |
| Gradient | 2-100% B in 7.0 min |
| Method D | |
| Column | Macherey-Nagel CC125/4 Nucleosil 100-3 C18 HD |
| Column Temperature | 30° C. |
| Eluents | A: H₂O, B: acetonitrile, both containing 0.1% TFA |
| Flow Rate | 1.0 mL/min |
| Gradient | 20-100% B in 7.0 min |
| Method E | |
| System | Agilent 1100 Series with Waters Micromass ZQ |
| Column | XBridge C18, 3 × 30 mm, 2.5 micron |
| Eluents | A: H2O, containing 5% acetonitril and 0.8% HCOOH B: acetonitrile, containing 0.6% HCOOH |
| Flow Rate | 1.4-2.4 mL/min |
| Gradient | 10-95% B in 2.4 min (E1) or 1-95% B in 2.9 min (E2) |
| Method F | |
| Column | Macherey-Nagel CC125/4 Nucleosil 100-3 C18 HD |
| Column Temperature | 30° C. |
| Eluents | A: H₂O, B: acetonitrile, both containing 0.1% TFA |
| Flow Rate | 1.0 mL/min |
| Gradient | 2-100% B in 7.0 min then 2 min by 100% B |
| Method G | |
| Column | Acquity UPLC BEH C18/2.1 * 50 mm/1.7 μm |
| Column Temperature | 40° C. |
| Eluents | A: H₂O, B: acetonitrile, both containing 0.1% TFA |
| Flow Rate | 1.0 mL/min |
| Gradient | 0.1 min 2% B; 2 to 100% B in 1.5 min; 0.4 min 100% B |

Abbreviations
AIBN α,α'-azo-isobutyronitrile
Ar Argon
Bn benzyl
Boc tert-butoxycarbonyl
DCM dichloromethane
DIPEA diisopropyl-ethyl-amine
DME 1,2-dimethoxyethane
DMF N,N-dimethylformamide
DMSO dimethyl sulfoxide
h hour(s)
HATU 2-(1H-7-Azabenzotriazol-1-yl)-1,1,3,3-tetramethyluronium hexafluorophosphate
HPLC High Performance Liquid Chromatography
HV high vacuum
Isolute Isolute® HM-N by International Solvent Technology Ltd., U.K.
LAH lithium aluminium hydride
mL millilitre(s)
min minute(s)
MS-ES electrospray mass spectrometry
MW microwave
$R_f$ ratio of fronts in TLC
rt room temperature
TBTU [(Benzotriazol-1-yloxy)-dimethylamino-methylene]-dimethyl-ammonium tetrafluoro borate
TBDPS tert-butyldiphenylsilyl
TFA trifluoroacetic acid
THF tetrahydrofuran
TLC thin layer chromatography
$t_R$ retention time
UV Ultraviolet
Starting Materials:
Several aryl bromides and anilines as used according to Scheme 1-3 have been purchased from commercial sources where practicable. Otherwise, the aryl bromides and anilines/aminoheterocycles are being prepared according to the exemplified general procedures:

General procedure I for the synthesis of aryl bromide building blocks (in the following formula exemplified for 2-(4-bromo-phenyl)-1-morpholin-4-yl-ethanone)

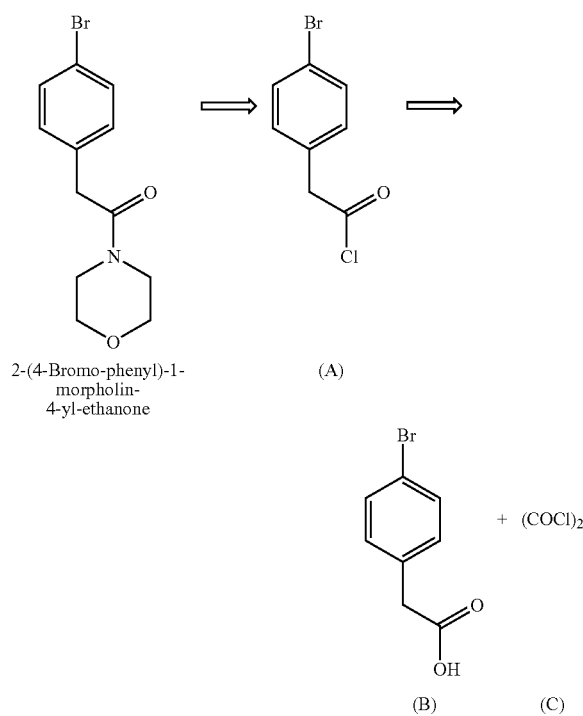

The compound shown on the left above, 2-(4-bromo-phenyl)-1-morpholin-4-yl-ethanone, is obtained by reaction of the corresponding acid chloride (A), (4-bromo-phenyl)-acetyl chloride, with morpholine and Et₃N in DCM at rt. The product is obtained in high yield. The intermediate acid chloride (A) is obtained by reaction of (4-bromo-phenyl)-acetic acid (B) and oxalyl chloride (C) in DCM at rt and using DMF as reaction initiator. The intermediate (A) is obtained in good yield.

Alternatively, amide bond formation can be achieved by coupling of the appropriate carboxylic acid (B) and the appropriate amine in the presence of HATU and N-methyl morpholine in DMF at rt.

The following aryl bromides used in the examples below are synthesized analogously, using the appropriate starting materials:
2-(4-Bromo-phenyl)-1-(4-methyl-piperazin-1-yl)-ethanone
(4-Bromo-2-fluoro-phenyl)-morpholin-4-yl-methanone
(4-Bromo-2-fluoro-phenyl)-(4-methyl-piperazin-1-yl)-methanone
2-(4-Bromo-2-fluoro-phenyl)-1-(1,1-dioxido-thiomorpholin-4-yl)-ethanone
[1-(4-Bromo-phenyl)-cyclopropyl]-(4-ethyl-piperazin-1-yl)-methanone
(4-Bromo-phenyl)-morpholin-4-yl-methanone
(4-Bromo-phenyl)-(4-methyl-piperazin-1-yl)-methanone
(4-Bromo-phenyl)-pyrrolidin-1-yl-methanone
4-Bromo-N-(2-morpholin-4-yl-ethyl)-benzamide
4-Bromo-N-(1-ethyl-pyrrolidin-2-ylmethyl)-benzamide
(4-Bromo-phenyl)-(1,1-dioxido-thiomorpholin-4-yl)-methanone
(5-Bromo-pyridin-2-yl)-(1,1-dioxido-thiomorpholin-4-yl)-methanone
(6-Bromo-pyridin-3-yl)-(1,1-dioxido-thiomorpholin-4-yl)-methanone
(4-Bromo-2,6-difluoro-phenyl)-(1,1-dioxido-thiomorpholin-4-yl)-methanone
(4-Bromo-2,6-difluoro-phenyl)-morpholin-4-yl-methanone
(4-Bromo-2,6-difluoro-phenyl)-(4-methyl-piperazin-1-yl)-methanone
(4-Bromo-2-chloro-phenyl)-morpholin-4-yl-methanone
(4-Bromo-2-methyl-phenyl)-morpholin-4-yl-methanone
(4-Bromo-3-fluoro-phenyl)-morpholin-4-yl-methanone
(6-Bromo-pyridin-3-yl)-morpholin-4-yl-methanone
(5-Bromo-pyridin-2-yl)-morpholin-4-yl-methanone
(3-Bromo-phenyl)-(4-methyl-piperazin-1-yl)-methanone
2-(4-Bromo-phenyl)-2-methyl-1-morpholin-4-yl-propan-1-one
[1-(4-Bromo-phenyl)-cyclopropyl]-morpholin-4-yl-methanone
[1-(4-Bromo-phenyl)-cyclopropyl]-(4-methyl-piperazin-1-yl)-methanone
(5-Bromo-pyridin-2-yl)-morpholin-4-yl-methanone
(5-Bromo-pyridin-2-yl)-(4-methyl-piperazin-1-yl)-methanone
2-(4-Bromo-phenyl)-1-[4-(2-hydroxy-ethyl)-piperazin-1-yl]-ethanone
4-Bromo-2-fluoro-N-(2-morpholin-4-yl-ethyl)-benzamide
4-Bromo-2-fluoro-N-[2-(4-methyl-piperazin-1-yl)-ethyl]-benzamide
(4-Bromo-2-fluoro-phenyl)-(4-dimethylamino-piperidin-1-yl)-methanone
(4-Bromo-phenyl)-[4-(2-hydroxy-ethyl)-piperazin-1-yl]-methanone
(4-Bromo-2-fluoro-phenyl)-(1,1-Dioxido-thiomorpholin-4-yl)-methanone
(4-Bromo-3-fluoro-phenyl)-morpholin-4-yl-methanone General procedure II for the synthesis of aryl bromide building blocks (in the following formula exemplified for 4-(4-bromo-2-methyl-benzyl)-morpholine)

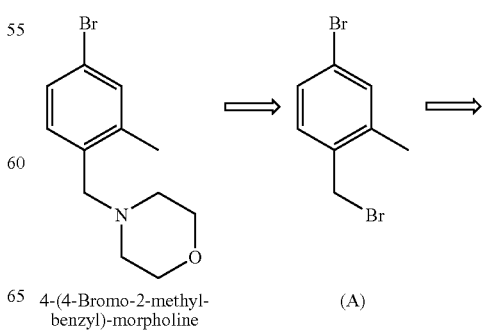

4-(4-Bromo-2-methyl-benzyl)-morpholine (A)

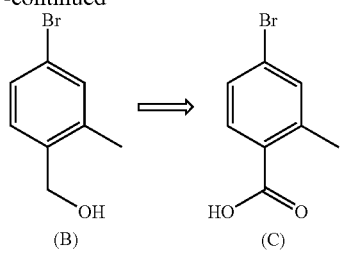

The compound shown on the left above, 4-(4-Bromo-2-methyl-benzyl)-morpholine, is obtained by reaction of the corresponding benzyl bromide (A), 4-bromo-1-bromomethyl-2-methyl-benzene, with morpholine in DMF at rt. The product is obtained in high yield. The intermediate benzyl bromide (A) is obtained by reaction of (4-bromo-2-methyl-phenyl)-methanol (B) with PPh$_3$ and CBr$_4$ in DCM at rt. The intermediate (A) is obtained in high yield. The intermediate benzyl alcohol B is obtained by reduction of the corresponding carboxylic acid (C), 4-bromo-2-methyl-benzoic acid with LAH in THF. The intermediate (B) is obtained in good yield.

The following aryl bromides used in the examples below are synthesized analogously, using the appropriate corresponding starting materials:

4-(4-Bromo-2-fluoro-benzyl)-morpholine
4-(4-Bromo-2-chloro-benzyl)-morpholine
4-(4-Bromo-2-methyl-benzyl)-morpholine
4-(4-Bromo-2,6-difluoro-benzyl)-morpholine
4-[1-(4-Bromo-phenyl)-ethyl]-morpholine
4-(6-Bromo-pyridin-3-ylmethyl)-morpholine
4-(5-Bromo-pyridin-2-ylmethyl)-morpholine
4-[2-(4-Bromo-phenyl)-ethyl]-morpholine
1-(4-Bromo-2-fluoro-benzyl)-4-ethyl-piperazine
1-(4-Bromo-2,6-difluoro-benzyl)-4-ethyl-piperazine
4-(4-Bromo-2,6-difluoro-benzyl)-1-ethyl-piperazin-2-one
1-[4-(4-Bromo-2,6-difluoro-benzyl)-piperazin-1-yl]-ethanone
4-(4-Bromo-2,6-difluoro-benzyl)-thiomorpholine 1,1-dioxide
4-(4-Bromo-2-fluoro-benzyl)-thiomorpholine 1,1-dioxide
4-(4-Bromo-2-chloro-benzyl)-thiomorpholine 1,1-dioxide
1-(4-Bromo-2,6-difluoro-benzyl)-4-methyl-piperazine
1-(4-Bromo-2,6-difluoro-benzyl)-4-isopropyl-piperazine
1-(4-Bromo-2,6-difluoro-benzyl)-4-cyclopropyl-piperazine
4-(4-Bromo-2,6-difluoro-benzyl)-3,3-dimethyl-morpholine
4-(4-Bromo-2,6-difluoro-benzyl)-1-methyl-piperazin-2-one
4-(4-Bromo-2,6-difluoro-benzyl)-piperazin-2-one
8-(4-Bromo-2,6-difluoro-benzyl)-2,5-dioxa-8-aza-spiro[3.5]nonane
4-(4-Bromo-2,6-difluoro-benzyl)-cis-2,6-dimethyl-morpholine
1-(4-Bromo-2,6-difluoro-benzyl)-pyrrolidin-2-one
1-(4-Bromo-2,6-difluoro-benzyl)-3-methoxy-azetidine
4-(4-Bromo-2,6-difluoro-benzyl)-morpholin-3-one General procedure III for the synthesis of aniline building blocks (in the following formula exemplified for (4-amino-phenyl)-morpholin-4-yl-methanone)

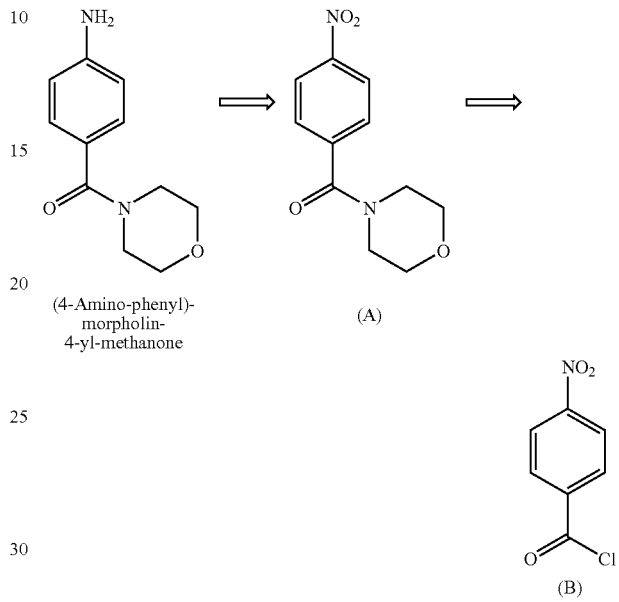

The compound shown on the left above, (4-amino-phenyl)-morpholin-4-yl-methanone, is obtained by hydrogenation of the corresponding nitro-compound (A), morpholin-4-yl-(4-nitro-phenyl)-methanone, with Pd/C or Raney-Nickel and H$_2$ or NH$_4$CO$_2$H in MeOH at rt. Alternatively, the nitro group reduction can be achieved with SnCl$_2$ in EtOH at 90° C. The intermediate nitro compound (A) is obtained by the reaction of 4-nitro-benzoyl chloride (B) and morpholine and Et$_3$N in DCM at rt. The intermediate (A) is obtained in good yield. When needed, analogs of (B) are obtained from the corresponding carboxylic acid derivatives heated to reflux for 2 hrs with thionylchloride or oxalylchloride in DCM or dichloroethane.

Alternatively, amide bond formation can be achieved by coupling of the appropriate carboxylic acid derivative (B) and the appropriate amine in the presence of TBTU and Et$_3$N in THF at 0° C. to rt.

The following anilines used in the examples below are synthesized analogously, using the appropriate corresponding starting materials:

4-Amino-N-(1-methyl-piperidin-4-yl)-benzamide
(4-Amino-phenyl)-(4-dimethylamino-piperidin-1-yl)-methanone
4-Amino-N-(2-morpholin-4-yl-ethyl)-benzamide
4-Amino-N-(1-ethyl-pyrrolidin-2-ylmethyl)-benzamide
(4-Amino-2-fluoro-phenyl)-(4-methyl-piperazin-1-yl)-methanone
(4-Amino-2-chloro-phenyl)-(4-methyl-piperazin-1-yl)-methanone
(4-Amino-2-methyl-phenyl)-(4-methyl-piperazin-1-yl)-methanone
(4-Amino-2-trifluoromethyl-phenyl)-(4-methyl-piperazin-1-yl)-methanone
(4-Amino-2-methyl-phenyl)-morpholin-4-yl-methanone (4-Amino-2-methyl-phenyl)-pyrrolidin-1-yl-methanone
(5-Amino-2-fluoro-phenyl)-(4-methyl-piperazin-1-yl)-methanone
(5-Amino-2-fluoro-phenyl)-morpholin-4-yl-methanone
5-Amino-N-(1-ethyl-pyrrolidin-2-ylmethyl)-2-fluoro-benzamide
4-(4-Amino-benzoyl)-piperazine-1-carboxylic acid tert-butyl ester
(4-Amino-pyridin-2-yl)-(4-methyl-piperazin-1-yl)-methanone
(4-Amino-pyridin-2-yl)-(2,5-dioxa-8-aza-spiro[3.5]non-8-yl)-methanone
4-Amino-pyridin-2-yl)-(cis-3,5-dimethyl-piperazin-1-yl)-methanone
4-(4-Amino-pyridine-2-carbonyl)-piperazine-1-carboxylic acid tert-butyl ester
(5-Amino-2-methyl-phenyl)-(4-methyl-piperazin-1-yl)-methanone
(5-Amino-2-methyl-phenyl)-(cis-3,5-dimethyl-piperazin-1-yl)-methanone General procedure IV for the synthesis of aniline building blocks (in the following formula exemplified for (4-amino-phenyl)-(4-methyl-piperazin-1-yl)-methanone)

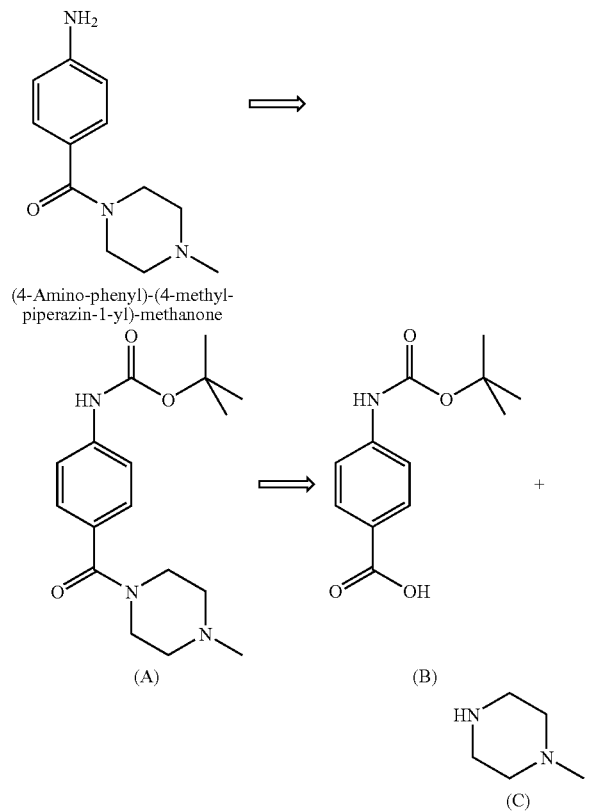

The compound shown on the left above, (4-amino-phenyl)-(4-methyl-piperazin-1-yl)-methanone, is obtained by treatment of intermediate (A), [4-(4-methyl-piperazine-1-carbonyl)-phenyl]-carbamic acid tert-butyl ester, with TFA in DCM at rt. The intermediate compound (A) is obtained by coupling of 4-tert-butoxycarbonylamino-benzoic acid (B) and N-methyl piperazine (C) in the presence of HATU and N-methyl morpholine in DCM at rt. The intermediate (A) is obtained in good yield.

The use of the Boc protecting group is not necessary for the preparation of certain aniline building blocks.

The following anilines used in the examples below are synthesized analogously, using the appropriate corresponding starting materials:

4-Amino-N-(2-dimethylamino-ethyl)-N-methyl-benzamide
4-Amino-N-(2-dimethylamino-ethyl)-benzamide
4-Amino-N-(2-hydroxy-ethyl)-benzamide
(5-Amino-pyridin-2-yl)-morpholin-4-yl-methanone
(3-Amino-phenyl)-morpholin-4-yl-methanone
(3-Amino-phenyl)-(4-methyl-piperazin-1-yl)-methanone
3-Amino-N-(2-dimethylamino-ethyl)-benzamide
2-(3-Amino-phenyl)-1-(4-methyl-piperazin-1-yl)-ethanone
2-(3-Amino-phenyl)-1-(4-ethyl-piperazin-1-yl)-ethanone
(4-Amino-phenyl)-(4-ethyl-piperazin-1-yl)-methanone
(5-Amino-pyridin-3-yl)-morpholin-4-yl-methanone
(3-Amino-phenyl)-(cis-3,5-dimethyl-piperazin-1-yl)-methanone
(3-Amino-phenyl)-(4-cyclopropyl-piperazin-1-yl)-methanone
(5-Amino-pyridin-2-yl)-(4-methyl-piperazin-1-yl)-methanone General procedure V for the synthesis of aniline building blocks (in the following formula exemplified for 3-(2-dimethylamino-ethoxy)-4-methoxy-phenylamine)

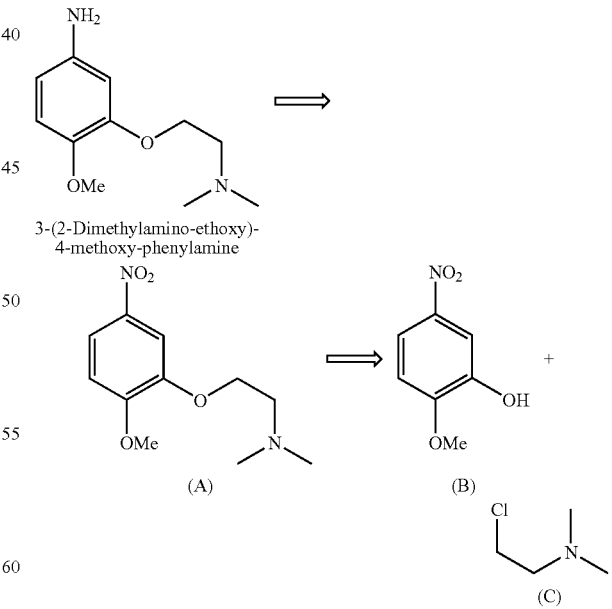

The compound shown on the left above, 3-(2-dimethylamino-ethoxy)-4-methoxy-phenylamine, is obtained by treatment of intermediate (A), [2-(2-methoxy-5-nitro-phenoxy)-ethyl]-dimethyl-amine, with Pd/C and $NH_4CO_2H$ in MeOH/THF at rt. The intermediate compound (A) is obtained by alkylation of 2-methoxy-5-nitro-phenol (B) with (2-chloro-ethyl)-dimethyl-amine (C) in the presence of NaH in DMF at 150° C.

The following anilines used in the examples below are synthesized analogously, using the appropriate corresponding starting materials:
3-(3-Dimethylamino-propoxy)-4-methoxy-phenylamine
4-Methoxy-3-(2-pyrrolidin-1-yl-ethoxy)-phenylamine
4-Methoxy-3-(2-morpholin-4-yl-ethoxy)-phenylamine
3-(2-Morpholin-4-yl-ethoxy)-phenylamine
3-[2-(4-Methyl-piperazin-1-yl)-ethoxy]-phenylamine
3-(2-Diethylamino-ethoxy)-phenylamine
4-(2-Diethylamino-ethoxy)-phenylamine
4-(2-Morpholin-4-yl-ethoxy)-phenylamine
4-(2-Pyrrolidin-1-yl-ethoxy)-phenylamine
3,5-Dimethyl-4-(2-morpholin-4-yl-ethoxy)-phenylamine General procedure VI for the synthesis of aniline building blocks (in the following formula exemplified for 4-(cis-3,5-dimethyl-piperazin-1-ylmethyl)-phenylamine)

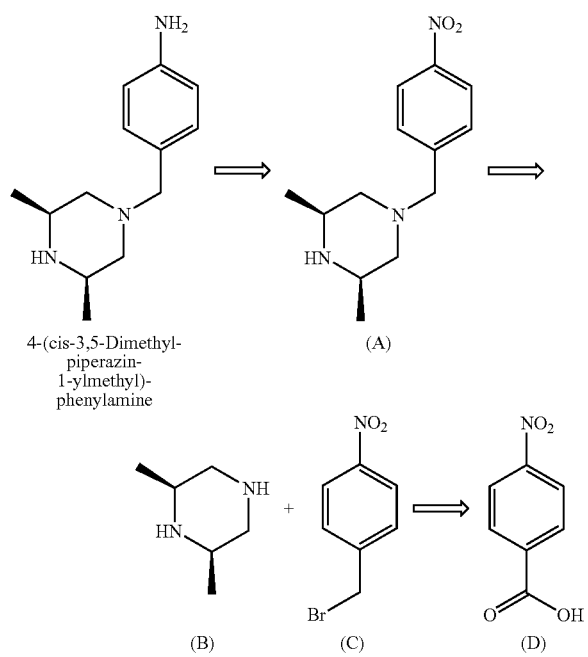

The compound shown on the left above, 4-(cis-3,5-dimethyl-piperazin-1-ylmethyl)-phenylamine, is obtained by treatment of intermediate (A), cis-3,5-dimethyl-1-(4-nitro-benzyl)-piperazine, with SnCl$_2$ hydrate in MeOH at rt. Alternatively, the nitro group reduction can be achieved with Pd/C or Raney-Nickel and H$_2$ or NH$_4$CO$_2$H in MeOH at rt. The intermediate compound (A) is obtained by reaction of cis-2,6-dimethyl-piperazine (B) with 1-bromomethyl-4-nitro-benzene (C) in the presence of Et$_3$N or DIPEA in DMF at rt.

Where needed, the (substituted) benzyl bromide (C) is synthesized from the corresponding carboxylic acid (D) via reduction to the alcohol and conversion to the halogen compound.

The following anilines used in the examples below are synthesized analogously, using the appropriate corresponding starting materials:

4-((2R,5S)-2,5-Dimethyl-piperazin-1-ylmethyl)-phenylamine (racemic)
4-(4-Amino-benzyl)-piperazin-2-one
4-(4, 7-Diaza-spiro[2.5]oct-7-ylmethyl)-phenylamine
4-(4-Amino-benzyl)-piperazine-1-carboxylic acid tert-butyl ester
1-[4-(4-Amino-benzyl)-piperazin-1-yl]-ethanone
4-(4-Cyclopropyl-piperazin-1-ylmethyl)-phenylamine
4-Methyl-3-(4-methyl-piperazin-1-ylmethyl)-phenylamine
4-Methyl-3-morpholin-4-ylmethyl-phenylamine
5-(4-Ethyl-piperazin-1-ylmethyl)-pyridin-2-ylamine
4-Methyl-3-(4-methyl-piperazin-1-ylmethyl)-phenylamine
4-(5-Amino-2-methyl-benzyl)-piperazine-1-carboxylic acid tert-butyl ester
4-(5-Amino-2-methyl-benzyl)-piperazin-2-one
4-(4-Amino-benzyl)-1-methyl-piperazin-2-one
4-(4-Methyl-piperazin-1-ylmethyl)-phenylamine
3-(cis-3,5-Dimethyl-piperazin-1-ylmethyl)-4-methyl-phenylamine
3-(2,5-Dioxa-8-aza-spiro[3.5]non-8-ylmethyl)-4-methyl-phenylamine
3-(4-Cyclopropyl-piperazin-1-ylmethyl)-4-methyl-phenylamine
4-(4-Amino-pyridin-2-ylmethyl)-piperazine-1-carboxylic acid tert-butyl ester
3-(4,7-Diaza-spiro[2.5]oct-7-ylmethyl)-4-methyl-phenylamine
3-((2R,5S)-2,5-Dimethyl-piperazin-1-ylmethyl)-4-methyl-phenylamine (racemic)
3-(3,3-Dimethyl-piperazin-1-ylmethyl)-4-methyl-phenylamine
3-(3,3-Difluoro-pyrrolidin-1-ylmethyl)-4-methyl-phenylamine
1-(5-Amino-2-methyl-benzyl)-azetidin-3-ol
4-(5-Amino-2-methyl-benzyl)-1-methyl-piperazin-2-one
3-[4-(2-Dimethylamino-ethyl)-piperazin-1-ylmethyl]-4-methyl-phenylamine
4-(5-Amino-2-methyl-benzyl)-3-oxo-piperazine-1-carboxylic acid tert-butyl ester
1-(5-Amino-2-chloro-benzyl)-azetidin-3-ol
4-(5-Amino-2-chloro-benzyl)-piperazine-1-carboxylic acid tert-butyl ester
4-Methyl-3-(3-trifluoromethyl-piperazin-1-ylmethyl)-phenylamine (racemic)
3-(3-Methoxy-azetidin-1-ylmethyl)-4-methyl-phenylamine
1-(5-Amino-2-methyl-benzyl)-pyrrolidin-3-ol
3-Imidazol-1-ylmethyl-4-methyl-phenylamine
4-Methyl-3-pyrazol-1-ylmethyl-phenylamine
4-Methyl-3-[1,2,4]triazol-4-ylmethyl-phenylamine
3-(3-Methoxy-pyrrolidin-1-ylmethyl)-4-methyl-phenylamine
3-(5-Amino-2-methyl-benzyloxy)-azetidine-1-carboxylic acid tert-butyl ester
[1-(5-Amino-2-methyl-benzyl)-pyrrolidin-3-yl]-dimethyl-amine
3-(7-Aza-bicyclo[2.2.1]hept-7-ylmethyl)-4-methyl-phenylamine
4-(4-Amino-2-methyl-benzyl)-piperazine-1-carboxylic acid tert-butyl ester
4-(cis-3,5-Dimethyl-piperazin-1-ylmethyl)-3-methyl-phenylamine
4-(3,3-Difluoro-pyrrolidin-1-ylmethyl)-phenylamine
6-(4-Methyl-piperazin-1-ylmethyl)-pyridin-3-ylamine
4-(3,3-Dimethyl-piperazin-1-ylmethyl)-phenylamine
4-(3-Trifluoromethyl-piperazin-1-ylmethyl)-phenylamine (racemic)

4-(cis-3,5-Dimethyl-piperazin-1-ylmethyl)-2-fluoro-phenylamine
1-(4-Amino-benzyl)-azetidin-3-ol
6-Morpholin-4-ylmethyl-pyridin-3-ylamine
6-Piperazin-1-ylmethyl-pyridin-3-ylamine
4-Chloro-3-(4-methyl-piperazin-1-ylmethyl)-phenylamine
4-(4-Amino-benzyl)-3-oxo-piperazine-1-carboxylic acid tert-butyl ester
4-(5-Amino-pyridin-2-ylmethyl)-1-methyl-piperazin-2-one
4-(3-Methoxy-pyrrolidin-1-ylmethyl)-phenylamine
1-(5-Amino-pyridin-2-ylmethyl)-pyrrolidin-3-ol (racemic)
4-Methyl-3-(7-methyl-2,7-diaza-spiro[4.4]non-2-yl methyl)-phenylamine
4-Methyl-3-(4-methyl-pyrazol-1-ylmethyl)-phenylamine
2-[1-(5-Amino-2-methyl-benzyl)-1H-pyrazol-4-yl]-ethanol Alternatively, (A) is obtained by the reaction of 2-bromomethyl-1-methyl-4-nitro-benzene (C) with sodium azide in ethanol/water 1:2 at rt overnight, followed by triazole formation with dimethyl-prop-2-ynyl-amine in tert-butanol/water 1:1 in presence of copper (I) sulfate (0.15 eq.) and L-(+)-sodium ascorbate (0.3 eq.).

3-(4-Dimethylaminomethyl-[1,2,3]triazol-1-ylmethyl)-4-methyl-phenylamine
[1-(5-Amino-2-methyl-benzyl)-1H-[1,2,3]triazol-4-yl]-methanol Alternatively, (B) is obtained from the reaction of 3-oxo-piperazine-1-carboxylic acid tert-butyl ester activated with sodium hydride with (2-bromo-ethyl)-dimethyl-amine in DMF. The resulting material is then Boc-deprotected in dioxane with HCl to give (B) as HCl salt.

4-(5-Amino-2-methyl-benzyl)-1-(2-dimethylamino-ethyl)-piperazin-2-one

General procedure VII for the synthesis of aniline building blocks (in the following formula exemplified for 6-(cis-3,5-dimethyl-piperazin-1-yl)-pyridin-3-ylamine)

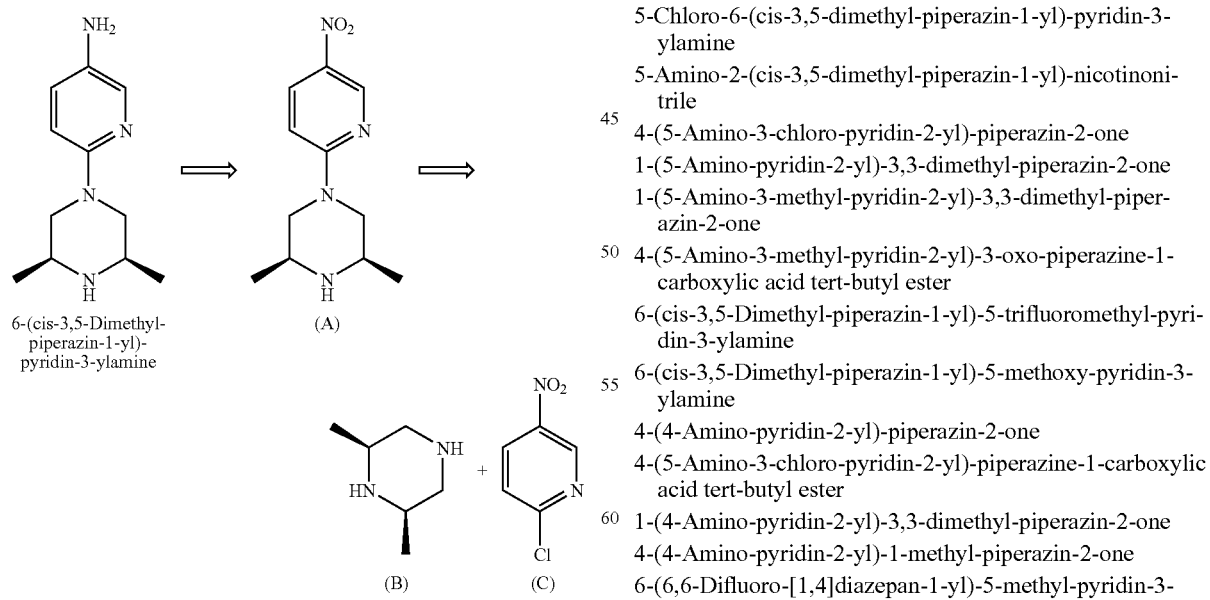

din-2-yl)-piperazine, with H$_2$ (or ammonium formate) and Pd/C (or Raney-Nickel) in MeOH (and THF) at rt. The intermediate compound (A) is obtained by reaction of cis-2,6-dimethyl-piperazine (B) with 2-chloro-5-nitro-pyridine (C) in the presence of Et$_3$N in THF at rt to 70° C.

Alternatively, in case (B) is an alcohol, 2-bromo-5-nitro-pyridine, or 2-chloro-4-nitro-pyridine-1-oxide for some of the meta-substituted derivatives, is used as (C) in presence of KOtBu or Cs$_2$CO$_3$ or NaH in DMA or THF at rt to 80° C.

The following anilines used in the examples below are synthesized analogously, using the appropriate corresponding starting materials:

6-((2R,5S)-2,5-Dimethyl-piperazin-1-yl)-pyridin-3-ylamine (racemic)
6-(4,7-Diaza-spiro[2.5]oct-7-yl)-pyridin-3-ylamine
2-[4-(5-Amino-pyridin-2-yl)-piperazin-1-yl]-ethanol
2-(4,7-Diaza-spiro[2.5]oct-7-yl)-pyridin-4-ylamine
2-(4-Methyl-piperazin-1-yl)-pyrimidin-5-ylamine
6-Isopropoxy-pyridin-3-ylamine
4-(4-Amino-pyridin-2-yloxymethyl)-piperidine-1-carboxylic acid tert-butyl ester
6-(cis-3,5-dimethyl-piperazin-1-yl)-5-methyl-pyridin-3-ylamine
5-Chloro-6-(cis-3,5-dimethyl-piperazin-1-yl)-pyridin-3-ylamine
2-(4-Cyclopropyl-piperazin-1-yl)-pyridin-4-ylamine
6-(4-Cyclopropyl-piperazin-1-yl)-pyridin-3-ylamine
6-[4-(2-Dimethylamino-ethyl)-piperazin-1-yl]-pyridin-3-ylamine
6-(3-Trifluoromethyl-piperazin-1-yl)-pyridin-3-ylamine (racemic)
4-(5-Amino-pyridin-2-yl)-3-oxo-piperazine-1-carboxylic acid tert-butyl ester
4-(5-Amino-3-methyl-pyridin-2-yl)-piperazine-1-carboxylic acid tert-butyl ester
6-(3,3-Dimethyl-piperazin-1-yl)-5-methyl-pyridin-3-ylamine
5-Chloro-6-(cis-3,5-dimethyl-piperazin-1-yl)-pyridin-3-ylamine
5-Amino-2-(cis-3,5-dimethyl-piperazin-1-yl)-nicotinonitrile
4-(5-Amino-3-chloro-pyridin-2-yl)-piperazin-2-one
1-(5-Amino-pyridin-2-yl)-3,3-dimethyl-piperazin-2-one
1-(5-Amino-3-methyl-pyridin-2-yl)-3,3-dimethyl-piperazin-2-one
4-(5-Amino-3-methyl-pyridin-2-yl)-3-oxo-piperazine-1-carboxylic acid tert-butyl ester
6-(cis-3,5-Dimethyl-piperazin-1-yl)-5-trifluoromethyl-pyridin-3-ylamine
6-(cis-3,5-Dimethyl-piperazin-1-yl)-5-methoxy-pyridin-3-ylamine
4-(4-Amino-pyridin-2-yl)-piperazin-2-one
4-(5-Amino-3-chloro-pyridin-2-yl)-piperazine-1-carboxylic acid tert-butyl ester
1-(4-Amino-pyridin-2-yl)-3,3-dimethyl-piperazin-2-one
4-(4-Amino-pyridin-2-yl)-1-methyl-piperazin-2-one
6-(6,6-Difluoro-[1,4]diazepan-1-yl)-5-methyl-pyridin-3-ylamine (B obtained from WO2003042172 p. 51)
6-(2-Morpholin-4-yl-ethoxy)-pyridin-3-ylamine
3-(5-Amino-pyridin-2-yloxy)-azetidine-1-carboxylic acid tert-butyl ester The compound shown on the left above, 6-(cis-3,5-dimethyl-piperazin-1-yl)-pyridin-3-ylamine, is obtained by treatment of intermediate (A), cis-3,5-dimethyl-1-(5-nitro-pyri- 6-(Tetrahydro-pyran-4-yloxy)-pyridin-3-ylamine
6-(2-Methoxy-ethoxy)-pyridin-3-ylamine
6-(Tetrahydro-pyran-4-ylmethoxy)-pyridin-3-ylamine
6-[2-(tert-Butyl-diphenyl-silanyloxy)-ethoxy]-pyridin-3-ylamine
3-(5-Amino-pyridin-2-yloxy)-pyrrolidine-1-carboxylic acid tert-butyl ester
6-[3-(tert-Butyl-diphenyl-silanyloxy)-pyrrolidin-1-yl]-pyridin-3-ylamine
2-(Tetrahydro-pyran-4-yloxy)-pyridin-4-ylamine
2-(2-Morpholin-4-yl-ethoxy)-pyridin-4-ylamine
2-(3-Trifluoromethyl-piperazin-1-yl)-pyridin-4-ylamine (racemic)
5-(4-Methyl-piperazin-1-yl)-pyridin-2-ylamine General procedure VIII for the synthesis of aniline building blocks (in the following formula exemplified for 4-(4-Ethyl-piperazin-1-yl)-3-methyl-phenylamine)

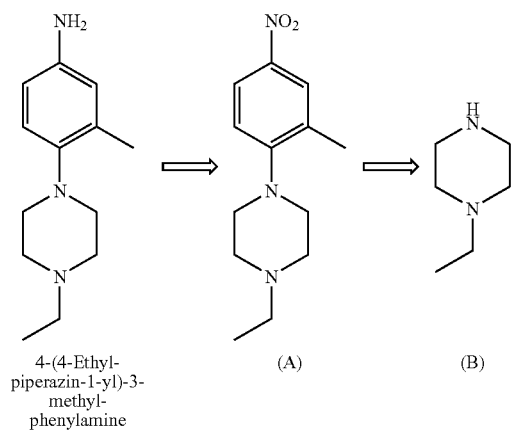

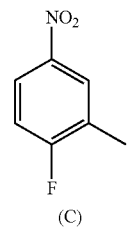

(C)

The compound shown on the left above, 4-(4-ethyl-piperazin-1-yl)-3-methyl-phenylamine, is obtained by treatment of intermediate (A), 1-ethyl-4-(2-methyl-4-nitro-phenyl)-piperazine, with $H_2$ (or ammonium formate) and Pd/C in MeOH (and THF) at rt. The intermediate compound (A) is obtained by reaction of N-ethyl-piperazine (B) with 1-fluoro-2-methyl-4-nitro-benzene (C) in dimethylacetamide (DMA) at 110° C. for 20 hours.

General procedure IX for the synthesis of aminopyrazole building blocks (in the following formula exemplified for 1-(2-methoxy-ethyl)-1H-pyrazol-4-ylamine)

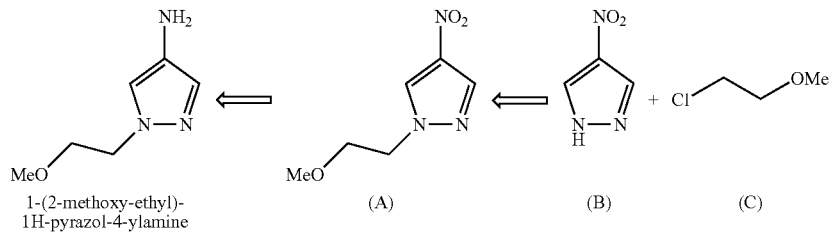

The compound shown on the left above, 1-(2-methoxy-ethyl)-1H-pyrazol-4-ylamine, is obtained by treatment of intermediate (A), 1-(2-methoxy-ethyl)-4-nitro-1H-pyrazole, with ammonium formate and Pd/C in MeOH at rt. The intermediate compound (A) is obtained by alkylation of 4-nitro-1H-pyrazole (B) with 1-chloro-2-methoxy-ethane (C) in the presence of NaH in DMF at 95° C.

The following aminopyrazole used in the examples below is synthesized analogously, using the appropriate corresponding starting materials:

4-(4-Amino-pyrazol-1-yl)-piperidine-1-carboxylic acid tert-butyl ester

General procedure X for the synthesis of aniline building blocks (in the following formula exemplified for 2-(4-methyl-piperazin-1-ylmethyl)-pyridin-4-ylamine)

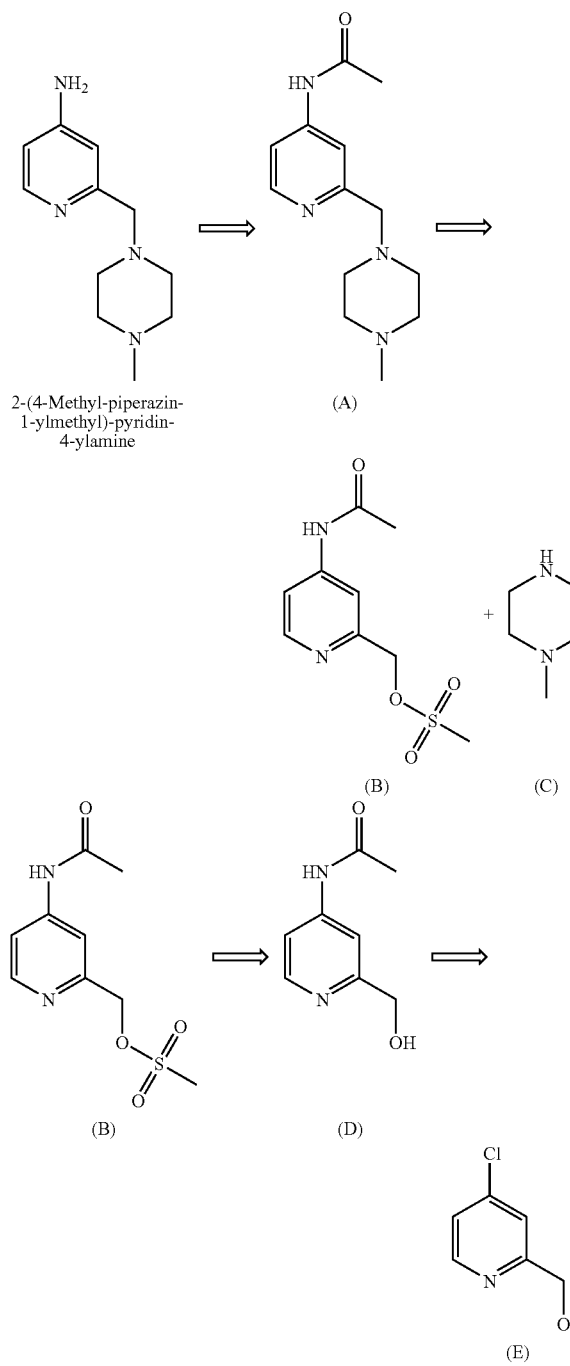

The compound shown on the left above, 2-(4-methyl-piperazin-1-ylmethyl)-pyridin-4-ylamine), is obtained by treatment of intermediate (A), N-[2-(4-methyl-piperazin-1-ylmethyl)-pyridin-4-yl]-acetamide, with KOH in EtOH/water 2:1 at 100° C. for 4 h. The intermediate compound (A) is obtained by reaction of N-methyl-piperazine (C) with methanesulfonic acid 4-acetylamino-pyridin-2-ylmethyl ester (B) in DCM at rt in the presence of DIPEA. The intermediate compound (B) is obtained from the reaction of N-(2-hydroxymethyl-pyridin-4-yl)-acetamide (D) with methanesulfonyl chloride in the presence of Et₃N in DCM (or with SOCl₂ in 1,2-dichloroethane with a small amount of DMF for the chloride analog of (B)). Intermediate (D) is obtained from the treatment of (4-chloro-pyridin-2-yl)-methanol with acetamide in presence of Pd(OAc)₂, 4,5-bis-diphenylphosphanyl-9,9-dimethyl-9H-xanthene and cesium carbonate in dioxane and DMF at 130° C. in the microwave oven for 1 h.

The following anilines used in the examples below are synthesized analogously, using the appropriate corresponding starting materials:

2-(cis-3,5-Dimethyl-piperazin-1-ylmethyl)-pyridin-4-ylamine

2-[4-(2-Dimethylamino-ethyl)-piperazin-1-ylmethyl]-pyridin-4-ylamine 4-(4-Amino-pyridin-2-ylmethyl)-1-methyl-piperazin-2-one 2-(3,3-Difluoro-pyrrolidin-1-ylmethyl)-pyridin-4-ylamine 2-(4-Cyclopropyl-piperazin-1-ylmethyl)-pyridin-4-ylamine 2-(3-Trifluoromethyl-piperazin-1-yl methyl)-pyridin-4-ylamine (racemic)

4-(4-Amino-pyridin-2-ylmethyl)-3-oxo-piperazine-1-carboxylic acid tert-butyl ester 1-(4-Amino-pyridin-2-ylmethyl)-pyrrolidin-3-ol 2-(3-Methoxy-pyrrolidin-1-ylmethyl)-pyridin-4-ylamine 2-(3-Dimethylamino-pyrrolidin-1-ylmethyl)-pyridin-4-ylamine General procedure XI for the synthesis of aniline building blocks (in the following formula exemplified for (S)-3-(4-Amino-phenyl)-morpholine-4-carboxylic acid tert-butyl ester)

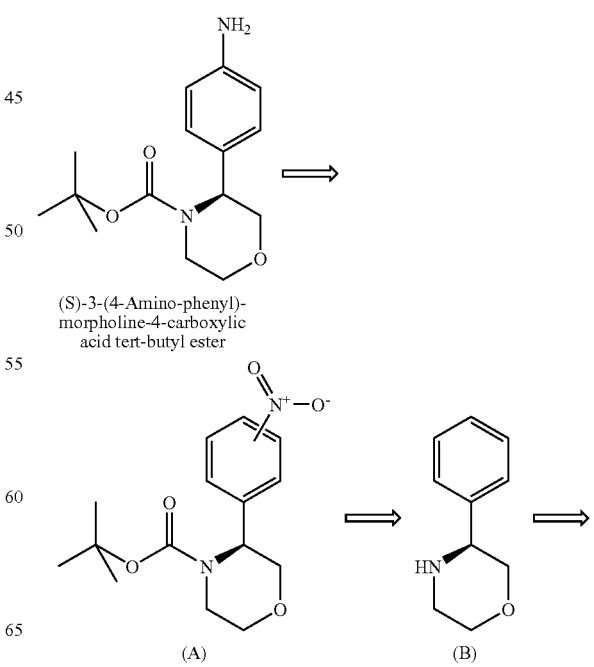

-continued

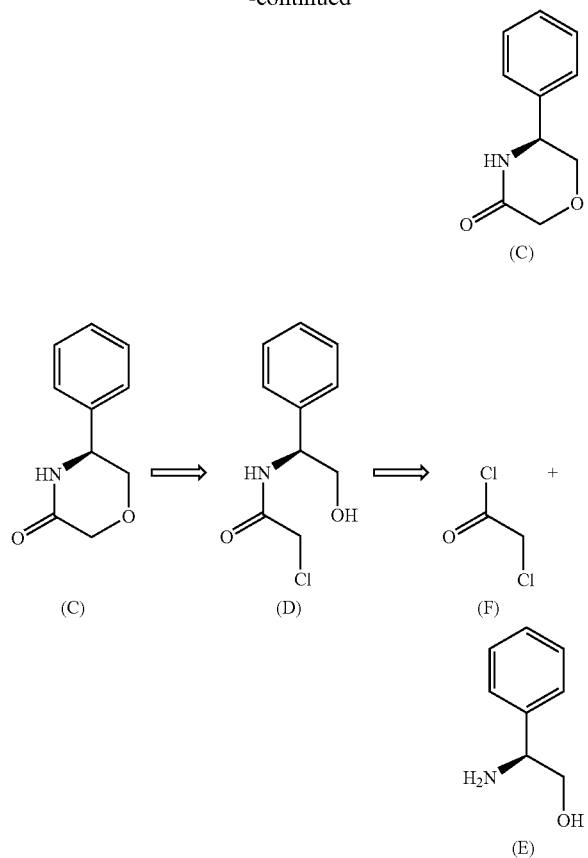

The compound shown on the left above, (S)-3-(4-amino-phenyl)-morpholine-4-carboxylic acid tert-butyl ester, is obtained from the hydrogenation of intermediate (A) with hydrazine hydrate in ethanol in presence of Raney-Nickel under argon atmosphere at rt, followed by separation of the $NO_2$-regioisomers. To obtain the intermediate compound (A) (mixture of regioisomers), a solution of (S)-3-phenyl-morpholine (B) in DCM is slowly dropped into fuming nitric acid in DCM at −45° C. After 1 h, the reaction is quenched slowly with an aq. sol. of NaOH followed by a DCM/aq. bicarbonate work-up. The resulting material is purified on silica column chromatography and then Boc protected with Boc-anhydride in DCM at rt.

The intermediate compound (B) is obtained from the reduction of (S)-5-phenyl-morpholin-3-one (C) with LAH in THF at rt. The morpholine derivative compound (C) is obtained from the ring closing of 2-chloro-N-((S)-2-hydroxy-1-phenyl-ethyl)-acetamide (D) in presence of sodium hydride in THF/toluene 1:1 at 0° C. to rt. The intermediate compound (D) results from the slow addition of chloro-acetyl chloride (F) dissolved in DCM to (S)-2-amino-2-phenyl-ethanol (E) in THF in presence of $Et_3N$ at 0° C. to rt.

The following anilines used in the examples below are synthesized analogously, using the appropriate corresponding starting materials:

2-(4-Amino-phenyl)-morpholine-4-carboxylic acid tert-butyl ester (racemic)

(S)-3-(3-Amino-phenyl)-morpholine-4-carboxylic acid tert-butyl ester

EXAMPLE 1

(3,4-Diethoxy-phenyl)-[7-(4-methanesulfonyl-phenyl)-7H-pyrrolo[2,3-d]pyrimidin-2-yl]-amine (1)

The compound is prepared according to Scheme 1.

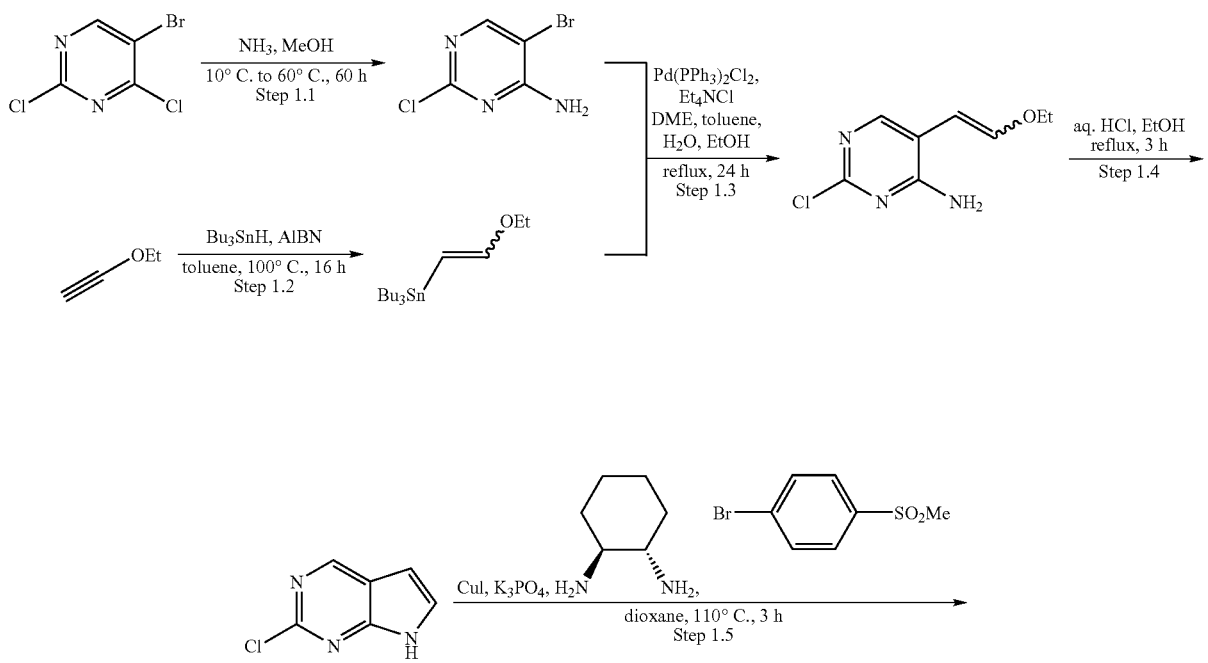

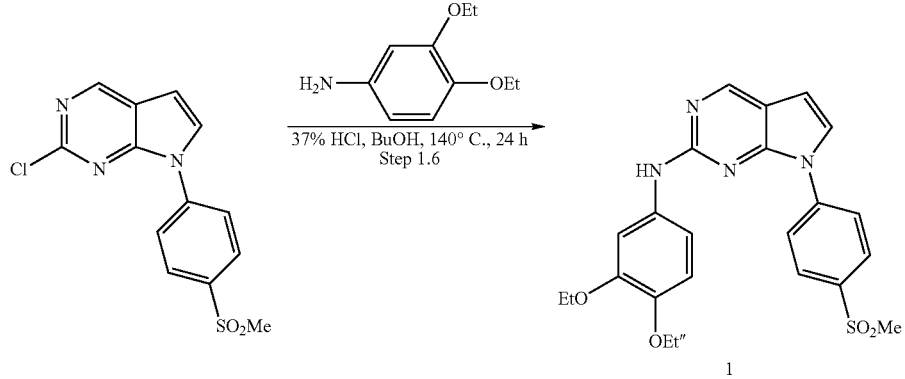

Step 1.1: 5-Bromo-2-chloro-pyrimidin-4-ylamine 2,4-Dichloro-5-bromopyrimidine (200 g, 0.88 mol) is added slowly to NH$_3$ (1000 ml, 7 M in MeOH) while the reaction mixture is kept below 10° C. The reaction mixture is stirred at rt for 2 h, heated to 60° C. for 2 h, and then cooled again to rt and stirred for 55 h. It is concentrated under reduced pressure, and the residue is suspended in H$_2$O (500 ml). The aqueous layer is extracted with EtOAc (3×) and the combined organic layers are dried over MgSO$_4$, filtered, and concentrated under reduced pressure to yield the title compound as a white solid.

Step 1.2: 1-Ethoxy-propene

To a solution of ethoxyethyne (120 g, 0.69 mol, 40% in hexane) in toluene (1500 mL) is added slowly tributyltin hydride (190 g, 0.65 mol) and AIBN (4.6 g, 0.028 mol). The reaction mixture is heated to 100° C. for 16 h. The reaction mixture is concentrated under reduced pressure and dried under HV. The brown residual oil (80% purity of title compound) is used for next step without purification.

Step 1.3: 2-Chloro-5-(2-ethoxy-vinyl)-pyrimidin-4-ylamine

5-Bromo-2-chloro-pyrimidin-4-ylamine (88.0 g, 0.43 mol), 1-ethoxy-propene (220 g, 0.49 mol), Pd(PPh$_3$)$_2$Cl$_2$ (35.0 g, 0.05 mol) and Et$_4$NCl (67.0 g, 0.40 mol) are suspended in solvent (750 mL, DME/toluene/H$_2$O/EtOH 10:1:3:6) under nitrogen. The reaction mixture is heated to reflux for 24 h, cooled to rt, and then diluted with water. The aqueous layer is extracted with EtOAc (3×). The combined organic layers are dried over MgSO$_4$, filtered, and concentrated under reduced pressure. The residue is purified by column chromatography (SiO$_2$, gradient elution, EtOAc/petroleumether 1:10>1:4) to yield the title compound as a yellow solid.

Step 1.4: 2-Chloro-7H-pyrrolo[2,3-d]pyrimidine

To a solution of 2-Chloro-5-(2-ethoxy-vinyl)-pyrimidin-4-ylamine (38.0 g, 0.19 mol) in ETOH (1000 ml) is added concentrated aqueous HCl (37%, 100 g, 1.00 mol) at rt. The reaction mixture is heated to reflux for 3 h and then evaporated to dryness under reduced pressure. Aqueous sodium carbonate solution (5%, 500 mL) is added to the residue, and the mixture is extracted with EtOAc (3×). The combined organic layers are dried over MgSO$_4$, filtered, and concentrated under reduced pressure. The residue is recrystallized from hexane/ether (4/1, 250 ml) to give the title compound as an off-white solid.

Step 1.5: 2-Chloro-7-(4-methanesulfonyl-phenyl)-7H-pyrrolo[2,3-d]pyrimidine

In a seal tube, 2-chloro-7H-pyrrolo[2,3-d]pyrimidine (600 mg, 3.56 mmol), 4-bromophenylmethylsulfone (700 mg, 4.10 mmol), CuI (239 mg, 1.23 mmol), and K$_3$PO$_4$ (2.67 g, 12.3 mmol) are suspended in 1,4-dioxane (30 mL). Then, trans-1,2-diaminocyclohexane (149 µL, 1.23 mmol) is added at rt. The reaction vial is flushed with Ar and the mixture is heated to 110° C. for 3 h. After cooling to rt, the reaction mixture is concentrated under reduce pressure. The residue is suspended in EtOAc and washed with saturated aqueous NaCl solution (3×). The organic layer is dried over MgSO$_4$, filtered, and concentrated under reduced pressure. The solid residue is triturated with small amounts of EtOAc to yield the title compound as a brown solid.

Step 1.6: (3,4-Diethoxy-phenyl)-[7-(4-methanesulfonyl-phenyl)-7H-pyrrolo[2,3-d]pyrimidin-2-yl]-amine (1)

To a suspension of 2-chloro-7-(4-methanesulfonyl-phenyl)-7H-pyrrolo[2,3-d]pyrimidine (30.0 mg, 0.093 mmol) in BuOH (1.5 mL) is added 3,4-diethoxyaniline (41.0 mg, 0.220 mmol) and concentrated aqueous HCl (37%, 23.0 µL, 0.232 mmol). The reaction mixture is heated to 140° C. for 24 h, cooled to rt, and concentrated under reduce pressure. The residue is purified by reverse phase prep-HPLC (Waters) to afford the title compound (1) as a yellow solid. HPLC: $t_R$=1.61 min (Method A); MS-ES: (M+H)$^+$=453.

EXAMPLE 2

{4-[7-(3,5-Difluoro-4-morpholin-4-ylmethyl-phenyl)-7H-pyrrolo[2,3-d]pyrimidin-2-ylamino]-phenyl}-(4-methyl-piperazin-1-yl)-methanone (2)

The compound is prepared according to Scheme 2.

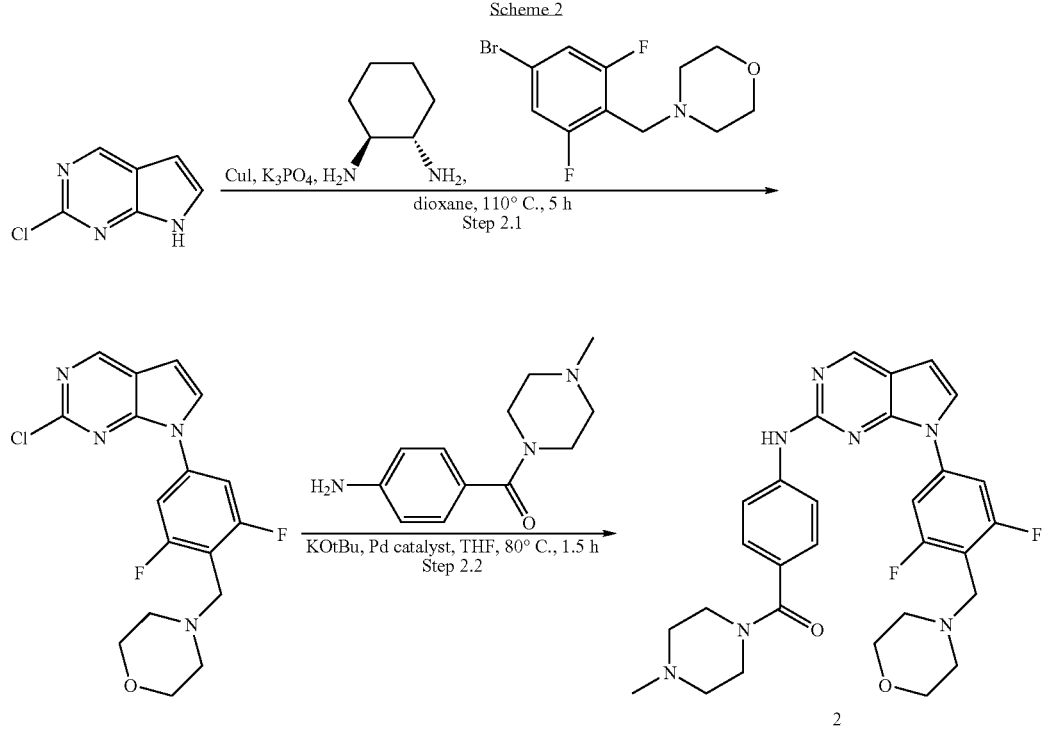

Step 2.1: 2-Chloro-7-(3,5-difluoro-4-morpholin-4-ylmethyl-phenyl)-7H-pyrrolo[2,3-d]pyrimidine In a sealed tube, 2-chloro-7H-pyrrolo[2,3-d]pyrimidine (200 mg, 1.24 mmol), 4-(4-bromo-2,6-difluoro-benzyl)-morpholine (418 mg, 1.36 mmol), CuI (72.1 mg, 0.371 mmol), and $K_3PO_4$ (804 mg, 3.71 mmol) are suspended in 1,4-dioxane (8 mL). Then, trans-1,2-diaminocyclohexane (45.0 µL, 0.371 mmol) is added at rt. The reaction vial is flushed with Ar and the mixture is heated to 110° C. for 5 h. After cooling to rt, the reaction mixture is diluted with EtOAc and the organic layer is washed with saturated aqueous $Na_2CO_3$ solution (2×). The organic layer is dried over $Na_2SO_4$, filtered, and concentrated under reduced pressure. The residue is purified by column chromatography ($SiO_2$, gradient elution, hexane/EtOAc 100:0→30:70) to yield the title compound as a white solid.

Step 2.2: {4-[7-(3,5-Difluoro-4-morpholin-4-ylmethyl-phenyl)-7H-pyrrolo[2,3-d]pyrimidin-2-ylamino]-phenyl}-(4-methyl-piperazin-1-yl)-methanone (2)

In a sealed tube, 2-chloro-7-(3,5-difluoro-4-morpholin-4-ylmethyl-phenyl)-7H-pyrrolo[2,3-d]pyrimidine (50.0 mg, 0.130 mmol), (4-Amino-phenyl)-(4-methyl-piperazin-1-yl)-methanone (42.1 mg, 0.182 mmol), KOtBu (21.1 mg, 0.182 mmol) and SK-CC02-A (12.5 mg, 0.020 mmol, Pd catalyst 2-(Dimethylaminomethyl)-ferrocen-1-yl-palladium(II)-chlorid Dinorbornylphosphin Complex, Fluka No. 44696) are suspended in THF (2 ml) under Ar. The reaction mixture is stirred at 80° C. for 1.5 h, cooled to rt, and then filtered through a Celite plug. The filtrate is concentrated under reduce pressure. The residue is purified by reverse phase prep-HPLC (Waters) to afford the title compound (2) as a white solid. HPLC: $t_R$=0.89 min (Method A); MS-ES: $(M+H)^+$=548.

EXAMPLE 3

(4-Isopropoxy-phenyl)-[7-(4-methanesulfonyl-phenyl)-7H-pyrrolo[2.3-d]pyrimidin-2-yl]-amine (3)

The compound is prepared according to Scheme 3.

Scheme 3

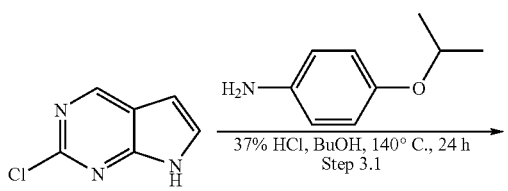

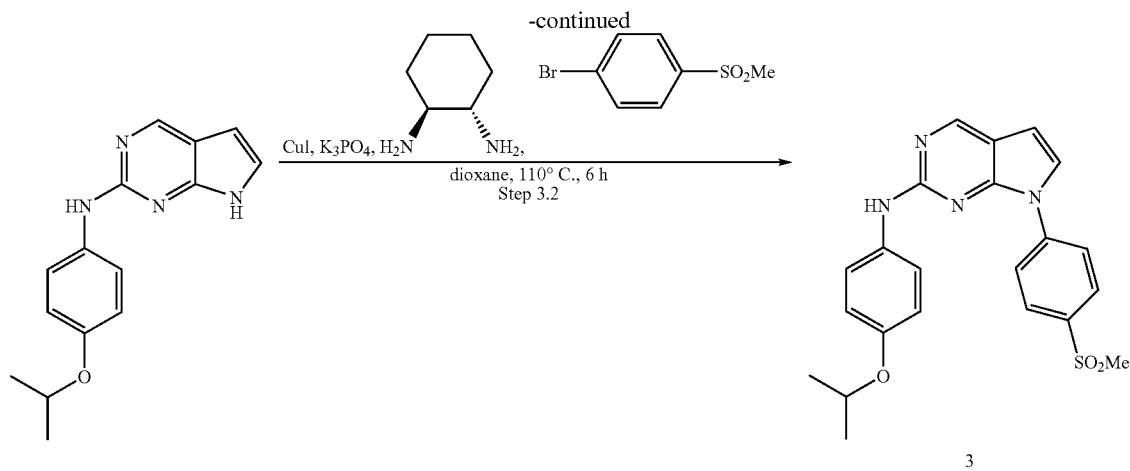

Step 3.1: (4-Isopropoxy-phenyl)-(7H-pyrrolo[2,3-d]pyrimidin-2-yl)-amine

To a suspension of 2-chloro-7H-pyrrolo[2,3-d]pyrimidine (700 mg, 4.33 mmol) in BuOH (10 mL) is added 4-isopropoxyaniline (1.31 g, 8.66 mmol) and concentrated aqueous HCl (37%, 1.28 mL, 13.0 mmol). The reaction mixture is heated to 140° C. for 24 h, cooled to rt, and concentrated under reduce pressure. The residue is dissolved in EtOAc and the organic layer is washed with saturated aqueous $Na_2CO_3$ solution (2×). The organic layer is dried over $Na_2SO_4$, filtered, and concentrated under reduced pressure. The residue solid residue is triturated with hexane to yield the title compound as an off-white solid.

Step 3.2: (4-Isopropoxy-phenyl)-[7-(4-methanesulfonyl-phenyl)-7H-pyrrolo[2,3-d]pyrimidin-2-yl]-amine (3)

In a sealed tube, (4-Isopropoxy-phenyl)-(7H-pyrrolo[2,3-d]pyrimidin-2-yl)-amine (350 mg, 1.17 mmol), 4-bromophenylmethylsulfone (552 mg, 2.35 mmol), CuI (68.4 mg, 0.352 mmol), and $K_3PO_4$ (763 mg, 3.52 mmol) are suspended in 1,4-dioxane (10 mL). Then, trans-1,2-diaminocyclohexane (42.7 μL, 0.352 mmol) is added at rt. The reaction vial is flushed with Ar and the mixture is heated to 110° C. for 6 h. After cooling to rt, the reaction mixture is diluted with EtOAc and the organic layer is washed with saturated aqueous NaCl solution (3×). The organic layer is dried over $Na_2SO_4$, filtered, and concentrated under reduced pressure. The residue is purified by reverse phase prep-HPLC (Waters) to afford the title compound (3) as an off-white solid. HPLC: $t_R$=1.67 min (Method A); MS-ES: $(M+H)^+$=423.

EXAMPLE 4

[7-(4-Methanesulfonyl-phenyl)-7H-pyrrolo[2,3-d]pyrimidin-2-yl]-(3,4,5-trimethoxy-phenyl)-amine

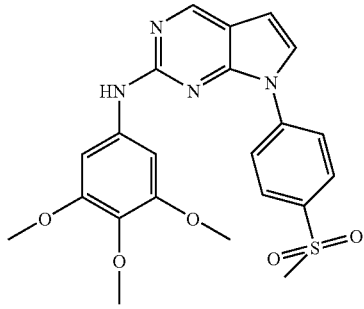 [SMILES: COc1cc(Nc2ncc3ccn(-c4ccc(S(C)(=O)=O)cc4)c3n2)cc(OC)c1OC]

The compound is prepared analogous to Example 1. HPLC: $t_R$=1.48 min (Method A); MS-ES: $(M+H)^+$=455.

EXAMPLE 5

(3,4-Dimethoxy-phenyl)-[7-(4-methanesulfonyl-phenyl)-7H-pyrrolo[2,3-d]pyrimidin-2-yl]-amine

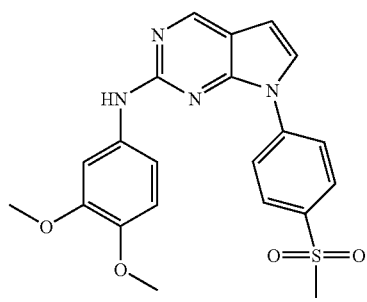 [SMILES: COc1ccc(Nc2ncc3ccn(-c4ccc(S(C)(=O)=O)cc4)c3n2)cc1OC]

The compound is prepared analogous to Example 3. HPLC: $t_R$=1.37 min (Method A); MS-ES: $(M+H)^+$=425.

EXAMPLE 6

N-tert-Butyl-4-[2-(3,4-dimethoxy-phenylamino)-pyrrolo[2,3-d]pyrimidin-7-yl]-benzenesulfonamide

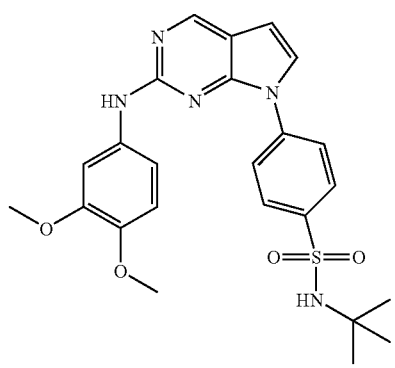 [SMILES: COc1ccc(Nc2ncc3ccn(-c4ccc(S(=O)(=O)NC(C)(C)C)cc4)c3n2)cc1OC]

The compound is prepared analogous to Example 3. HPLC: $t_R$=1.73 min (Method A); MS-ES: $(M+H)^+$=482.

EXAMPLE 7

N-tert-Butyl-4-[2-(3,4-dimethoxy-phenylamino)-pyrrolo[2,3-d]pyrimidin-7-yl]-benzamide

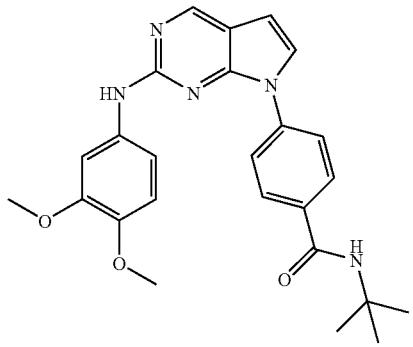 [SMILES: COc1ccc(Nc2ncc3ccn(-c4ccc(C(=O)NC(C)(C)C)cc4)c3n2)cc1OC]

The compound is prepared analogous to Example 3. HPLC: $t_R$=1.71 min (Method A); MS-ES: (M+H)$^+$=446.

EXAMPLE 8

N-tert-Butyl-4-[2-(3,4,5-trimethoxy-phenylamino)-pyrrolo[2,3-d]pyrimidin-7-yl]-benzenesulfonamide

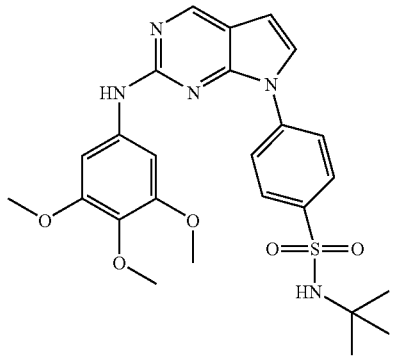 [SMILES: COc1cc(Nc2ncc3ccn(-c4ccc(S(=O)(=O)NC(C)(C)C)cc4)c3n2)cc(OC)c1OC]

The compound is prepared analogous to Example 3. HPLC: $t_R$=1.83 min (Method A); MS-ES: (M+H)$^+$=512.

EXAMPLE 9

N-tert-Butyl-4-[2-(3,4,5-trimethoxy-phenylamino)-pyrrolo[2,3-d]pyrimidin-7-yl]-benzamide

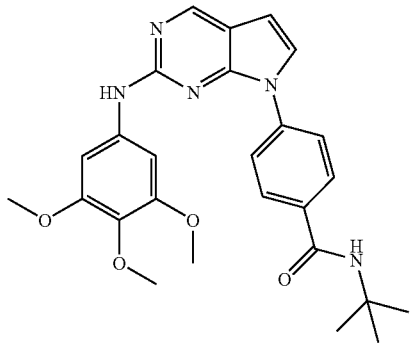 [SMILES: COc1cc(Nc2ncc3ccn(-c4ccc(C(=O)NC(C)(C)C)cc4)c3n2)cc(OC)c1OC]

The compound is prepared analogous to Example 3. HPLC: $t_R$=1.81 min (Method A); MS-ES: (M+H)$^+$=476.

EXAMPLE 10

N,N-Dimethyl-4-[2-(3,4,5-trimethoxy-phenylamino)-pyrrolo[2,3-d]pyrimidin-7-yl]-benzenesulfonamide

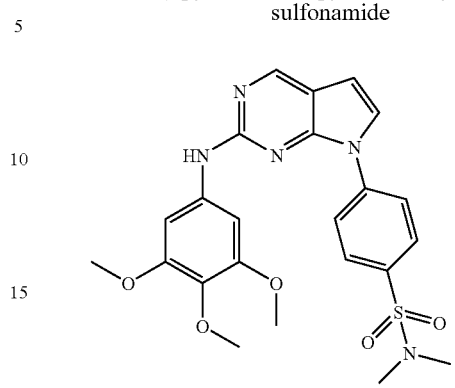

The compound is prepared analogous to Example 3. HPLC: $t_R$=1.69 min (Method A); MS-ES: (M+H)$^+$=484.

EXAMPLE 11

(4,5-Dimethoxy-2-methyl-phenyl)-[7-(4-methanesulfonyl-phenyl)-7H-pyrrolo[2,3-d]pyrimidin-2-yl]-amine

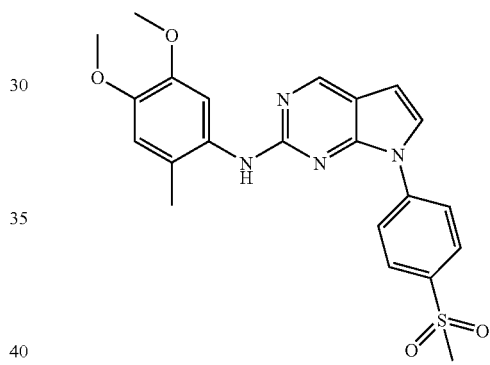

The compound is prepared analogous to Example 1. HPLC: $t_R$=1.32 min (Method A); MS-ES: (M+H)$^+$=439.

EXAMPLE 12

[7-(4-Methanesulfonyl-phenyl)-7H-pyrrolo[2,3-d]pyrimidin-2-yl]-(3-methyl-1,2,3,4,4a,5-hexahydro-7H-6-oxa-3,11b-diaza-dibenzo[a,c]cyclohepten-9-yl)-amine

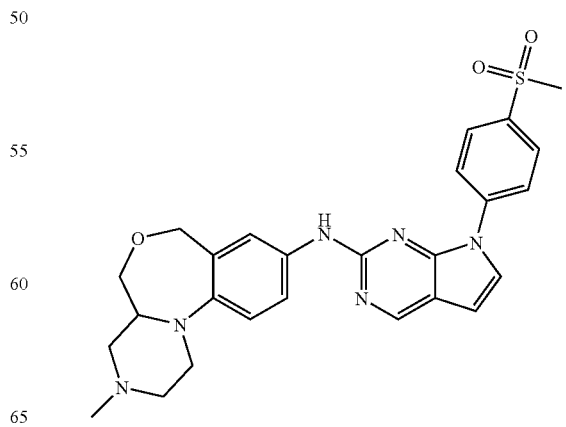

The compound is prepared analogous to Example 1. HPLC: $t_R$=1.06 min (Method A); MS-ES: (M+H)$^+$=505.

EXAMPLE 13

4-{4-[7-(4-Methanesulfonyl-phenyl)-7H-pyrrolo[2,3-d]pyrimidin-2-ylamino]-phenyl}-piperazine-1-carboxylic acid diethylamide

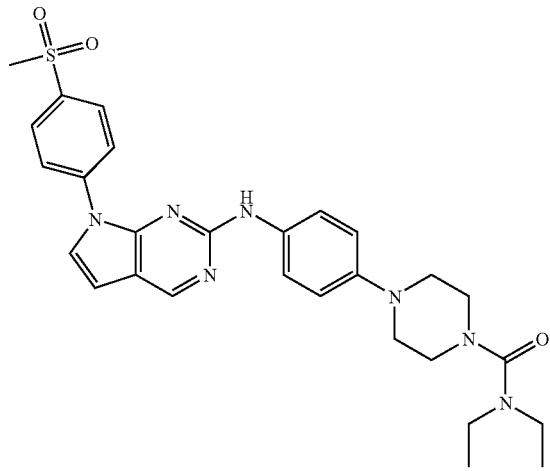 [SMILES: CCN(CC)C(=O)N1CCN(c2ccc(Nc3ncc4ccn(-c5ccc(S(C)(=O)=O)cc5)c4n3)cc2)CC1]

The compound is prepared analogous to Example 1. HPLC: $t_R$=1.44 min (Method A); MS-ES: (M+H)$^+$=548.

EXAMPLE 14

[7-(4-Methanesulfonyl-phenyl)-7H-pyrrolo[2,3-d]pyrimidin-2-yl]-(2,2,3,3-tetrafluoro-2,3-dihydro-benzo[1,4]dioxin-6-yl)-amine

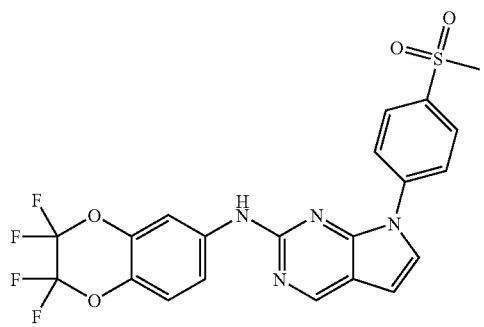 [SMILES: CS(=O)(=O)c1ccc(-n2ccc3cnc(Nc4ccc5c(c4)OC(F)(F)C(F)(F)O5)nc32)cc1]

The compound is prepared analogous to Example 1. HPLC: $t_R$=2.30 min (Method A); MS-ES: (M+H)$^+$=495.

EXAMPLE 15

Benzo[1,3]dioxol-5-yl-[7-(4-methanesulfonyl-phenyl)-7H-pyrrolo[2,3-d]pyrimidin-2-yl]-amine

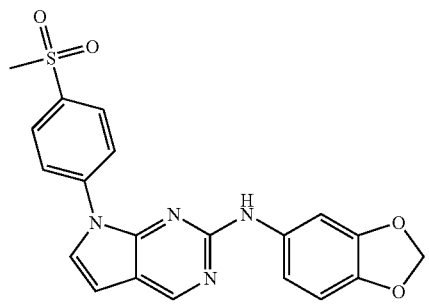 [SMILES: CS(=O)(=O)c1ccc(-n2ccc3cnc(Nc4ccc5c(c4)OCO5)nc32)cc1]

The compound is prepared analogous to Example 1. HPLC: $t_R$=1.42 min (Method A); MS-ES: (M+H)$^+$=409.

EXAMPLE 16

[7-(4-Methanesulfonyl-phenyl)-7H-pyrrolo[2,3-d]pyrimidin-2-yl]-[4-(1-methyl-piperidin-4-yl)-phenyl]-amine

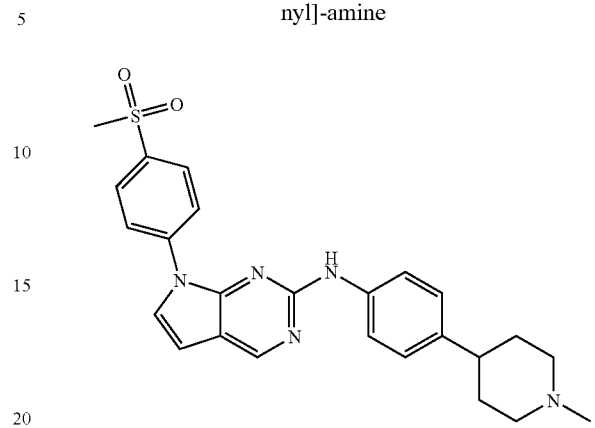

The compound is prepared analogous to Example 1. HPLC: $t_R$=1.08 min (Method A); MS-ES: (M+H)$^+$=462.

EXAMPLE 17

[7-(4-Methanesulfonyl-phenyl)-7H-pyrrolo[2,3-d]pyrimidin-2-yl]-[3-(4-methyl-piperazin-1-yl)-phenyl]-amine

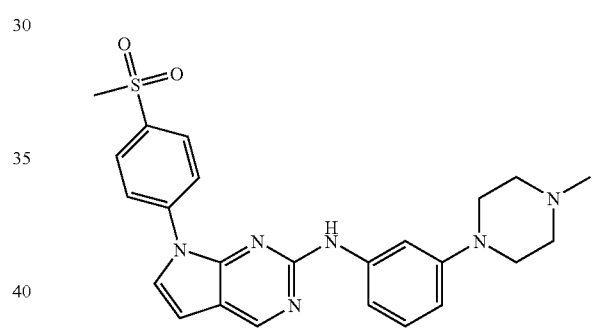

The compound is prepared analogous to Example 1. HPLC: $t_R$=1.09 min (Method A); MS-ES: (M+H)$^+$=463.

EXAMPLE 18

[7-(4-Methanesulfonyl-phenyl)-7H-pyrrolo[2,3-d]pyrimidin-2-yl]-[4-(4-methyl-piperazin-1-yl)-phenyl]-amine

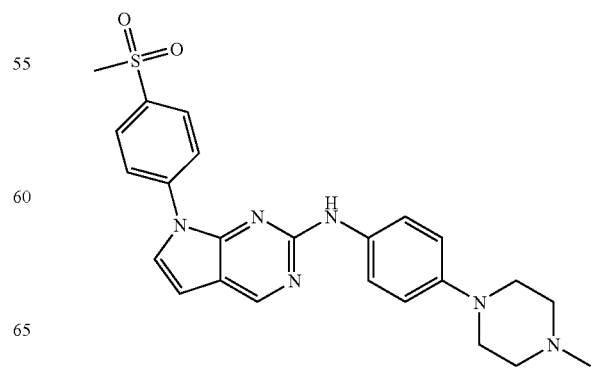

The compound is prepared analogous to Example 1. HPLC: $t_R$=0.98 min (Method A); MS-ES: (M+H)$^+$=463.

EXAMPLE 19

[7-(4-Methanesulfonyl-phenyl)-7H-pyrrolo[2,3-d]pyrimidin-2-yl]-phenyl-amine

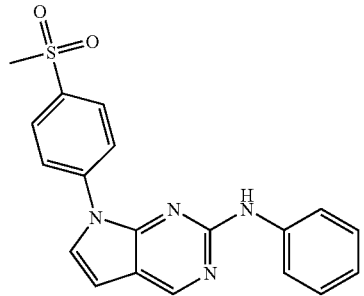 [SMILES: CS(=O)(=O)c1ccc(-n2ccc3cnc(Nc4ccccc4)nc32)cc1]

The compound is prepared analogous to Example 1. HPLC: $t_R$=1.46 min (Method A); MS-ES: (M+H)$^+$=365.

EXAMPLE 20

[7-(4-Methanesulfonyl-phenyl)-7H-pyrrolo[2,3-d]pyrimidin-2-yl]-(4-methoxy-phenyl)-amine

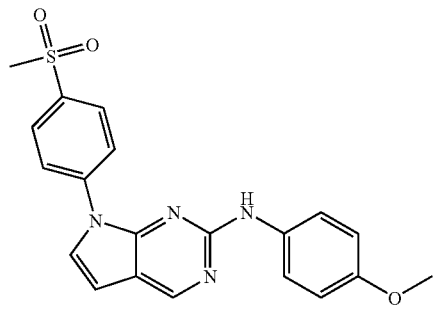

The compound is prepared analogous to Example 1. HPLC: $t_R$=1.41 min (Method A); MS-ES: (M+H)$^+$=395.

EXAMPLE 21

N-[7-(4-Methanesulfonyl-phenyl)-7H-pyrrolo[2,3-d]pyrimidin-2-yl]-N',N'-dimethyl-benzene-1,4-diamine

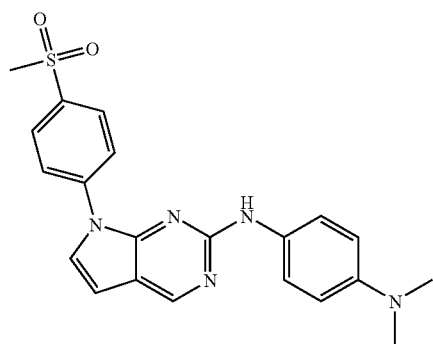

The compound is prepared analogous to Example 1. HPLC: $t_R$=1.07 min (Method A); MS-ES: (M+H)$^+$=408.

EXAMPLE 22

(2,4-Dimethoxy-phenyl)-[7-(4-methanesulfonyl-phenyl)-7H-pyrrolo[2,3-d]pyrimidin-2-yl]-amine

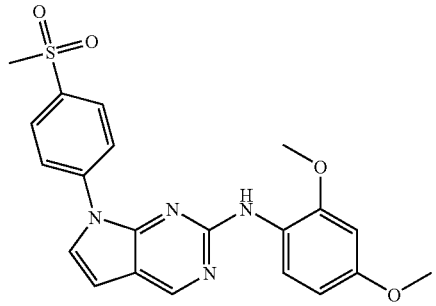

The compound is prepared analogous to Example 1. MS-ES: (M+H)$^+$=425.

EXAMPLE 23

(3,5-Dimethoxy-phenyl)-[7-(4-methanesulfonyl-phenyl)-7H-pyrrolo[2,3-d]pyrimidin-2-yl]-amine

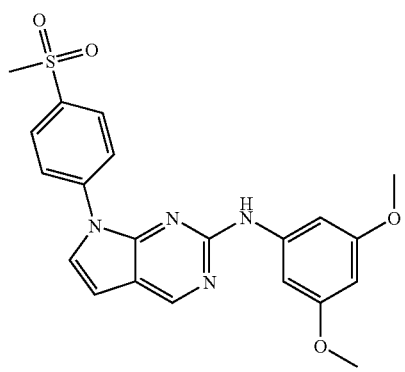

The compound is prepared analogous to Example 1. HPLC: $t_R$=1.62 min (Method A); MS-ES: (M+H)$^+$=425.

EXAMPLE 24

5-[7-(4-Methanesulfonyl-phenyl)-7H-pyrrolo[2,3-d]pyrimidin-2-ylamino]-2-methoxy-phenol

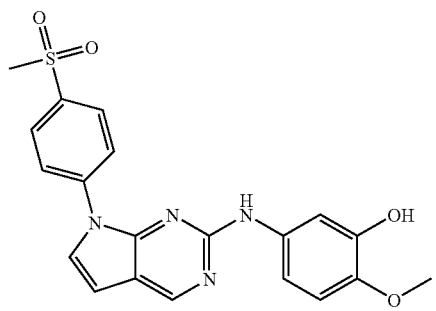

The compound is prepared analogous to Example 1.
HPLC: $t_R$=1.22 min (Method A); MS-ES: (M+H)$^+$=411.

EXAMPLE 25

[7-(4-Methanesulfonyl-phenyl)-7H-pyrrolo[2,3-d]pyrimidin-2-yl]-[4-methoxy-3-(4-methyl-piperazin-1-yl)-phenyl]-amine

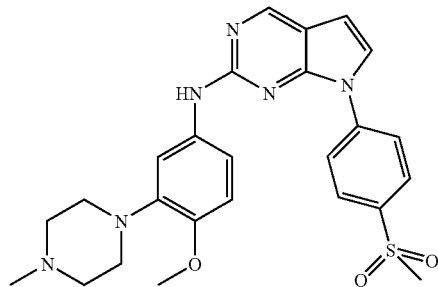 [SMILES: COc1ccc(Nc2ncc3ccn(-c4ccc(S(C)(=O)=O)cc4)c3n2)cc1N1CCN(C)CC1]

The compound is prepared analogous to Example 1.
HPLC: $t_R$=1.07 min (Method A); MS-ES: (M+H)$^+$=493.

EXAMPLE 26

[3-(2-Dimethylamino-ethoxy)-4-methoxy-phenyl]-[7-(4-methanesulfonyl-phenyl)-7H-pyrrolo[2,3-d]pyrimidin-2-yl]-amine

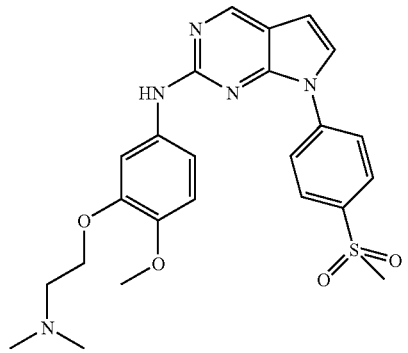 [SMILES: COc1ccc(Nc2ncc3ccn(-c4ccc(S(C)(=O)=O)cc4)c3n2)cc1OCCN(C)C]

The compound is prepared analogous to Example 1.
HPLC: $t_R$=1.09 min (Method A); MS-ES: (M+H)$^+$=482.

EXAMPLE 27

[3-(3-Dimethylamino-propoxy)-4-methoxy-phenyl]-[7-(4-methanesulfonyl-phenyl)-7H-pyrrolo[2,3-d]pyrimidin-2-yl]-amine

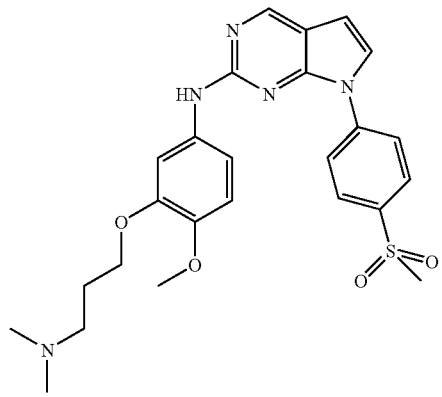 [SMILES: COc1ccc(Nc2ncc3ccn(-c4ccc(S(C)(=O)=O)cc4)c3n2)cc1OCCCN(C)C]

The compound is prepared analogous to Example 1.
HPLC: $t_R$=1.10 min (Method A); MS-ES: (M+H)$^+$=496.

EXAMPLE 28

{4-[7-(4-Methanesulfonyl-phenyl)-7H-pyrrolo[2,3-d]pyrimidin-2-ylamino]-phenyl}-(4-methyl-piperazin-1-yl)-methanone

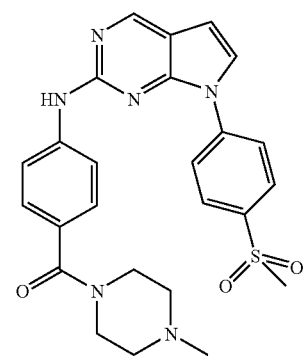 [SMILES: CN1CCN(C(=O)c2ccc(Nc3ncc4ccn(-c5ccc(S(C)(=O)=O)cc5)c4n3)cc2)CC1]

The compound is prepared analogous to Example 2.
HPLC: $t_R$=1.02 min (Method A); MS-ES: (M+H)$^+$=491.

EXAMPLE 29

[7-(4-Methanesulfonyl-phenyl)-7H-pyrrolo[2,3-d]pyrimidin-2-yl]-[4-methoxy-3-(2-morpholin-4-yl-ethoxy)-phenyl]-amine

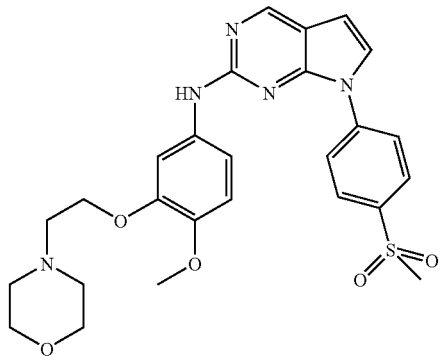 [SMILES: COc1ccc(Nc2ncc3ccn(-c4ccc(S(C)(=O)=O)cc4)c3n2)cc1OCCN1CCOCC1]

The compound is prepared analogous to Example 1.
HPLC: $t_R$=1.11 min (Method A); MS-ES: (M+H)$^+$=524.

EXAMPLE 30

{4-[7-(4-Methanesulfonyl-phenyl)-7H-pyrrolo[2,3-d]pyrimidin-2-ylamino]-phenyl}-morpholin-4-yl-methanone

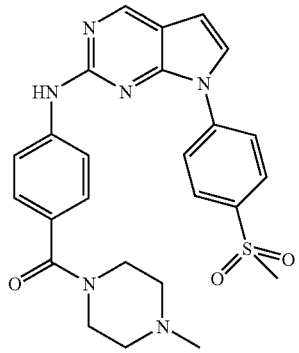 [SMILES: CN1CCN(C(=O)c2ccc(Nc3ncc4ccn(-c5ccc(S(C)(=O)=O)cc5)c4n3)cc2)CC1]

The compound is prepared analogous to Example 2.
HPLC: $t_R$=1.33 min (Method A); MS-ES: (M+H)$^+$=478.

EXAMPLE 31

[7-(4-Methanesulfonyl-phenyl)-7H-pyrrolo[2,3-d]pyrimidin-2-yl]-[4-methoxy-3-(2-pyrrolidin-1-yl-ethoxy)-phenyl]-amine

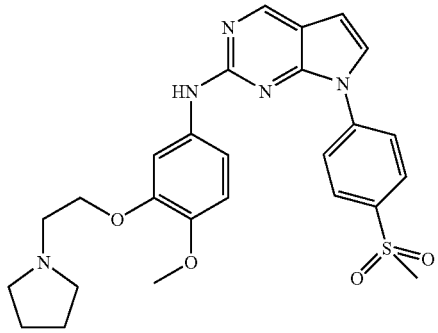 [SMILES: COc1ccc(Nc2ncc3ccn(-c4ccc(S(C)(=O)=O)cc4)c3n2)cc1OCCN1CCCC1]

The compound is prepared analogous to Example 1.
HPLC: $t_R$=1.13 min (Method A); MS-ES: (M+H)$^+$=508.

EXAMPLE 32

[7-(4-Methanesulfonyl-phenyl)-7H-pyrrolo[2,3-d]pyrimidin-2-yl]-{3-[2-(4-methyl-piperazin-1-yl)-ethoxy]-phenyl}-amine

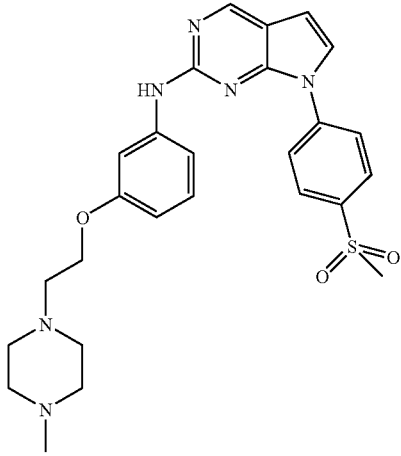 [SMILES: CN1CCN(CCOc2cccc(Nc3ncc4ccn(-c5ccc(S(C)(=O)=O)cc5)c4n3)c2)CC1]

The compound is prepared analogous to Example 1.
HPLC: $t_R$=1.05 min (Method A); MS-ES: (M+H)$^+$=507.

EXAMPLE 33

[4-(2-Diethylamino-ethoxy)-phenyl]-[7-(4-methanesulfonyl-phenyl)-7H-pyrrolo[2,3-d]pyrimidin-2-yl]-amine

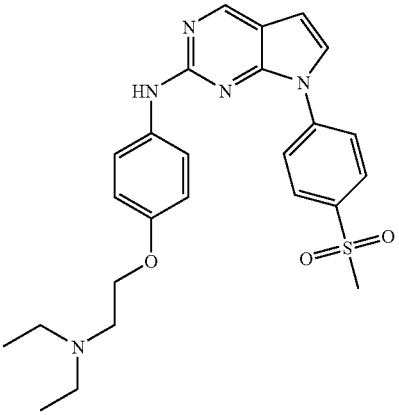 [SMILES: CCN(CC)CCOc1ccc(Nc2ncc3ccn(-c4ccc(S(C)(=O)=O)cc4)c3n2)cc1]

The compound is prepared analogous to Example 1.
HPLC: $t_R$=1.09 min (Method A); MS-ES: (M+H)$^+$=480.

EXAMPLE 34

[7-(4-Methanesulfonyl-phenyl)-7H-pyrrolo[2,3-d]pyrimidin-2-yl]-[4-(2-morpholin-4-yl-ethoxy)-phenyl]-amine

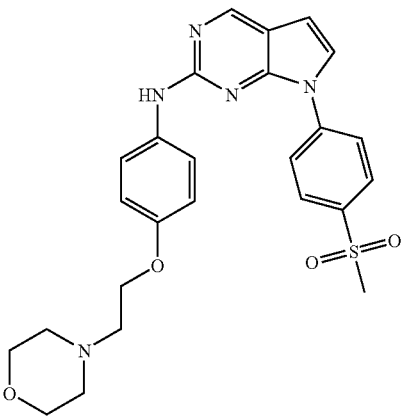 [SMILES: CS(=O)(=O)c1ccc(-n2ccc3cnc(Nc4ccc(OCCN5CCOCC5)cc4)nc32)cc1]

The compound is prepared analogous to Example 1.
HPLC: $t_R$=1.01 min (Method A); MS-ES: (M+H)$^+$=494.

EXAMPLE 35

[7-(4-Methanesulfonyl-phenyl)-7H-pyrrolo[2,3-d]pyrimidin-2-yl]-[3-(2-morpholin-4-yl-ethoxy)-phenyl]-amine

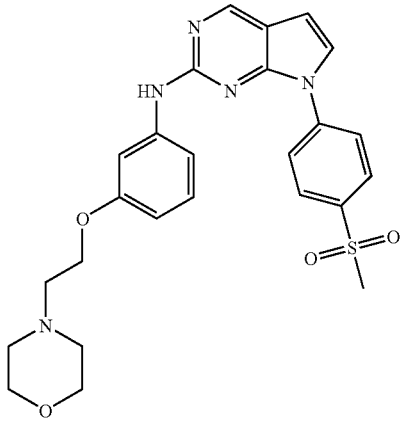 [SMILES: CS(=O)(=O)c1ccc(-n2ccc3cnc(Nc4cccc(OCCN5CCOCC5)c4)nc32)cc1]

The compound is prepared analogous to Example 1.
HPLC: $t_R$=1.13 min (Method A); MS-ES: (M+H)$^+$=494.

EXAMPLE 36

[3-(2-Diethylamino-ethoxy)-phenyl]-[7-(4-methanesulfonyl-phenyl)-7H-pyrrolo[2,3-d]pyrimidin-2-yl]-amine

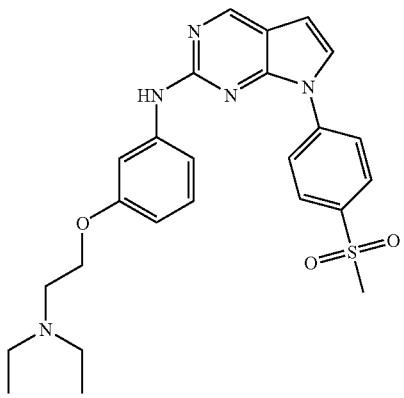 [SMILES: CCN(CC)CCOc1cccc(Nc2ncc3ccn(-c4ccc(S(C)(=O)=O)cc4)c3n2)c1]

The compound is prepared analogous to Example 1.
HPLC: $t_R$=1.20 min (Method A); MS-ES: (M+H)$^+$=480.

EXAMPLE 37

[7-(4-Methanesulfonyl-phenyl)-7H-pyrrolo[2,3-d]pyrimidin-2-yl]-(4-piperazin-1-yl-phenyl)-amine

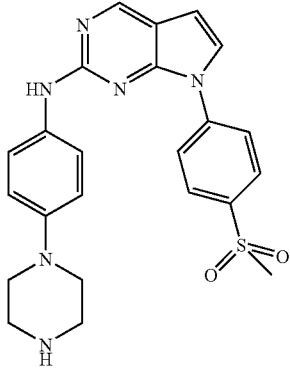 [SMILES: CS(=O)(=O)c1ccc(-n2ccc3cnc(Nc4ccc(N5CCNCC5)cc4)nc32)cc1]

The compound is prepared analogous to Example 1.
HPLC: $t_R$=0.98 min (Method A); MS-ES: (M+H)$^+$=449.

EXAMPLE 38

[7-(4-Methanesulfonyl-phenyl)-7H-pyrrolo[2,3-d]pyrimidin-2-yl]-[4-(4-methyl-piperazin-1-ylmethyl)-phenyl]-amine

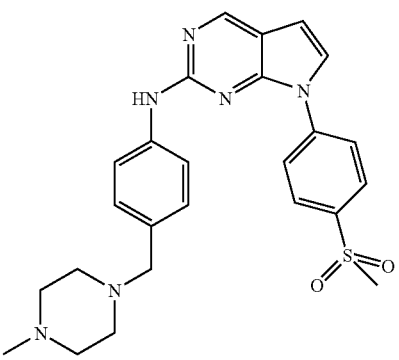 [SMILES: CN1CCN(Cc2ccc(Nc3ncc4ccn(-c5ccc(S(C)(=O)=O)cc5)c4n3)cc2)CC1]

The compound is prepared analogous to Example 2.
HPLC: $t_R$=0.98 min (Method A); MS-ES: (M+H)$^+$=477.

EXAMPLE 39

{3-[7-(4-Methanesulfonyl-phenyl)-7H-pyrrolo[2,3-d]pyrimidin-2-ylamino]-phenyl}-(4-methyl-piperazin-1-yl)-methanone

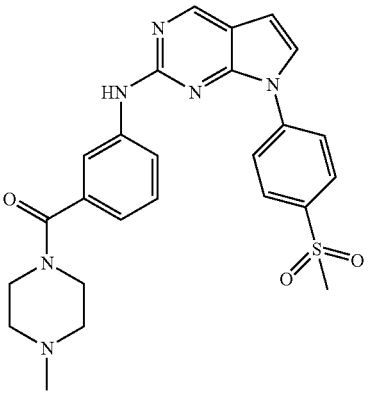 [SMILES: CN1CCN(C(=O)c2cccc(Nc3ncc4ccn(-c5ccc(S(C)(=O)=O)cc5)c4n3)c2)CC1]

The compound is prepared analogous to Example 2.
HPLC: $t_R$=1.02 min (Method A); MS-ES: (M+H)$^+$=491.

EXAMPLE 40

N-(2-Dimethylamino-ethyl)-4-[7-(4-methanesulfonyl-phenyl)-7H-pyrrolo[2,3-d]pyrimidin-2-ylamino]-benzamide

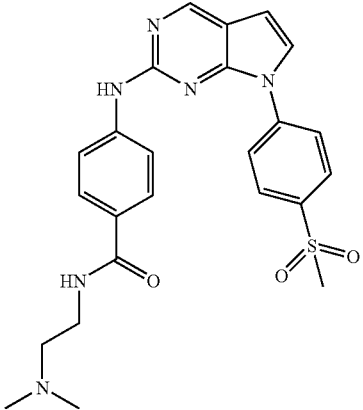 [SMILES: CN(C)CCNC(=O)c1ccc(Nc2ncc3ccn(-c4ccc(S(C)(=O)=O)cc4)c3n2)cc1]

The compound is prepared analogous to Example 2.
HPLC: $t_R$=1.10 min (Method A); MS-ES: (M+H)$^+$=479.

EXAMPLE 41

[7-(4-Methanesulfonyl-phenyl)-7H-pyrrolo[2,3-d]pyrimidin-2-yl]-(3-piperidin-1-ylmethyl-phenyl)-amine

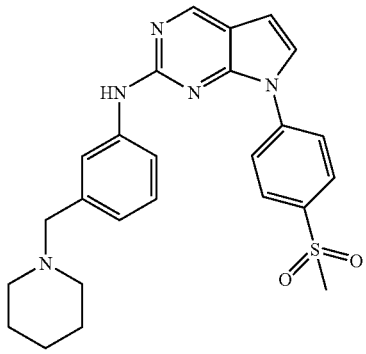 [SMILES: CS(=O)(=O)c1ccc(-n2ccc3cnc(Nc4cccc(CN5CCCCC5)c4)nc32)cc1]

The compound is prepared analogous to Example 2.
HPLC: $t_R$=1.16 min (Method A); MS-ES: (M+H)$^+$=462.

EXAMPLE 42

[7-(4-Methanesulfonyl-phenyl)-7H-pyrrolo[2,3-d]pyrimidin-2-yl]-(4-piperidin-1-ylmethyl-phenyl)-amine

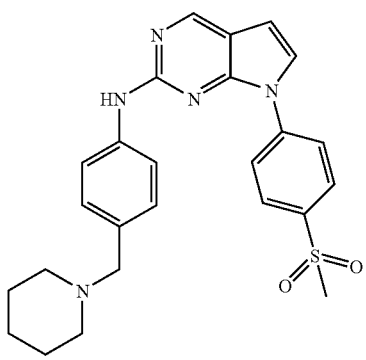 [SMILES: CS(=O)(=O)c1ccc(-n2ccc3cnc(Nc4ccc(CN5CCCCC5)cc4)nc32)cc1]

The compound is prepared analogous to Example 2.
HPLC: $t_R$=1.15 min (Method A); MS-ES: (M+H)$^+$=462.

EXAMPLE 43

(4-Imidazol-1-ylmethyl-phenyl)-[7-(4-methanesulfonyl-phenyl)-7H-pyrrolo[2,3-d]pyrimidin-2-yl]-amine

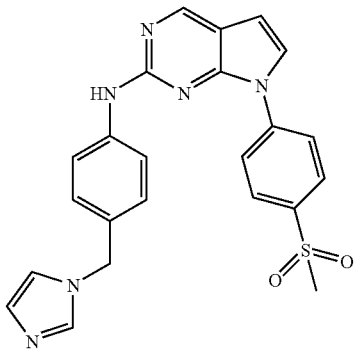 [SMILES: CS(=O)(=O)c1ccc(-n2ccc3cnc(Nc4ccc(Cn5ccnc5)cc4)nc32)cc1]

The compound is prepared analogous to Example 2.
HPLC: $t_R$=1.06 min (Method A); MS-ES: (M+H)$^+$=445.

EXAMPLE 44

[7-(4-Methanesulfonyl-phenyl)-7H-pyrrolo[2,3-d]pyrimidin-2-yl]-(4-morpholin-4-ylmethyl-phenyl)-amine

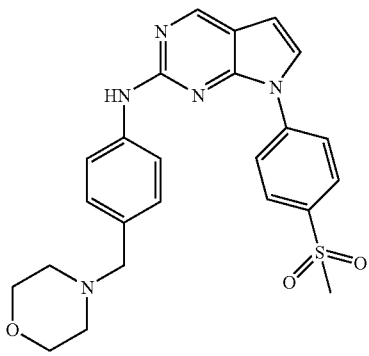 [SMILES: CS(=O)(=O)c1ccc(-n2ccc3cnc(Nc4ccc(CN5CCOCC5)cc4)nc32)cc1]

The compound is prepared analogous to Example 2.
HPLC: $t_R$=1.08 min (Method A); MS-ES: (M+H)$^+$=464.

EXAMPLE 45

4-{4-[7-(4-Methanesulfonyl-phenyl)-7H-pyrrolo[2,3-d]pyrimidin-2-ylamino]-benzyl}-piperazine-1-carboxylic acid tert-butyl ester

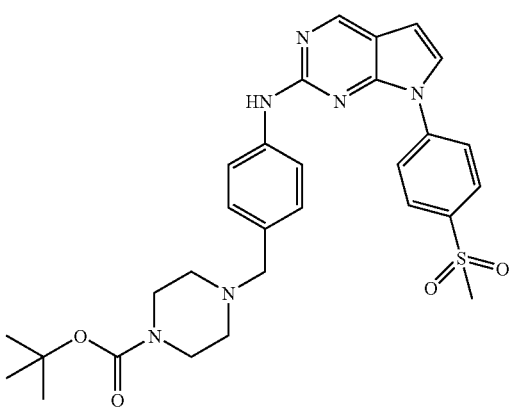 [SMILES: CC(C)(C)OC(=O)N1CCN(Cc2ccc(Nc3ncc4ccn(-c5ccc(S(C)(=O)=O)cc5)c4n3)cc2)CC1]

The compound is prepared analogous to Example 2. HPLC: $t_R$=1.41 min (Method A); MS-ES: (M+H)⁺=563.

EXAMPLE 46

2-{4-[7-(4-Methanesulfonyl-phenyl)-7H-pyrrolo[2,3-d]pyrimidin-2-ylamino]-phenyl}-pyrrolidine-1-carboxylic acid tert-butyl ester

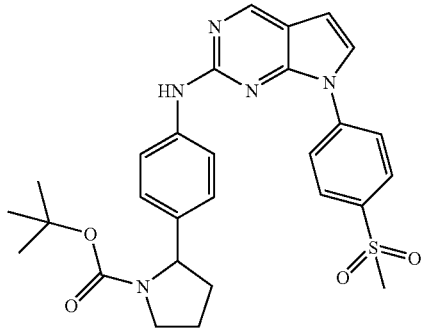 [SMILES: CC(C)(C)OC(=O)N1CCCC1c1ccc(Nc2ncc3ccn(-c4ccc(S(C)(=O)=O)cc4)c3n2)cc1]

The compound is prepared analogous to Example 2. HPLC: $t_R$=1.92 min (Method A); MS-ES: (M+H)⁺=534.

EXAMPLE 47

(3-Imidazol-1-ylmethyl-phenyl)-[7-(4-methanesulfonyl-phenyl)-7H-pyrrolo[2,3-d]pyrimidin-2-yl]-amine

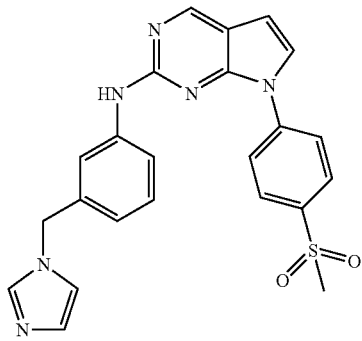 [SMILES: CS(=O)(=O)c1ccc(-n2ccc3cnc(Nc4cccc(Cn5ccnc5)c4)nc32)cc1]

The compound is prepared analogous to Example 2. HPLC: $t_R$=1.08 min (Method A); MS-ES: (M+H)⁺=445.

EXAMPLE 48

N-(2-Dimethylamino-ethyl)-3-[7-(4-methanesulfonyl-phenyl)-7H-pyrrolo[2,3-d]pyrimidin-2-ylamino]-N-phenyl-benzamide

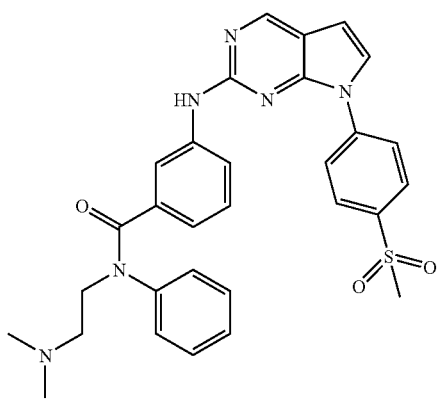 [SMILES: CN(C)CCN(C(=O)c1cccc(Nc2ncc3ccn(-c4ccc(S(C)(=O)=O)cc4)c3n2)c1)c1ccccc1]

The compound is prepared analogous to Example 2. HPLC: $t_R$=1.28 min (Method A); MS-ES: (M+H)⁺=555.

EXAMPLE 49

{3-[7-(4-Methanesulfonyl-phenyl)-7H-pyrrolo[2,3-d]pyrimidin-2-ylamino]-phenyl}-morpholin-4-yl-methanone

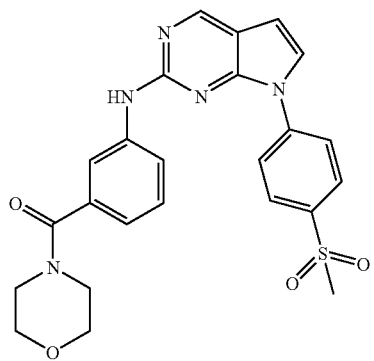 [SMILES: CS(=O)(=O)c1ccc(-n2ccc3cnc(Nc4cccc(C(=O)N5CCOCC5)c4)nc32)cc1]

The compound is prepared analogous to Example 2. HPLC: $t_R$=1.32 min (Method A); MS-ES: (M+H)⁺=478.

EXAMPLE 50

N-(2-Dimethylamino-ethyl)-3-[7-(4-methanesulfonyl-phenyl)-7H-pyrrolo[2,3-d]pyrimidin-2-ylamino]-benzamide

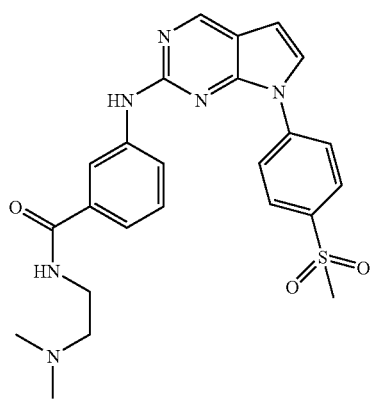 [SMILES: CN(C)CCNC(=O)c1cccc(Nc2ncc3ccn(-c4ccc(S(C)(=O)=O)cc4)c3n2)c1]

The compound is prepared analogous to Example 2. HPLC: $t_R$=1.04 min (Method A); MS-ES: (M+H)$^+$=479.

EXAMPLE 51

N-(2-Hydroxy-ethyl)-4-[7-(4-methanesulfonyl-phenyl)-7H-pyrrolo[2,3-d]pyrimidin-2-ylamino]-benzamide

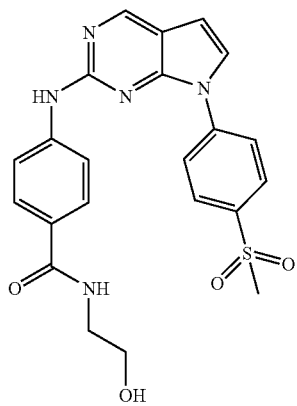 [SMILES: CS(=O)(=O)c1ccc(-n2ccc3cnc(Nc4ccc(C(=O)NCCO)cc4)nc32)cc1]

The compound is prepared analogous to Example 2. HPLC: $t_R$=1.17 min (Method A); MS-ES: (M+H)$^+$=452.

EXAMPLE 52

[7-(4-Methanesulfonyl-phenyl)-7H-pyrrolo[2,3-d]pyrimidin-2-yl]-(4-piperazin-1-ylmethyl-phenyl)-amine

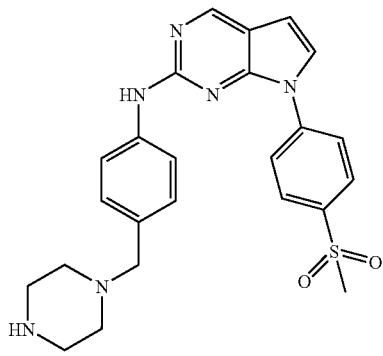 [SMILES: CS(=O)(=O)c1ccc(-n2ccc3cnc(Nc4ccc(CN5CCNCC5)cc4)nc32)cc1]

The compound is prepared by treatment of Example 45 with TFA in CH$_2$Cl$_2$ at rt. HPLC: $t_R$=1.08 min (Method A); MS-ES: (M+H)$^+$=464.

EXAMPLE 53

[7-(4-Methanesulfonyl-phenyl)-7H-pyrrolo[2,3-d]pyrimidin-2-yl]-(4-pyrrolidin-2-yl-phenyl)-amine

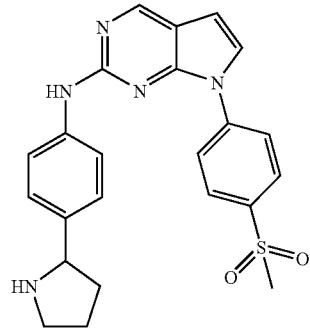 [SMILES: CS(=O)(=O)c1ccc(-n2ccc3cnc(Nc4ccc(C5CCCN5)cc4)nc32)cc1]

The compound is prepared by treatment of Example 46 with TFA in CH$_2$Cl$_2$ at rt. HPLC: $t_R$=1.09 min (Method A); MS-ES: (M+H)$^+$=434.

EXAMPLE 54

[7-(4-Methanesulfonyl-phenyl)-7H-pyrrolo[2,3-d]pyrimidin-2-yl]-(4-methoxymethyl-phenyl)-amine

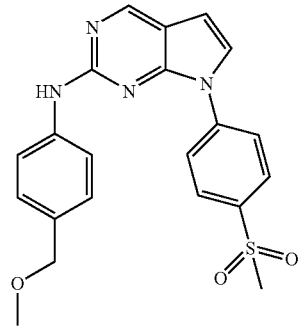 [SMILES: COCc1ccc(Nc2ncc3ccn(-c4ccc(S(C)(=O)=O)cc4)c3n2)cc1]

The compound is prepared analogous to Example 2.
HPLC: $t_R$=1.46 min (Method A); MS-ES: (M+H)$^+$=409.

EXAMPLE 55

(4-Fluoro-phenyl)-[7-(4-methanesulfonyl-phenyl)-7H-pyrrolo[2,3-d]pyrimidin-2-yl]-amine

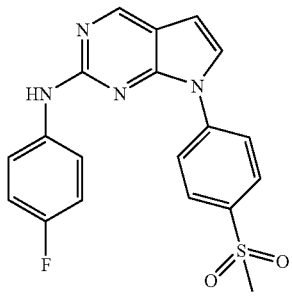 [SMILES: CS(=O)(=O)c1ccc(-n2ccc3cnc(Nc4ccc(F)cc4)nc32)cc1]

The compound is prepared analogous to Example 1.
HPLC: $t_R$=1.52 min (Method A); MS-ES: (M+H)$^+$=383.

EXAMPLE 56

{4-[2-(4-Fluoro-phenylamino)-pyrrolo[2,3-d]pyrimidin-7-yl]-phenyl}-(4-methyl-piperazin-1-yl)-methanone

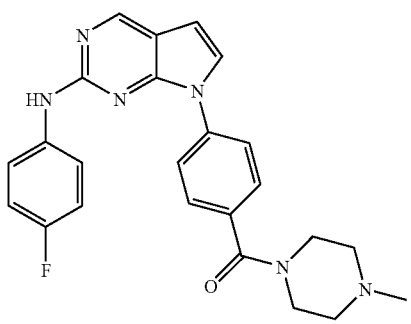 [SMILES: CN1CCN(C(=O)c2ccc(-n3ccc4cnc(Nc5ccc(F)cc5)nc43)cc2)CC1]

The compound is prepared analogous to Example 3.
HPLC: $t_R$=1.06 min (Method A); MS-ES: (M+H)$^+$=431.

EXAMPLE 57

{4-[2-(4-Fluoro-phenylamino)-pyrrolo[2,3-d]pyrimidin-7-yl]-phenyl}-pyrrolidin-1-yl-methanone

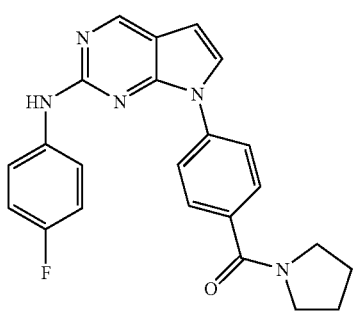 [SMILES: O=C(c1ccc(-n2ccc3cnc(Nc4ccc(F)cc4)nc32)cc1)N1CCCC1]

The compound is prepared analogous to Example 3.
HPLC: $t_R$=1.56 min (Method A); MS-ES: (M+H)$^+$=402.

EXAMPLE 58

{2-Fluoro-4-[2-(4-fluoro-phenylamino)-pyrrolo[2,3-d]pyrimidin-7-yl]-phenyl}-(4-methyl-piperazin-1-yl)-methanone

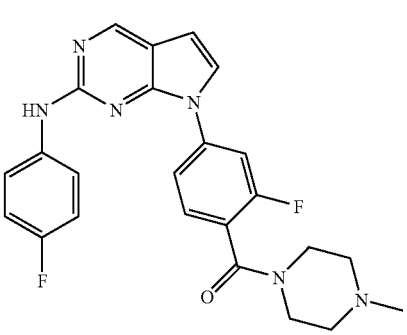 [SMILES: CN1CCN(C(=O)c2ccc(-n3ccc4cnc(Nc5ccc(F)cc5)nc43)cc2F)CC1]

The compound is prepared analogous to Example 3.
HPLC: $t_R$=1.11 min (Method A); MS-ES: (M+H)$^+$=449.

EXAMPLE 59

{2-Fluoro-4-[2-(4-fluoro-phenylamino)-pyrrolo[2,3-d]pyrimidin-7-yl]-phenyl}-morpholin-4-yl-methanone

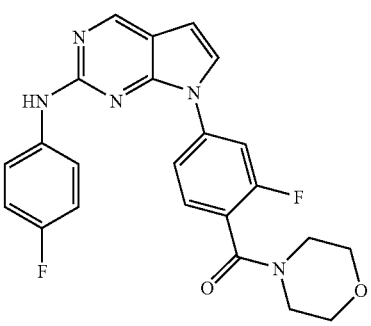 [SMILES: O=C(c1ccc(-n2ccc3cnc(Nc4ccc(F)cc4)nc32)cc1F)N1CCOCC1]

The compound is prepared analogous to Example 3.
HPLC: $t_R$=1.54 min (Method A); MS-ES: (M+H)$^+$=436.

EXAMPLE 60

1-{4-[2-(4-Fluoro-phenylamino)-pyrrolo[2,3-d]pyrimidin-7-yl]-phenyl}-ethanone

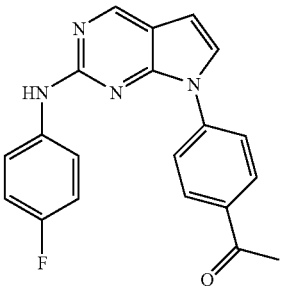 [SMILES: CC(=O)c1ccc(-n2ccc3cnc(Nc4ccc(F)cc4)nc32)cc1]

The compound is prepared analogous to Example 3.
HPLC: $t_R$=1.71 min (Method A); MS-ES: (M+H)$^+$=347.

EXAMPLE 61

{4-[2-(4-Fluoro-phenylamino)-pyrrolo[2,3-d]pyrimidin-7-yl]-phenyl}-morpholin-4-yl-methanone

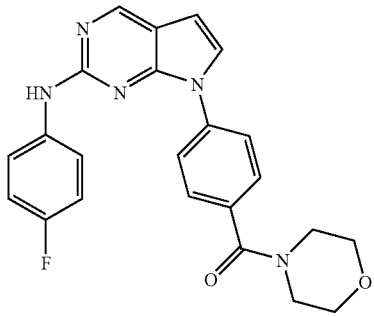 [SMILES: O=C(c1ccc(-n2ccc3cnc(Nc4ccc(F)cc4)nc32)cc1)N1CCOCC1]

The compound is prepared analogous to Example 3.
HPLC: $t_R$=1.42 min (Method A); MS-ES: (M+H)$^+$=418.

EXAMPLE 62

4-[2-(4-Fluoro-phenylamino)-pyrrolo[2,3-d]pyrimidin-7-yl]-N-(2-morpholin-4-yl-ethyl)-benzamide

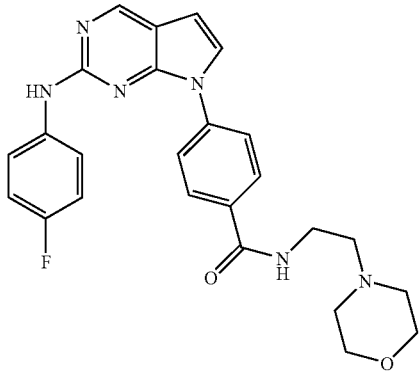 [SMILES: O=C(NCCN1CCOCC1)c1ccc(-n2ccc3cnc(Nc4ccc(F)cc4)nc32)cc1]

The compound is prepared analogous to Example 3.
HPLC: $t_R$=1.13 min (Method A); MS-ES: (M+H)$^+$=461.

EXAMPLE 63

N-(1-Ethyl-pyrrolidin-2-ylmethyl)-4-[2-(4-fluoro-phenylamino)-pyrrolo[2,3-d]pyrimidin-7-yl]-benzamide

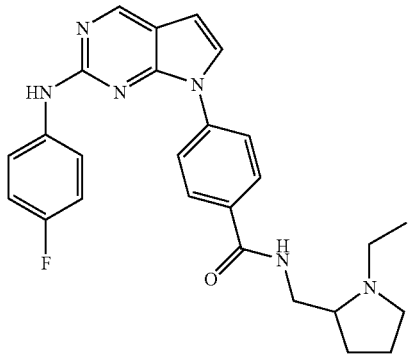 [SMILES: CCN1CCCC1CNC(=O)c1ccc(-n2ccc3cnc(Nc4ccc(F)cc4)nc32)cc1]

The compound is prepared analogous to Example 3.
HPLC: $t_R$=1.23 min (Method A); MS-ES: (M+H)$^+$=459.

EXAMPLE 64

[4-(1,1-Dioxido-thiomorpholin-4-ylmethyl)-phenyl]-[7-(4-methanesulfonyl-phenyl)-7H-pyrrolo[2,3-d]pyrimidin-2-yl]-amine

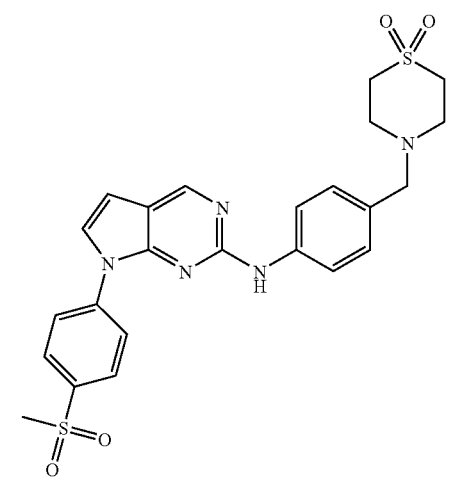 [SMILES: CS(=O)(=O)c1ccc(-n2ccc3cnc(Nc4ccc(CN5CCS(=O)(=O)CC5)cc4)nc32)cc1]

The compound is prepared analogous to Example 2.
HPLC: $t_R$=1.11 min (Method A); MS-ES: (M+H)$^+$=512.

EXAMPLE 65

N-(2-Dimethylamino-ethyl)-4-[7-(4-methanesulfonyl-phenyl)-7H-pyrrolo[2,3-d]pyrimidin-2-ylamino]-N-methyl-benzamide

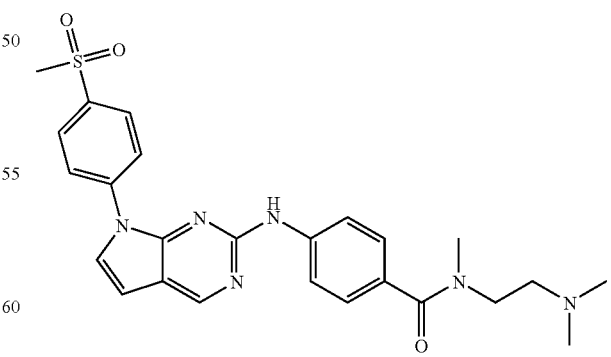

The compound is prepared analogous to Example 2.
HPLC: $t_R$=1.04 min (Method A); MS-ES: (M+H)$^+$=493.

EXAMPLE 66

(4-Dimethylamino-piperidin-1-yl)-{4-[7-(4-methanesulfonyl-phenyl)-7H-pyrrolo[2,3-d]pyrimidin-2-ylamino]-phenyl}-methanone

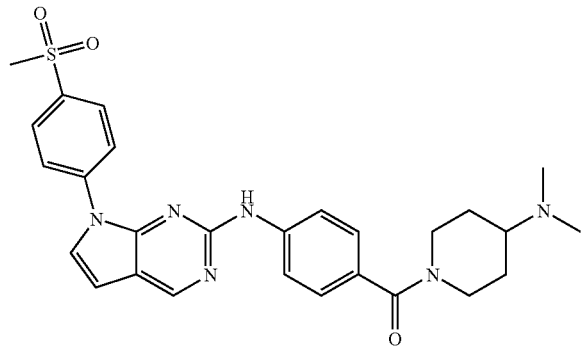

The compound is prepared analogous to Example 2.
HPLC: $t_R$=1.02 min (Method A); MS-ES: $(M+H)^+$=519.

EXAMPLE 67

4-[7-(4-Methanesulfonyl-phenyl)-7H-pyrrolo[2,3-d]pyrimidin-2-ylamino]-N-(2-morpholin-4-yl-ethyl)-benzamide

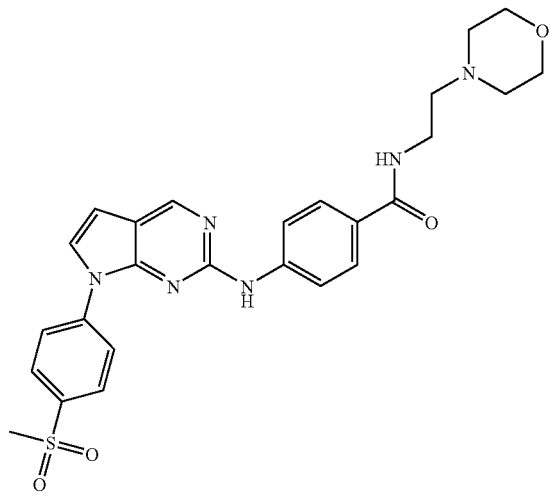 [SMILES: CS(=O)(=O)c1ccc(-n2ccc3cnc(Nc4ccc(C(=O)NCCN5CCOCC5)cc4)nc32)cc1]

The compound is prepared analogous to Example 2.
HPLC: $t_R$=1.10 min (Method A); MS-ES: $(M+H)^+$=521.

EXAMPLE 68

N-(1-Ethyl-pyrrolidin-2-ylmethyl)-4-[7-(4-methanesulfonyl-phenyl)-7H-pyrrolo[2,3-d]pyrimidin-2-ylamino]-benzamide

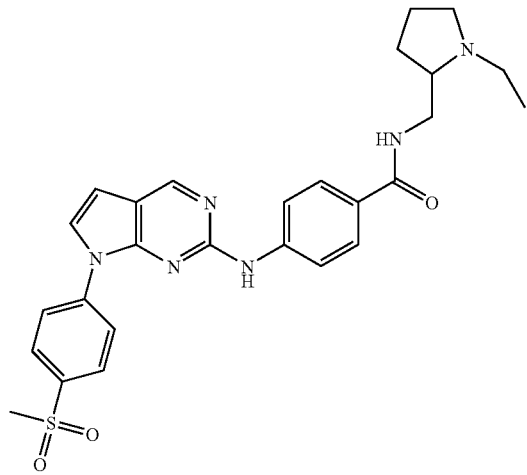 [SMILES: CCN1CCCC1CNC(=O)c1ccc(Nc2ncc3ccn(-c4ccc(S(C)(=O)=O)cc4)c3n2)cc1]

The compound is prepared analogous to Example 2.
HPLC: $t_R$=1.18 min (Method A); MS-ES: $(M+H)^+$=519.

EXAMPLE 69

4-{4-[7-(4-Methanesulfonyl-phenyl)-7H-pyrrolo[2,3-d]pyrimidin-2-ylamino]-benzoyl}-piperazine-1-carboxylic acid tert-butyl ester

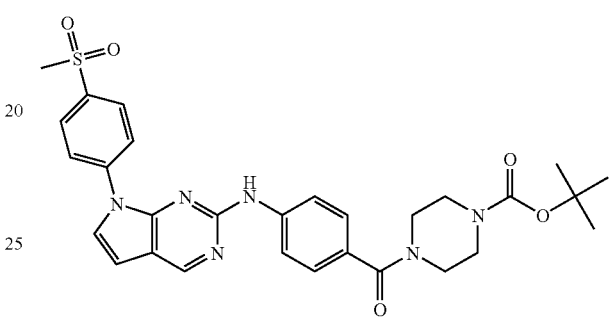

The compound is prepared analogous to Example 2.
HPLC: $t_R$=1.80 min (Method A); MS-ES: $(M+H)^+$=577.

EXAMPLE 70

2-{3-[7-(4-Methanesulfonyl-phenyl)-7H-pyrrolo[2,3-d]pyrimidin-2-ylamino]-phenyl}-1-(4-methyl-piperazin-1-yl)-ethanone The compound is prepared analogous to Example 2.
HPLC: $t_R$=1.03 min (Method A); MS-ES: $(M+H)^+$=505.

EXAMPLE 71

{2-Fluoro-4-[7-(4-methanesulfonyl-phenyl)-7H-pyrrolo[2,3-d]pyrimidin-2-ylamino]-phenyl}-(4-methyl-piperazin-1-yl)-methanone

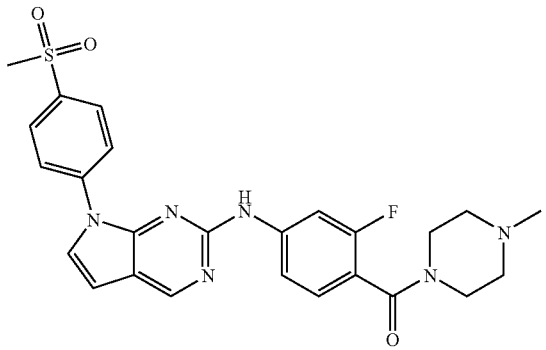

The compound is prepared analogous to Example 2. HPLC: $t_R$=1.13 min (Method A); MS-ES: (M+H)$^+$=509.

EXAMPLE 72

{4-[7-(4-Methanesulfonyl-phenyl)-7H-pyrrolo[2,3-d]pyrimidin-2-ylamino]-2-trifluoromethyl-phenyl}-(4-methyl-piperazin-1-yl)-methanone

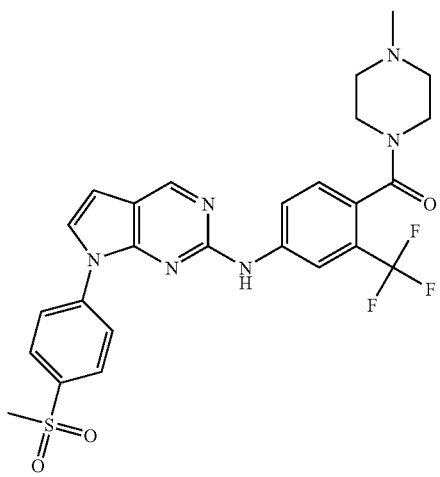 [SMILES: CN1CCN(C(=O)c2ccc(Nc3ncc4ccn(-c5ccc(S(C)(=O)=O)cc5)c4n3)cc2C(F)(F)F)CC1]

The compound is prepared analogous to Example 2. HPLC: $t_R$=1.23 min (Method A); MS-ES: (M+H)$^+$=559.

EXAMPLE 73

{4-[7-(4-Methanesulfonyl-phenyl)-7H-pyrrolo[2,3-d]pyrimidin-2-ylamino]-2-methyl-phenyl}-(4-methyl-piperazin-1-yl)-methanone

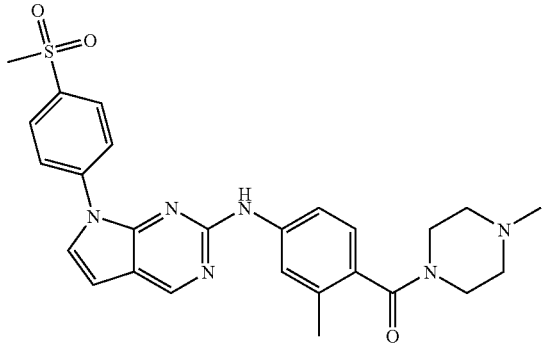

The compound is prepared analogous to Example 2. HPLC: $t_R$=1.02 min (Method A); MS-ES: (M+H)$^+$=505.

EXAMPLE 74

{4-[7-(4-Methanesulfonyl-phenyl)-7H-pyrrolo[2,3-d]pyrimidin-2-ylamino]-2-methyl-phenyl}-morpholin-4-yl-methanone

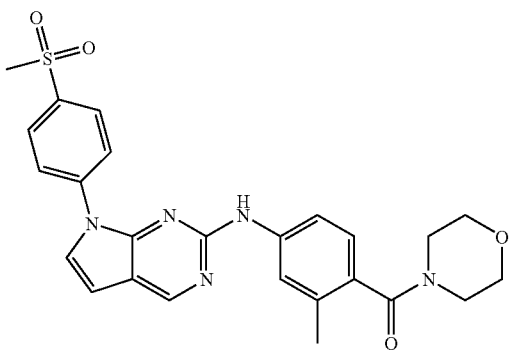 [SMILES: Cc1cc(Nc2ncc3ccn(-c4ccc(S(C)(=O)=O)cc4)c3n2)ccc1C(=O)N1CCOCC1]

The compound is prepared analogous to Example 2. HPLC: $t_R$=1.31 min (Method A); MS-ES: (M+H)$^+$=492.

EXAMPLE 75

{4-[7-(4-Methanesulfonyl-phenyl)-7H-pyrrolo[2,3-d]pyrimidin-2-ylamino]-2-methyl-phenyl}-pyrrolidin-1-yl-methanone

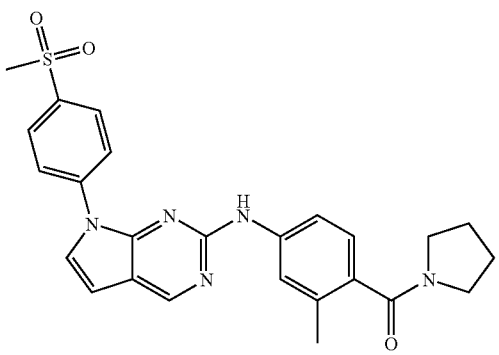 [SMILES: Cc1cc(Nc2ncc3ccn(-c4ccc(S(C)(=O)=O)cc4)c3n2)ccc1C(=O)N1CCCC1]

The compound is prepared analogous to Example 2. HPLC: $t_R$=1.42 min (Method A); MS-ES: (M+H)$^+$=476.

EXAMPLE 76

{2-Fluoro-5-[7-(4-methanesulfonyl-phenyl)-7H-pyrrolo[2,3-d]pyrimidin-2-ylamino]-phenyl}-(4-methyl-piperazin-1-yl)-methanone

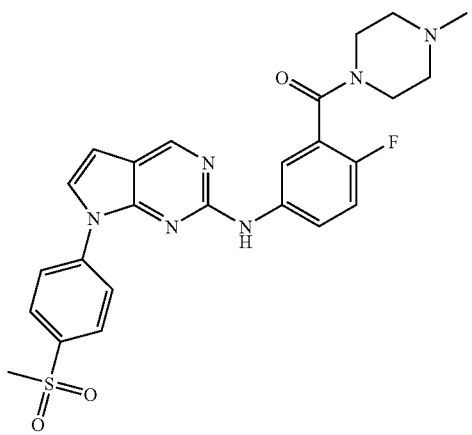

The compound is prepared analogous to Example 2. HPLC: $t_R$=1.06 min (Method A); MS-ES: (M+H)$^+$=509.

EXAMPLE 77

{2-Fluoro-5-[7-(4-methanesulfonyl-phenyl)-7H-pyrrolo[2,3-d]pyrimidin-2-ylamino]-phenyl}-morpholin-4-yl-methanone

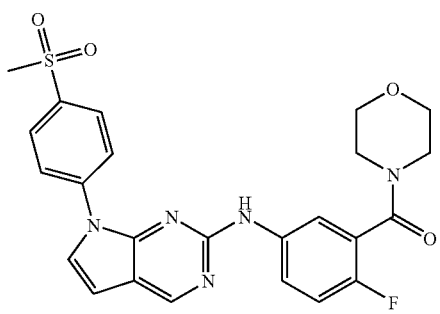 [SMILES: CS(=O)(=O)c1ccc(-n2ccc3cnc(Nc4ccc(F)c(C(=O)N5CCOCC5)c4)nc32)cc1]

The compound is prepared analogous to Example 2. HPLC: $t_R$=1.38 min (Method A); MS-ES: (M+H)$^+$=496.

EXAMPLE 78

N-(1-Ethyl-pyrrolidin-2-ylmethyl)-2-fluoro-5-[7-(4-methanesulfonyl-phenyl)-7H-pyrrolo[2,3-d]pyrimidin-2-ylamino]-benzamide

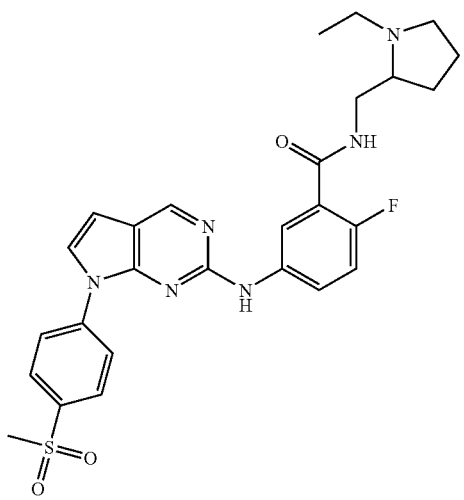 [SMILES: CCN1CCCC1CNC(=O)c1cc(Nc2ncc3ccn(-c4ccc(S(C)(=O)=O)cc4)c3n2)ccc1F]

The compound is prepared analogous to Example 2. HPLC: $t_R$=1.14 min (Method A); MS-ES: (M+H)$^+$=537.

EXAMPLE 79

1-{4-[7-(4-Methanesulfonyl-phenyl)-7H-pyrrolo[2,3-d]pyrimidin-2-ylamino]-phenyl}-ethanone

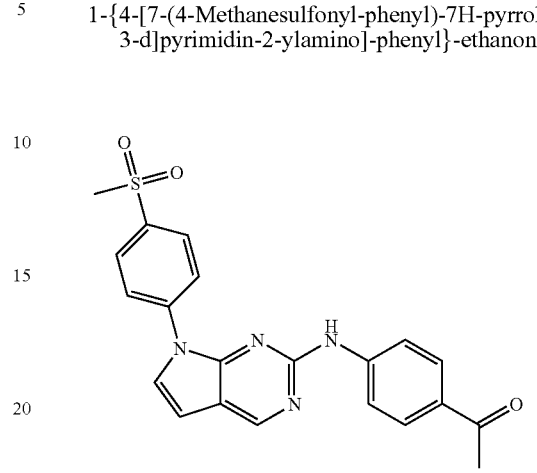

The compound is prepared analogous to Example 2. HPLC: $t_R$=1.61 min (Method A); MS-ES: (M+H)$^+$=407.

EXAMPLE 80

(4-Fluoro-3-trifluoromethyl-phenyl)-[7-(4-methanesulfonyl-phenyl)-7H-pyrrolo[2,3-d]pyrimidin-2-yl]-amine

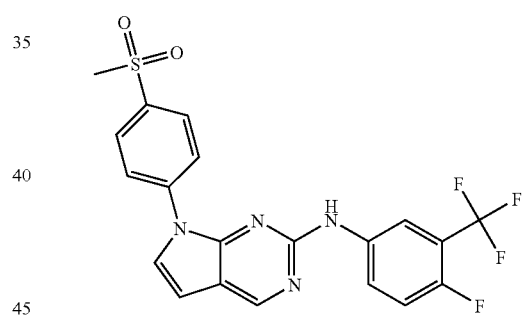

The compound is prepared analogous to Example 2. HPLC: $t_R$=2.01 min (Method A); MS-ES: (M+H)$^+$=451.

EXAMPLE 81

(4-Fluoro-3-methyl-phenyl)-[7-(4-methanesulfonyl-phenyl)-7H-pyrrolo[2,3-d]pyrimidin-2-yl]-amine

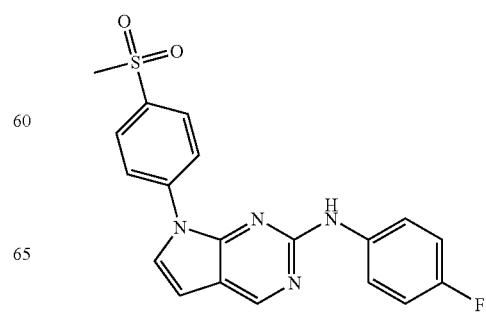

The compound is prepared analogous to Example 2.
HPLC: $t_R$=1.67 min (Method A); MS-ES: (M+H)$^+$=397.

EXAMPLE 82

{2,6-Difluoro-4-[2-(4-isopropoxy-phenylamino)-pyrrolo[2,3-d]pyrimidin-7-yl]-phenyl}-morpholin-4-yl-methanone

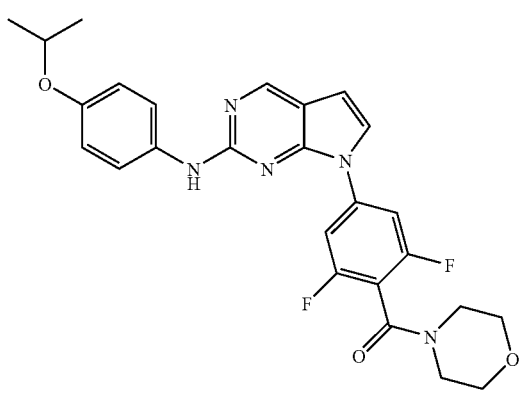 [SMILES: CC(C)Oc1ccc(Nc2ncc3ccn(-c4cc(F)c(C(=O)N5CCOCC5)c(F)c4)c3n2)cc1]

The compound is prepared analogous to Example 3.
HPLC: $t_R$=1.76 min (Method A); MS-ES: (M+H)$^+$=494.

EXAMPLE 83

2-{4-[2-(4-Isopropoxy-phenylamino)-pyrrolo[2,3-d]pyrimidin-7-yl]-phenyl}-2-methyl-1-morpholin-4-yl-propan-1-one

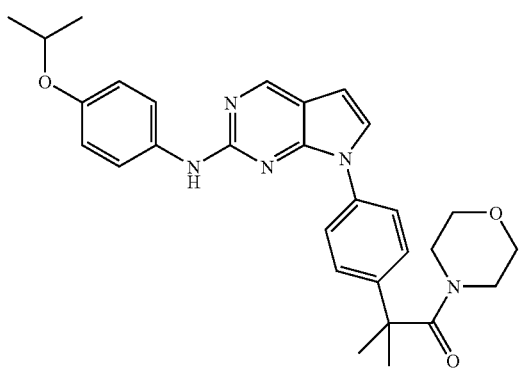 [SMILES: CC(C)Oc1ccc(Nc2ncc3ccn(-c4ccc(C(C)(C)C(=O)N5CCOCC5)cc4)c3n2)cc1]

The compound is prepared analogous to Example 3.
HPLC: $t_R$=1.79 min (Method A); MS-ES: (M+H)$^+$=500.

EXAMPLE 84

(1-{4-[2-(4-Isopropoxy-phenylamino)-pyrrolo[2,3-d]pyrimidin-7-yl]-phenyl}-cyclopropyl)-morpholin-4-yl-methanone

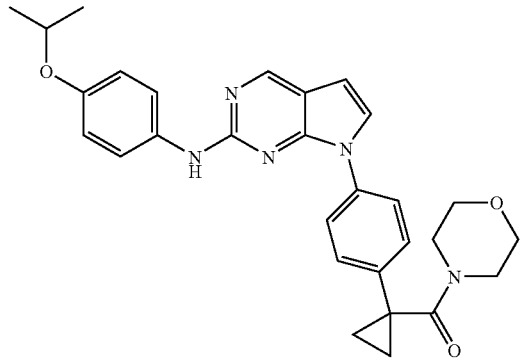 [SMILES: CC(C)Oc1ccc(Nc2ncc3ccn(-c4ccc(C5(C(=O)N6CCOCC6)CC5)cc4)c3n2)cc1]

The compound is prepared analogous to Example 3.
HPLC: $t_R$=1.69 min (Method A); MS-ES: (M+H)$^+$=498.

EXAMPLE 85

{2-Fluoro-4-[2-(4-isopropoxy-phenylamino)-pyrrolo[2,3-d]pyrimidin-7-yl]-phenyl}-(4-methyl-piperazin-1-yl)-methanone

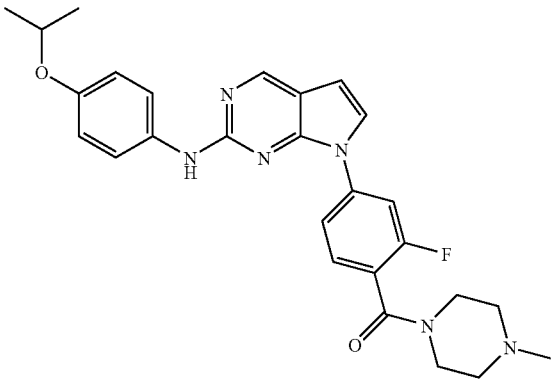 [SMILES: CC(C)Oc1ccc(Nc2ncc3ccn(-c4ccc(C(=O)N5CCN(C)CC5)c(F)c4)c3n2)cc1]

The compound is prepared analogous to Example 3.
HPLC: $t_R$=1.23 min (Method A); MS-ES: (M+H)$^+$=489.

EXAMPLE 86

11-{4-[2-(4-Isopropoxy-phenylamino)-pyrrolo[2,3-d]pyrimidin-7-yl]-phenyl}-ethanone

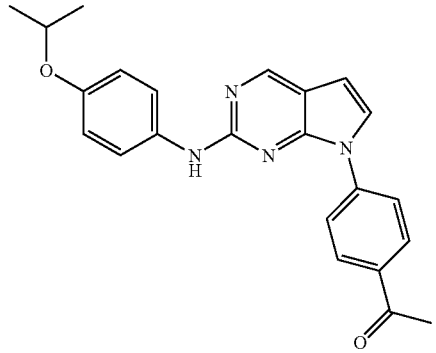 [SMILES: CC(=O)c1ccc(-n2ccc3cnc(Nc4ccc(OC(C)C)cc4)nc32)cc1]

The compound is prepared analogous to Example 3.
HPLC: $t_R$=1.83 min (Method A); MS-ES: (M+H)$^+$=387.

EXAMPLE 87

{4-[7-(4-Methanesulfonyl-phenyl)-7H-pyrrolo[2,3-d]pyrimidin-2-ylamino]-phenyl}-piperazin-1-yl-methanone

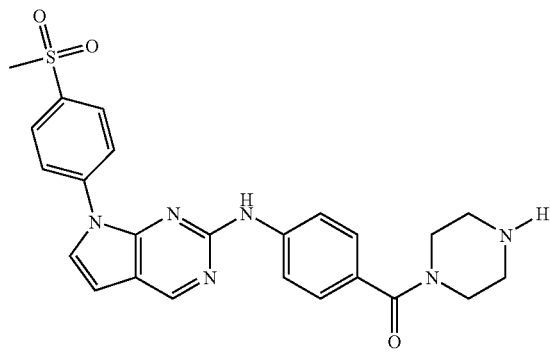 [SMILES: CS(=O)(=O)c1ccc(-n2ccc3cnc(Nc4ccc(C(=O)N5CCNCC5)cc4)nc32)cc1]

The compound is prepared by treatment of Example 69 with TFA in $CH_2Cl_2$ at rt. MS-ES: $(M+H)^+=477$.

EXAMPLE 88

{2-Fluoro-4-[2-(4-fluoro-3-methyl-phenylamino)-pyrrolo[2,3-d]pyrimidin-7-yl]-phenyl}-(4-methyl-piperazin-1-yl)-methanone

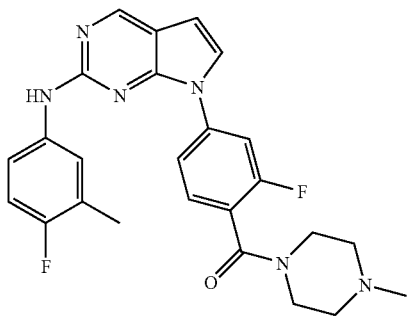 [SMILES: Cc1cc(Nc2ncc3ccn(-c4ccc(C(=O)N5CCN(C)CC5)c(F)c4)c3n2)ccc1F]

The compound is prepared analogous to Example 3. HPLC: $t_R=1.24$ min (Method A); MS-ES: $(M+H)^+=463$.

EXAMPLE 89

{2,6-Difluoro-4-[2-(4-fluoro-3-methyl-phenylamino)-pyrrolo[2,3-d]pyrimidin-7-yl]-phenyl}-morpholin-4-yl-methanone

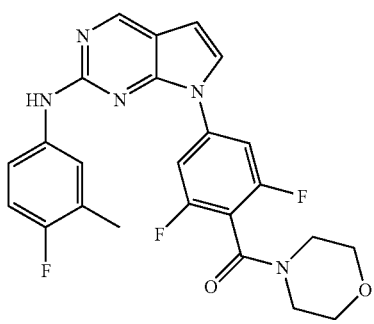 [SMILES: Cc1cc(Nc2ncc3ccn(-c4cc(F)c(C(=O)N5CCOCC5)c(F)c4)c3n2)ccc1F]

The compound is prepared analogous to Example 3. HPLC: $t_R=1.78$ min (Method A); MS-ES: $(M+H)^+=468$.

EXAMPLE 90

{2-Chloro-4-[2-(4-fluoro-3-methyl-phenylamino)-pyrrolo[2,3-d]pyrimidin-7-yl]-phenyl}-morpholin-4-yl-methanone

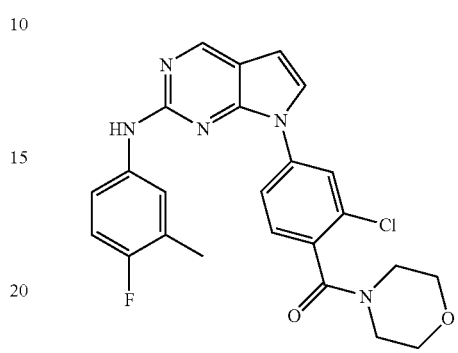

The compound is prepared analogous to Example 3. MS-ES: $(M+H)^+=466$.

EXAMPLE 91

{4-[2-(4-Fluoro-3-methyl-phenylamino)-pyrrolo[2,3-d]pyrimidin-7-yl]-2-methyl-phenyl}-morpholin-4-yl-methanone

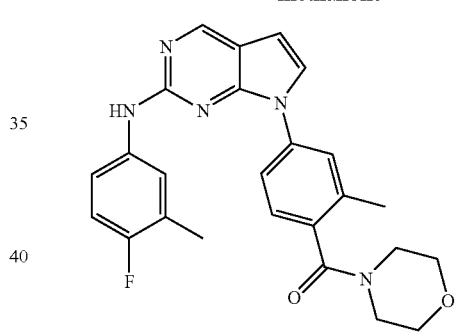

The compound is prepared analogous to Example 3. MS-ES: $(M+H)^+=446$.

EXAMPLE 92

{2-Fluoro-4-[2-(4-fluoro-3-methyl-phenylamino)-pyrrolo[2,3-d]pyrimidin-7-yl]-phenyl}-morpholin-4-yl-methanone

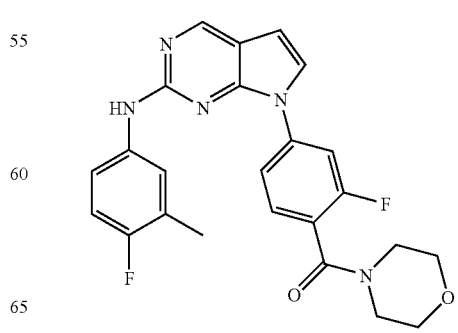

The compound is prepared analogous to Example 3. MS-ES: (M+H)⁺=450.

EXAMPLE 93

7-(4-Methanesulfonyl-phenyl)-7H-pyrrolo[2,3-d]pyrimidin-2-yl]-[3-(4-methyl-piperazin-1-ylmethyl)-phenyl]-amine

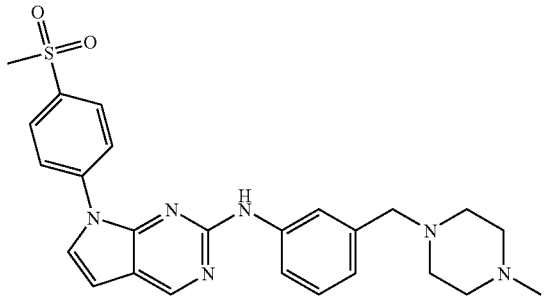

The compound is prepared analogous to Example 3. HPLC: t_R=1.02 min (Method A); MS-ES: (M+H)⁺=477.

EXAMPLE 94

{2-Chloro-4-[7-(4-methanesulfonyl-phenyl)-7H-pyrrolo[2,3-d]pyrimidin-2-ylamino]-phenyl}-(4-methyl-piperazin-1-yl)-methanone

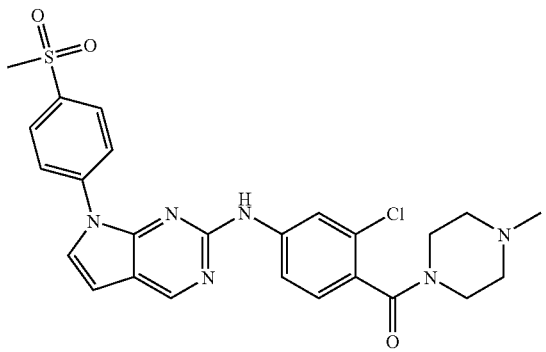

The compound is prepared analogous to Example 3. HPLC: t_R=1.15 min (Method A); MS-ES: (M+H)⁺=525.

EXAMPLE 95

4-[7-(4-Methanesulfonyl-phenyl)-7H-pyrrolo[2,3-d]pyrimidin-2-ylamino]-benzonitrile

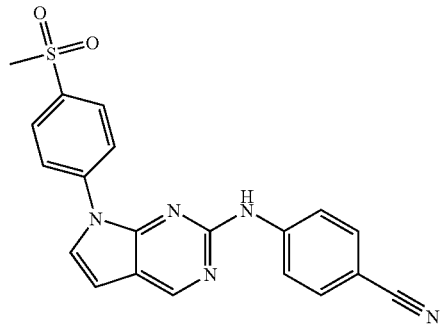 [SMILES: CS(=O)(=O)c1ccc(-n2ccc3cnc(Nc4ccc(C#N)cc4)nc32)cc1]

The compound is prepared analogous to Example 3. HPLC: t_R=1.77 min (Method A); MS-ES: (M+H)⁺=390.

EXAMPLE 96

4-[2-(4-Isopropoxy-phenylamino)-pyrrolo[2,3-d]pyrimidin-7-yl]-benzonitrile

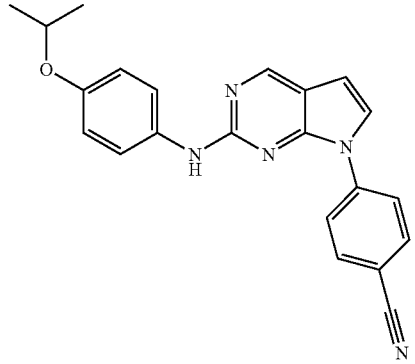 [SMILES: CC(C)Oc1ccc(Nc2ncc3ccn(-c4ccc(C#N)cc4)c3n2)cc1]

The compound is prepared analogous to Example 3. HPLC: t_R=1.90 min (Method A); MS-ES: (M+H)⁺=370.

EXAMPLE 97

[7-(3-Fluoro-4-morpholin-4-ylmethyl-phenyl)-7H-pyrrolo[2,3-d]pyrimidin-2-yl]-(4-isopropoxy-phenyl)-amine

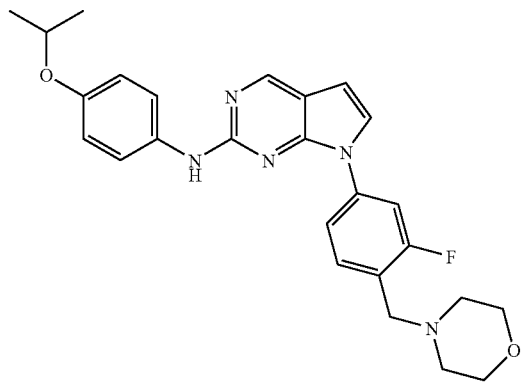

The compound is prepared analogous to Example 3. HPLC: t_R=1.27 min (Method A); MS-ES: (M+H)⁺=462.

EXAMPLE 98

{2-Fluoro-4-[2-(4-isopropoxy-phenylamino)-pyrrolo[2,3-d]pyrimidin-7-yl]-phenyl}-morpholin-4-yl-methanone

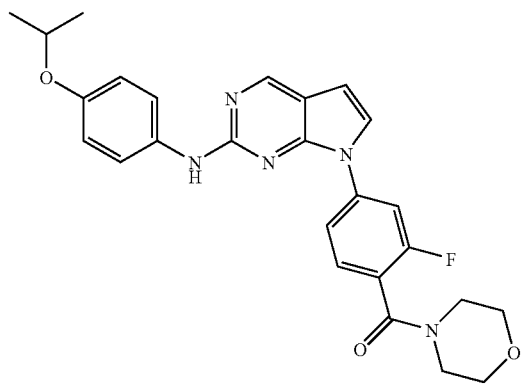 [SMILES: CC(C)Oc1ccc(Nc2ncc3ccn(-c4ccc(C(=O)N5CCOCC5)c(F)c4)c3n2)cc1]

The compound is prepared analogous to Example 3.
HPLC: $t_R$=1.64 min (Method A); MS-ES: (M+H)$^+$=476.

EXAMPLE 99

{2-Chloro-4-[2-(4-isopropoxy-phenylamino)-pyrrolo[2,3-d]pyrimidin-7-yl]-phenyl}-morpholin-4-yl-methanone

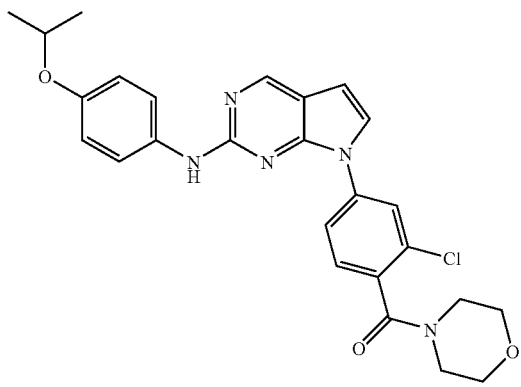

The compound is prepared analogous to Example 3.
HPLC: $t_R$=1.69 min (Method A); MS-ES: (M+H)$^+$=492.

EXAMPLE 100

{4-[2-(4-Isopropoxy-phenylamino)-pyrrolo[2,3-d]pyrimidin-7-yl]-2-methyl-phenyl}-morpholin-4-yl-methanone

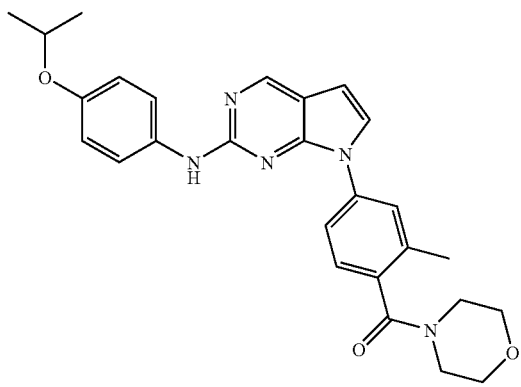

The compound is prepared analogous to Example 3.
HPLC: $t_R$=1.61 min (Method A); MS-ES: (M+H)$^+$=472.

EXAMPLE 101

2-{4-[2-(4-Isopropoxy-phenylamino)-pyrrolo[2,3-d]pyrimidin-7-yl]-phenyl}-1-(4-methyl-piperazin-1-yl)-ethanone

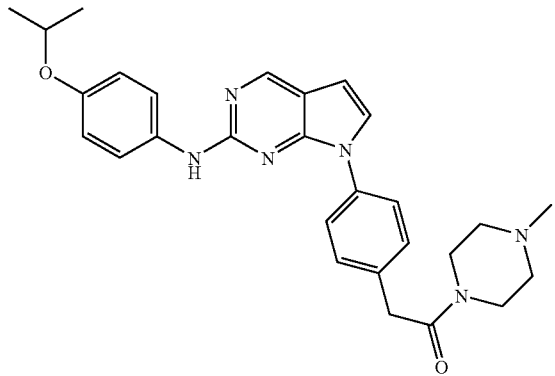 [SMILES: CC(C)Oc1ccc(Nc2ncc3ccn(-c4ccc(CC(=O)N5CCN(C)CC5)cc4)c3n2)cc1]

The compound is prepared analogous to Example 3.
HPLC: $t_R$=1.27 min (Method A); MS-ES: (M+H)$^+$=485.

EXAMPLE 102

2-{4-[2-(4-Isopropoxy-phenylamino)-pyrrolo[2,3-d]pyrimidin-7-yl]-phenyl}-1-morpholin-4-yl-ethanone

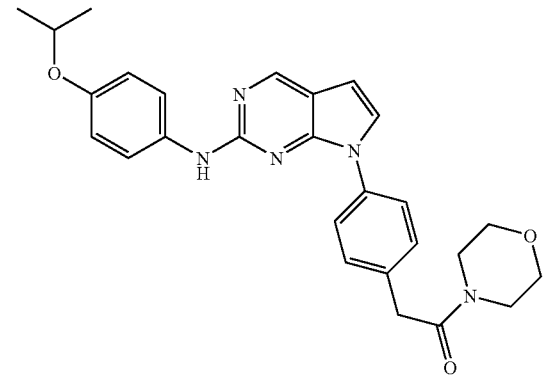 [SMILES: CC(C)Oc1ccc(Nc2ncc3ccn(-c4ccc(CC(=O)N5CCOCC5)cc4)c3n2)cc1]

The compound is prepared analogous to Example 3.
HPLC: $t_R$=1.60 min (Method A); MS-ES: (M+H)$^+$=472.

EXAMPLE 103

(1-{4-[2-(4-Isopropoxy-phenylamino)-pyrrolo[2,3-d]pyrimidin-7-yl]-phenyl}-cyclopropyl)-(4-methyl-piperazin-1-yl)-methanone

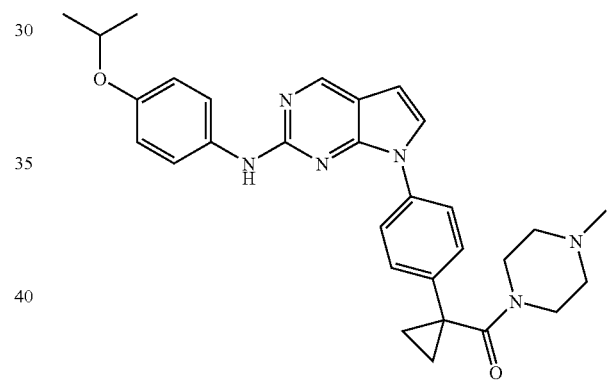

The compound is prepared analogous to Example 3.
HPLC: $t_R$=1.36 min (Method A); MS-ES: (M+H)$^+$=511.

EXAMPLE 104

1-{4-[2-(4-Isopropoxy-phenylamino)-pyrrolo[2,3-d]pyrimidin-7-yl]-phenyl}-piperazin-2-one

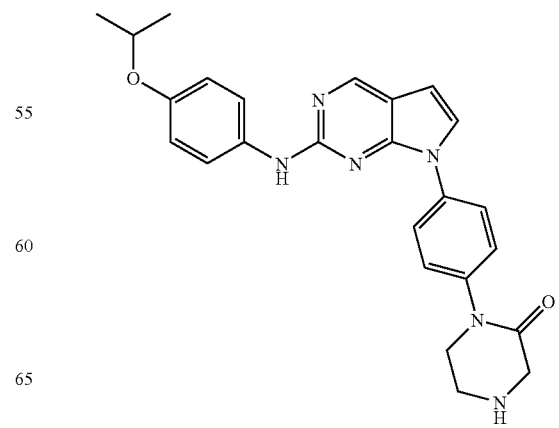

EXAMPLE 105
1-{4-[2-(4-Isopropoxy-phenylamino)-pyrrolo[2,3-d]pyrimidin-7-yl]-phenyl}-pyrrolidin-2-one

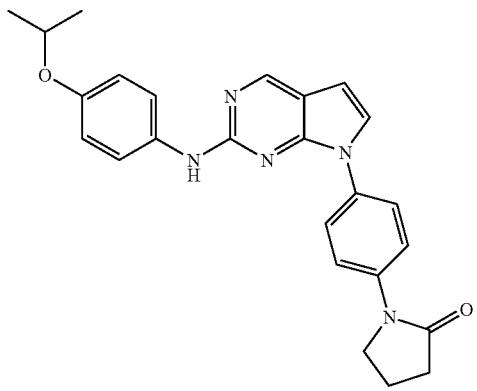 [SMILES: CC(C)Oc1ccc(Nc2ncc3ccn(-c4ccc(N5CCCC5=O)cc4)c3n2)cc1]

The compound is prepared analogous to Example 3.
HPLC: $t_R$=1.72 min (Method A); MS-ES: (M+H)$^+$=428.

EXAMPLE 106
{7-[4-(4-Ethyl-piperazin-1-ylmethyl)-3-fluoro-phenyl]-7H-pyrrolo[2,3-d]pyrimidin-2-yl}-(4-isopropoxy-phenyl)-amine

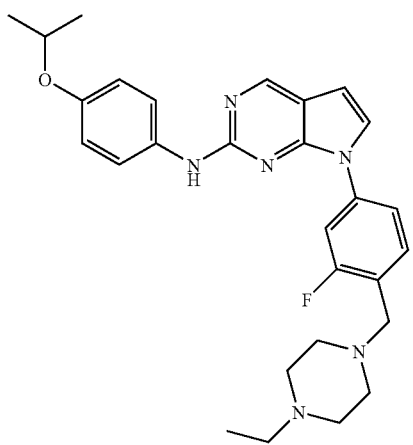 [SMILES: CCN1CCN(Cc2ccc(-n3ccc4cnc(Nc5ccc(OC(C)C)cc5)nc43)cc2F)CC1]

The compound is prepared analogous to Example 3.
HPLC: $t_R$=1.25 min (Method A); MS-ES: (M+H)$^+$=489.

EXAMPLE 107
(4-Isopropoxy-phenyl)-[7-(4-pyrrolidin-1-ylmethyl-phenyl)-7H-pyrrolo[2,3-d]pyrimidin-2-yl]-amine

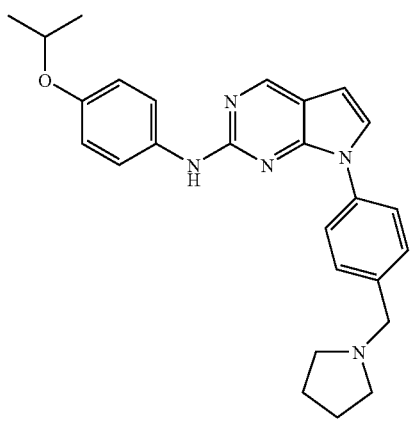 [SMILES: CC(C)Oc1ccc(Nc2ncc3ccn(-c4ccc(CN5CCCC5)cc4)c3n2)cc1]

The compound is prepared analogous to Example 3.
HPLC: $t_R$=1.27 min (Method A); MS-ES: (M+H)$^+$=428.

EXAMPLE 108
7-(4-[1,4]Diazepan-1-ylmethyl-3-fluoro-phenyl)-7H-pyrrolo[2,3-d]pyrimidin-2-yl]-(4-isopropoxy-phenyl)-amine

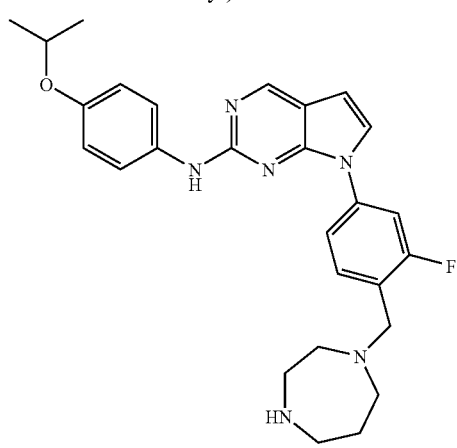

The compound is prepared analogous to Example 3.
HPLC: $t_R$=1.14 min (Method A); MS-ES: (M+H)$^+$=475.

EXAMPLE 109
(4-Isopropoxy-phenyl)-[7-(4-morpholin-4-ylmethyl-phenyl)-7H-pyrrolo[2,3-d]pyrimidin-2-yl]-amine

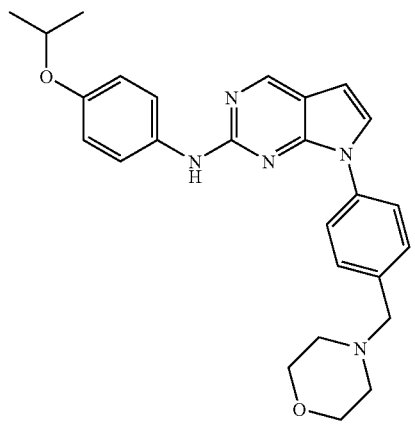 [SMILES: CC(C)Oc1ccc(Nc2ncc3ccn(-c4ccc(CN5CCOCC5)cc4)c3n2)cc1]

The compound is prepared analogous to Example 3.
HPLC: $t_R$=1.23 min (Method A); MS-ES: (M+H)$^+$=444.

EXAMPLE 110
[7-(3-Chloro-4-morpholin-4-yl methyl-phenyl)-7H-pyrrolo[2,3-d]pyrimidin-2-yl]-(4-isopropoxy-phenyl)-amine

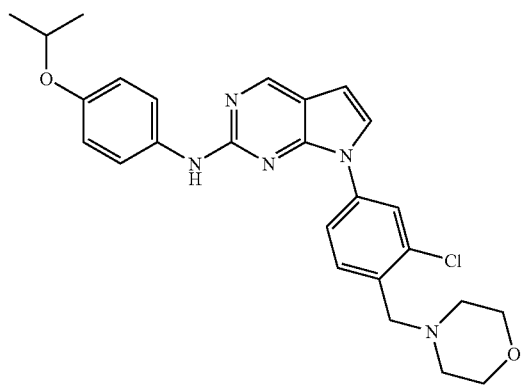 [SMILES: CC(C)Oc1ccc(Nc2ncc3ccn(-c4ccc(CN5CCOCC5)c(Cl)c4)c3n2)cc1]

The compound is prepared analogous to Example 3.
HPLC: $t_R$=1.33 min (Method A); MS-ES: (M+H)$^+$=478.

The compound is prepared analogous to Example 3.
HPLC: $t_R$=1.55 min (Method A); MS-ES: (M+H)$^+$=510.

EXAMPLE 111

(4-Isopropoxy-phenyl)-[7-(3-methyl-4-morpholin-4-ylmethyl-phenyl)-7H-pyrrolo[2,3-d]pyrimidin-2-yl]-amine

EXAMPLE 113

{7-[3-Chloro-4-(1,1-dioxido-thiomorpholin-4-ylmethyl)-phenyl]-7H-pyrrolo[2,3-d]pyrimidin-2-yl}-(4-isopropoxy-phenyl)-amine

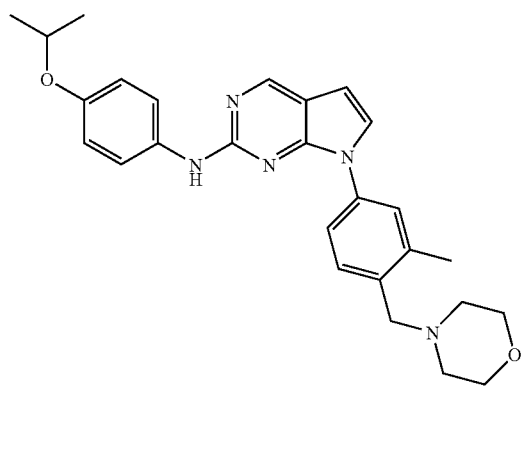 [SMILES: Cc1cc(-n2ccc3cnc(Nc4ccc(OC(C)C)cc4)nc32)ccc1CN1CCOCC1]

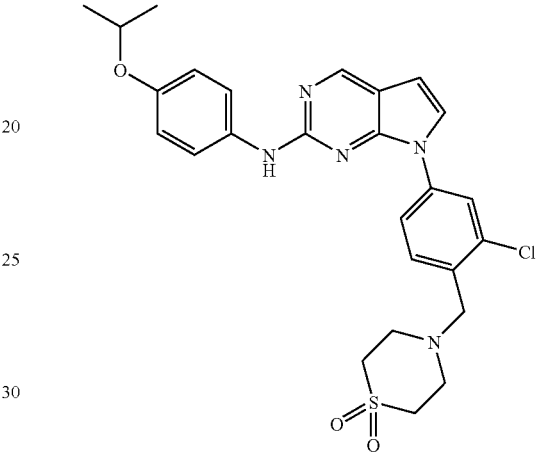

The compound is prepared analogous to Example 3.
HPLC: $t_R$=1.28 min (Method A); MS-ES: (M+H)$^+$=458.

EXAMPLE 112

{7-[4-(1,1-Dioxido-thiomorpholin-4-ylmethyl)-3-fluoro-phenyl]-7H-pyrrolo[2,3-d]pyrimidin-2-yl}-(4-isopropoxy-phenyl)-amine The compound is prepared analogous to Example 3.
HPLC: $t_R$=1.73 min (Method A); MS-ES: (M+H)$^+$=526.

EXAMPLE 114

1-{4-[2-(4-Isopropoxy-phenylamino)-pyrrolo[2,3-d]pyrimidin-7-yl]-phenyl}-ethanol

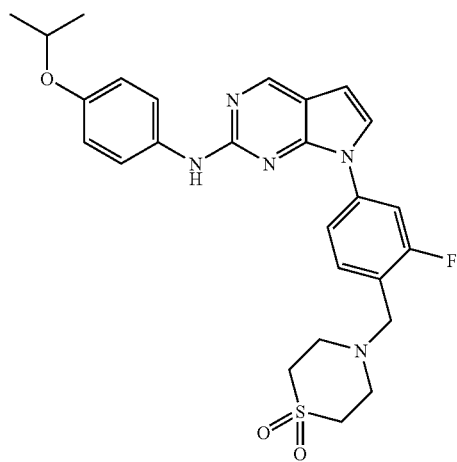 [SMILES: CC(C)Oc1ccc(Nc2ncc3ccn(-c4ccc(CN5CCS(=O)(=O)CC5)c(F)c4)c3n2)cc1]

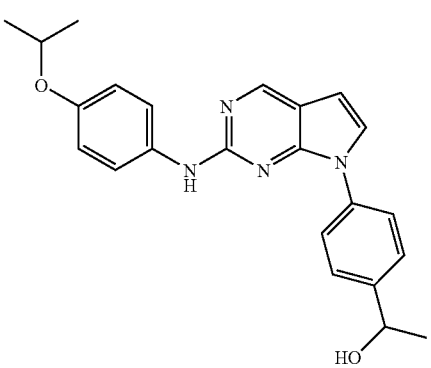 [SMILES: CC(C)Oc1ccc(Nc2ncc3ccn(-c4ccc(C(C)O)cc4)c3n2)cc1]

The compound is prepared analogous to Example 3. HPLC: $t_R$=1.63 min (Method A); MS-ES: (M+H)⁺=389.

EXAMPLE 115

(4-Isopropoxy-phenyl)-{7-[4-(2-morpholin-4-yl-ethyl)-phenyl]-7H-pyrrolo[2,3-d]pyrimidin-2-yl}-amine

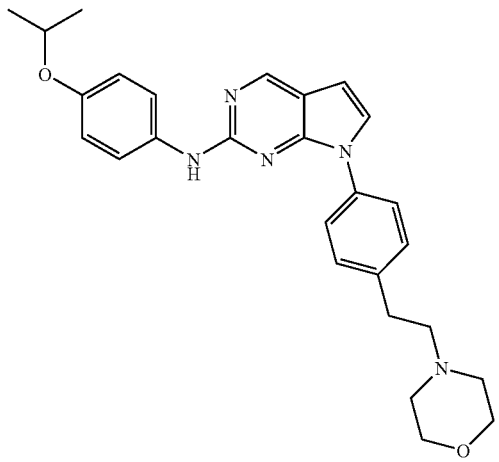 [SMILES: CC(C)Oc1ccc(Nc2ncc3ccn(-c4ccc(CCN5CCOCC5)cc4)c3n2)cc1]

The compound is prepared analogous to Example 3. HPLC: $t_R$=1.27 min (Method A); MS-ES: (M+H)⁺=458.

EXAMPLE 116

{4-[2-(3-Chloro-4-methyl-phenylamino)-pyrrolo[2,3-d]pyrimidin-7-yl]-2,6-difluoro-phenyl}-morpholin-4-yl-methanone

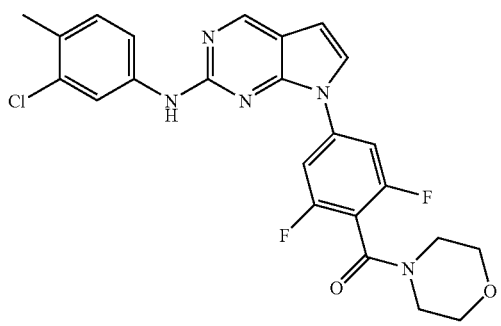 [SMILES: Cc1ccc(Nc2ncc3ccn(-c4cc(F)c(C(=O)N5CCOCC5)c(F)c4)c3n2)cc1Cl]

The compound is prepared analogous to Example 3. HPLC: $t_R$=2.03 min (Method A); MS-ES: (M+H)⁺=484.

EXAMPLE 117

(1-{4-[2-(3-Chloro-4-methyl-phenylamino)-pyrrolo[2,3-d]pyrimidin-7-yl]-phenyl}-cyclopropyl)-(4-methyl-piperazin-1-yl)-methanone

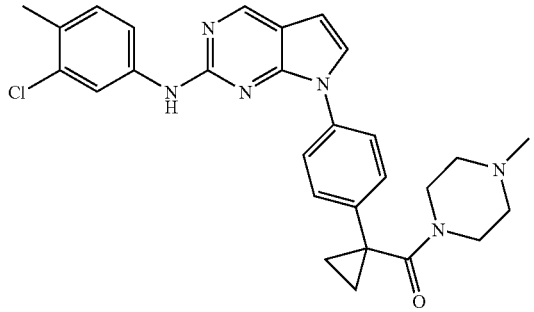

The compound is prepared analogous to Example 3. HPLC: $t_R$=1.47 min (Method A); MS-ES: (M+H)⁺=501.

EXAMPLE 118

(3-Chloro-4-methyl-phenyl)-[7-(3-fluoro-4-morpholin-4-ylmethyl-phenyl)-7H-pyrrolo[2,3-d]pyrimidin-2-yl]-amine

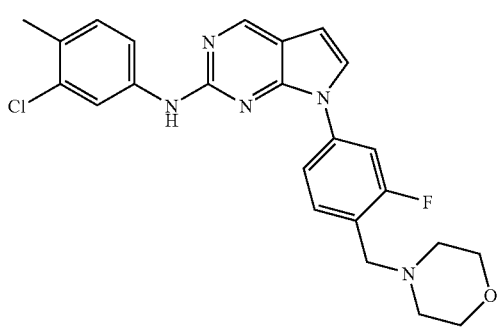 [SMILES: Cc1ccc(Nc2ncc3ccn(-c4ccc(CN5CCOCC5)c(F)c4)c3n2)cc1Cl]

The compound is prepared analogous to Example 3. MS-ES: (M+H)⁺=452.

EXAMPLE 119

(3-Chloro-4-methyl-phenyl)-[7-(4-morpholin-4-ylmethyl-phenyl)-7H-pyrrolo[2,3-d]pyrimidin-2-yl]-amine

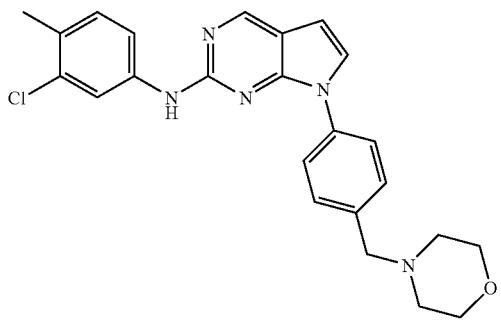 [SMILES: Cc1ccc(Nc2ncc3ccn(-c4ccc(CN5CCOCC5)cc4)c3n2)cc1Cl]

The compound is prepared analogous to Example 3. HPLC: $t_R$=1.33 min (Method A); MS-ES: (M+H)⁺=434.

EXAMPLE 120

(3-Chloro-4-methyl-phenyl)-{7-[4-(4-ethyl-piperazin-1-ylmethyl)-3-fluoro-phenyl]-7H-pyrrolo[2,3-d]pyrimidin-2-yl}-amine

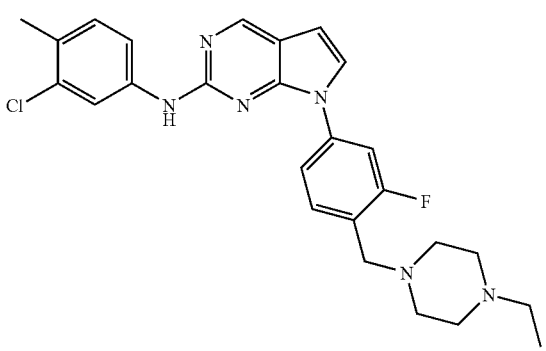 [SMILES: CCN1CCN(Cc2ccc(-n3ccc4cnc(Nc5ccc(C)c(Cl)c5)nc43)cc2F)CC1]

The compound is prepared analogous to Example 3.
HPLC: $t_R$=1.38 min (Method A); MS-ES: (M+H)$^+$=479.

EXAMPLE 121

(3-Chloro-4-methyl-phenyl)-{7-[4-(1,1-dioxido-thiomorpholin-4-ylmethyl)-3-fluoro-phenyl]-7H-pyrrolo[2,3-d]pyrimidin-2-yl}-amine

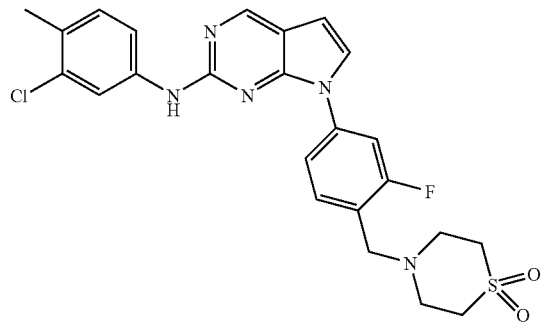 [SMILES: Cc1ccc(Nc2ncc3ccn(-c4ccc(CN5CCS(=O)(=O)CC5)c(F)c4)c3n2)cc1Cl]

The compound is prepared analogous to Example 3.
HPLC: $t_R$=1.73 min (Method A); MS-ES: (M+H)$^+$=500.

EXAMPLE 122

(1-{4-[2-(4-Fluoro-3-methyl-phenylamino)-pyrrolo[2,3-d]pyrimidin-7-yl]-phenyl}-cyclopropyl)-(4-methyl-piperazin-1-yl)-methanone

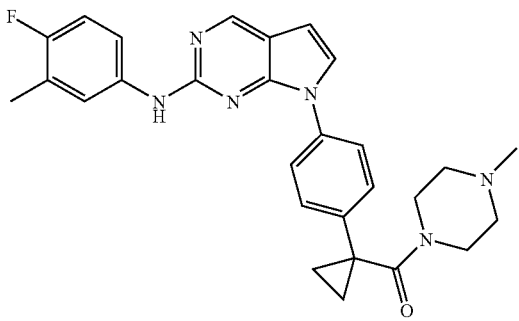 [SMILES: Cc1cc(Nc2ncc3ccn(-c4ccc(C5(C(=O)N6CCN(C)CC6)CC5)cc4)c3n2)ccc1F]

The compound is prepared analogous to Example 3.
HPLC: $t_R$=1.33 min (Method A); MS-ES: (M+H)$^+$=485.

EXAMPLE 123

(4-Fluoro-3-methyl-phenyl)-[7-(4-morpholin-4-ylmethyl-phenyl)-7H-pyrrolo[2,3-d]pyrimidin-2-yl]-amine

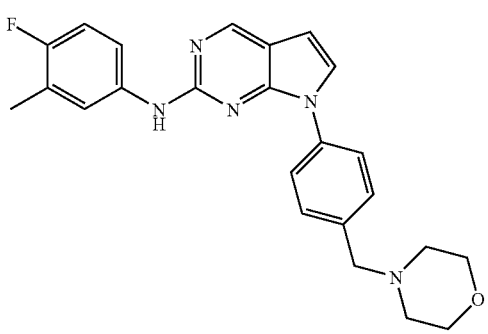 [SMILES: Cc1cc(Nc2ncc3ccn(-c4ccc(CN5CCOCC5)cc4)c3n2)ccc1F]

The compound is prepared analogous to Example 3.
HPLC: $t_R$=1.18 min (Method A); MS-ES: (M+H)$^+$=418.

EXAMPLE 124

{7-[4-(4-Ethyl-piperazin-1-ylmethyl)-3-fluoro-phenyl]-7H-pyrrolo[2,3-d]pyrimidin-2-yl}-(4-fluoro-3-methyl-phenyl)-amine

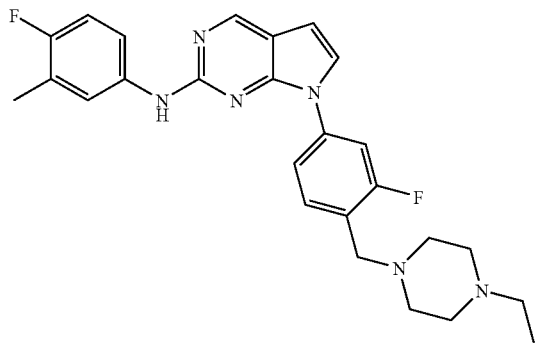 [SMILES: CCN1CCN(Cc2ccc(-n3ccc4cnc(Nc5ccc(F)c(C)c5)nc43)cc2F)CC1]

The compound is prepared analogous to Example 3.
HPLC: $t_R$=1.24 min (Method A); MS-ES: (M+H)$^+$=463.

EXAMPLE 125

{7-[4-(1,1-Dioxido-thiomorpholin-4-ylmethyl)-3-fluoro-phenyl]-7H-pyrrolo[2,3-d]pyrimidin-2-yl}-(4-fluoro-3-methyl-phenyl)-amine

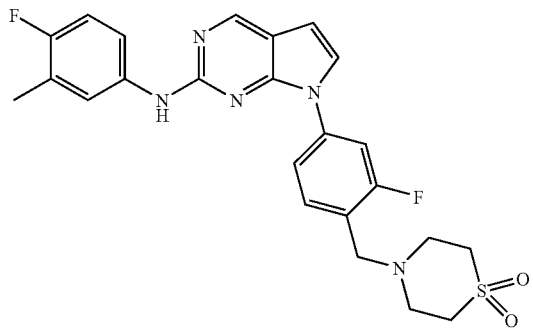 [SMILES: Cc1cc(Nc2ncc3ccn(-c4ccc(CN5CCS(=O)(=O)CC5)c(F)c4)c3n2)ccc1F]

The compound is prepared analogous to Example 3.
HPLC: $t_R$=1.53 min (Method A); MS-ES: (M+H)$^+$=484.

EXAMPLE 126

[7-(3,5-Difluoro-4-morpholin-4-ylmethyl-phenyl)-7H-pyrrolo[2,3-d]pyrimidin-2-yl]-(4-isopropoxy-phenyl)-amine

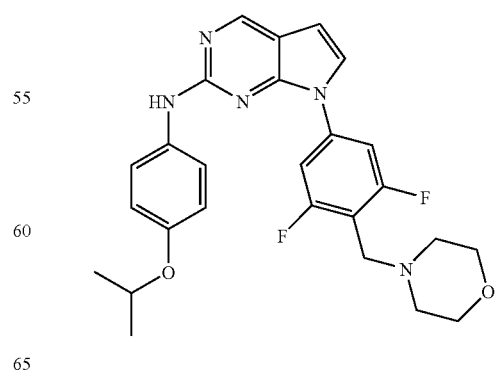

The compound is prepared analogous to Example 3.
HPLC: $t_R$=1.32 min (Method A); MS-ES: (M+H)$^+$=480.

EXAMPLE 127

(4-Fluoro-3-methyl-phenyl)-[7-(3-fluoro-4-morpholin-4-ylmethyl-phenyl)-7H-pyrrolo[2,3-d]pyrimidin-2-yl]-amine

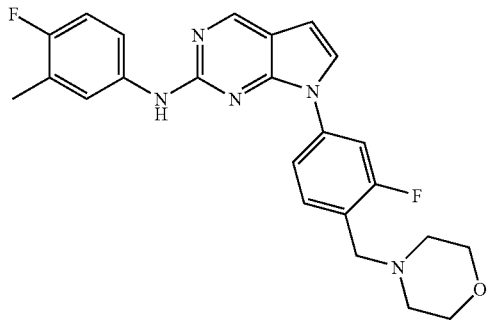 [SMILES: Cc1cc(Nc2ncc3ccn(-c4ccc(CN5CCOCC5)c(F)c4)c3n2)ccc1F]

The compound is prepared analogous to Example 3. HPLC: $t_R$=1.26 min (Method A); MS-ES: $(M+H)^+$=436.

EXAMPLE 128

(3-Chloro-4-methyl-phenyl)-[7-(3,5-difluoro-4-morpholin-4-ylmethyl-phenyl)-7H-pyrrolo[2,3-d]pyrimidin-2-yl]-amine

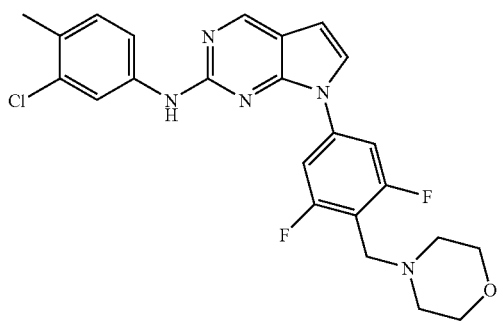 [SMILES: Cc1ccc(Nc2ncc3ccn(-c4cc(F)c(CN5CCOCC5)c(F)c4)c3n2)cc1Cl]

The compound is prepared analogous to Example 3. HPLC: $t_R$=1.48 min (Method A); MS-ES: $(M+H)^+$=470.

EXAMPLE 129

(3-Chloro-4-methyl-phenyl)-{7-[4-(1,1-dioxido-thiomorpholin-4-ylmethyl)-3,5-difluoro-phenyl]-7H-pyrrolo[2,3-d]pyrimidin-2-yl}-amine

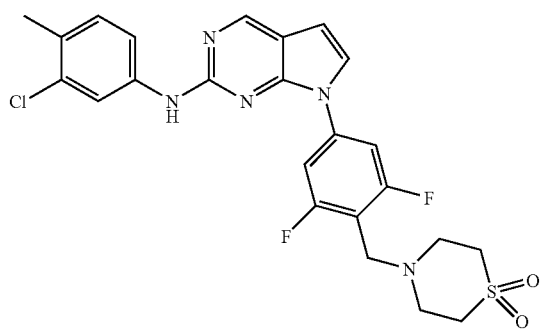 [SMILES: Cc1ccc(Nc2ncc3ccn(-c4cc(F)c(CN5CCS(=O)(=O)CC5)c(F)c4)c3n2)cc1Cl]

The compound is prepared analogous to Example 3. HPLC: $t_R$=1.96 min (Method A); MS-ES: $(M+H)^+$=518.

EXAMPLE 130

(3-Chloro-4-methyl-phenyl)-{7-[4-(4-ethyl-piperazin-1-ylmethyl)-3,5-difluoro-phenyl]-7H-pyrrolo[2,3-d]pyrimidin-2-yl}-amine

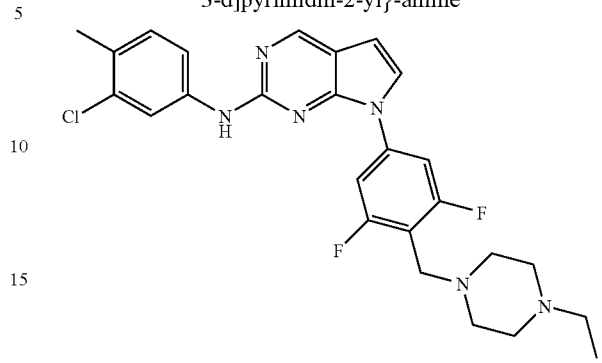

The compound is prepared analogous to Example 3. HPLC: $t_R$=1.51 min (Method A); MS-ES: $(M+H)^+$=497.

EXAMPLE 131

[7-(3,5-Difluoro-4-morpholin-4-ylmethyl-phenyl)-7H-pyrrolo[2,3-d]pyrimidin-2-yl]-(4-fluoro-3-methyl-phenyl)-amine

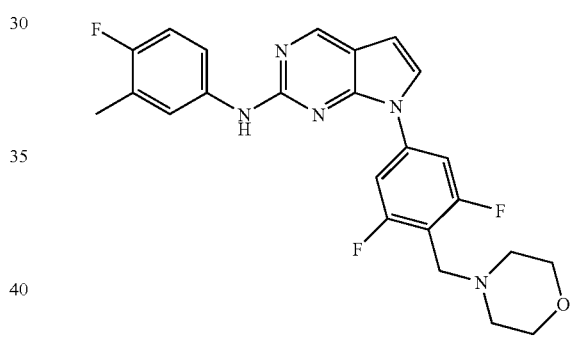

The compound is prepared analogous to Example 3. HPLC: $t_R$=1.39 min (Method A); MS-ES: $(M+H)^+$=454.

EXAMPLE 132

{7-[4-(4-Ethyl-piperazin-1-ylmethyl)-3,5-difluoro-phenyl]-7H-pyrrolo[2,3-d]pyrimidin-2-yl}-(4-fluoro-3-methyl-phenyl)-amine

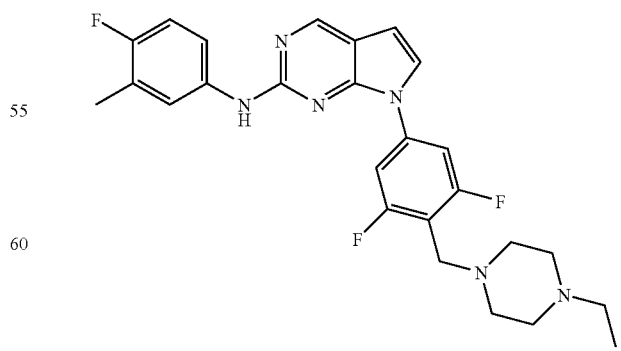

The compound is prepared analogous to Example 3. HPLC: $t_R$=1.35 min (Method A); MS-ES: $(M+H)^+$=481.

EXAMPLE 133

1-(4-{2,6-Difluoro-4-[2-(4-fluoro-3-methyl-phenylamino)-pyrrolo[2,3-d]pyrimidin-7-yl]-benzyl}-piperazin-1-yl)-ethanone

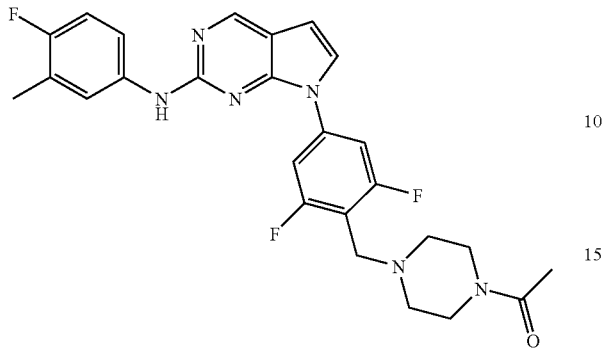

The compound is prepared analogous to Example 3. HPLC: $t_R$=1.26 min (Method A); MS-ES: (M+H)$^+$=495.

EXAMPLE 134

4-{2,6-Difluoro-4-[2-(4-fluoro-3-methyl-phenylamino)-pyrrolo[2,3-d]pyrimidin-7-yl]-benzyl}-1-ethyl-piperazin-2-one

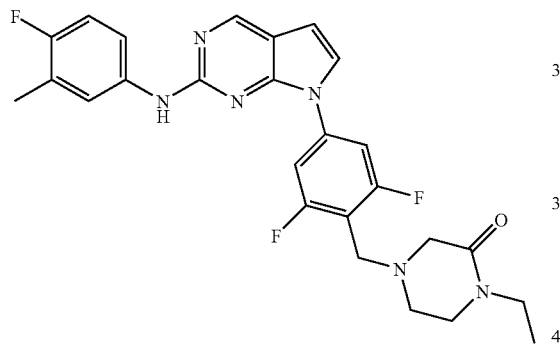

The compound is prepared analogous to Example 3. HPLC: $t_R$=1.43 min (Method A); MS-ES: (M+H)$^+$=495.

EXAMPLE 135

[7-(3,5-Difluoro-4-morpholin-4-ylmethyl-phenyl)-7H-pyrrolo[2,3-d]pyrimidin-2-yl]-(4-methoxymethyl-phenyl)-amine

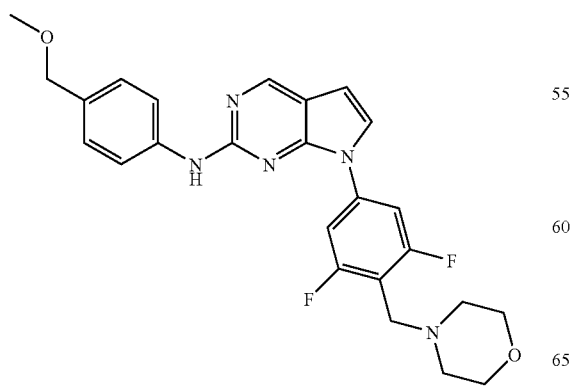

The compound is prepared analogous to Example 2. HPLC: $t_R$=1.15 min (Method A); MS-ES: (M+H)$^+$=466.

EXAMPLE 136

4-[7-(3,5-Difluoro-4-morpholin-4-ylmethyl-phenyl)-7H-pyrrolo[2,3-d]pyrimidin-2-ylamino]-benzonitrile

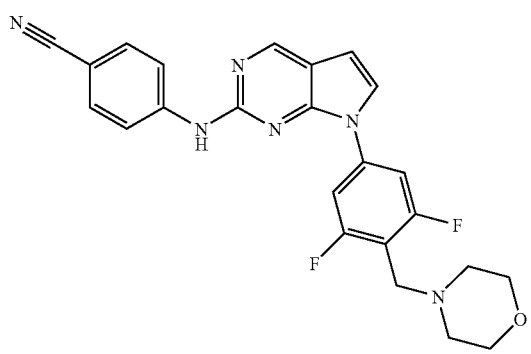 [SMILES: N#Cc1ccc(Nc2ncc3ccn(-c4cc(F)c(CN5CCOCC5)c(F)c4)c3n2)cc1]

The compound is prepared analogous to Example 2. HPLC: $t_R$=1.38 min (Method A); MS-ES: (M+H)$^+$=447.

EXAMPLE 137

{7-[4-(1,1-Dioxido-thiomorpholin-4-ylmethyl)-3,5-difluoro-phenyl]-7H-pyrrolo[2,3-d]pyrimidin-2-yl}-(4-fluoro-3-methyl-phenyl)-amin

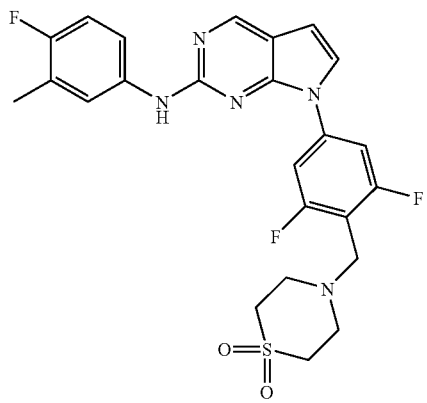 [SMILES: Cc1cc(Nc2ncc3ccn(-c4cc(F)c(CN5CCS(=O)(=O)CC5)c(F)c4)c3n2)ccc1F]

The compound is prepared analogous to Example 3. HPLC: $t_R$=1.71 min (Method A); MS-ES: (M+H)$^+$=502.

EXAMPLE 138

{4-[7-(3,5-Difluoro-4-morpholin-4-ylmethyl-phenyl)-7H-pyrrolo[2,3-d]pyrimidin-2-ylamino]-phenyl}-morpholin-4-yl-methanone

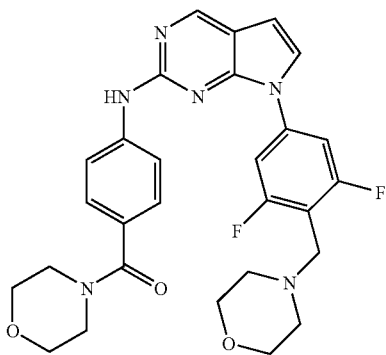 [SMILES: O=C(c1ccc(Nc2ncc3ccn(-c4cc(F)c(CN5CCOCC5)c(F)c4)c3n2)cc1)N1CCOCC1]

The compound is prepared analogous to Example 2. HPLC: $t_R$=1.08 min (Method A); MS-ES: (M+H)$^+$=535.

EXAMPLE 139

[7-(4-Methanesulfinylmethyl-phenyl)-7H-pyrrolo[2,3-d]pyrimidin-2-yl]-p-tolyl-amine

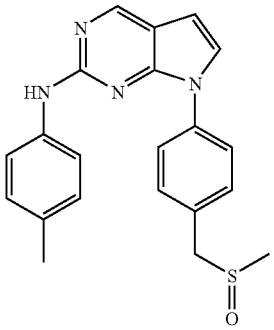 [SMILES: Cc1ccc(Nc2ncc3ccn(-c4ccc(CS(C)=O)cc4)c3n2)cc1]

The compound is prepared analogous to Example 3. HPLC: $t_R$=7.96 min. (Method B); MS-ES: (M+H)$^+$=377; TLC***: $R_f$=0.22

EXAMPLE 140

[7-(4-Methanesulfonylmethyl-phenyl)-7H-pyrrolo[2,3-d]pyrimidin-2-yl]-p-tolyl-amine

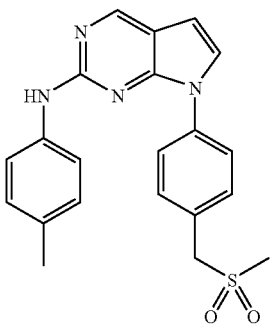 [SMILES: Cc1ccc(Nc2ncc3ccn(-c4ccc(CS(C)(=O)=O)cc4)c3n2)cc1]

The compound is prepared analogous to Example 3. HPLC: $t_R$=8.23 min. (Method B); MS-ES: (M+H)$^+$=393; TLC***: $R_f$=0.42

EXAMPLE 141

1-Morpholin-4-yl-2-[4-(2-p-tolylamino-pyrrolo[2,3-d]pyrimidin-7-yl)-phenyl]-ethanone

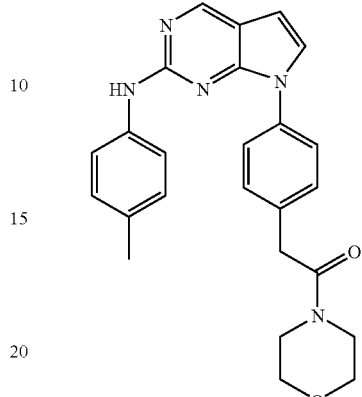

The compound is prepared analogous to Example 3. HPLC: $t_R$=8.36 min. (Method B); MS-ES: (M+H)$^+$=428; TLCt: $R_f$=0.14

EXAMPLE 142

2-{4-[2-(4-Fluoro-3-methoxy-phenylamino)-pyrrolo[2,3-d]pyrimidin-7-yl]-phenyl}-1-morpholin-4-yl-ethanone

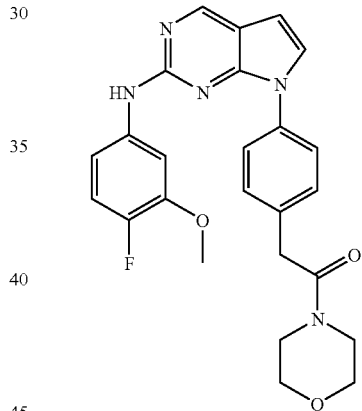

The compound is prepared analogous to Example 3. HPLC: $t_R$=8.27 min. (Method B); MS-ES: (M+H)$^+$=462; TLC‡: $R_f$=0.23

EXAMPLE 143

1-Morpholin-4-yl-2-[4-(2-phenylamino-pyrrolo[2,3-d]pyrimidin-7-yl)-phenyl]-ethanone

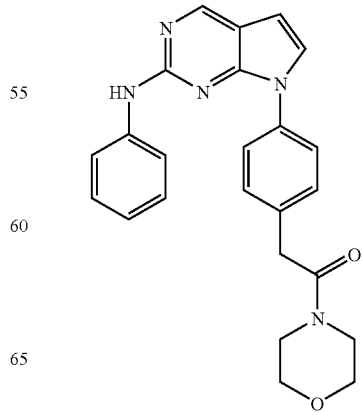

The compound is prepared analogous to Example 3.
HPLC: $t_R$=8.04 min. (Method B); MS-ES: (M+H)$^+$=414;
TLC$^‡$: R$_f$=0.11

EXAMPLE 144

1-Morpholin-4-yl-2-{4-[2-(4-trifluoromethyl-phenylamino)-pyrrolo[2,3-d]pyrimidin-7-yl]-phenyl}-ethanone

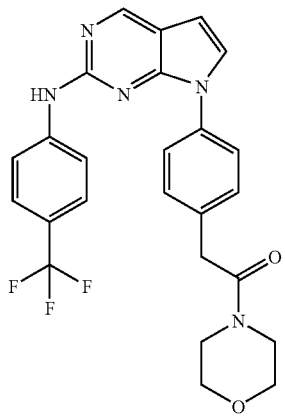 [SMILES: O=C(Cc1ccc(-n2ccc3cnc(Nc4ccc(C(F)(F)F)cc4)nc32)cc1)N1CCOCC1]

The compound is prepared analogous to Example 3.
HPLC: $t_R$=9.22 min. (Method B); MS-ES: (M+H)$^+$=482;
TLC$^‡$: R$_f$=0.12

EXAMPLE 145

1-(4-Methyl-piperazin-1-yl)-2-{4-[2-(4-trifluoromethyl-phenylamino)-pyrrolo[2,3-d]pyrimidin-7-yl]-phenyl}-ethanone

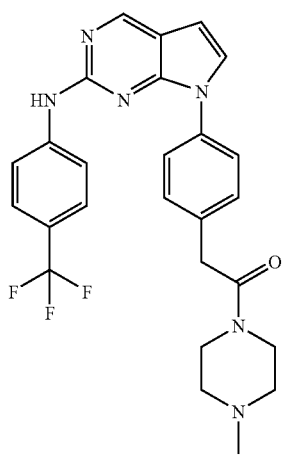 [SMILES: CN1CCN(C(=O)Cc2ccc(-n3ccc4cnc(Nc5ccc(C(F)(F)F)cc5)nc43)cc2)CC1]

The compound is prepared analogous to Example 3.
HPLC: $t_R$=8.15 min. (Method B); MS-ES: (M+H)$^+$=495;
TLC*: R$_f$=0.29

EXAMPLE 146

[7-(4-Morpholin-4-ylmethyl-phenyl)-7H-pyrrolo[2,3-d]pyrimidin-2-yl]-p-tolyl-amine

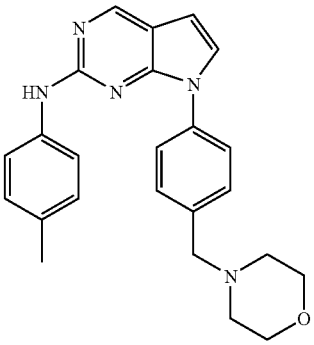 [SMILES: Cc1ccc(Nc2ncc3ccn(-c4ccc(CN5CCOCC5)cc4)c3n2)cc1]

The compound is prepared analogous to Example 3.
HPLC: $t_R$=7.28 min. (Method B); MS-ES: (M+H)$^+$=400;
TLC$^‡$: R$_f$=0.17

EXAMPLE 147

(3,4-Diethoxy-phenyl)-[7-(4-morpholin-4-ylmethyl-phenyl)-7H-pyrrolo[2,3-d]pyrimidin-2-yl]-amine

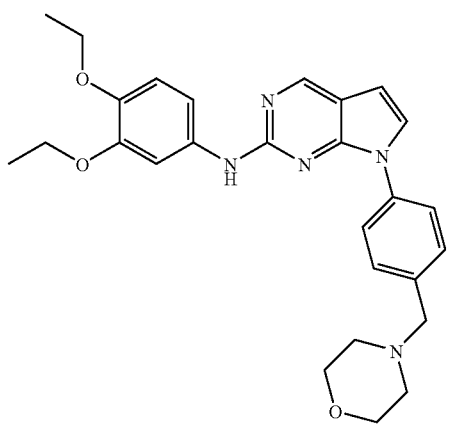 [SMILES: CCOc1ccc(Nc2ncc3ccn(-c4ccc(CN5CCOCC5)cc4)c3n2)cc1OCC]

The compound is prepared analogous to Example 3.
HPLC: $t_R$=7.47 min. (Method B); MS-ES: (M+H)$^+$=474

EXAMPLE 148

2-{4-[2-(3,4-Dimethyl-phenylamino)-pyrrolo[2,3-d]pyrimidin-7-yl]-phenyl}-1-(4-methyl-piperazin-1-yl)-ethanone

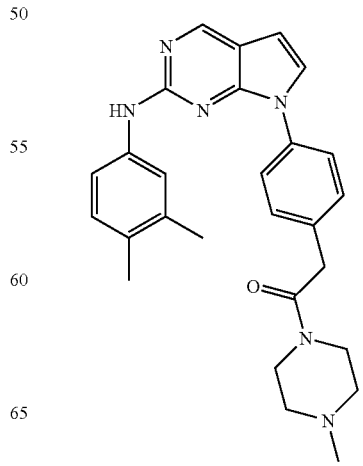

The compound is prepared analogous to Example 3.
HPLC: $t_R$=7.50 min. (Method B); MS-ES: (M+H)$^+$=455;
TLC*: $R_f$=0.36

EXAMPLE 149

1-(4-Methyl-piperazin-1-yl)-2-[4-(2-p-tolylamino-pyrrolo[2,3-d]pyrimidin-7-yl)-phenyl]-ethanone

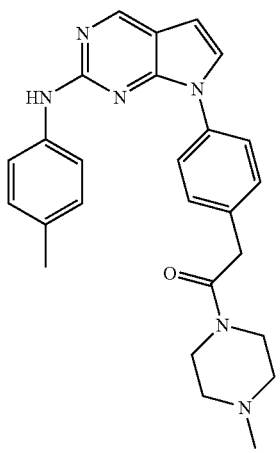 [SMILES: Cc1ccc(Nc2ncc3ccn(-c4ccc(CC(=O)N5CCN(C)CC5)cc4)c3n2)cc1]

The compound is prepared analogous to Example 3.
HPLC: $t_R$=7.25 min. (Method B); MS-ES: (M+H)$^+$=441;
TLC*: $R_f$=0.37

EXAMPLE 150

2-{4-[2-(4-Fluoro-3-methoxy-phenylamino)-pyrrolo[2,3-d]pyrimidin-7-yl]-phenyl}-1-(4-methyl-piperazin-1-yl)-ethanone

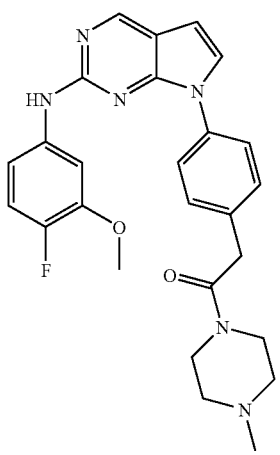 [SMILES: COc1cc(Nc2ncc3ccn(-c4ccc(CC(=O)N5CCN(C)CC5)cc4)c3n2)ccc1F]

The compound is prepared analogous to Example 3.
HPLC: $t_R$=7.21 min. (Method B); MS-ES: (M+H)$^+$=475;
TLC*: $R_f$=0.36

EXAMPLE 151

{2-Fluoro-4-[2-(4-fluoro-3-methoxy-phenylamino)-pyrrolo[2,3-d]pyrimidin-7-yl]-phenyl}-morpholin-4-yl-methanone

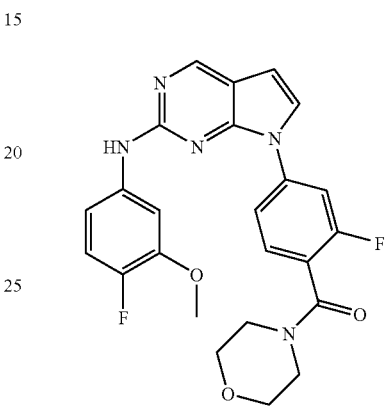

The compound is prepared analogous to Example 3.
HPLC: $t_R$=8.40 min. (Method B); MS-ES: (M+H)$^+$=466;
TLC‡: $R_f$=0.16

EXAMPLE 152

{4-[2-(3,4-Dimethyl-phenylamino)-pyrrolo[2,3-d]pyrimidin-7-yl]-2-fluoro-phenyl}-morpholin-4-yl-methanone

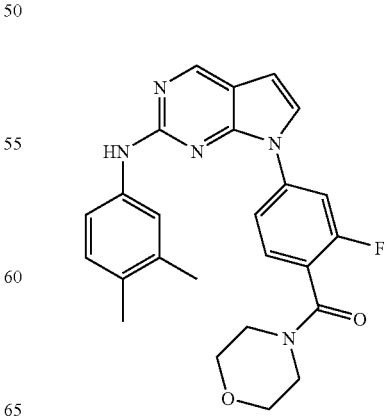

The compound is prepared analogous to Example 3.
HPLC: $t_R$=8.76 min. (Method B); MS-ES: (M+H)$^+$=446;
TLC$^‡$: $R_f$=0.26

EXAMPLE 153

(4-{7-[4-(1,1-Dioxido-thiomorpholin-4-ylmethyl)-phenyl]-7H-pyrrolo[2,3-d]pyrimidin-2-ylamino}-phenyl)-morpholin-4-yl-methanone

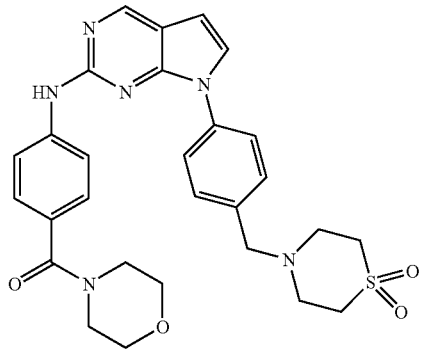 [SMILES: O=C(c1ccc(Nc2ncc3ccn(-c4ccc(CN5CCS(=O)(=O)CC5)cc4)c3n2)cc1)N1CCOCC1]

The compound is prepared analogous to Example 2.
HPLC: $t_R$=7.03 min. (Method B); MS-ES: (M+H)$^+$=547;
TLC**: $R_f$=0.29

EXAMPLE 154

{2-Fluoro-4-[2-(4-fluoro-3-methoxy-phenylamino)-pyrrolo[2,3-d]pyrimidin-7-yl]-phenyl}-(4-methyl-piperazin-1-yl)-methanone

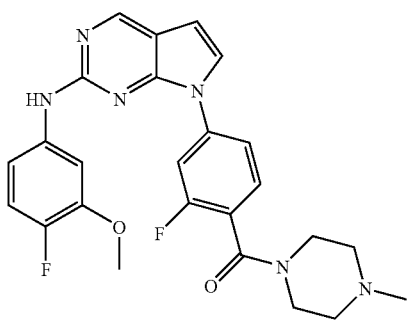 [SMILES: COc1cc(Nc2ncc3ccn(-c4ccc(C(=O)N5CCN(C)CC5)c(F)c4)c3n2)ccc1F]

The compound is prepared analogous to Example 3.
HPLC: $t_R$=7.26 min. (Method B); MS-ES: (M+H)$^+$=479;
TLC**: $R_f$=0.23

EXAMPLE 155

{4-[2-(3,4-Dimethyl-phenylamino)-pyrrolo[2,3-d]pyrimidin-7-yl]-2-fluoro-phenyl}-(4-methyl-piperazin-1-yl)-methanone

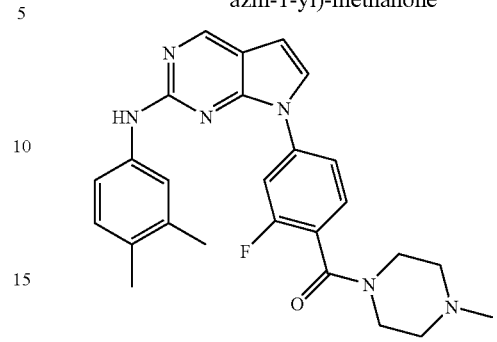

The compound is prepared analogous to Example 3.
HPLC: $t_R$=7.45 min. (Method B); MS-ES: (M+H)$^+$=459;
TLC**: $R_f$=0.31

EXAMPLE 156

2-{4-[2-(3,4-Dimethyl-phenylamino)-pyrrolo[2,3-d]pyrimidin-7-yl]-2-fluoro-phenyl}-1-(1,1-dioxido-1-thiomorpholin-4-yl)-ethanone

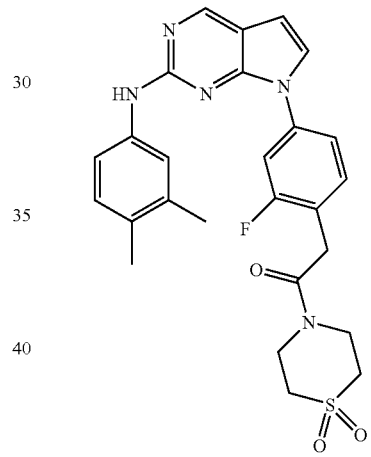

The compound is prepared analogous to Example 3.
HPLC: $t_R$=8.51 min. (Method B); MS-ES: (M+H)$^+$=508;
TLC**: $R_f$=0.67

EXAMPLE 157

{4-[7-(3-Fluoro-4-morpholin-4-ylmethyl-phenyl)-7H-pyrrolo[2,3-d]pyrimidin-2-ylamino]-phenyl}-morpholin-4-yl-methanone

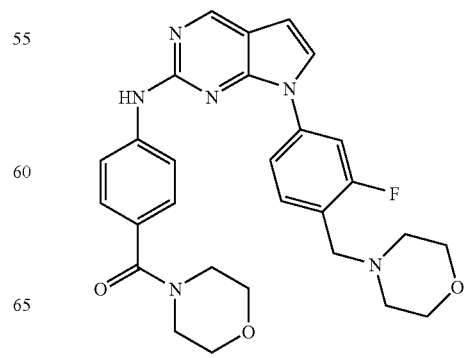

The compound is prepared analogous to Example 2.
HPLC: $t_R$=7.03 min. (Method B); MS-ES: (M+H)$^+$=517;
TLC*: $R_f$=0.29

EXAMPLE 158

{2-Fluoro-4-[7-(3-fluoro-4-morpholin-4-ylmethyl-
phenyl)-7H-pyrrolo[2,3-d]pyrimidin-2-ylamino]-
phenyl}-(4-methyl-piperazin-1-yl)-methanone

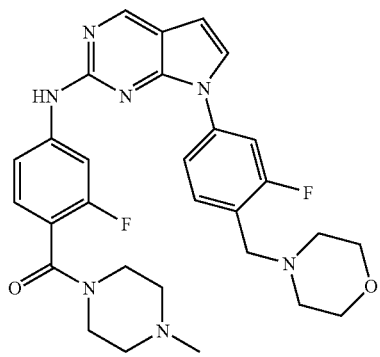 [SMILES: CN1CCN(C(=O)c2ccc(Nc3ncc4ccn(-c5ccc(CN6CCOCC6)c(F)c5)c4n3)cc2F)CC1]

The compound is prepared analogous to Example 3.
HPLC: $t_R$=6.71 min. (Method B); MS-ES: (M+H)$^+$=548;
TLC*: $R_f$=0.57

EXAMPLE 159

(1-{4-[2-(3,4-Dimethyl-phenylamino)-pyrrolo[2,3-d]
pyrimidin-7-yl]-phenyl}-cyclopropyl)-(4-ethyl-pip-
erazin-1-yl)-methanone

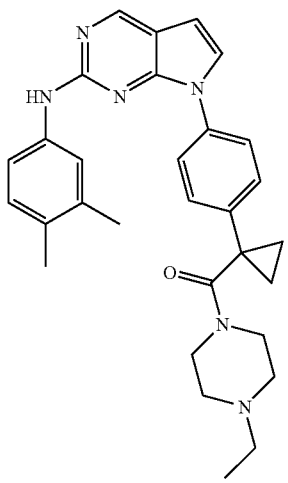 [SMILES: CCN1CCN(C(=O)C2(c3ccc(-n4ccc5cnc(Nc6ccc(C)c(C)c6)nc54)cc3)CC2)CC1]

The compound is prepared analogous to Example 3.
HPLC: $t_R$=8.20 min. (Method B); MS-ES: (M+H)$^+$=495;
TLC**: $R_f$=0.11

EXAMPLE 160

(3,4-Dimethyl-phenyl)-[7-(4-morpholin-4-ylmethyl-
phenyl)-7H-pyrrolo[2,3-d]pyrimidin-2-yl]-amine

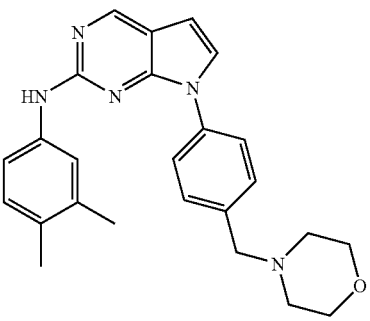 [SMILES: Cc1ccc(Nc2ncc3ccn(-c4ccc(CN5CCOCC5)cc4)c3n2)cc1C]

The compound is prepared analogous to Example 3.
HPLC: $t_R$=7.80 min. (Method B); MS-ES: (M+H)$^+$=414;
TLC**: $R_f$=0.21

EXAMPLE 161

2-{4-[2-(3,4-Dimethyl-phenylamino)-6-methyl-pyr-
rolo[2,3-d]pyrimidin-7-yl]-phenyl}-1-(4-methyl-
piperazin-1-yl)-ethanone

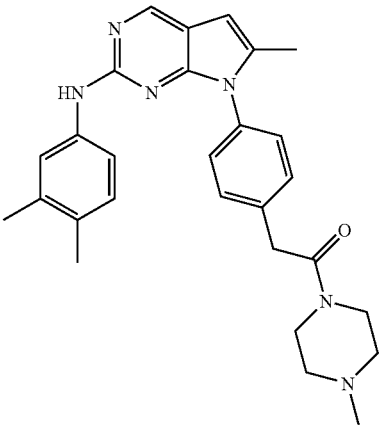 [SMILES: Cc1ccc(Nc2ncc3cc(C)n(-c4ccc(CC(=O)N5CCN(C)CC5)cc4)c3n2)cc1C]

The compound is prepared analogous to Example 3. But
during the synthesis of the pyrrolopyrimidine core, tributyl-
(1-propynyl)-tin was used instead of tributyl-(2-ethoxy-vi-
nyl)-stannane as described in Example 1 to obtain 2-chloro- 6-methyl-7H-pyrrolo[2,3-d]pyrimidine. HPLC: $t_R$=7.76 min. (Method B); MS-ES: (M+H)$^+$=469; TLC**: $R_f$=0.31

EXAMPLE 162

2-{4-[2-(4-Fluoro-3-methoxy-phenylamino)-6-methyl-pyrrolo[2,3-d]pyrimidin-7-yl]-phenyl}-1-(4-methyl-piperazin-1-yl)-ethanone

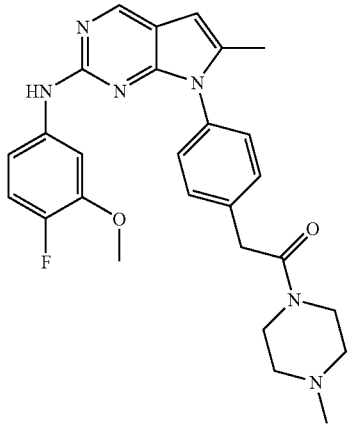 [SMILES: COc1cc(Nc2ncc3cc(C)n(-c4ccc(CC(=O)N5CCN(C)CC5)cc4)c3n2)ccc1F]

The compound is prepared analogous to Example 3. But during the synthesis of the pyrrolopyrimidine core, tributyl-(1-propynyl)-tin was used instead of tributyl-(2-ethoxy-vinyl)-stannane as described in Example 1 to obtain 2-chloro-6-methyl-7H-pyrrolo[2,3-d]pyrimidine. HPLC: $t_R$=7.31 min. (Method B); MS-ES: (M+H)$^+$=489; TLC***: $R_f$=0.20

EXAMPLE 163

(3,4-Dimethyl-phenyl)-[7-(3-fluoro-4-morpholin-4-ylmethyl-phenyl)-6-methyl-7H-pyrrolo[2,3-d]pyrimidin-2-yl]-amine

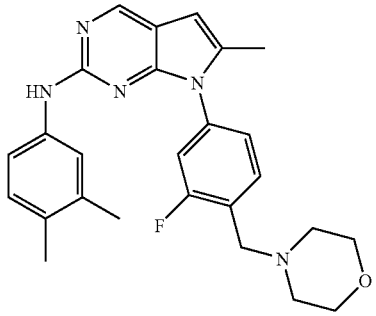 [SMILES: Cc1ccc(Nc2ncc3cc(C)n(-c4ccc(CN5CCOCC5)c(F)c4)c3n2)cc1C]

The compound is prepared analogous to Example 3. But during the synthesis of the pyrrolopyrimidine core, tributyl-(1-propynyl)-tin was used instead of tributyl-(2-ethoxy-vinyl)-stannane as described in Example 1 to obtain 2-chloro-6-methyl-7H-pyrrolo[2,3-d]pyrimidine. HPLC: $t_R$=7.58 min. (Method B); MS-ES: (M+H)$^+$=446; TLC***: $R_f$=0.40

EXAMPLE 164

(4-Fluoro-3-methoxy-phenyl)-[7-(3-fluoro-4-morpholin-4-ylmethyl-phenyl)-6-methyl-7H-pyrrolo[2,3-d]pyrimidin-2-yl]-amine

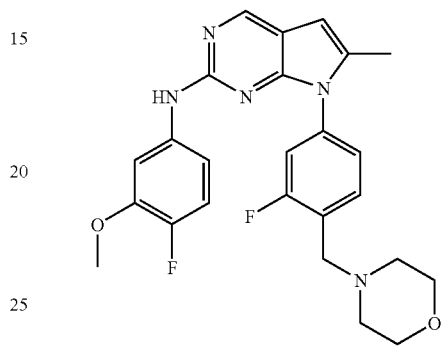

The compound is prepared analogous to Example 3. But during the synthesis of the pyrrolopyrimidine core, tributyl-(1-propynyl)-tin was used instead of tributyl-(2-ethoxy-vinyl)-stannane as described in Example 1 to obtain 2-chloro-6-methyl-7H-pyrrolo[2,3-d]pyrimidine. HPLC: $t_R$=7.23 min. (Method B); MS-ES: (M+H)$^+$=466; TLC***: $R_f$=0.32

EXAMPLE 165

2-{4-[2-(3,4-Diethoxy-phenylamino)-pyrrolo[2,3-d]pyrimidin-7-yl]-phenyl}-1-(4-ethyl-piperazin-1-yl)-ethanone

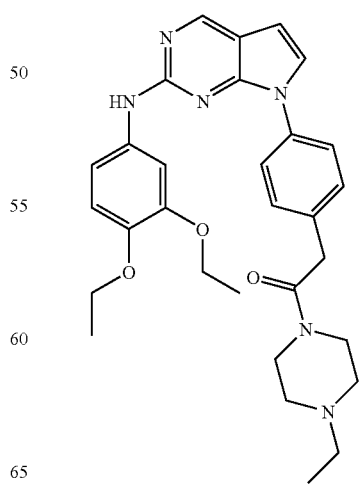

The compound is prepared analogous to Example 3. HPLC: $t_R$=7.53 min. (Method B); MS-ES: (M+H)$^+$=529; TLC*: $R_f$=0.43

EXAMPLE 166

2-{4-[2-(3,4-Dimethyl-phenylamino)-pyrrolo[2,3-d]pyrimidin-7-yl]-phenyl}-1-morpholin-4-yl-ethanone

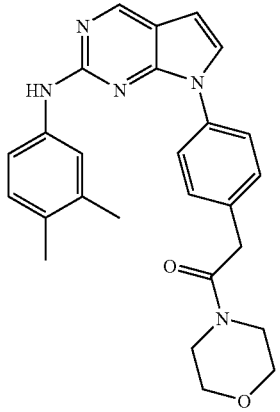 [SMILES: Cc1ccc(Nc2ncc3ccn(-c4ccc(CC(=O)N5CCOCC5)cc4)c3n2)cc1C]

The compound is prepared analogous to Example 3. HPLC: $t_R$=8.63 min. (Method B); MS-ES: (M+H)$^+$=442; TLC**: $R_f$=0.30

EXAMPLE 167

2-{4-[2-(3,4-Diethoxy-phenylamino)-6-methyl-pyrrolo[2,3-d]pyrimidin-7-yl]-phenyl}-1-(4-methyl-piperazin-1-yl)-ethanone

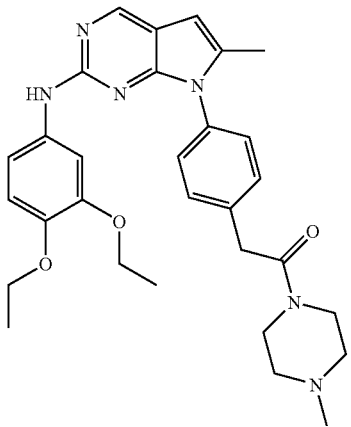 [SMILES: CCOc1ccc(Nc2ncc3cc(C)n(-c4ccc(CC(=O)N5CCN(C)CC5)cc4)c3n2)cc1OCC]

The compound is prepared analogous to Example 3. But during the synthesis of the pyrrolopyrimidine core, tributyl-(1-propynyl)-tin was used instead of tributyl-(2-ethoxy-vinyl)-stannane as described in Example 1 to obtain 2-chloro-6-methyl-7H-pyrrolo[2,3-d]pyrimidine. HPLC: $t_R$=7.52 min. (Method B); MS-ES: (M+H)$^+$=529; TLC*: $R_f$=0.50

EXAMPLE 168

(3,4-Diethoxy-phenyl)-[7-(3-fluoro-4-morpholin-4-ylmethyl-phenyl)-6-methyl-7H-pyrrolo[2,3-d]pyrimidin-2-yl]-amine

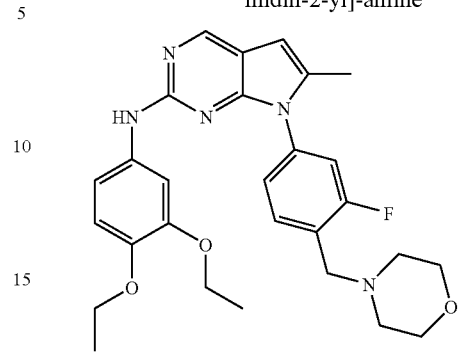

The compound is prepared analogous to Example 3. But during the synthesis of the pyrrolopyrimidine core, tributyl-(1-propynyl)-tin was used instead of tributyl-(2-ethoxy-vinyl)-stannane as described in Example 1 to obtain 2-chloro-6-methyl-7H-pyrrolo[2,3-d]pyrimidine. HPLC: $t_R$=7.49 min. (Method B); MS-ES: (M+H)$^+$=506; TLC***: $R_f$=0.24

EXAMPLE 169

{4-[2-(3,4-Dimethyl-phenylamino)-pyrrolo[2,3-d]pyrimidin-7-yl]-phenyl}-morpholin-4-yl-methanone

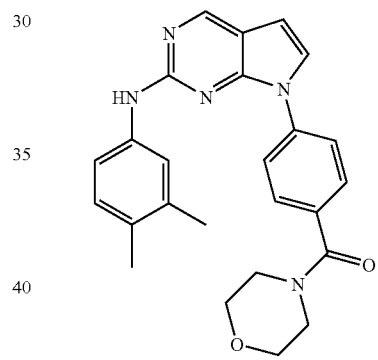

The compound is prepared analogous to Example 3. HPLC: $t_R$=8.54 min. (Method B); MS-ES: (M+H)$^+$=428; TLC*: $R_f$=0.66

EXAMPLE 170

{4-[2-(3,4-Dimethyl-phenylamino)-pyrrolo[2,3-d]pyrimidin-7-y]-phenyl}-(4-methyl-piperazin-1-yl)-methanone

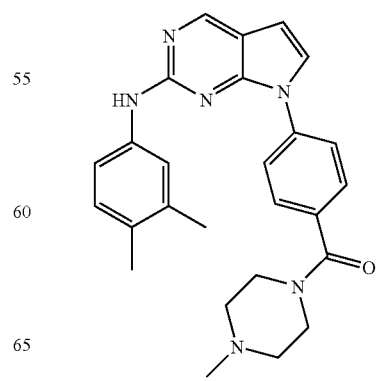

The compound is prepared analogous to Example 3.
HPLC: $t_R$=7.36 min. (Method B); MS-ES: (M+H)$^+$=441;
TLC**: $R_f$=0.18

EXAMPLE 171

{4-[7-(3,5-Difluoro-4-morpholin-4-ylmethyl-phenyl)-7H-pyrrolo[2,3-d]pyrimidin-2-ylamino]-phenyl}-(4-ethyl-piperazin-1-yl)-methanone

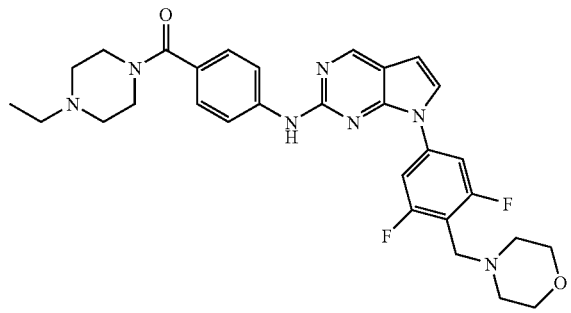 [SMILES: CCN1CCN(C(=O)c2ccc(Nc3ncc4ccn(-c5cc(F)c(CN6CCOCC6)c(F)c5)c4n3)cc2)CC1]

The compound is prepared analogous to Example 2.
HPLC: $t_R$=0.93 min (Method A); MS-ES: (M+H)$^+$=562.

EXAMPLE 172

2-{3-[7-(3,5-Difluoro-4-morpholin-4-ylmethyl-phenyl)-7H-pyrrolo[2,3-d]pyrimidin-2-ylamino]-phenyl}-1-(4-ethyl-piperazin-1-yl)-ethanone

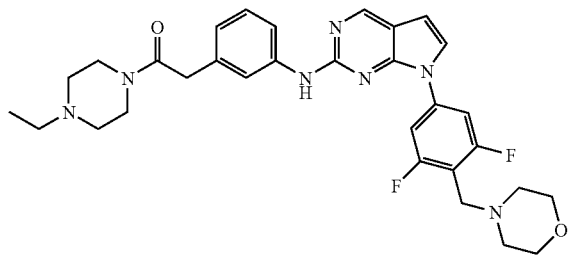 [SMILES: CCN1CCN(C(=O)Cc2cccc(Nc3ncc4ccn(-c5cc(F)c(CN6CCOCC6)c(F)c5)c4n3)c2)CC1]

The compound is prepared analogous to Example 2.
HPLC: $t_R$=0.93 min (Method A); MS-ES: (M+H)$^+$=576.

EXAMPLE 173

[7-(3,5-Difluoro-4-morpholin-4-ylmethyl-phenyl)-7H-pyrrolo[2,3-d]pyrimidin-2-yl]-[4-(4-methyl-piperazin-1-ylmethyl)-phenyl]-amine

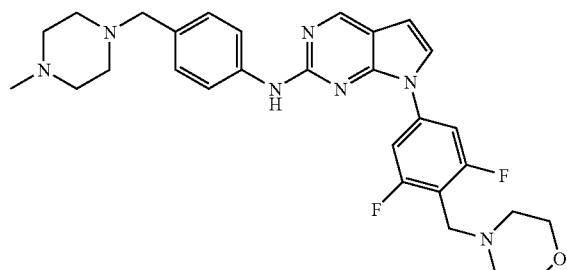

The compound is prepared analogous to Example 2.
HPLC: $t_R$=0.93 min (Method A); MS-ES: (M+H)$^+$=534.

EXAMPLE 174

[7-(3,5-Difluoro-4-morpholin-4-ylmethyl-phenyl)-7H-pyrrolo[2,3-d]pyrimidin-2-yl]-[3-(4-methyl-piperazin-1-yl)-phenyl]-amine

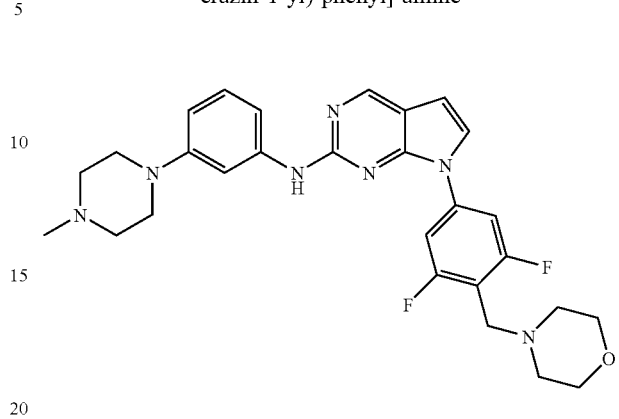

The compound is prepared analogous to Example 2.
HPLC: $t_R$=0.93 min (Method A); MS-ES: (M+H)$^+$=520.

EXAMPLE 175

{4-[7-(3-Chloro-4-morpholin-4-ylmethyl-phenyl)-7H-pyrrolo[2,3-d]pyrimidin-2-ylamino]-phenyl}-morpholin-4-yl-methanone

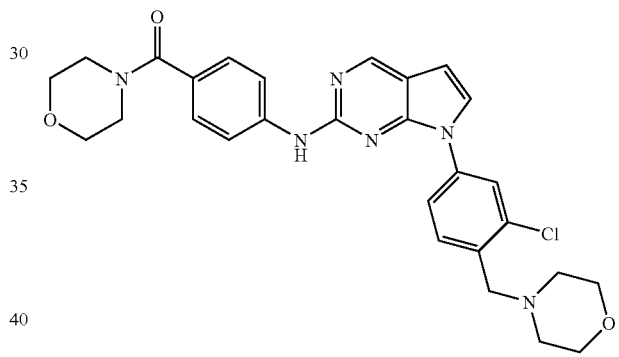

The compound is prepared analogous to Example 2.
HPLC: $t_R$=1.13 min (Method A); MS-ES: (M+H)$^+$=533.

EXAMPLE 176

[7-(3-Chloro-4-morpholin-4-yl methyl-phenyl)-7H-pyrrolo[2,3-d]pyrimidin-2-yl]-(4-methoxymethyl-phenyl)-amine

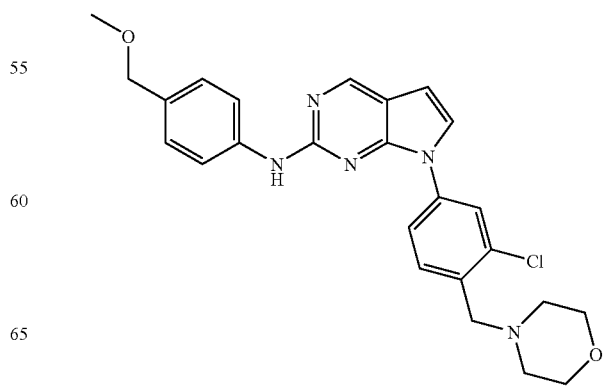

The compound is prepared analogous to Example 2.
HPLC: $t_R$=1.19 min (Method A); MS-ES: (M+H)⁺=464.

EXAMPLE 177

[7-(3-Chloro-4-morpholin-4-ylmethyl-phenyl)-7H-pyrrolo[2,3-d]pyrimidin-2-yl]-(3,4-diethoxy-phenyl)-amine

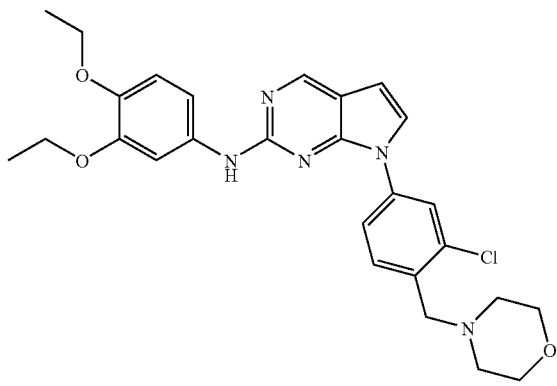 [SMILES: CCOc1ccc(Nc2ncc3ccn(-c4ccc(CN5CCOCC5)c(Cl)c4)c3n2)cc1OCC]

The compound is prepared analogous to Example 2.
HPLC: $t_R$=1.28 min (Method A); MS-ES: (M+H)⁺=508.

EXAMPLE 178

{4-[7-(3,5-Difluoro-4-pyrrolidin-1-ylmethyl-phenyl)-7H-pyrrolo[2,3-d]pyrimidin-2-ylamino]-phenyl}-morpholin-4-yl-methanone

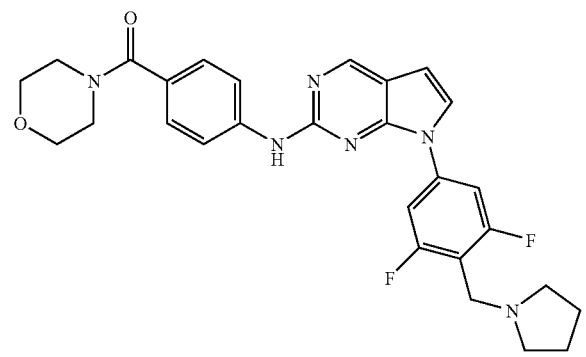 [SMILES: O=C(c1ccc(Nc2ncc3ccn(-c4cc(F)c(CN5CCCC5)c(F)c4)c3n2)cc1)N1CCOCC1]

The compound is prepared analogous to Example 2.
HPLC: $t_R$=1.13 min (Method A); MS-ES: (M+H)⁺=519.

EXAMPLE 179

[7-(3,5-Difluoro-4-pyrrolidin-1-ylmethyl-phenyl)-7H-pyrrolo[2,3-d]pyrimidin-2-yl]-(4-methoxymethyl-phenyl)-amine

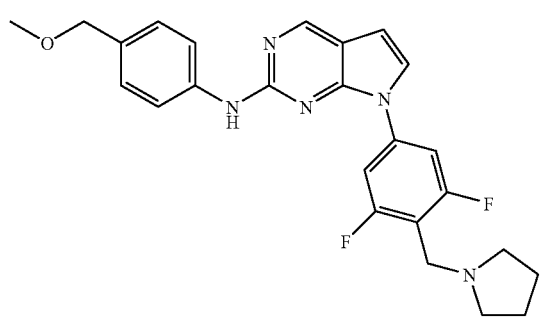 [SMILES: COCc1ccc(Nc2ncc3ccn(-c4cc(F)c(CN5CCCC5)c(F)c4)c3n2)cc1]

The compound is prepared analogous to Example 2.
HPLC: $t_R$=1.21 min (Method A); MS-ES: (M+H)⁺=450.

EXAMPLE 180

{7-[4-(1,1-Dioxido-thiomorpholin-4-ylmethyl)-3,5-difluoro-phenyl]-7H-pyrrolo[2,3-d]pyrimidin-2-yl}-phenyl-amine

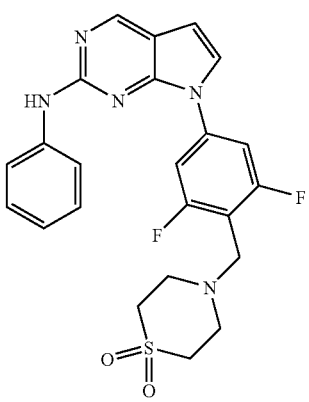 [SMILES: O=S1(=O)CCN(Cc2c(F)cc(-n3ccc4cnc(Nc5ccccc5)nc43)cc2F)CC1]

The compound is prepared analogous to Example 2.
HPLC: $t_R$=1.53 min (Method A); MS-ES: (M+H)⁺=470.

EXAMPLE 181

{7-[4-(1,1-Dioxido-thiomorpholin-4-ylmethyl)-3,5-difluoro-phenyl]-7H-pyrrolo[2,3-d]pyrimidin-2-yl}-pyridin-2-yl-amine

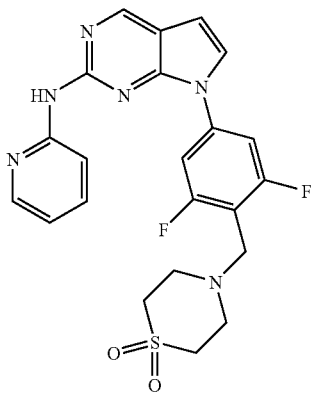 [SMILES: O=S1(=O)CCN(Cc2c(F)cc(-n3ccc4cnc(Nc5ccccn5)nc43)cc2F)CC1]

The compound is prepared analogous to Example 2.
HPLC: $t_R$=1.20 min (Method A); MS-ES: (M+H)⁺=471.

EXAMPLE 182

{7-[4-(1,1-Dioxido-thiomorpholin-4-ylmethyl)-3,5-difluoro-phenyl]-7H-pyrrolo[2,3-d]pyrimidin-2-yl}-pyridin-3-yl-amine

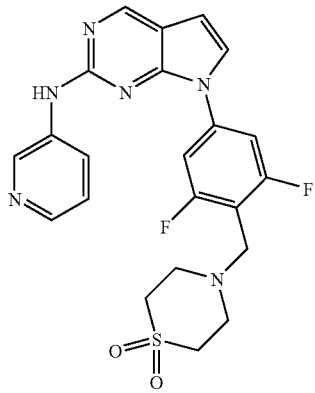 [SMILES: O=S1(=O)CCN(Cc2c(F)cc(-n3ccc4cnc(Nc5cccnc5)nc43)cc2F)CC1]

The compound is prepared analogous to Example 2.
HPLC: $t_R$=1.17 min (Method A); MS-ES: (M+H)$^+$=471.

EXAMPLE 183

{7-[4-(1,1-Dioxido-thiomorpholin-4-ylmethyl)-3,5-difluoro-phenyl]-7H-pyrrolo[2,3-d]pyrimidin-2-yl}-pyridin-4-yl-amine

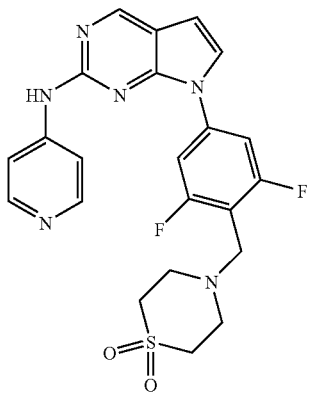 [SMILES: O=S1(=O)CCN(Cc2c(F)cc(-n3ccc4cnc(Nc5ccncc5)nc43)cc2F)CC1]

The compound is prepared analogous to Example 2.
HPLC: $t_R$=1.21 min (Method A); MS-ES: (M+H)$^+$=471.

EXAMPLE 184

{7-[4-(1,1-Dioxido-thiomorpholin-4-ylmethyl)-3,5-difluoro-phenyl]-7H-pyrrolo[2,3-d]pyrimidin-2-yl}-(4-methoxymethyl-phenyl)-amine

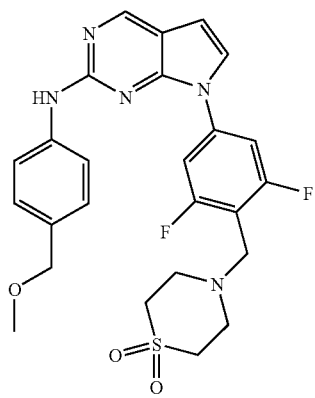 [SMILES: COCc1ccc(Nc2ncc3ccn(-c4cc(F)c(CN5CCS(=O)(=O)CC5)c(F)c4)c3n2)cc1]

The compound is prepared analogous to Example 2.
HPLC: $t_R$=1.52 min (Method A); MS-ES: (M+H)$^+$=514.

EXAMPLE 185

4-{7-[4-(1,1-Dioxido-thiomorpholin-4-ylmethyl)-3,5-difluoro-phenyl]-7H-pyrrolo[2,3-d]pyrimidin-2-ylamino}-benzonitrile

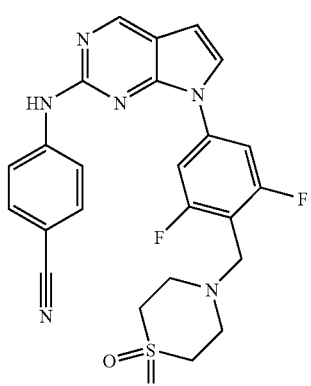

The compound is prepared analogous to Example 2.
HPLC: $t_R$=1.78 min (Method A); MS-ES: (M+H)$^+$=495.

EXAMPLE 186

(4-{7-[4-(1,1-Dioxido-thiomorpholin-4-ylmethyl)-3,5-difluoro-phenyl]-7H-pyrrolo[2,3-d]pyrimidin-2-ylamino}-2-trifluoromethyl-phenyl)-(4-methyl-piperazin-1-yl)-methanone

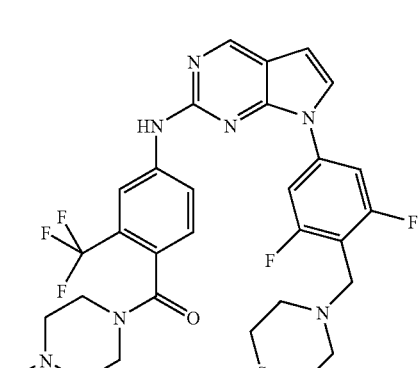

The compound is prepared analogous to Example 2.
HPLC: $t_R$=1.35 min (Method A); MS-ES: (M+H)$^+$=664.

EXAMPLE 187

(4-{7-[4-(1,1-Dioxido-thiomorpholin-4-ylmethyl)-3,5-difluoro-phenyl]-7H-pyrrolo[2,3-d]pyrimidin-2-ylamino}-phenyl)-morpholin-4-yl-methanone

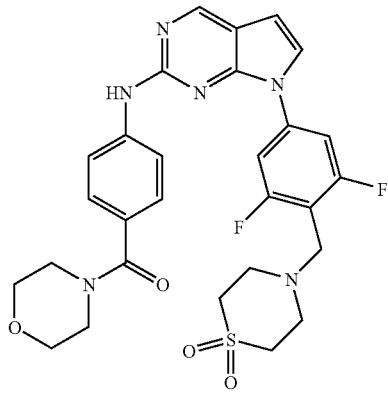 [SMILES: O=C(c1ccc(Nc2ncc3ccn(-c4cc(F)c(CN5CCS(=O)(=O)CC5)c(F)c4)c3n2)cc1)N1CCOCC1]

The compound is prepared analogous to Example 2. HPLC: $t_R$=1.36 min (Method A); MS-ES: (M+H)$^+$=583.

EXAMPLE 188

{7-[4-(1,1-Dioxido-thiomorpholin-4-ylmethyl)-3,5-difluoro-phenyl]-7H-pyrrolo[2,3-d]pyrimidin-2-yl}-[4-(4-ethyl-piperazin-1-ylmethyl)-phenyl]-amine

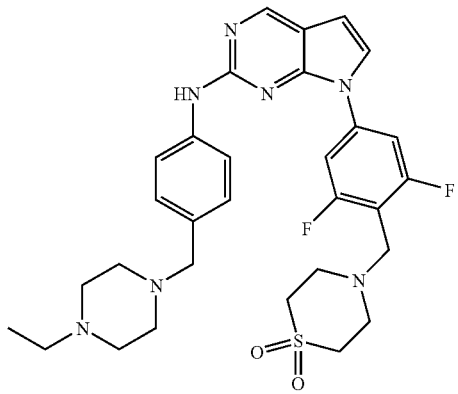 [SMILES: CCN1CCN(Cc2ccc(Nc3ncc4ccn(-c5cc(F)c(CN6CCS(=O)(=O)CC6)c(F)c5)c4n3)cc2)CC1]

The compound is prepared analogous to Example 2. HPLC: $t_R$=1.14 min (Method A); MS-ES: (M+H)$^+$=596.

EXAMPLE 189

{2,6-Difluoro-4-[2-(4-methoxymethyl-phenylamino)-pyrrolo[2,3-d]pyrimidin-7-yl]-phenyl}-(4-methyl-piperazin-1-yl)-methanone

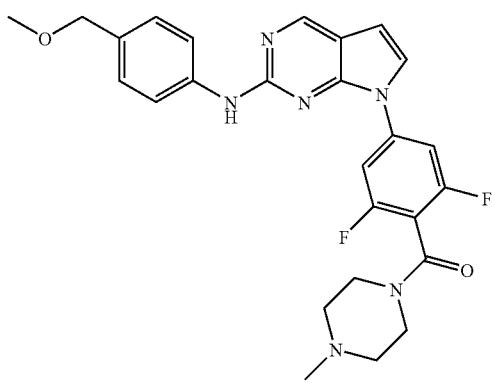 [SMILES: COCc1ccc(Nc2ncc3ccn(-c4cc(F)c(C(=O)N5CCN(C)CC5)c(F)c4)c3n2)cc1]

The compound is prepared analogous to Example 2. HPLC: $t_R$=1.18 min (Method A); MS-ES: (M+H)$^+$=493.

EXAMPLE 190

(4-{2-[4-(1,1-Dioxido-thiomorpholin-4-ylmethyl)-phenylamino]-pyrrolo[2,3-d]pyrimidin-7-yl}-2,6-difluoro-phenyl)-(4-methyl-piperazin-1-yl)-methanone

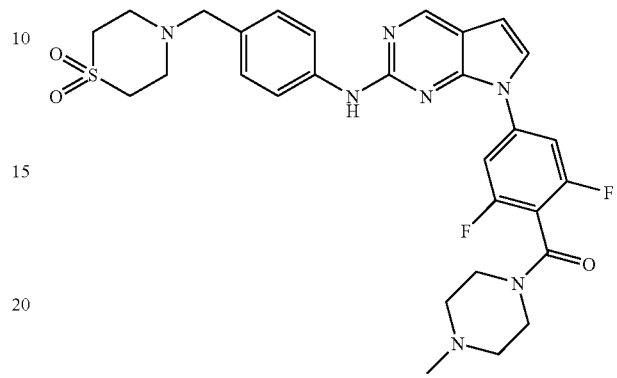

The compound is prepared analogous to Example 2. HPLC: $t_R$=0.98 min (Method A); MS-ES: (M+H)$^+$=596.

EXAMPLE 191

(4-{2-[4-(4-Ethyl-piperazin-1-ylmethyl)-phenylamino]-pyrrolo[2,3-d]pyrimidin-7-yl}-2,6-difluoro-phenyl)-(4-methyl-piperazin-1-yl)-methanone

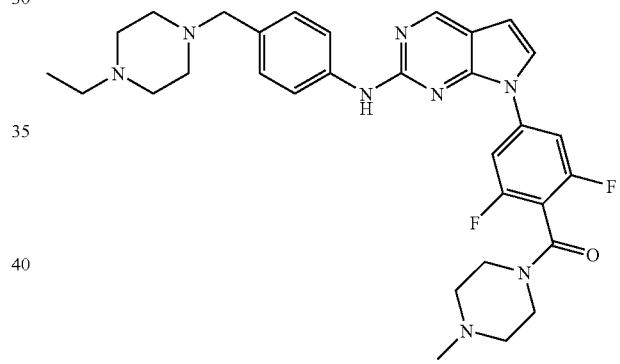

The compound is prepared analogous to Example 2. HPLC: $t_R$=0.93 min (Method A); MS-ES: (M+H)$^+$=575.

EXAMPLE 192

{2,6-Difluoro-4-[2-(4-morpholin-4-ylmethyl-phenylamino)-pyrrolo[2,3-d]pyrimidin-7-yl]-phenyl}-(4-methyl-piperazin-1-yl)-methanone

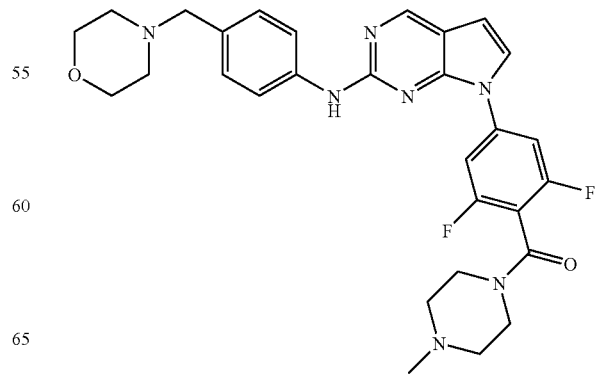

The compound is prepared analogous to Example 2.
HPLC: $t_R$=0.96 min (Method A); MS-ES: (M+H)$^+$=548.

EXAMPLE 193

(4-Isopropoxy-phenyl)-{7-[4-(1-morpholin-4-yl-ethyl)-phenyl]-7H-pyrrolo[2,3-d]pyrimidin-2-yl}-amine (racemic)

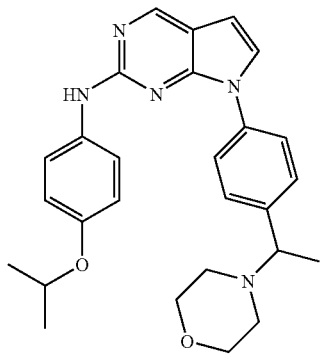 [SMILES: CC(C)Oc1ccc(Nc2ncc3ccn(-c4ccc(C(C)N5CCOCC5)cc4)c3n2)cc1]

The compound is prepared analogous to Example 2.
HPLC: $t_R$=1.28 min (Method A); MS-ES: (M+H)$^+$=458.

EXAMPLE 194

{7-[4-(1,1-Dioxido-thiomorpholin-4-ylmethyl)-3,5-difluoro-phenyl]-7H-pyrrolo[2,3-d]pyrimidin-2-yl}-(4-isopropoxy-phenyl)-amine

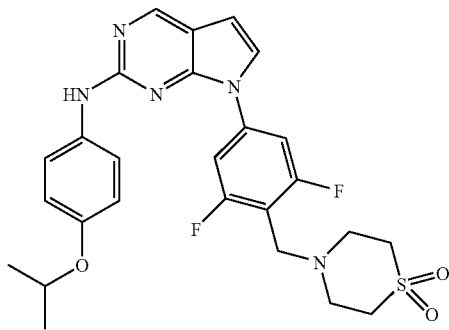 [SMILES: CC(C)Oc1ccc(Nc2ncc3ccn(-c4cc(F)c(CN5CCS(=O)(=O)CC5)c(F)c4)c3n2)cc1]

The compound is prepared analogous to Example 2.
HPLC: $t_R$=1.73 min (Method A); MS-ES: (M+H)$^+$=528.

EXAMPLE 195

{5-[7-(3,5-Difluoro-4-morpholin-4-ylmethyl-phenyl)-7H-pyrrolo[2,3-d]pyrimidin-2-ylamino]-pyridin-2-yl}-morpholin-4-yl-methanone

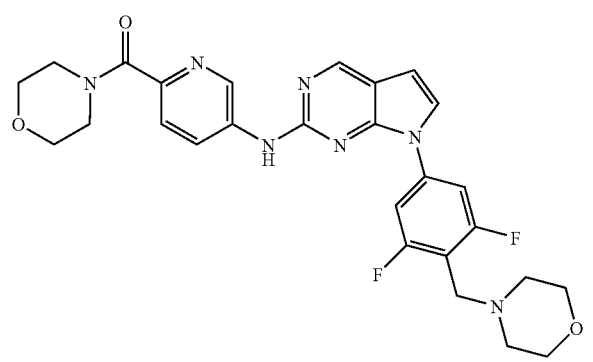 [SMILES: O=C(c1ccc(Nc2ncc3ccn(-c4cc(F)c(CN5CCOCC5)c(F)c4)c3n2)cn1)N1CCOCC1]

The compound is prepared analogous to Example 2.
HPLC: $t_R$=1.07 min (Method A); MS-ES: (M+H)$^+$=536.

EXAMPLE 196

[7-(3,5-Difluoro-4-morpholin-4-ylmethyl-phenyl)-7H-pyrrolo[2,3-d]pyrimidin-2-yl]-[4-(4-ethyl-piperazin-1-ylmethyl)-phenyl]-amine

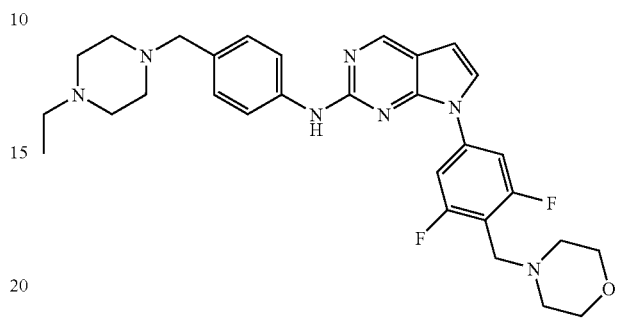

The compound is prepared analogous to Example 2.
HPLC: $t_R$=0.92 min (Method A); MS-ES: (M+H)$^+$=548.

EXAMPLE 197

[7-(3,5-Difluoro-4-morpholin-4-ylmethyl-phenyl)-7H-pyrrolo[2,3-d]pyrimidin-2-yl]-(4-morpholin-4-ylmethyl-phenyl)-amine

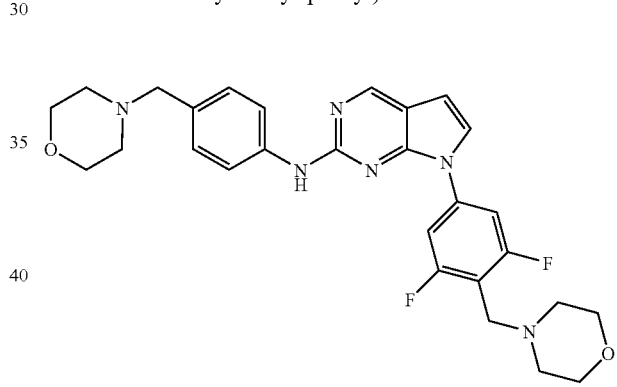

The compound is prepared analogous to Example 2.
HPLC: $t_R$=0.94 min (Method A); MS-ES: (M+H)$^+$=521.

EXAMPLE 198

[7-(3,5-Difluoro-4-morpholin-4-ylmethyl-phenyl)-7H-pyrrolo[2,3-d]pyrimidin-2-yl]-(3-morpholin-4-ylmethyl-phenyl)-amine

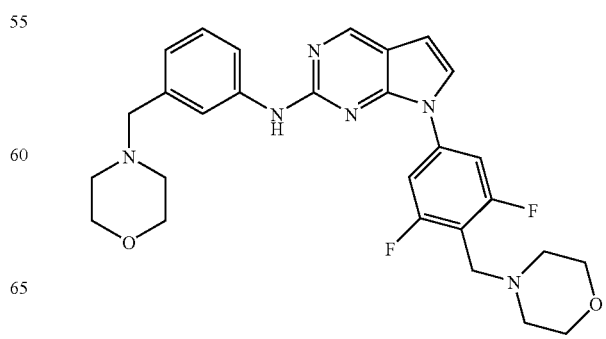

The compound is prepared analogous to Example 2.
HPLC: $t_R$=0.94 min (Method A); MS-ES: (M+H)$^+$=521.

EXAMPLE 199

[7-(3,5-Difluoro-4-morpholin-4-ylmethyl-phenyl)-7H-pyrrolo[2,3-d]pyrimidin-2-yl]-[3-(4-methyl-piperazin-1-ylmethyl)-phenyl]-amine

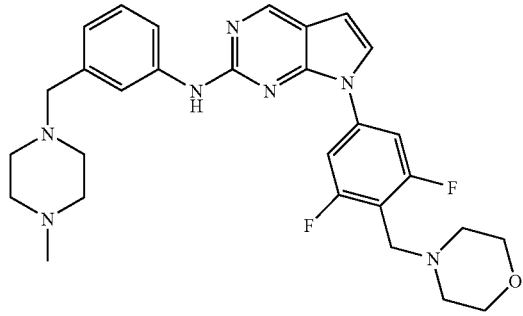 [SMILES: CN1CCN(Cc2cccc(Nc3ncc4ccn(-c5cc(F)c(CN6CCOCC6)c(F)c5)c4n3)c2)CC1]

The compound is prepared analogous to Example 2.
HPLC: $t_R$=0.93 min (Method A); MS-ES: (M+H)$^+$=534.

EXAMPLE 200

[7-(3,5-Difluoro-4-morpholin-4-ylmethyl-phenyl)-7H-pyrrolo[2,3-d]pyrimidin-2-yl]-[4-(4-methyl-piperazin-1-ylmethyl)-3-trifluoromethyl-phenyl]-amine

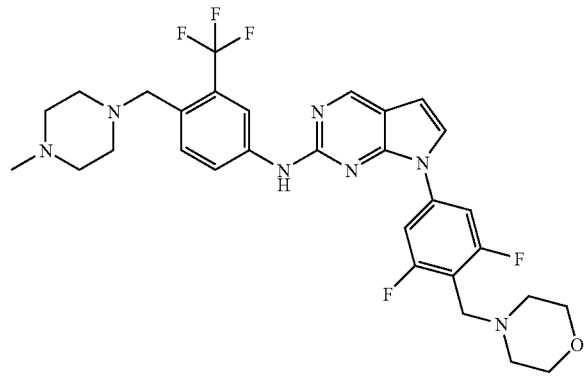 [SMILES: CN1CCN(Cc2ccc(Nc3ncc4ccn(-c5cc(F)c(CN6CCOCC6)c(F)c5)c4n3)cc2C(F)(F)F)CC1]

The compound is prepared analogous to Example 2.
HPLC: $t_R$=1.17 min (Method A); MS-ES: (M+H)$^+$=602.

EXAMPLE 201

{4-[7-(3.5-Difluoro-4-morpholin-4-ylmethyl-phenyl)-7H-pyrrolo[2,3-d]pyrimidin-2-ylamino]-2-trifluoromethyl-phenyl}-(4-methyl-piperazin-1-yl)-methanone

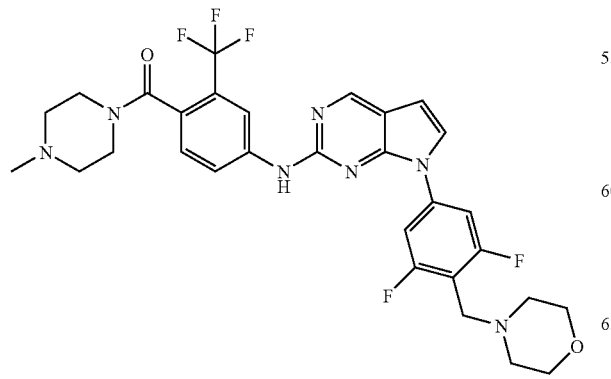

The compound is prepared analogous to Example 2.
HPLC: $t_R$=1.08 min (Method A); MS-ES: (M+H)$^+$=616.

EXAMPLE 202

{3-[7-(3 5-Difluoro-4-morpholin-4-ylmethyl-phenyl)-7H-pyrrolo[2,3-d]pyrimidin-2-ylamino]-phenyl}-morpholin-4-yl-methanone

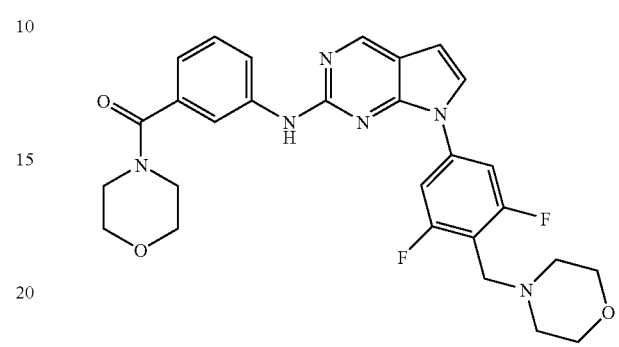

The compound is prepared analogous to Example 2.
HPLC: $t_R$=1.09 min (Method A); MS-ES: (M+H)$^+$=535.

EXAMPLE 203

{3-[7-(3,5-Difluoro-4-morpholin-4-ylmethyl-phenyl)-7H-pyrrolo[2,3-d]pyrimidin-2-ylamino]-phenyl}-(4-methyl-piperazin-1-yl)-methanone

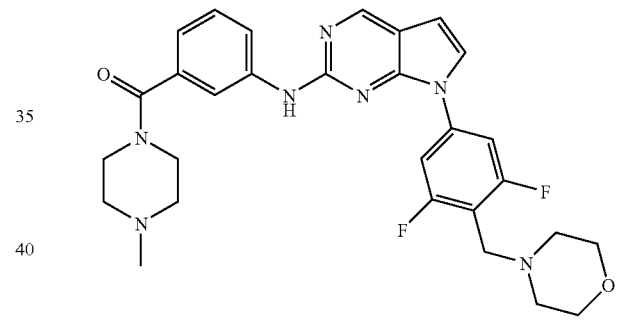

The compound is prepared analogous to Example 2.
HPLC: $t_R$=0.89 min (Method A); MS-ES: (M+H)$^+$=548.

EXAMPLE 204

(2,6-Difluoro-4-{2-[4-(4-methyl-piperazin-1-ylmethyl)-3-trifluoromethyl-phenylamino]-pyrrolo[2,3-d]pyrimidin-7-yl}-phenyl)-morpholin-4-yl-methanone

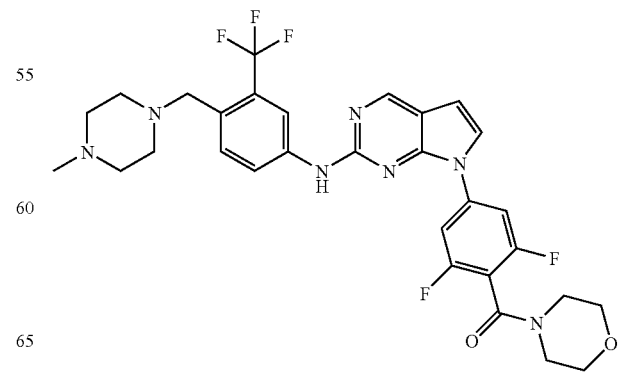

The compound is prepared analogous to Example 2.
HPLC: $t_R$=1.43 min (Method A); MS-ES: (M+H)$^+$=616.

EXAMPLE 205

(2,6-Difluoro-4-{2-[4-(4-methyl-piperazin-1-ylmethyl)-phenylamino]-pyrrolo[2,3-d]pyrimidin-7-yl}-phenyl)-morpholin-4-yl-methanone

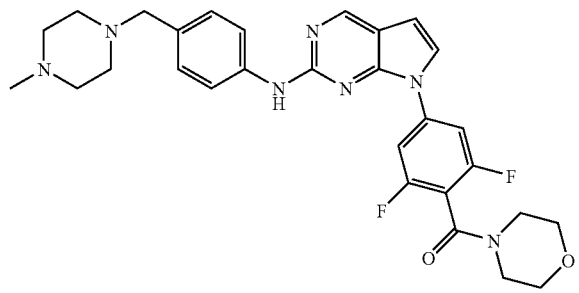 [SMILES: CN1CCN(Cc2ccc(Nc3ncc4ccn(-c5cc(F)c(C(=O)N6CCOCC6)c(F)c5)c4n3)cc2)CC1]

The compound is prepared analogous to Example 2.
HPLC: $t_R$=1.10 min (Method A); MS-ES: (M+H)$^+$=548.

EXAMPLE 206

{2,6-Difluoro-4-[2-(4-morpholin-4-ylmethyl-phenylamino)-pyrrolo[2,3-d]pyrimidin-7-yl]-phenyl}-morpholin-4-yl-methanone

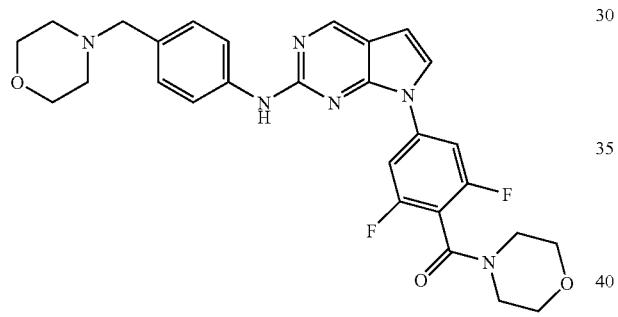

The compound is prepared analogous to Example 2.
HPLC: $t_R$=1.17 min (Method A); MS-ES: (M+H)$^+$=535.

EXAMPLE 207

(2,6-Difluoro-4-{2-[3-(4-methyl-piperazin-1-yl)-phenylamino]-pyrrolo[2,3-d]pyrimidin-7-yl}-phenyl)-morpholin-4-yl-methanone

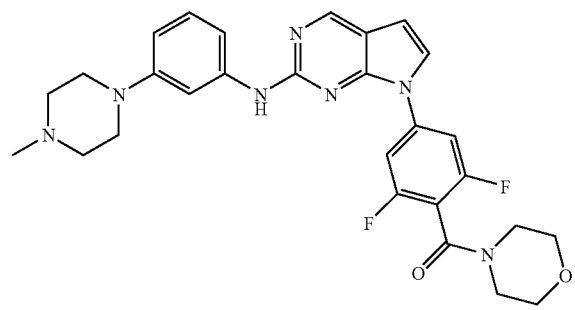 [SMILES: CN1CCN(c2cccc(Nc3ncc4ccn(-c5cc(F)c(C(=O)N6CCOCC6)c(F)c5)c4n3)c2)CC1]

The compound is prepared analogous to Example 2.
HPLC: $t_R$=1.20 min (Method A); MS-ES: (M+H)$^+$=534.

EXAMPLE 208

[7-(3,5-Difluoro-4-morpholin-4-ylmethyl-phenyl)-7H-pyrrolo[2,3-d]pyrimidin-2-yl]-phenyl-amine

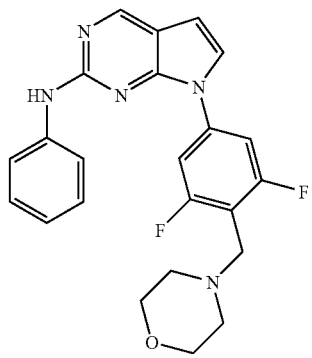 [SMILES: Fc1cc(-n2ccc3cnc(Nc4ccccc4)nc32)cc(F)c1CN1CCOCC1]

The compound is prepared analogous to Example 2.
HPLC: $t_R$=1.16 min (Method A); MS-ES: (M+H)$^+$=422.

EXAMPLE 209

[7-(3,5-Difluoro-4-morpholin-4-ylmethyl-phenyl)-7H-pyrrolo[2,3-d]pyrimidin-2-yl]-pyridin-2-yl-amine

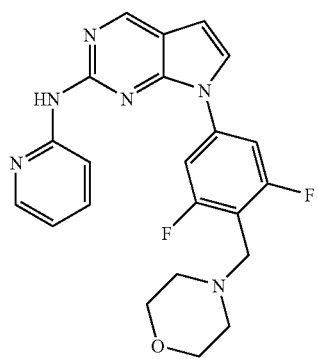 [SMILES: Fc1cc(-n2ccc3cnc(Nc4ccccn4)nc32)cc(F)c1CN1CCOCC1]

The compound is prepared analogous to Example 2.
HPLC: $t_R$=0.95 min (Method A); MS-ES: (M+H)$^+$=423.

EXAMPLE 210

[7-(3,5-Difluoro-4-morpholin-4-ylmethyl-phenyl)-7H-pyrrolo[2,3-d]pyrimidin-2-yl]-pyridin-3-yl-amine

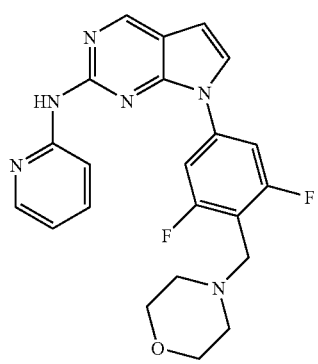 [SMILES: Fc1cc(-n2ccc3cnc(Nc4ccccn4)nc32)cc(F)c1CN1CCOCC1]

The compound is prepared analogous to Example 2. HPLC: $t_R$=0.93 min (Method A); MS-ES: (M+H)$^+$=423.

EXAMPLE 211

[7-(3,5-Difluoro-4-morpholin-4-ylmethyl-phenyl)-7H-pyrrolo[2,3-d]pyrimidin-2-yl]-pyridin-4-yl-amine

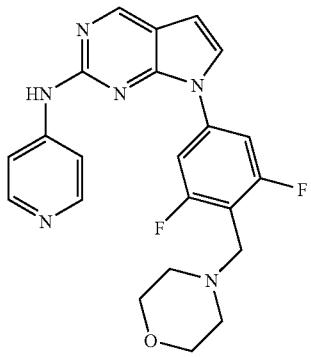 [SMILES: Fc1cc(-n2ccc3cnc(Nc4ccncc4)nc32)cc(F)c1CN1CCOCC1]

The compound is prepared analogous to Example 2. HPLC: $t_R$=0.96 min (Method A); MS-ES: (M+H)$^+$=423.

EXAMPLE 212

2-{4-[2-(3,4-Dimethyl-phenylamino)-pyrrolo[2,3-d]pyrimidin-7-yl]-phenyl}-1-[4-(2-hydroxy-ethyl)-piperazin-1-yl]-ethanone

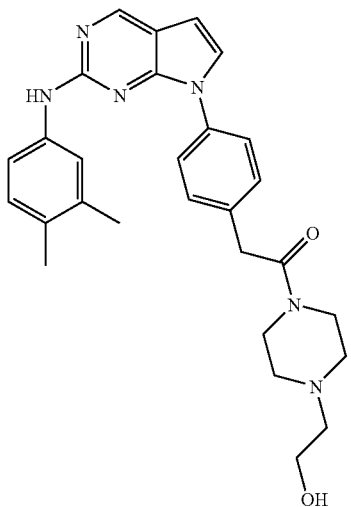 [SMILES: Cc1ccc(Nc2ncc3ccn(-c4ccc(CC(=O)N5CCN(CCO)CC5)cc4)c3n2)cc1C]

The compound is prepared analogous to Example 3 (scheme 3). HPLC: $t_R$=7.59 min. (Method B); MS-ES: (M+H)$^+$=485; TLC**: $R_f$=0.17

EXAMPLE 213

{2,6-Difluoro-4-[2-(4-fluoro-3-methyl-phenylamino)-pyrrolo[2,3-d]pyrimidin-7-yl]-phenyl}-morpholin-4-yl-methanone

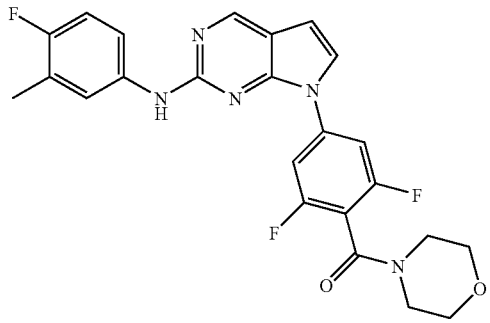 [SMILES: Cc1cc(Nc2ncc3ccn(-c4cc(F)c(C(=O)N5CCOCC5)c(F)c4)c3n2)ccc1F]

The compound is prepared analogous to Example 3. HPLC: $t_R$=1.78 min (Method A); MS-ES: (M+H)$^+$=468.

EXAMPLE 214

[2,6-Difluoro-4-(2-phenylamino-pyrrolo[2,3-d]pyrimidin-7-yl)-phenyl]-morpholin-4-yl-methanone

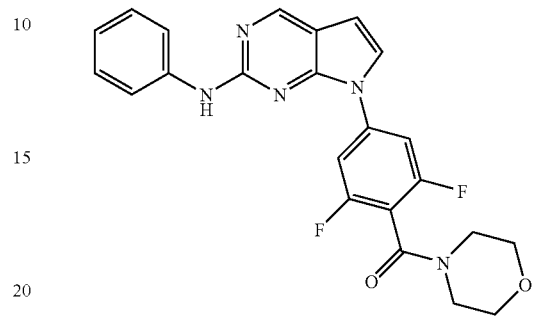

The compound is prepared analogous to Example 2. HPLC: $t_R$=1.60 min (Method A); MS-ES: (M+H)$^+$=436.

EXAMPLE 215

{2,6-Difluoro-4-[2-(pyridin-2-ylamino)-pyrrolo[2,3-d]pyrimidin-7-yl]-phenyl}-morpholin-4-yl-methanone

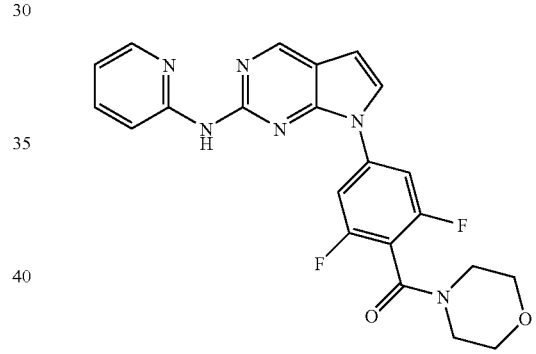

The compound is prepared analogous to Example 2. HPLC: $t_R$=1.24 min (Method A); MS-ES: (M+H)$^+$=437.

EXAMPLE 216

{2,6-Difluoro-4-[2-(pyridin-3-ylamino)-pyrrolo[2,3-d]pyrimidin-7-yl]-phenyl}-morpholin-4-yl-methanone

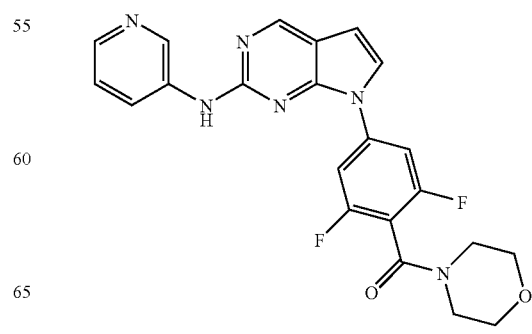

The compound is prepared analogous to Example 2.
HPLC: $t_R$=1.22 min (Method A); MS-ES: (M+H)$^+$=437.

EXAMPLE 217

{2,6-Difluoro-4-[2-(pyridin-4-ylamino)-pyrrolo[2,3-d]pyrimidin-7-yl]-phenyl}-morpholin-4-yl-methanone

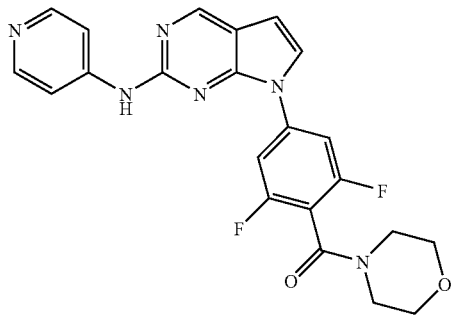 [SMILES: O=C(c1c(F)cc(-n2ccc3cnc(Nc4ccncc4)nc32)cc1F)N1CCOCC1]

The compound is prepared analogous to Example 2.
HPLC: $t_R$=1.24 min (Method A); MS-ES: (M+H)$^+$=437.

EXAMPLE 218

{2,6-Difluoro-4-[2-(pyrimidin-4-ylamino)-pyrrolo[2,3-d]pyrimidin-7-yl]-phenyl}-morpholin-4-yl-methanone

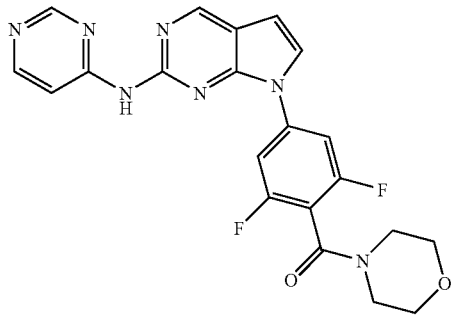 [SMILES: O=C(c1c(F)cc(-n2ccc3cnc(Nc4ccncn4)nc32)cc1F)N1CCOCC1]

The compound is prepared analogous to Example 2.
HPLC: $t_R$=1.15 min (Method A); MS-ES: (M+H)$^+$=438.

EXAMPLE 219

{2,6-Difluoro-4-[2-(6-methyl-pyridin-3-ylamino)-pyrrolo[2,3-d]pyrimidin-7-yl]-phenyl}-morpholin-4-yl-methanone

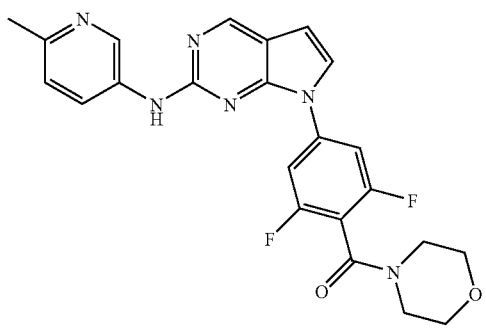 [SMILES: Cc1ccc(Nc2ncc3ccn(-c4cc(F)c(C(=O)N5CCOCC5)c(F)c4)c3n2)cn1]

The compound is prepared analogous to Example 2.
HPLC: $t_R$=1.26 min (Method A); MS-ES: (M+H)$^+$=451.

EXAMPLE 220

{2,6-Difluoro-4-[2-(4-fluoro-3-methyl-phenylamino)-pyrrolo[2,3-d]pyrimidin-7-yl]-phenyl}-morpholin-4-yl-methanone

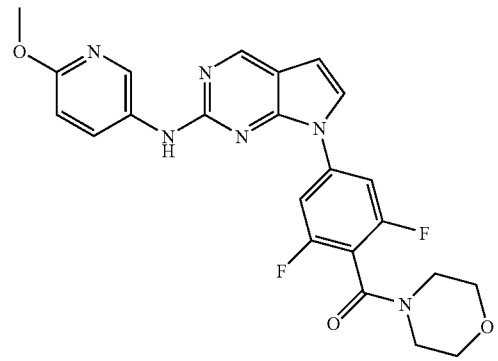 [SMILES: COc1ccc(Nc2ncc3ccn(-c4cc(F)c(C(=O)N5CCOCC5)c(F)c4)c3n2)cn1]

The compound is prepared analogous to Example 2.
HPLC: $t_R$=1.39 min (Method A); MS-ES: (M+H)$^+$=467.

EXAMPLE 221

{2,6-Difluoro-4-[2-(4-fluoro-3-methyl-phenylamino)-pyrrolo[2,3-d]pyrimidin-7-yl]-phenyl}-morpholin-4-yl-methanone

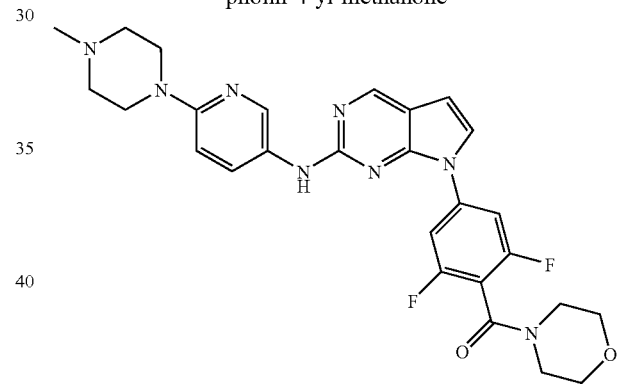

The compound is prepared analogous to Example 2.
HPLC: $t_R$=1.05 min (Method A); MS-ES: (M+H)$^+$=535.

EXAMPLE 222

{4-[2-(5,6-Dimethyl-pyridin-2-ylamino)-pyrrolo[2,3-d]pyrimidin-7-yl]-2-fluoro-phenyl}-morpholin-4-yl-methanone

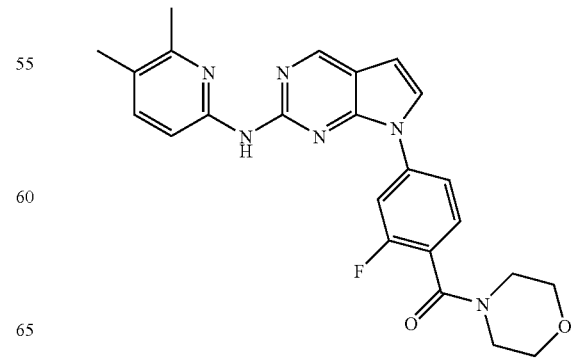

The compound is prepared analogous to Example 2.
HPLC: $t_R$=1.33 min (Method A); MS-ES: (M+H)⁺=447.

EXAMPLE 223

{2,6-Difluoro-4-[2-(4-fluoro-3-methyl-phenylamino)-pyrrolo[2,3-d]pyrimidin-7-yl]-phenyl}-morpholin-4-yl-methanone

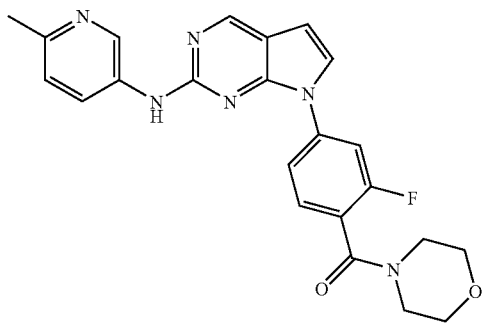 [SMILES: Cc1ccc(Nc2ncc3ccn(-c4ccc(C(=O)N5CCOCC5)c(F)c4)c3n2)cn1]

The compound is prepared analogous to Example 2.
HPLC: $t_R$=1.21 min (Method A); MS-ES: (M+H)⁺=433.

EXAMPLE 224

{2-Fluoro-4-[2-(pyridin-3-ylamino)-pyrrolo[2,3-d]pyrimidin-7-yl]-phenyl}-morpholin-4-yl-methanone

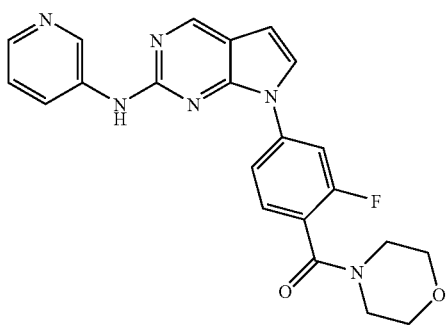 [SMILES: O=C(c1ccc(-n2ccc3cnc(Nc4cccnc4)nc32)cc1F)N1CCOCC1]

The compound is prepared analogous to Example 2.
HPLC: $t_R$=1.17 min (Method A); MS-ES: (M+H)⁺=419.

EXAMPLE 225

{2-Fluoro-4-[2-(6-methoxy-pyridin-3-ylamino)-pyrrolo[2,3-d]pyrimidin-7-yl]-phenyl}-morpholin-4-yl-methanone

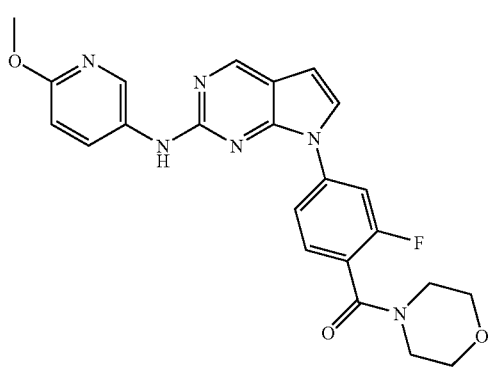 [SMILES: COc1ccc(Nc2ncc3ccn(-c4ccc(C(=O)N5CCOCC5)c(F)c4)c3n2)cn1]

The compound is prepared analogous to Example 2.
HPLC: $t_R$=1.29 min (Method A); MS-ES: (M+H)⁺=449.

EXAMPLE 226

{2-Fluoro-4-[2-(6-isopropoxy-pyridin-3-ylamino)-pyrrolo[2,3-d]pyrimidin-7-yl]-phenyl}-morpholin-4-yl-methanone

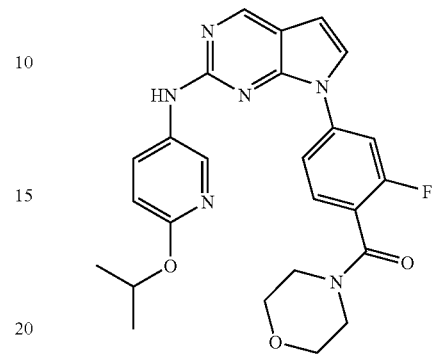

The compound is prepared analogous to Example 2.
HPLC: $t_R$=1.52 min (Method A); MS-ES: (M+H)⁺=477.

EXAMPLE 227

{2-Fluoro-4-[2-(6-trifluoromethyl-pyridin-3-ylamino)-pyrrolo[2,3-d]pyrimidin-7-yl]-phenyl}-morpholin-4-yl-methanone

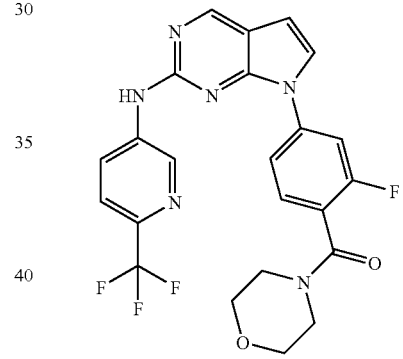

The compound is prepared analogous to Example 2.
HPLC: $t_R$=1.91 min (Method A); MS-ES: (M+H)⁺=487.

EXAMPLE 228

5-{7-[3-Fluoro-4-(morpholine-4-carbonyl)-phenyl]-7H-pyrrolo[2,3-d]pyrimidin-2-ylamino}-pyridine-2-carbonitrile

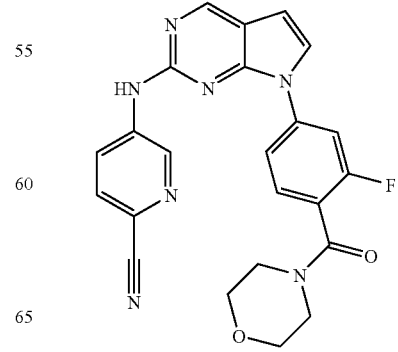

The compound is prepared analogous to Example 2.
HPLC: $t_R$=1.71 min (Method A); MS-ES: (M+H)$^+$=444.

EXAMPLE 229

[7-(4-Methanesulfonyl-phenyl)-7H-pyrrolo[2,3-d]pyrimidin-2-yl]-(6-methyl-pyridin-3-yl)-amine

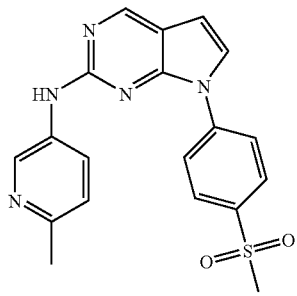 [SMILES: Cc1ccc(Nc2ncc3ccn(-c4ccc(S(C)(=O)=O)cc4)c3n2)cn1]

The compound is prepared analogous to Example 2.
HPLC: $t_R$=1.15 min (Method A); MS-ES: (M+H)$^+$=380.

EXAMPLE 230

[7-(4-Methanesulfonyl-phenyl)-7H-pyrrolo[2,3-d]pyrimidin-2-yl]-(6-methoxy-pyridin-3-yl)-amine

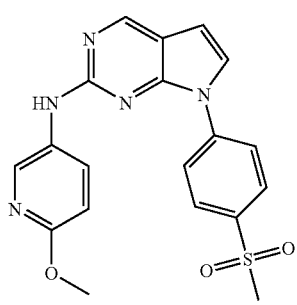 [SMILES: COc1ccc(Nc2ncc3ccn(-c4ccc(S(C)(=O)=O)cc4)c3n2)cn1]

The compound is prepared analogous to Example 2.
HPLC: $t_R$=1.26 min (Method A); MS-ES: (M+H)$^+$=396.

EXAMPLE 231

{4-[2-(4-Isopropoxy-phenylamino)-pyrrolo[2,3-d]pyrimidin-7-yl]-phenyl}-morpholin-4-yl-methanone

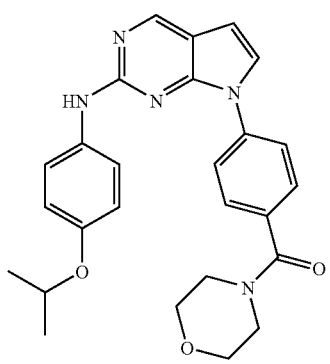 [SMILES: CC(C)Oc1ccc(Nc2ncc3ccn(-c4ccc(C(=O)N5CCOCC5)cc4)c3n2)cc1]

The compound is prepared analogous to Example 2.
HPLC: $t_R$=1.57 min (Method A); MS-ES: (M+H)$^+$=458.

EXAMPLE 232

{4-[2-(6-Isopropoxy-pyridin-3-ylamino)-pyrrolo[2,3-d]pyrimidin-7-yl-phenyl}-morpholin-4-yl-methanone

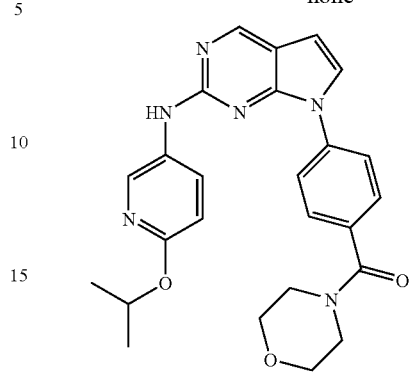

The compound is prepared analogous to Example 2.
HPLC: $t_R$=1.42 min (Method A); MS-ES: (M+H)$^+$=459.

EXAMPLE 233

{4-[2-(3-Fluoro-4-methyl-phenylamino)-pyrrolo[2,3-d]pyrimidin-7-yl]-phenyl}-morpholin-4-yl-methanone

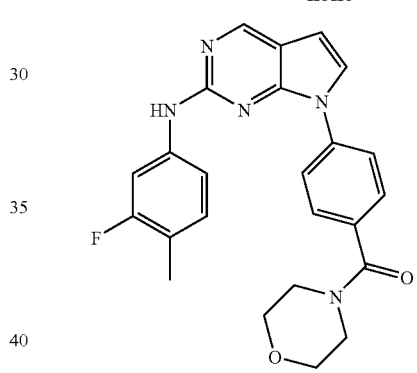

The compound is prepared analogous to Example 2.
HPLC: $t_R$=1.64 min (Method A); MS-ES: (M+H)$^+$=432.

EXAMPLE 234

{4-[2-(6-Methoxy-pyridin-3-ylamino)-pyrrolo[2,3-d]pyrimidin-7-yl]-phenyl}-morpholin-4-yl-methanone

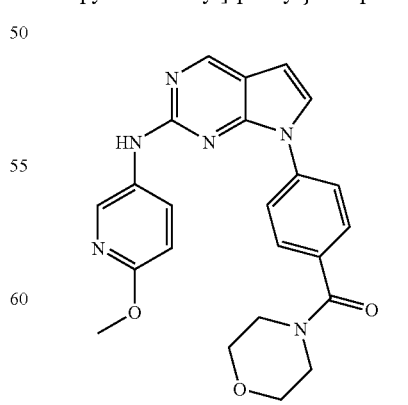

The compound is prepared analogous to Example 2.
HPLC: $t_R$=1.20 min (Method A); MS-ES: (M+H)$^+$=431.

EXAMPLE 235

5-{7-[4-(Morpholine-4-carbonyl)-phenyl]-7H-pyrrolo[2,3-d]pyrimidin-2-ylamino}-pyridine-2-carbonitrile

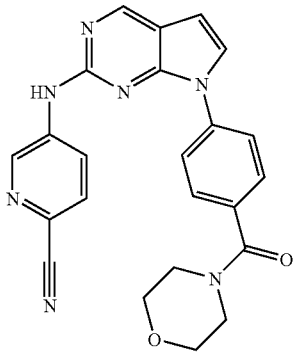 [SMILES: N#Cc1ccc(Nc2ncc3ccn(-c4ccc(C(=O)N5CCOCC5)cc4)c3n2)cn1]

The compound is prepared analogous to Example 2.
HPLC: $t_R$=1.55 min (Method A); MS-ES: (M+H)$^+$=426.

EXAMPLE 236

Morpholin-4-yl-{4-[2-(6-trifluoromethyl-pyridin-3-ylamino)-pyrrolo[2,3-d]pyrimidin-7-yl]-phenyl}-methanone

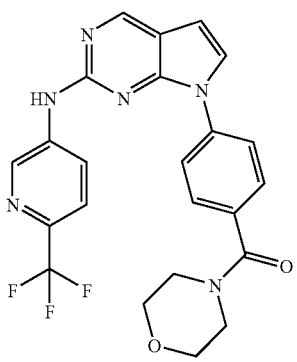 [SMILES: O=C(c1ccc(-n2ccc3cnc(Nc4ccc(C(F)(F)F)nc4)nc32)cc1)N1CCOCC1]

The compound is prepared analogous to Example 2.
HPLC: $t_R$=1.76 min (Method A); MS-ES: (M+H)$^+$=469.

EXAMPLE 237

4-{7-[4-(Morpholine-4-carbonyl)-phenyl]-7H-pyrrolo[2,3-d]pyrimidin-2-ylamino}-benzonitrile

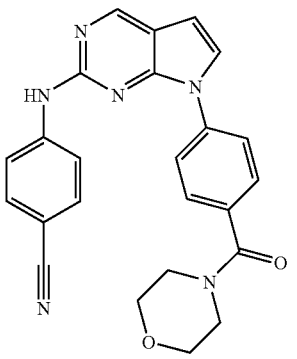 [SMILES: N#Cc1ccc(Nc2ncc3ccn(-c4ccc(C(=O)N5CCOCC5)cc4)c3n2)cc1]

The compound is prepared analogous to Example 2.
HPLC: $t_R$=1.58 min (Method A); MS-ES: (M+H)$^+$=425.

EXAMPLE 238

{4-[2-(6-Methyl-pyridin-3-ylamino)-pyrrolo[2,3-d]pyrimidin-7-yl]-phenyl}-morpholin-4-yl-methanone

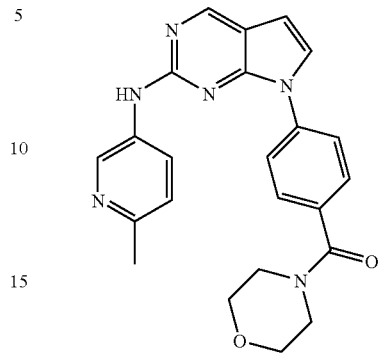

The compound is prepared analogous to Example 2.
HPLC: $t_R$=1.13 min (Method A); MS-ES: (M+H)$^+$=415.

EXAMPLE 239

{4-[2-(4-Methoxymethyl-phenylamino)-pyrrolo[2,3-d]pyrimidin-7-yl]-phenyl}-morpholin-4-yl-methanone

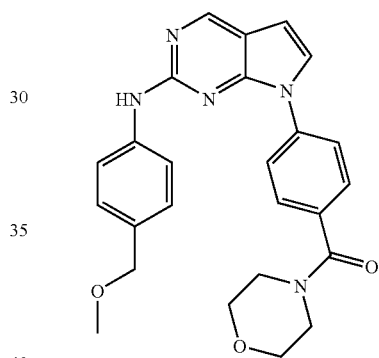

The compound is prepared analogous to Example 2.
HPLC: $t_R$=1.36 min (Method A); MS-ES: (M+H)$^+$=444.

EXAMPLE 240

{4-[2-(3-Methoxy-4-methyl-phenylamino)-pyrrolo[2,3-d]pyrimidin-7-yl]-phenyl}-morpholin-4-yl-methanone

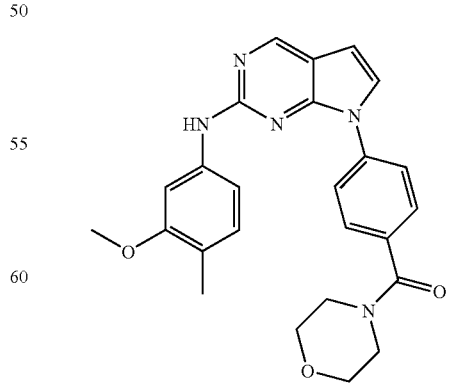

The compound is prepared analogous to Example 2.
HPLC: $t_R$=1.57 min (Method A); MS-ES: (M+H)$^+$=444.

EXAMPLE 241

{2,6-Difluoro-4-[2-(1-methyl-1H-pyrazol-4-ylamino)-pyrrolo[2,3-d]pyrimidin-7-yl]-phenyl}-morpholin-4-yl-methanone

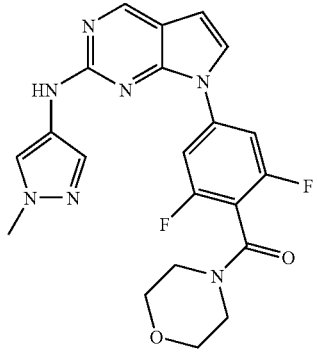 [SMILES: Cn1cc(Nc2ncc3ccn(-c4cc(F)c(C(=O)N5CCOCC5)c(F)c4)c3n2)cn1]

The compound is prepared analogous to Example 2. HPLC: $t_R$=1.18 min (Method A); MS-ES: (M+H)$^+$=440.

EXAMPLE 242

{2,6-Difluoro-4-[2-(5-methyl-pyridin-3-ylamino)-pyrrolo[2,3-d]pyrimidin-7-yl]-phenyl}-morpholin-4-yl-methanone

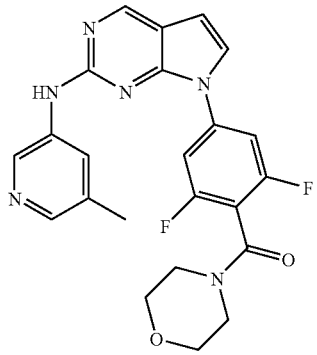 [SMILES: Cc1cncc(Nc2ncc3ccn(-c4cc(F)c(C(=O)N5CCOCC5)c(F)c4)c3n2)c1]

The compound is prepared analogous to Example 2. HPLC: $t_R$=1.27 min (Method A); MS-ES: (M+H)$^+$=451.

EXAMPLE 243

(2,6-Difluoro-4-{2-[2-(4-methyl-piperazin-1-yl)-pyridin-4-ylamino]-pyrrolo[2,3-d]pyrimidin-7-yl}-phenyl)-morpholin-4-yl-methanone

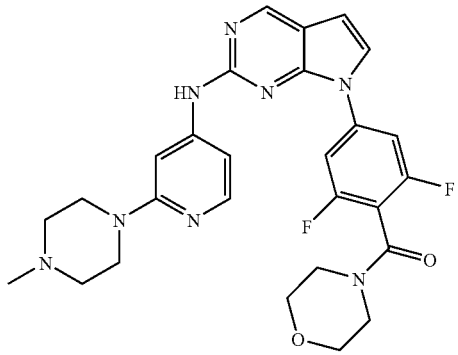 [SMILES: CN1CCN(c2cc(Nc3ncc4ccn(-c5cc(F)c(C(=O)N6CCOCC6)c(F)c5)c4n3)ccn2)CC1]

The compound is prepared analogous to Example 2. HPLC: $t_R$=1.13 min (Method A); MS-ES: (M+H)$^+$=535.

EXAMPLE 244

[7-(3-Fluoro-4-methanesulfonyl-phenyl)-7H-pyrrolo[2,3-d]pyrimidin-2-yl]-[4-(4-methyl-piperazin-1-ylmethyl)-phenyl]-amine

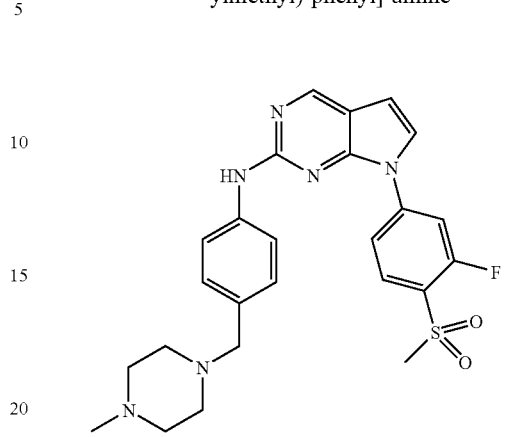

The compound is prepared analogous to Example 2. MS-ES: (M+H)$^+$=495.

EXAMPLE 245

(2,6-Difluoro-4-{2-[3-(4-methyl-piperazin-1-ylmethyl)-phenylamino]-pyrrolo[2,3-d]pyrimidin-7-yl}-phenyl)-morpholin-4-yl-methanone

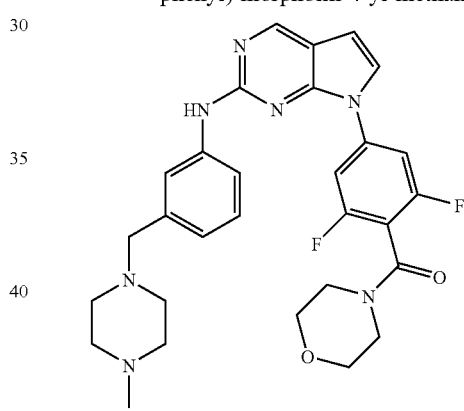

The compound is prepared analogous to Example 2. HPLC: $t_R$=1.13 min (Method A); MS-ES: (M+H)$^+$=548.

EXAMPLE 246

{2,6-Difluoro-4-[2-(thiazol-2-ylamino)-pyrrolo[2,3-d]pyrimidin-7-yl]-phenyl}-morpholin-4-yl-methanone

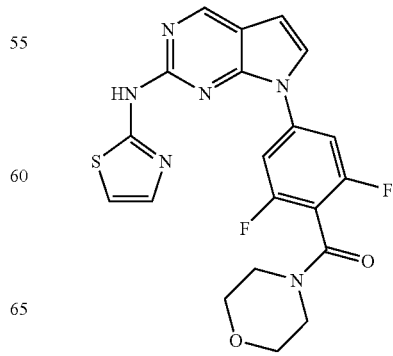

The compound is prepared analogous to Example 2.
HPLC: $t_R$=1.26 min (Method A); MS-ES: (M+H)⁺=443.

EXAMPLE 247

[7-(3,5-Difluoro-4-morpholin-4-ylmethyl-phenyl)-7H-pyrrolo[2,3-d]pyrimidin-2-yl]-(1-methyl-1H-pyrazol-4-yl)-amine

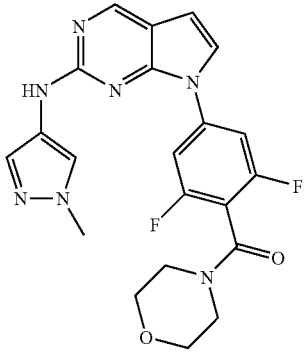 [SMILES: Cn1cc(Nc2ncc3ccn(-c4cc(F)c(C(=O)N5CCOCC5)c(F)c4)c3n2)cn1]

The compound is prepared analogous to Example 2.
HPLC: $t_R$=0.85 min (Method A); MS-ES: (M+H)⁺=426.

EXAMPLE 248

{5-[7-(3,5-Difluoro-4-morpholin-4-ylmethyl-phenyl)-7H-pyrrolo[2,3-d]pyrimidin-2-ylamino]-pyridin-3-yl}-morpholin-4-yl-methanone

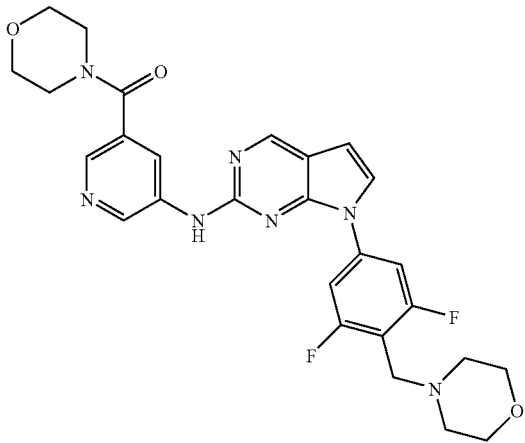 [SMILES: O=C(c1cncc(Nc2ncc3ccn(-c4cc(F)c(CN5CCOCC5)c(F)c4)c3n2)c1)N1CCOCC1]

The compound is prepared analogous to Example 2.
HPLC: $t_R$=0.97 min (Method A); MS-ES: (M+H)⁺=536.

EXAMPLE 249

(1,1-Dioxido-thiomorpholin-4-yl)-{4-[2-(6-methyl-pyridin-3-ylamino)-pyrrolo[2,3-d]pyrimidin-7-yl]-phenyl}-methanone

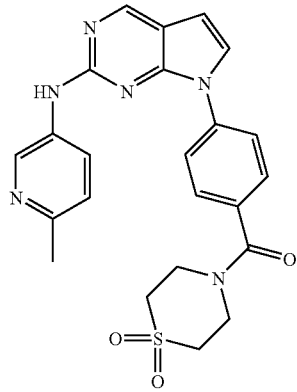 [SMILES: Cc1ccc(Nc2ncc3ccn(-c4ccc(C(=O)N5CCS(=O)(=O)CC5)cc4)c3n2)cn1]

The compound is prepared analogous to Example 2.
HPLC: $t_R$=1.09 min (Method A); MS-ES: (M+H)⁺=463.

EXAMPLE 250

(1,1-Dioxido-thiomorpholin-4-yl)-{4-[2-(6-methoxy-pyridin-3-ylamino)-pyrrolo[2,3-d]pyrimidin-7-yl]-phenyl}-methanone

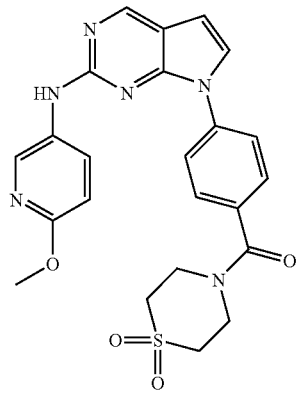 [SMILES: COc1ccc(Nc2ncc3ccn(-c4ccc(C(=O)N5CCS(=O)(=O)CC5)cc4)c3n2)cn1]

The compound is prepared analogous to Example 2.
HPLC: $t_R$=1.15 min (Method A); MS-ES: (M+H)⁺=479.

The compound is prepared analogous to Example 2.
HPLC: $t_R$=0.90 min (Method A); MS-ES: (M+H)⁺=470.

EXAMPLE 251

(2,6-Difluoro-4-{2-[1-(2-methoxy-ethyl)-1H-pyrazol-4-ylamino]-pyrrolo[2,3-d]pyrimidin-7-yl}-phenyl)-morpholin-4-yl-methanone

EXAMPLE 253

{4-[2-(1-Methyl-1H-pyrazol-4-ylamino)-pyrrolo[2,3-d]pyrimidin-7-yl]-phenyl}-morpholin-4-yl-methanone

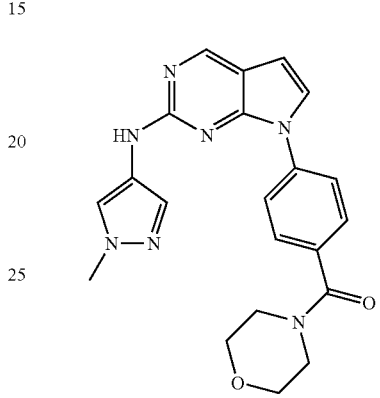

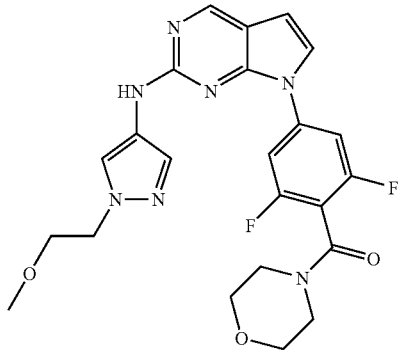 [SMILES: COCCn1cc(Nc2ncc3ccn(-c4cc(F)c(C(=O)N5CCOCC5)c(F)c4)c3n2)cn1]

The compound is prepared analogous to Example 2.
HPLC: $t_R$=1.05 min (Method A); MS-ES: (M+H)⁺=404.

The compound is prepared analogous to Example 2.
HPLC: $t_R$=1.23 min (Method A); MS-ES: (M+H)⁺=484.

EXAMPLE 254

7-(3,5-Difluoro-4-morpholin-4-ylmethyl-phenyl)-7H-pyrrolo[2,3-d]pyrimidin-2-yl]-[4-(cis-3,5-dimethyl-piperazin-1-ylmethyl)-phenyl]-amine

EXAMPLE 252

[7-(3,5-Difluoro-4-morpholin-4-ylmethyl-phenyl)-7H-pyrrolo[2,3-d]pyrimidin-2-yl]-[1-(2-methoxy-ethyl)-1H-pyrazol-4-yl]-amine

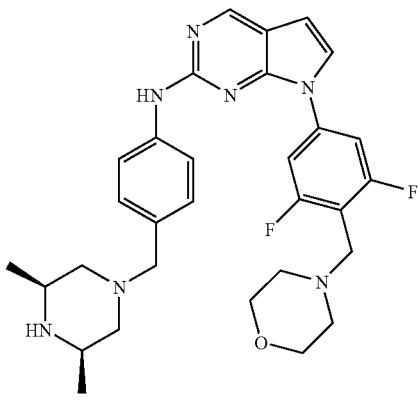

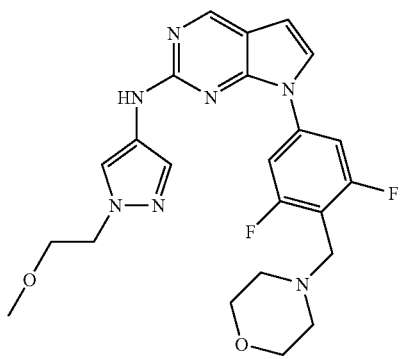 [SMILES: COCCn1cc(Nc2ncc3ccn(-c4cc(F)c(CN5CCOCC5)c(F)c4)c3n2)cn1]

155

The compound is prepared analogous to Example 2.
HPLC: $t_R$=0.92 min (Method A); MS-ES: (M+H)$^+$=548.

EXAMPLE 255

(4-{2-[4-(cis-3,5-Dimethyl-piperazin-1-ylmethyl)-phenylamino]-pyrrolo[2,3-d]pyrimidin-7-yl}-2,6-difluoro-phenyl)-morpholin-4-yl-methanone

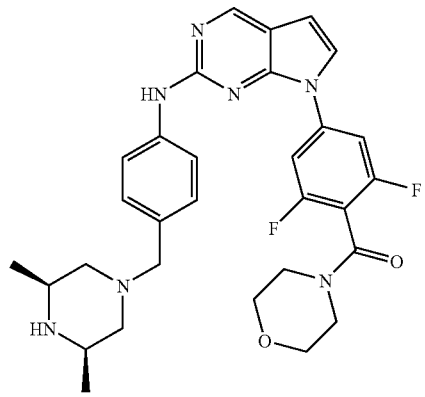 [SMILES: C[C@@H]1CN(Cc2ccc(Nc3ncc4ccn(-c5cc(F)c(C(=O)N6CCOCC6)c(F)c5)c4n3)cc2)C[C@H](C)N1]

The compound is prepared analogous to Example 2.
HPLC: $t_R$=1.11 min (Method A); MS-ES: (M+H)$^+$=562.

EXAMPLE 256

4-(4,7-Diaza-spiro[2.5]oct-7-ylmethyl)-phenyl]-[7-(3,5-difluoro-4-morpholin-4-ylmethyl-phenyl)-7H-pyrrolo[2,3-d]pyrimidin-2-yl]-amine

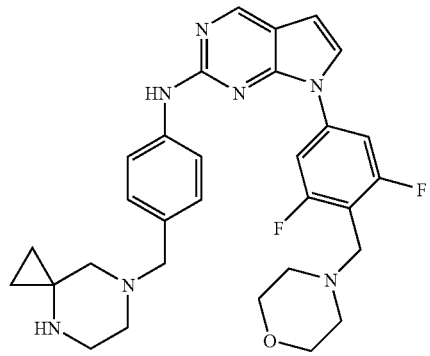 [SMILES: Fc1cc(-n2ccc3cnc(Nc4ccc(CN5CCNC6(CC6)C5)cc4)nc32)cc(F)c1CN1CCOCC1]

156

The compound is prepared analogous to Example 2.
HPLC: $t_R$=0.90 min (Method A); MS-ES: (M+H)$^+$=546.

EXAMPLE 257

4-{2-[4-(4,7-Diaza-spiro[2.5]oct-7-yl methyl)-phenylamino]-pyrrolo[2,3-d]pyrimidin-7-yl}-2,6-difluoro-phenyl)-morpholin-4-yl-methanone

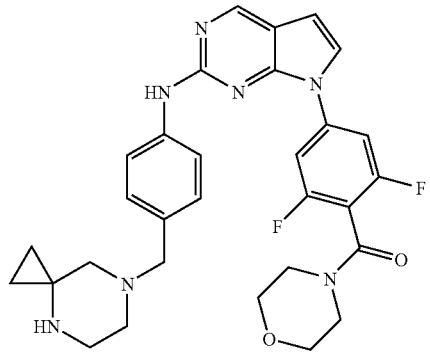 [SMILES: O=C(c1c(F)cc(-n2ccc3cnc(Nc4ccc(CN5CCNC6(CC6)C5)cc4)nc32)cc1F)N1CCOCC1]

The compound is prepared analogous to Example 2.
HPLC: $t_R$=1.08 min (Method A); MS-ES: (M+H)$^+$=560.

EXAMPLE 258

4-{4-[7-(3,5-Difluoro-4-morpholin-4-ylmethyl-phenyl)-7H-pyrrolo[2,3-d]pyrimidin-2-ylamino]-benzyl}-piperazin-2-one

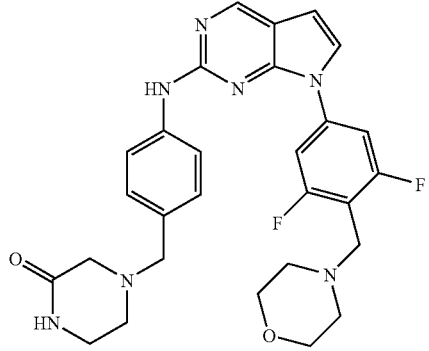 [SMILES: O=C1CN(Cc2ccc(Nc3ncc4ccn(-c5cc(F)c(CN6CCOCC6)c(F)c5)c4n3)cc2)CCN1]

The compound is prepared analogous to Example 2.
HPLC: $t_R$=0.87 min (Method A); MS-ES: (M+H)$^+$=534.

EXAMPLE 259

4-(4-{7-[3,5-Difluoro-4-(morpholine-4-carbonyl)-phenyl]-7H-pyrrolo[2,3-d]pyrimidin-2-ylamino}-benzyl)-piperazin-2-one

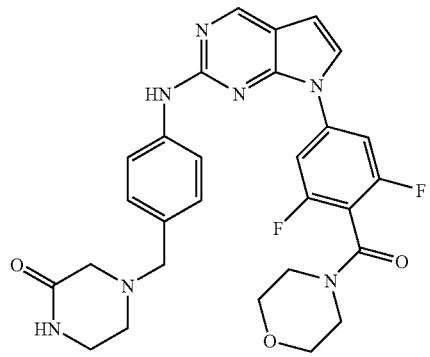 [SMILES: O=C1CN(Cc2ccc(Nc3ncc4ccn(-c5cc(F)c(C(=O)N6CCOCC6)c(F)c5)c4n3)cc2)CCN1]

The compound is prepared analogous to Example 2.
HPLC: $t_R$=1.11 min (Method A); MS-ES: (M+H)$^+$=548.

EXAMPLE 260

[7-(3,5-Difluoro-4-morpholin-4-ylmethyl-phenyl)-7H-pyrrolo[2,3-d]pyrimidin-2-yl]-[4-((2S,5R)-2,5-dimethyl-piperazin-1-ylmethyl)-phenyl]-amine (racemic)

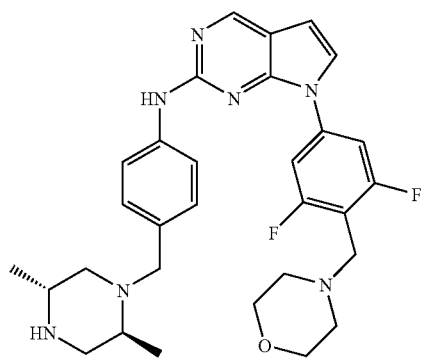 [SMILES: C[C@@H]1CN(Cc2ccc(Nc3ncc4ccn(-c5cc(F)c(CN6CCOCC6)c(F)c5)c4n3)cc2)[C@@H](C)CN1]

The compound is prepared analogous to Example 2.
HPLC: $t_R$=0.93 min (Method A); MS-ES: (M+H)$^+$=548.

EXAMPLE 261

(4-{2-[4-((2S,5R)-2,5-Dimethyl-piperazin-1-ylmethyl)-phenylamino]-pyrrolo[2,3-d]pyrimidin-7-yl}-2,6-difluoro-phenyl)-morpholin-4-yl-methanone (racemic)

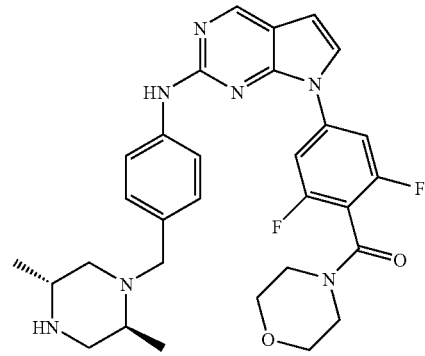 [SMILES: C[C@@H]1CN(Cc2ccc(Nc3ncc4ccn(-c5cc(F)c(C(=O)N6CCOCC6)c(F)c5)c4n3)cc2)[C@@H](C)CN1]

The compound is prepared analogous to Example 2.
HPLC: $t_R$=1.12 min (Method A); MS-ES: (M+H)$^+$=562.

EXAMPLE 262

{2,6-Difluoro-4-[2-(6-piperazin-1-yl-pyridin-3-ylamino)-pyrrolo[2,3-d]pyrimidin-7-yl]-phenyl}-morpholin-4-yl-methanone

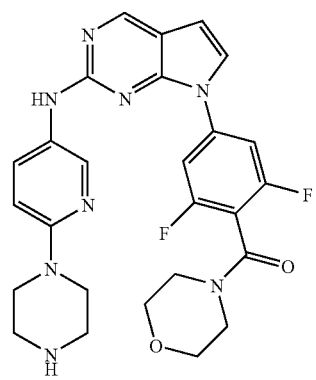 [SMILES: O=C(c1c(F)cc(-n2ccc3cnc(Nc4ccc(N5CCNCC5)nc4)nc32)cc1F)N1CCOCC1]

The compound is prepared analogous to Example 2, using a Boc-protected piperazine derivative in Step 2.2, Final deprotection is achieved with TFA in CH$_2$Cl$_2$ at rt. MS-ES: (M+H)$^+$=521.

EXAMPLE 263

[7-(3,5-Difluoro-4-morpholin-4-ylmethyl-phenyl)-7H-pyrrolo[2,3-d]pyrimidin-2-yl]-(6-piperazin-1-yl-pyridin-3-yl)-amine

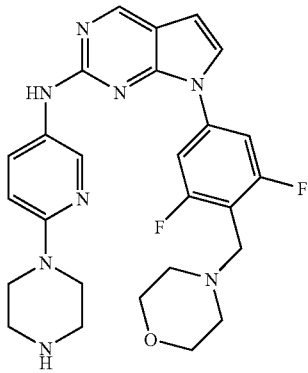 [SMILES: Fc1cc(-n2ccc3cnc(Nc4ccc(N5CCNCC5)nc4)nc32)cc(F)c1CN1CCOCC1]

The compound is prepared analogous to Example 2, using a Boc-protected piperazine derivative in Step 2.2, Final deprotection is achieved with TFA in CH$_2$Cl$_2$ at rt. MS-ES: (M+H)$^+$=507.

EXAMPLE 264

[2,6-Difluoro-4-(2-{6-[4-(2-hydroxy-ethyl)-piperazin-1-yl]-pyridin-3-ylamino}-pyrrolo[2,3-d]pyrimidin-7-yl)-phenyl]-morpholin-4-yl-methanone

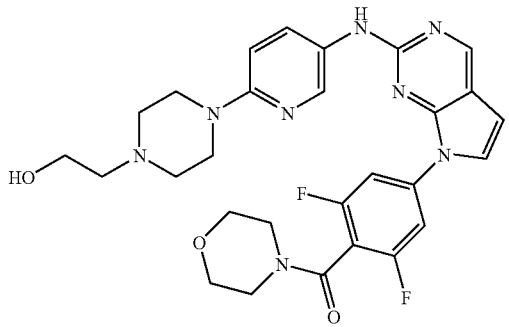 [SMILES: O=C(c1c(F)cc(-n2ccc3cnc(Nc4ccc(N5CCN(CCO)CC5)nc4)nc32)cc1F)N1CCOCC1]

The compound is prepared analogous to Example 2. HPLC: t$_R$=4.37 min (Method C); MS-ES: (M+H)$^+$=565.

EXAMPLE 265

2-(4-{5-[7-(3,5-Difluoro-4-morpholin-4-ylmethyl-phenyl)-7H-pyrrolo[2,3-d]pyrimidin-2-ylamino]-pyridin-2-yl}-piperazin-1-yl)-ethanol

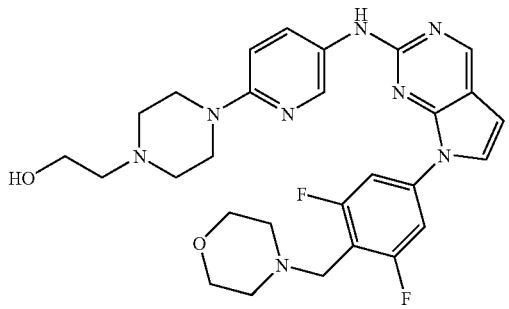 [SMILES: OCCN1CCN(c2ccc(Nc3ncc4ccn(-c5cc(F)c(CN6CCOCC6)c(F)c5)c4n3)cn2)CC1]

The compound is prepared analogous to Example 2. HPLC: t$_R$=3.91 min (Method C); MS-ES: (M+H)$^+$=551.

EXAMPLE 266

(4-{2-[6-(cis-3,5-Dimethyl-piperazin-1-yl)-pyridin-3-ylamino]-pyrrolo[2,3-d]pyrimidin-7-yl}-2,6-difluoro-phenyl)-morpholin-4-yl-methanone

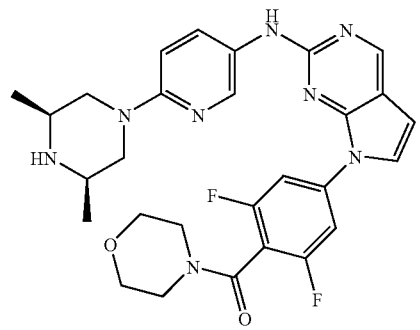 [SMILES: C[C@@H]1CN(c2ccc(Nc3ncc4ccn(-c5cc(F)c(C(=O)N6CCOCC6)c(F)c5)c4n3)cn2)C[C@H](C)N1]

The compound is prepared analogous to Example 2. HPLC: t$_R$=4.37 min (Method C); MS-ES: (M+H)$^+$=549.

EXAMPLE 267

[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-pyridin-3-yl]-amine

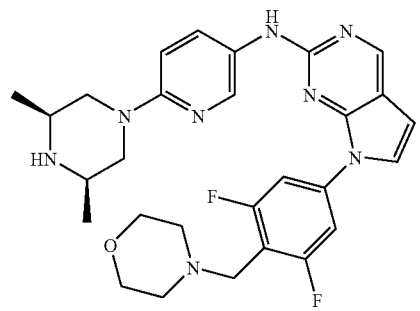 [SMILES: C[C@@H]1CN(c2ccc(Nc3ncc4ccn(-c5cc(F)c(CN6CCOCC6)c(F)c5)c4n3)cn2)C[C@H](C)N1]

The compound is prepared analogous to Example 2. HPLC: t$_R$=3.99 min (Method C); MS-ES: (M+H)$^+$=535.

EXAMPLE 268

(4-{2-[6-(4,7-Diaza-spiro[2.5]oct-7-yl)-pyridin-3-ylamino]-pyrrolo[2,3-d]pyrimidin-7-yl}-2,6-difluoro-phenyl)-morpholin-4-yl-methanone

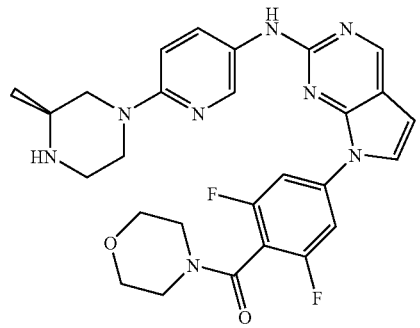 [SMILES: C[C@H]1CN(c2ccc(Nc3ncc4ccn(-c5cc(F)c(C(=O)N6CCOCC6)c(F)c5)c4n3)cn2)CCN1]

The compound is prepared analogous to Example 2. HPLC: t$_R$=4.43 min (Method C); MS-ES: (M+H)$^+$=547.

EXAMPLE 269

(4-{2-[6-((2R,5S)-2,5-Dimethyl-piperazin-1-yl)-pyridin-3-ylamino]-pyrrolo[2,3-d]pyrimidin-7-yl}-2,6-difluoro-phenyl)-morpholin-4-yl-methanone (racemic)

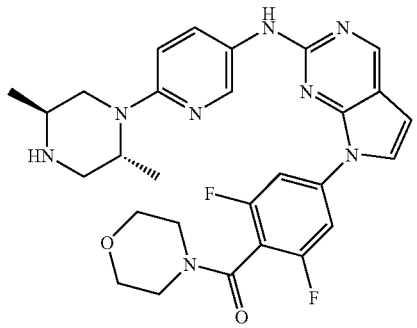 [SMILES: C[C@@H]1CN[C@@H](C)CN1c1ccc(Nc2ncc3ccn(-c4cc(F)c(C(=O)N5CCOCC5)c(F)c4)c3n2)cn1]

The compound is prepared analogous to Example 2. HPLC: $t_R$=4.46 min (Method C); MS-ES: (M+H)$^+$=549.

EXAMPLE 270

[6-(4,7-Diaza-spiro[2.5]oct-7-yl)-pyridin-3-yl]-[7-(3,5-difluoro-4-morpholin-4-ylmethyl-phenyl)-7H-pyrrolo[2,3-d]pyrimidin-2-yl]-amine

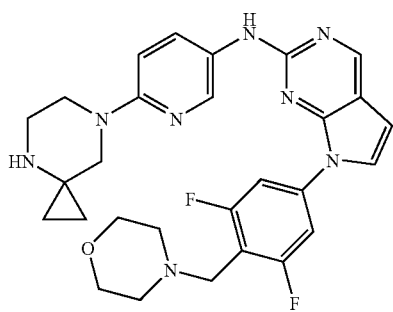 [SMILES: Fc1cc(-n2ccc3cnc(Nc4ccc(N5CCNC6(CC6)C5)nc4)nc32)cc(F)c1CN1CCOCC1]

The compound is prepared analogous to Example 2. HPLC: $t_R$=3.99 min (Method C); MS-ES: (M+H)$^+$=533.

EXAMPLE 271

[7-(3,5-Difluoro-4-morpholin-4-ylmethyl-phenyl)-7H-pyrrolo[2,3-d]pyrimidin-2-yl]-[6-((2R,5S)-2,5-dimethyl-piperazin-1-yl)-pyridin-3-yl]-amine (racemic)

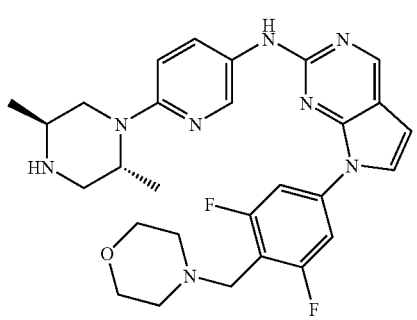 [SMILES: C[C@@H]1CN[C@@H](C)CN1c1ccc(Nc2ncc3ccn(-c4cc(F)c(CN5CCOCC5)c(F)c4)c3n2)cn1]

The compound is prepared analogous to Example 2. HPLC: $t_R$=4.02 min (Method C); MS-ES: (M+H)$^+$=535.

EXAMPLE 272

[6-(4,7-Diaza-spiro[2.5]oct-7-yl)-pyridin-3-yl]-[7-(4-methanesulfonyl-phenyl)-7H-pyrrolo[2,3-d]pyrimidin-2-yl]-amine

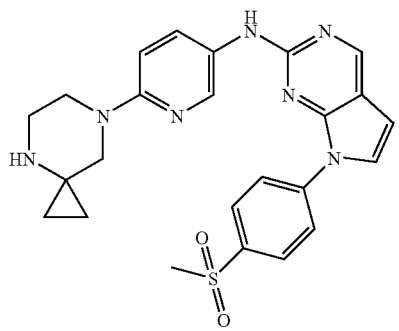 [SMILES: CS(=O)(=O)c1ccc(-n2ccc3cnc(Nc4ccc(N5CCNC6(CC6)C5)nc4)nc32)cc1]

The compound is prepared analogous to Example 2. HPLC: $t_R$=4.23 min (Method C); MS-ES: (M+H)$^+$=476.

EXAMPLE 273

[6-(cis-3,5-Dimethyl-piperazin-1-yl)-pyridin-3-yl]-[7-(4-methanesulfonyl-phenyl)-7H-pyrrolo[2,3-d]pyrimidin-2-yl]-amine

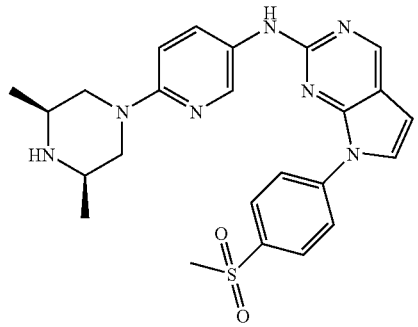 [SMILES: C[C@@H]1CN(c2ccc(Nc3ncc4ccn(-c5ccc(S(C)(=O)=O)cc5)c4n3)cn2)C[C@H](C)N1]

The compound is prepared analogous to Example 2. HPLC: $t_R$=4.29 min (Method C); MS-ES: (M+H)$^+$=478.

EXAMPLE 274

[6-((2R,5S)-2,5-Dimethyl-piperazin-1-yl)-pyridin-3-yl]-[7-(4-methanesulfonyl-phenyl)-7H-pyrrolo[2,3-d]pyrimidin-2-yl]-amine (racemic)

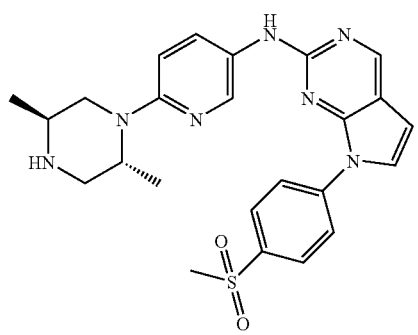 [SMILES: C[C@@H]1CN[C@@H](C)CN1c1ccc(Nc2ncc3ccn(-c4ccc(S(C)(=O)=O)cc4)c3n2)cn1]

The compound is prepared analogous to Example 2.
HPLC: $t_R$=4.30 min (Method C); MS-ES: (M+H)$^+$=478.

EXAMPLE 275

[2-(4,7-Diaza-spiro[2.5]oct-7-yl)-pyridin-4-yl]-[7-(4-methanesulfonyl-phenyl)-7H-pyrrolo[2,3-d]pyrimidin-2-yl]-amine

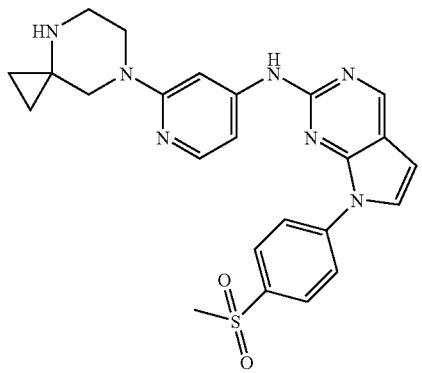 [SMILES: CS(=O)(=O)c1ccc(-n2ccc3cnc(Nc4ccnc(N5CCNC6(CC6)C5)c4)nc32)cc1]

The compound is prepared analogous to Example 2.
HPLC: $t_R$=4.43 min (Method C); MS-ES: (M+H)$^+$=476.

EXAMPLE 276

[7-(4-Methanesulfonyl-phenyl)-7H-pyrrolo[2,3-d]pyrimidin-2-yl]-[2-(4-methyl-piperazin-1-yl)-pyrimidin-5-yl]-amine

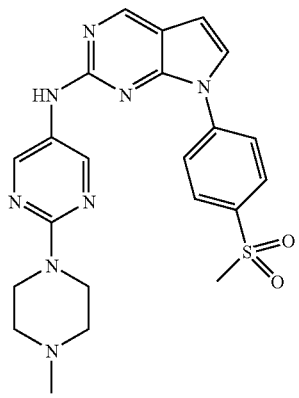 [SMILES: CN1CCN(c2ncc(Nc3ncc4ccn(-c5ccc(S(C)(=O)=O)cc5)c4n3)cn2)CC1]

The compound is prepared analogous to Example 2. MS-ES: (M+H)$^+$=465.

EXAMPLE 277

Cyclopropyl-(4-{2-[6-(4-methyl-piperazin-1-yl)-pyridin-3-ylamino]-pyrrolo[2,3-d]pyrimidin-7-yl}-phenyl)-methanol

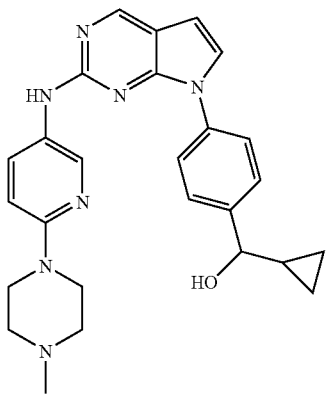 [SMILES: CN1CCN(c2ccc(Nc3ncc4ccn(-c5ccc(C(O)C6CC6)cc5)c4n3)cn2)CC1]

The compound is prepared analogous to Example 3.
HPLC: $t_R$=3.20 min (Method D); MS-ES: (M+H)$^+$=456.

EXAMPLE 278

4-{2-[6-(4-Methyl-piperazin-1-yl)-pyridin-3-ylamino]-pyrrolo[2,3-d]pyrimidin-7-yl}-benzonitrile

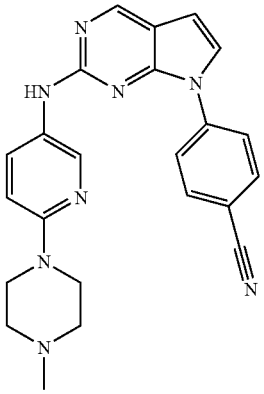 [SMILES: CN1CCN(c2ccc(Nc3ncc4ccn(-c5ccc(C#N)cc5)c4n3)cn2)CC1]

The compound is prepared analogous to Example 3.
HPLC: $t_R$=3.21 min (Method D); MS-ES: (M+H)$^+$=411.

EXAMPLE 279

1-(4-{2-[6-(4-Methyl-piperazin-1-yl)-pyridin-3-ylamino]-pyrrolo[2,3-d]pyrimidin-7-yl}-phenyl)-ethanol

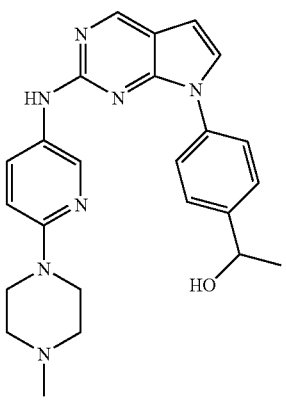 [SMILES: CC(O)c1ccc(-n2ccc3cnc(Nc4ccc(N5CCN(C)CC5)nc4)nc32)cc1]

The compound is prepared analogous to Example 3.
HPLC: $t_R$=2.80 min (Method D); MS-ES: (M+H)$^+$=430.

EXAMPLE 280

(2,6-Difluoro-4-{2-[6-(4-methyl-piperazin-1-yl)-pyridin-3-ylamino]-pyrrolo[2,3-d]pyrimidin-7-yl}-phenyl)-methanol

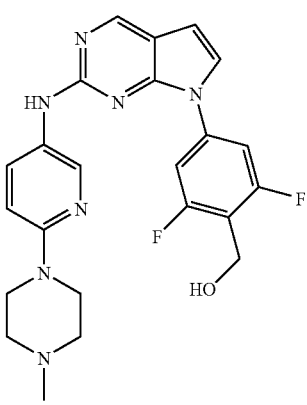 [SMILES: CN1CCN(c2ccc(Nc3ncc4ccn(-c5cc(F)c(CO)c(F)c5)c4n3)cn2)CC1]

The compound is prepared analogous to Example 3. HPLC: $t_R$=2.83 min (Method D); MS-ES: (M+H)$^+$=452.

EXAMPLE 281

(4-{2-[2-(4,7-Diaza-spiro[2.5]oct-7-yl)-pyridin-4-ylamino]-pyrrolo[2,3-d]pyrimidin-7-yl}-2,6-difluoro-phenyl)-morpholin-4-yl-methanone

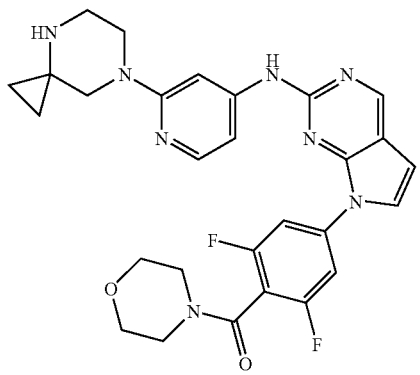 [SMILES: O=C(c1c(F)cc(-n2ccc3cnc(Nc4ccnc(N5CCNC6(CC6)C5)c4)nc32)cc1F)N1CCOCC1]

The compound is prepared analogous to Example 2. HPLC: $t_R$=4.61 min (Method C); MS-ES: (M+H)$^+$=547.

EXAMPLE 282

[7-(4-Methanesulfonyl-phenyl)-7H-pyrrolo[2,3-d]pyrimidin-2-yl]-(6-piperazin-1-yl-pyridin-3-yl)-amine

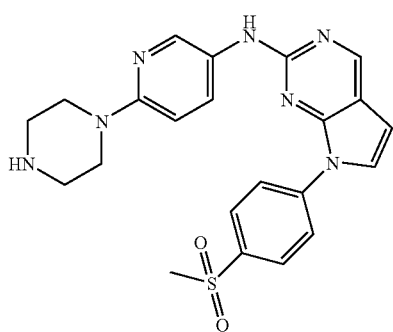 [SMILES: CS(=O)(=O)c1ccc(-n2ccc3cnc(Nc4ccc(N5CCNCC5)nc4)nc32)cc1]

The compound is prepared analogous to Example 2, using a Boc-protected piperazine derivative in Step 2.2, Final deprotection is achieved with 4N HCl in dioxan at rt. HPLC: $t_R$=4.19 min (Method C); MS-ES: (M+H)$^+$=450.

EXAMPLE 283

1-(4-{2-[6-(4-Methyl-piperazin-1-yl)-pyridin-3-ylamino]-pyrrolo[2,3-d]pyrimidin-7-yl}-phenyl)-pyrrolidin-2-one

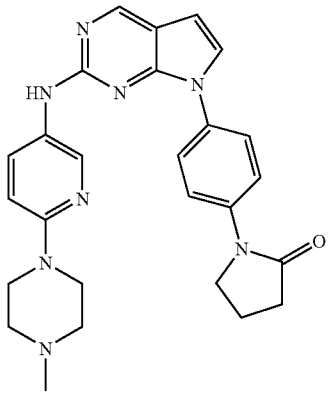 [SMILES: CN1CCN(c2ccc(Nc3ncc4ccn(-c5ccc(N6CCCC6=O)cc5)c4n3)cn2)CC1]

The compound is prepared analogous to Example 3. HPLC: $t_R$=3.03 min (Method D); MS-ES: (M+H)$^+$=469.

EXAMPLE 284

2-(4-{2-[4-(4-Ethyl-piperazin-1-yl)-3-methyl-phenylamino]-pyrrolo[2,3-d]pyrimidin-7-yl}-phenyl)-1-(4-methyl-piperazin-1-yl)-ethanone

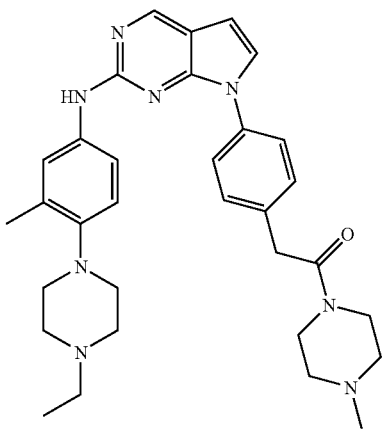 [SMILES: CCN1CCN(c2ccc(Nc3ncc4ccn(-c5ccc(CC(=O)N6CCN(C)CC6)cc5)c4n3)cc2C)CC1]

The compound is prepared analogous to Example 3. HPLC: $t_R$=6.74 min (Method B); MS-ES: (M+H)$^+$=553; TLC**: $R_f$=0.10

EXAMPLE 285

[4-(4-Ethyl-piperazin-1-yl)-3-methyl-phenyl]-[7-(3-fluoro-4-morpholin-4-ylmethyl-phenyl)-7H-pyrrolo[2,3-d]pyrimidin-2-yl]-amine

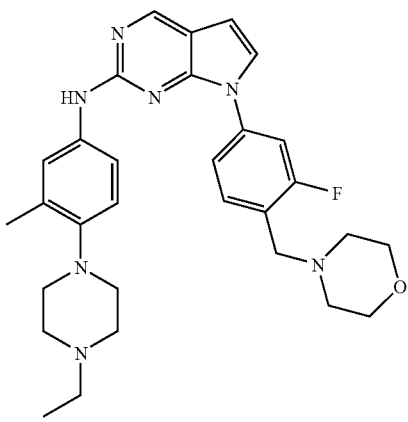 [SMILES: CCN1CCN(c2ccc(Nc3ncc4ccn(-c5ccc(CN6CCOCC6)c(F)c5)c4n3)cc2C)CC1]

The compound is prepared analogous to Example 3. HPLC: $t_R$=6.75 min. (Method B); MS-ES: (M+H)$^+$=530; TLC**: $R_f$=0.21

EXAMPLE 286

2-{4-[2-(3,4-Diethoxy-phenylamino)-6-methyl-pyrrolo[2,3-d]pyrimidin-7-yl]-2-fluoro-phenyl}-1-(1,1-dioxido-thiomorpholin-4-yl)-ethanone

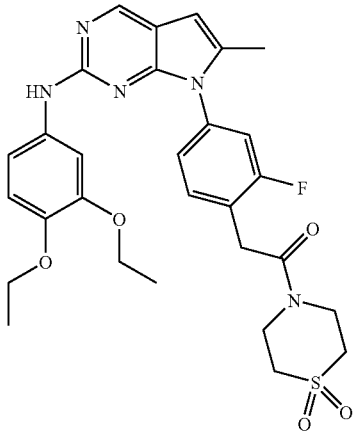 [SMILES: CCOc1ccc(Nc2ncc3cc(C)n(-c4ccc(CC(=O)N5CCS(=O)(=O)CC5)c(F)c4)c3n2)cc1OCC]

The compound is prepared analogous to Example 3. But instead of using 2-cloro-7H-pyrrolo[2,3-d]pyrimidine, 2-chloro-6-methyl-7H-pyrrolo[2,3-d]pyrimidine is used in the first step. This starting material is obtained by using tributyl-(1-propynyl)tin in the Stille coupling in the synthesis for the pyrrolopyrimidine as exemplified in the reaction scheme of Example 1. HPLC: $t_R$=8.46 min. (Method B); MS-ES: $(M+H)^+$=582; TLC**: $R_f$=0.51

EXAMPLE 287

{4-[2-(3,4-Diethoxy-phenylamino)-6-methyl-pyrrolo[2,3-d]pyrimidin-7-yl]-2-fluoro-phenyl}-morpholin-4-yl-methanone

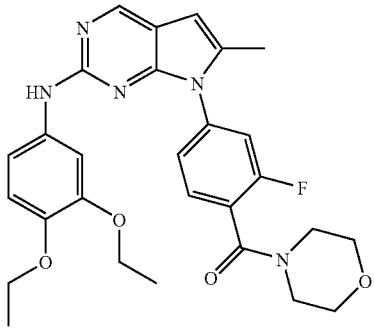 [SMILES: CCOc1ccc(Nc2ncc3cc(C)n(-c4ccc(C(=O)N5CCOCC5)c(F)c4)c3n2)cc1OCC]

The compound is prepared analogous to Example 3. But instead of using 2-cloro-7H-pyrrolo[2,3-d]pyrimidine, 2-chloro-6-methyl-7H-pyrrolo[2,3-d]pyrimidine is used in the first step. This starting material is obtained by using tributyl-(1-propynyl)tin in the Stille coupling in the synthesis for the pyrrolopyrimidine as exemplified in the reaction scheme of Example 1. HPLC: $t_R$=8.59 min. (Method B); MS-ES: $(M+H)^+$=520; TLC‡: $R_f$=0.22

EXAMPLE 288

{2-Fluoro-4-[2-(4-morpholin-4-ylmethyl-phenylamino)-pyrrolo[2,3-d]pyrimidin-7-yl]-phenyl}-morpholin-4-yl-methanone

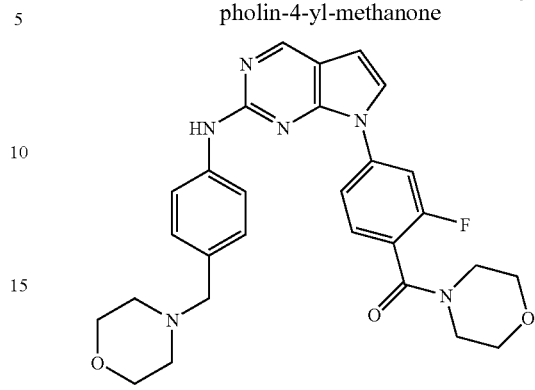

The compound is prepared analogous to Example 2. HPLC: $t_R$=7.22 min. (Method B); MS-ES: $(M+H)^+$=517; TLC*: $R_f$=0.37

EXAMPLE 289

[7-(3,5-Difluoro-4-morpholin-4-ylmethyl-phenyl)-7H-pyrrolo[2,3-d]pyrimidin-2-yl]-(3,4-dimethyl-phenyl)-amine

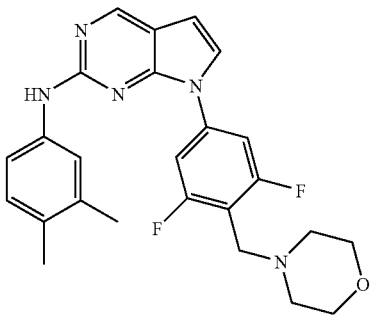 [SMILES: Cc1ccc(Nc2ncc3ccn(-c4cc(F)c(CN5CCOCC5)c(F)c4)c3n2)cc1C]

The compound is prepared analogous to Example 3. HPLC: $t_R$=7.85 min. (Method B); MS-ES: $(M+H)^+$=450; TLC‡: $R_f$=0.41

EXAMPLE 290

(3,4-Dimethyl-phenyl)-{7-[4-(1,1-dioxido-thiomorpholin-4-ylmethyl)-3,5-difluoro-phenyl]-7H-pyrrolo[2,3-d]pyrimidin-2-yl}-amine

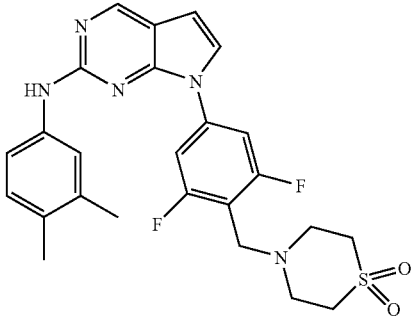 [SMILES: Cc1ccc(Nc2ncc3ccn(-c4cc(F)c(CN5CCS(=O)(=O)CC5)c(F)c4)c3n2)cc1C]

The compound is prepared analogous to Example 3. HPLC: $t_R$=8.88 min. (Method B); MS-ES: $(M+H)^+$=498; TLC‡: $R_f$=0.32

EXAMPLE 291

{4-[2-(3,4-Dimethyl-phenylamino)-pyrrolo[2,3-d]pyrimidin-7-yl]-2-fluoro-phenyl}-(1,1-dioxido-thiomorpholin-4-yl)-methanone

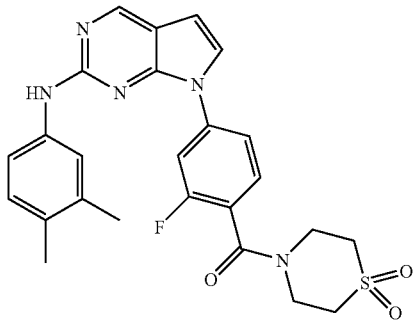 [SMILES: Cc1ccc(Nc2ncc3ccn(-c4ccc(C(=O)N5CCS(=O)(=O)CC5)c(F)c4)c3n2)cc1C]

The compound is prepared analogous to Example 3. HPLC: $t_R$=8.49 min. (Method B); MS-ES: (M+H)$^+$=494; TLC$^‡$: $R_f$=0.28

EXAMPLE 292

1-(1,1-Dioxido-thiomorpholin-4-yl)-2-(4-{2-[4-(4-ethyl-piperazin-1-yl)-3-methyl-phenylamino]-pyrrolo[2,3-d]pyrimidin-7-yl}-2-fluoro-phenyl)-ethanone

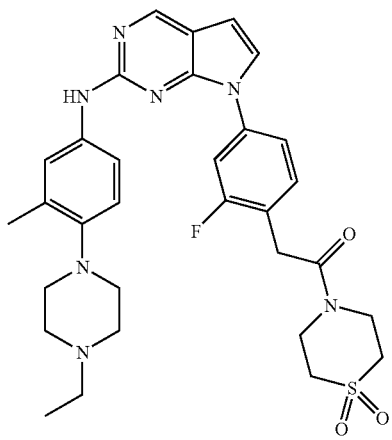 [SMILES: CCN1CCN(c2ccc(Nc3ncc4ccn(-c5ccc(CC(=O)N6CCS(=O)(=O)CC6)c(F)c5)c4n3)cc2C)CC1]

The compound is prepared analogous to Example 3. HPLC: $t_R$=7.37 min. (Method B); MS-ES: (M+H)$^+$=606; TLC**: $R_f$=0.34

EXAMPLE 293

(4-{2-[4-(4-Ethyl-piperazin-1-yl)-3-methyl-phenylamino]-pyrrolo[2,3-d]pyrimidin-7-yl}-2-fluoro-phenyl)-morpholin-4-yl-methanone

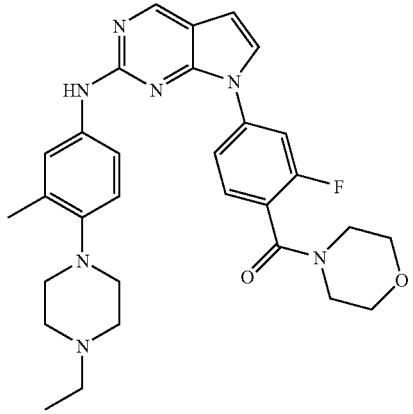 [SMILES: CCN1CCN(c2ccc(Nc3ncc4ccn(-c5ccc(C(=O)N6CCOCC6)c(F)c5)c4n3)cc2C)CC1]

The compound is prepared analogous to Example 3. HPLC: $t_R$=7.47 min. (Method B); MS-ES: (M+H)$^+$=544; TLC**: $R_f$=0.35

EXAMPLE 294

{4-[2-(3,4-Dimethyl-phenylamino)-pyrrolo[2,3-d]pyrimidin-7-yl]-2-methyl-phenyl}-morpholin-4-yl-methanone

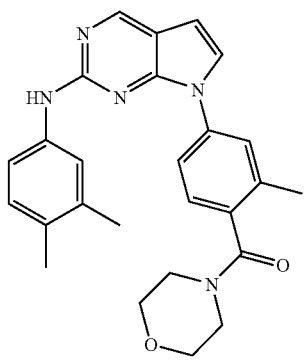 [SMILES: Cc1ccc(Nc2ncc3ccn(-c4ccc(C(=O)N5CCOCC5)c(C)c4)c3n2)cc1C]

The compound is prepared analogous to Example 3. HPLC: $t_R$=8.66 min. (Method B); MS-ES: (M+H)$^+$=442; TLC**: $R_f$=0.48

EXAMPLE 295

{4-[2-(4-Chloro-3-methoxy-phenylamino)-pyrrolo[2,3-d]pyrimidin-7-yl]-2-fluoro-phenyl}-morpholin-4-yl-methanone

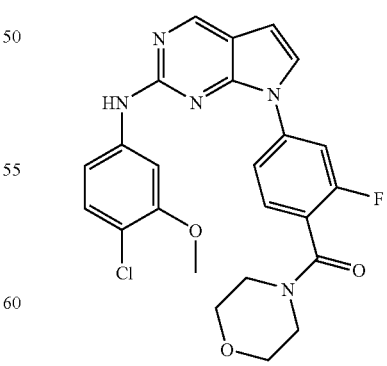

The compound is prepared analogous to Example 3. HPLC: $t_R$=8.95 min. (Method B); MS-ES: (M+H)$^+$=482; TLC**: $R_f$=0.46

EXAMPLE 296

{4-[2-(4-Fluoro-3-methoxy-phenylamino)-pyrrolo[2,3-d]pyrimidin-7-yl]-2-methyl-phenyl}-morpholin-4-yl-methanone

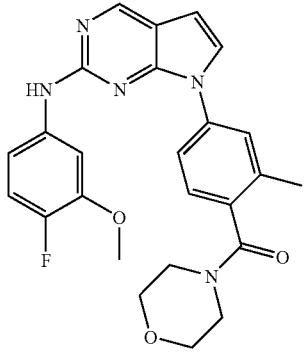 [SMILES: COc1cc(Nc2ncc3ccn(-c4ccc(C(=O)N5CCOCC5)c(C)c4)c3n2)ccc1F]

The compound is prepared analogous to Example 3.
HPLC: $t_R$=8.29 min. (Method B); MS-ES: (M+H)$^+$=462; TLC**: $R_f$=0.25

EXAMPLE 297

4-[2-(3,4-Dimethyl-phenylamino)-pyrrolo[2,3-d]pyrimidin-7-yl]-2-fluoro-N-(2-morpholin-4-yl-ethyl)-benzamide

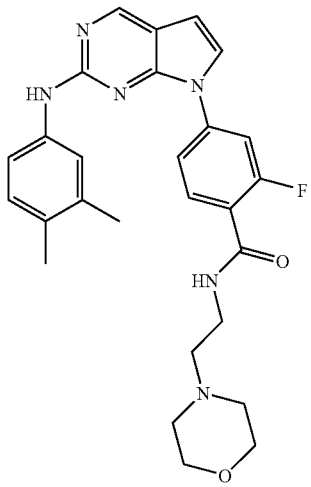 [SMILES: Cc1ccc(Nc2ncc3ccn(-c4ccc(C(=O)NCCN5CCOCC5)c(F)c4)c3n2)cc1C]

The compound is prepared analogous to Example 3.
HPLC: $t_R$=7.71 min. (Method B); MS-ES: (M+H)$^+$=489; TLC**: $R_f$=0.33

EXAMPLE 298

4-[2-(3,4-Dimethyl-phenylamino)-pyrrolo[2,3-d]pyrimidin-7-yl]-2-fluoro-N-[2-(4-methyl-piperazin-1-yl)-ethyl]-benzamide

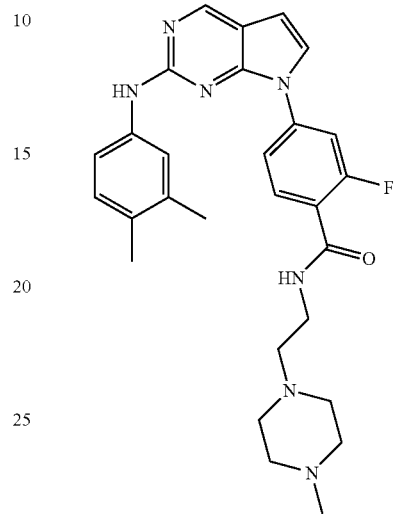

The compound is prepared analogous to Example 3.
HPLC: $t_R$=7.37 min. (Method B); MS-ES: (M+H)$^+$=502; TLC*: $R_f$=0.24

EXAMPLE 299

(4-Dimethylamino-piperidin-1-yl)-{4-[2-(3,4-dimethyl-phenylamino)-pyrrolo[2,3-d]pyrimidin-7-yl]-2-fluoro-phenyl}-methanone

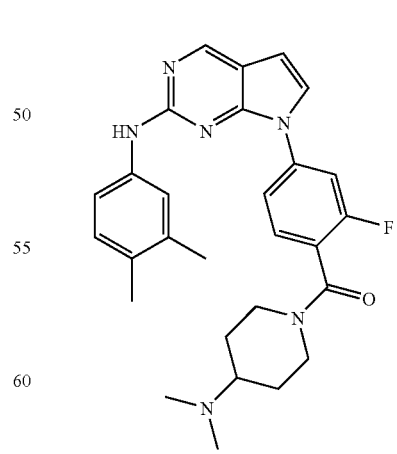

The compound is prepared analogous to Example 3.
HPLC: $t_R$=7.67 min. (Method B); MS-ES: (M+H)$^+$=487; TLC*: $R_f$=0.30

EXAMPLE 300

{4-[2-(3,4-Dimethyl-phenylamino)-pyrrolo[2,3-d]pyrimidin-7-yl]-phenyl}-[4-(2-hydroxy-ethyl)-piperazin-1-yl]-methanone

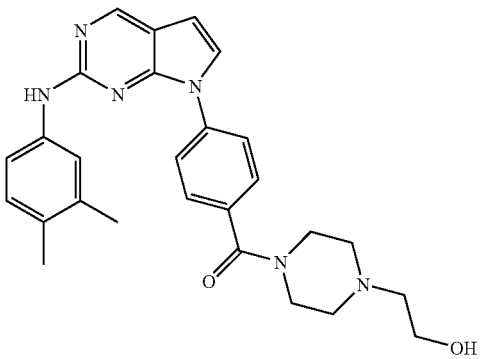 [SMILES: Cc1ccc(Nc2ncc3ccn(-c4ccc(C(=O)N5CCN(CCO)CC5)cc4)c3n2)cc1C]

The compound is prepared analogous to Example 3. HPLC: $t_R$=7.27 min. (Method B); MS-ES: (M+H)$^+$=471; TLC*: $R_f$=0.50

EXAMPLE 301

2-{4-[2-(1-Methyl-1H-pyrazol-4-ylamino)-pyrrolo[2,3-d]pyrimidin-7-yl]-phenyl}-1-morpholin-4-yl-ethanone

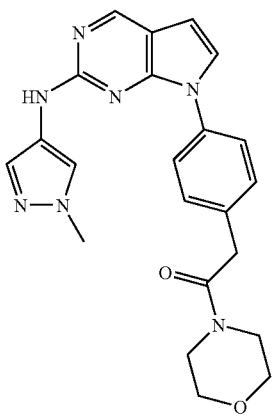 [SMILES: Cn1cc(Nc2ncc3ccn(-c4ccc(CC(=O)N5CCOCC5)cc4)c3n2)cn1]

The compound is prepared analogous to Example 3. HPLC: $t_R$=7.25 min. (Method B); MS-ES: (M+H)$^+$=418; TLC*: $R_f$=0.55

EXAMPLE 302

{2-Fluoro-4-[2-(1-methyl-1H-pyrazol-4-ylamino)-pyrrolo[2,3-d]pyrimidin-7-yl]-phenyl}-morpholin-4-yl-methanone

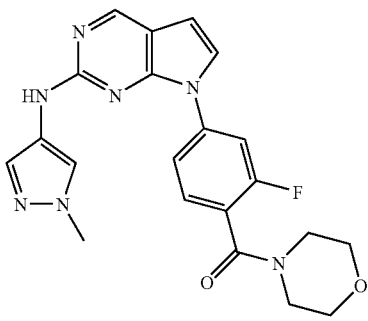 [SMILES: Cn1cc(Nc2ncc3ccn(-c4ccc(C(=O)N5CCOCC5)c(F)c4)c3n2)cn1]

The compound is prepared analogous to Example 3. HPLC: $t_R$=7.23 min. (Method B); MS-ES: (M+H)$^+$=422; TLC*: $R_f$=0.50

EXAMPLE 303

{2-Fluoro-4-[2-(3-methoxy-4-methyl-phenylamino)-pyrrolo[2,3-d]pyrimidin-7-yl]-phenyl}-morpholin-4-yl-methanone

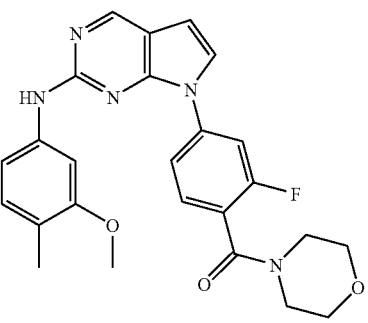 [SMILES: COc1cc(Nc2ncc3ccn(-c4ccc(C(=O)N5CCOCC5)c(F)c4)c3n2)ccc1C]

The compound is prepared analogous to Example 3. HPLC: $t_R$=8.67 min. (Method B); MS-ES: (M+H)$^+$=462; TLC*: $R_f$=0.59

EXAMPLE 304

{7-[3,5-Difluoro-4-(4-methyl-piperazin-1-ylmethyl)-phenyl]-7H-pyrrolo[2,3-d]pyrimidin-2-yl}-(3,4-dimethyl-phenyl)-amine

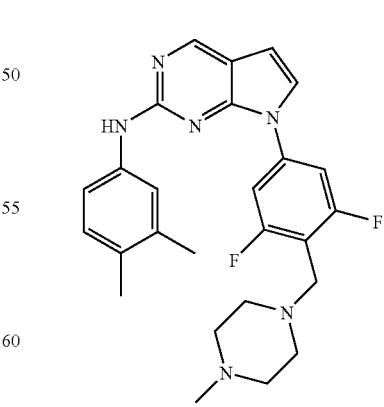

The compound is prepared analogous to Example 3. HPLC: $t_R$=7.97 min. (Method B); MS-ES: (M+H)$^+$=463; TLC**: $R_f$=0.17

EXAMPLE 305

{7-[3,5-Difluoro-4-(4-isopropyl-piperazin-1-ylmethyl)-phenyl]-7H-pyrrolo[2,3-d]pyrimidin-2-yl}-(3,4-dimethyl-phenyl)-amine

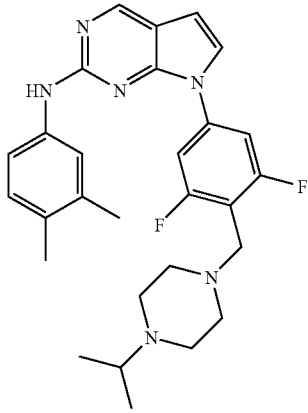 [SMILES: Cc1ccc(Nc2ncc3ccn(-c4cc(F)c(CN5CCN(C(C)C)CC5)c(F)c4)c3n2)cc1C]

The compound is prepared analogous to Example 3. HPLC: $t_R$=8.15 min. (Method B); MS-ES: (M+H)$^+$=491; TLC**: $R_f$=0.32

EXAMPLE 306

{7-[4-(4-Cyclopropyl-piperazin-1-yl methyl)-3,5-difluoro-phenyl]-7H-pyrrolo[2,3-d]pyrimidin-2-yl}-(3,4-dimethyl-phenyl)-amine

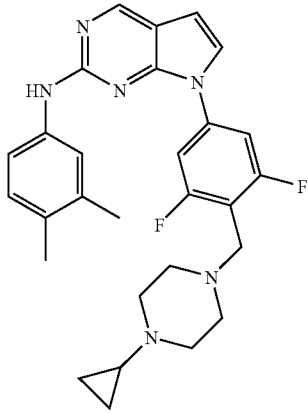 [SMILES: Cc1ccc(Nc2ncc3ccn(-c4cc(F)c(CN5CCN(C6CC6)CC5)c(F)c4)c3n2)cc1C]

The compound is prepared analogous to Example 3. HPLC: $t_R$=8.50 min. (Method B); MS-ES: (M+H)$^+$=489; TLC**: $R_f$=0.50

EXAMPLE 307

[7-(3,5-Difluoro-4-morpholin-4-ylmethyl-phenyl)-7H-pyrrolo[2,3-d]pyrimidin-2-yl]-(3-methoxy-4-methyl-phenyl)-amine

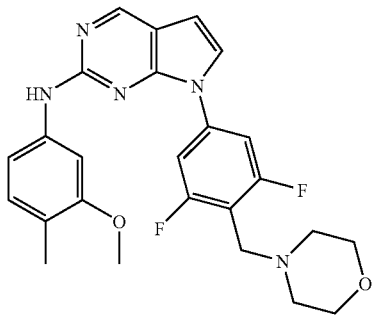 [SMILES: COc1cc(Nc2ncc3ccn(-c4cc(F)c(CN5CCOCC5)c(F)c4)c3n2)ccc1C]

The compound is prepared analogous to Example 3. HPLC: $t_R$=7.80 min. (Method B); MS-ES: (M+H)$^+$=466; TLC*: $R_f$=0.77

EXAMPLE 308

{7-[4-(1,1-Dioxido-thiomorpholin-4-ylmethyl)-3,5-difluoro-phenyl]-7H-pyrrolo[2,3-d]pyrimidin-2-yl}-(3-methoxy-4-methyl-phenyl)-amine

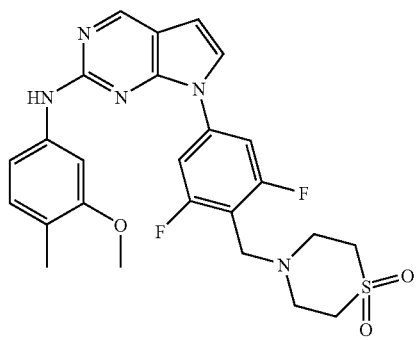 [SMILES: COc1cc(Nc2ncc3ccn(-c4cc(F)c(CN5CCS(=O)(=O)CC5)c(F)c4)c3n2)ccc1C]

The compound is prepared analogous to Example 3. HPLC: $t_R$=8.81 min. (Method B); MS-ES: (M+H)$^+$=514; TLC*: $R_f$=0.67

EXAMPLE 309

{7-[4-(3,3-Dimethyl-morpholin-4-ylmethyl)-3,5-difluoro-phenyl]-7H-pyrrolo[2,3-d]pyrimidin-2-yl}-(3,4-dimethyl-phenyl)-amine

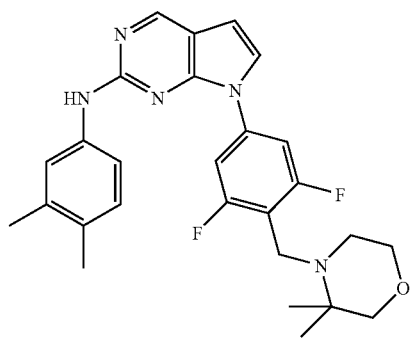 [SMILES: Cc1ccc(Nc2ncc3ccn(-c4cc(F)c(CN5CCOCC5(C)C)c(F)c4)c3n2)cc1C]

The compound is prepared analogous to Example 3. HPLC: $t_R$=8.23 min. (Method B); MS-ES: (M+H)$^+$=478; TLC*: $R_f$=0.80

EXAMPLE 310

4-{4-[2-(3,4-Dimethyl-phenylamino)-pyrrolo[2,3-d]pyrimidin-7-yl]-2,6-difluoro-benzyl}-1-methyl-piperazin-2-one

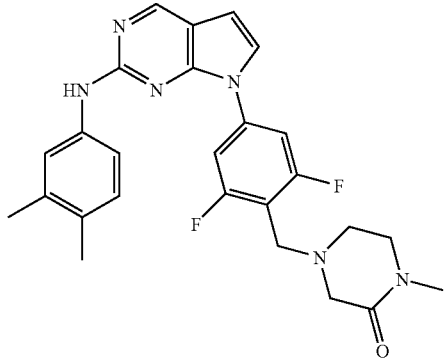

The compound is prepared analogous to Example 3. HPLC: $t_R$=8.05 min. (Method B); MS-ES: (M+H)$^+$=477; TLC*: $R_f$=0.67

EXAMPLE 311

{4-[2-(1,5-Dimethyl-1H-pyrazol-3-ylamino)-pyrrolo[2,3-d]pyrimidin-7-yl]-2-fluoro-phenyl}-morpholin-4-yl-methanone

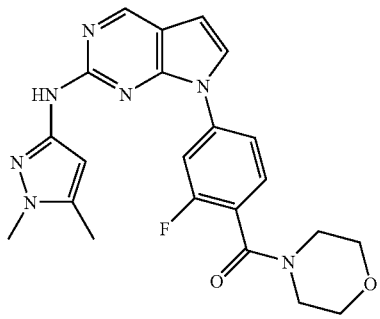 [SMILES: Cc1cc(Nc2ncc3ccn(-c4ccc(C(=O)N5CCOCC5)c(F)c4)c3n2)nn1C]

The compound is prepared analogous to Example 3. HPLC: $t_R$=7.94 min. (Method B); MS-ES: (M+H)$^+$=436; TLC*: $R_f$=0.37

EXAMPLE 312

4-{4-[2-(3,4-Dimethyl-phenylamino)-pyrrolo[2,3-d]pyrimidin-7-yl]-2,6-difluoro-benzyl}-piperazin-2-one

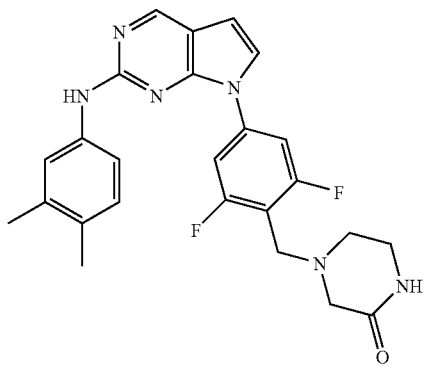 [SMILES: Cc1ccc(Nc2ncc3ccn(-c4cc(F)c(CN5CCNC(=O)C5)c(F)c4)c3n2)cc1C]

The compound is prepared analogous to Example 3. HPLC: $t_R$=7.81 min. (Method B); MS-ES: (M+H)$^+$=463; TLC*: $R_f$=0.61

EXAMPLE 313

{2-Fluoro-4-[2-(4-piperazin-1-ylmethyl-phenylamino)-pyrrolo[2,3-d]pyrimidin-7-yl]-phenyl}-morpholin-4-yl-methanone

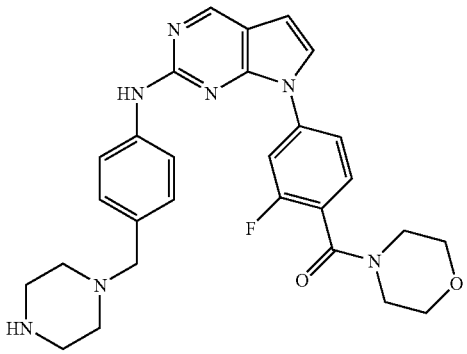 [SMILES: O=C(c1ccc(-n2ccc3cnc(Nc4ccc(CN5CCNCC5)cc4)nc32)cc1F)N1CCOCC1]

The compound is prepared analogous to Example 2. The final product is obtained by cleaving the Boc-protecting group under acidic conditions (4 M HCl in dioxane). HPLC: $t_R$=6.83 min. (Method B); MS-ES: (M+H)$^+$=516

EXAMPLE 314

{2,6-Difluoro-4-[2-(4-piperazin-1-ylmethyl-phenylamino)-pyrrolo[2,3-d]pyrimidin-7-yl]-phenyl}-morpholin-4-yl-methanone

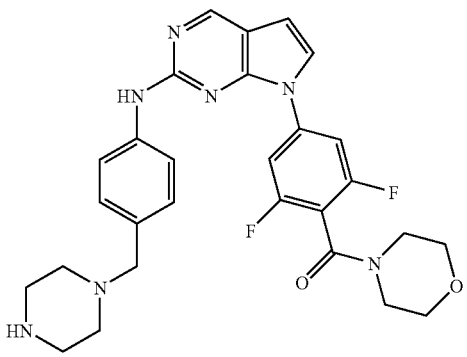 [SMILES: O=C(c1c(F)cc(-n2ccc3cnc(Nc4ccc(CN5CCNCC5)cc4)nc32)cc1F)N1CCOCC1]

The compound is prepared analogous to Example 2. The final product is obtained by cleaving the Boc-protecting group under acidic conditions (4 M HCl in dioxane). HPLC: $t_R$=7.00 min. (Method B); MS-ES: (M+H)$^+$=534

EXAMPLE 315

[7-(3,5-Difluoro-4-morpholin-4-ylmethyl-phenyl)-7H-pyrrolo[2,3-d]pyrimidin-2-yl]-(4-piperazin-1-ylmethyl-phenyl)-amine

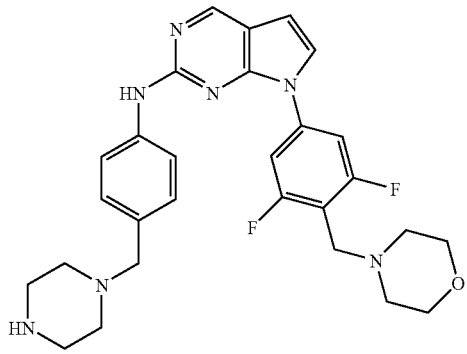 [SMILES: Fc1cc(-n2ccc3cnc(Nc4ccc(CN5CCNCC5)cc4)nc32)cc(F)c1CN1CCOCC1]

The compound is prepared analogous to Example 2. The final product is obtained by cleaving the Boc-protecting group under acidic conditions (4 M HCl in dioxane). HPLC: $t_R$=6.60 min. (Method B); MS-ES: (M+H)$^+$=520

EXAMPLE 316

[7-(3,5-Difluoro-4-morpholin-4-ylmethyl-phenyl)-7H-pyrrolo[2,3-d]pyrimidin-2-yl]-[5-(4-ethyl-piperazin-1-ylmethyl)-pyridin-2-yl]-amine

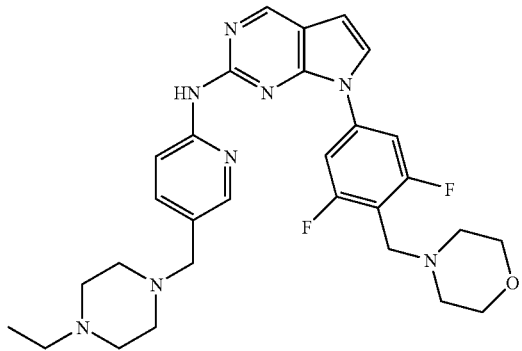 [SMILES: CCN1CCN(Cc2ccc(Nc3ncc4ccn(-c5cc(F)c(CN6CCOCC6)c(F)c5)c4n3)nc2)CC1]

The compound is prepared analogous to Example 2. HPLC: $t_R$=6.42 min. (Method B); MS-ES: (M+H)$^+$=549; TLC*: $R_f$=0.11

EXAMPLE 317

[5-(4-Ethyl-piperazin-1-ylmethyl)-pyridin-2-yl]-[7-(4-methanesulfonyl-phenyl)-7H-pyrrolo[2,3-d]pyrimidin-2-yl]-amine

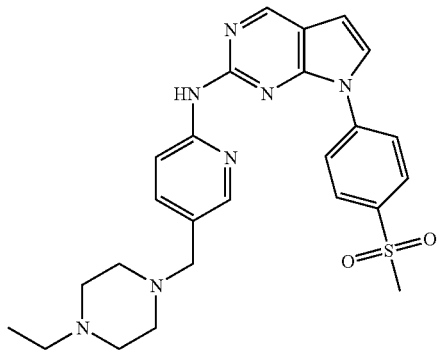 [SMILES: CCN1CCN(Cc2ccc(Nc3ncc4ccn(-c5ccc(S(C)(=O)=O)cc5)c4n3)nc2)CC1]

The compound is prepared analogous to Example 2. HPLC: $t_R$=6.91 min. (Method B); MS-ES: (M+H)$^+$=492

EXAMPLE 318

1-(4-{4-[7-(3,5-Difluoro-4-morpholin-4-ylmethyl-phenyl)-7H-pyrrolo[2,3-d]pyrimidin-2-ylamino]-benzyl}-piperazin-1-yl)-ethanone

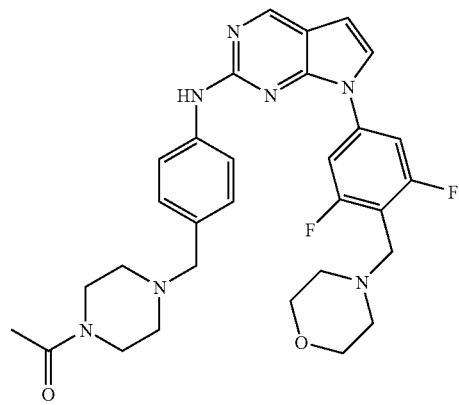 [SMILES: CC(=O)N1CCN(Cc2ccc(Nc3ncc4ccn(-c5cc(F)c(CN6CCOCC6)c(F)c5)c4n3)cc2)CC1]

The compound is prepared analogous to Example 2. HPLC: $t_R$=6.61 min. (Method B); MS-ES: (M+H)$^+$=562; TLC*: $R_f$=0.25

EXAMPLE 319

1-(4-{4-[7-(4-Methanesulfonyl-phenyl)-7H-pyrrolo[2,3-d]pyrimidin-2-ylamino]-benzyl}-piperazin-1-yl)-ethanone

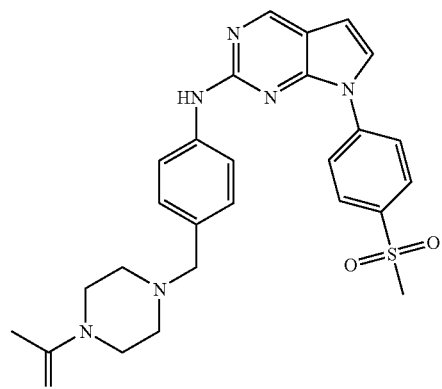

The compound is prepared analogous to Example 2. HPLC: $t_R$=7.01 min. (Method B); MS-ES: (M+H)$^+$=505; TLC*: $R_f$=0.21

EXAMPLE 320

4-{4-[7-(3,5-Difluoro-4-morpholin-4-ylmethyl-phenyl)-7H-pyrrolo[2,3-d]pyrimidin-2-ylamino]-pyrazol-1-yl}-piperidine-1-carboxylic acid tert-butyl ester

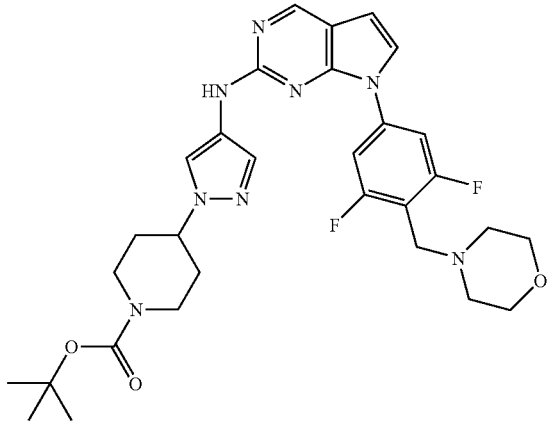 [SMILES: CC(C)(C)OC(=O)N1CCC(n2cc(Nc3ncc4ccn(-c5cc(F)c(CN6CCOCC6)c(F)c5)c4n3)cn2)CC1]

The compound is prepared analogous to Example 2. HPLC: $t_R$=8.04 min. (Method B); MS-ES: (M+H)$^+$=595; TLC*: $R_f$=0.43

EXAMPLE 321

[7-(3,5-Difluoro-4-morpholin-4-ylmethyl-phenyl)-7H-pyrrolo[2,3-d]pyrimidin-2-yl]-(1-piperidin-4-yl-1H-pyrazol-4-yl)-amine

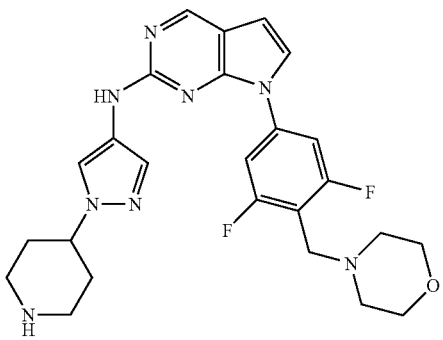 [SMILES: Fc1cc(-n2ccc3cnc(Nc4cnn(C5CCNCC5)c4)nc32)cc(F)c1CN1CCOCC1]

The compound is prepared from Example 320 by cleaving the Boc-protecting group under acidic conditions (4 M HCl in dioxane). HPLC: $t_R$=6.13 min. (Method B); MS-ES: (M+H)$^+$= 495

EXAMPLE 322

1-[4-(4-{7-[3-Fluoro-4-(morpholine-4-carbonyl)-phenyl]-7H-pyrrolo[2,3-d]pyrimidin-2-ylamino}-benzyl)-piperazin-1-yl]-ethanone

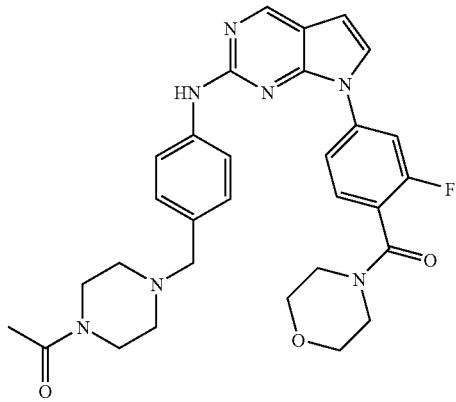 [SMILES: CC(=O)N1CCN(Cc2ccc(Nc3ncc4ccn(-c5ccc(C(=O)N6CCOCC6)c(F)c5)c4n3)cc2)CC1]

The compound is prepared analogous to Example 2. HPLC: $t_R$=7.23 min. (Method B); MS-ES: (M+H)$^+$=558; TLC*: $R_f$=0.25

EXAMPLE 323

1-[4-(4-{7-[3,5-Difluoro-4-(morpholine-4-carbonyl)-phenyl]-7H-pyrrolo[2,3-d]pyrimidin-2-ylamino}-benzyl)-piperazin-1-yl]-ethanone

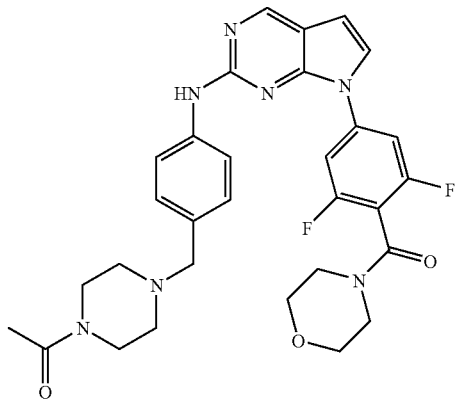 [SMILES: CC(=O)N1CCN(Cc2ccc(Nc3ncc4ccn(-c5cc(F)c(C(=O)N6CCOCC6)c(F)c5)c4n3)cc2)CC1]

The compound is prepared analogous to Example 2. HPLC: $t_R$=7.46 min. (Method B); MS-ES: (M+H)$^+$=576; TLC*: $R_f$=0.18

EXAMPLE 324

[2-Fluoro-4-(2-p-tolylamino-pyrrolo[2,3-d]pyrimidin-7-yl)-phenyl]-morpholin-4-yl-methanone

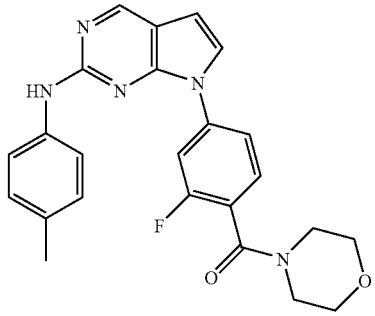 [SMILES: Cc1ccc(Nc2ncc3ccn(-c4ccc(C(=O)N5CCOCC5)c(F)c4)c3n2)cc1]

The compound is prepared analogous to Example 3. HPLC: $t_R$=8.47 min. (Method B); MS-ES: (M+H)$^+$=432

EXAMPLE 325

[7-(3,5-Difluoro-4-morpholin-4-ylmethyl-phenyl)-7H-pyrrolo[2,3-d]pyrimidin-2-yl]-p-tolyl-amine

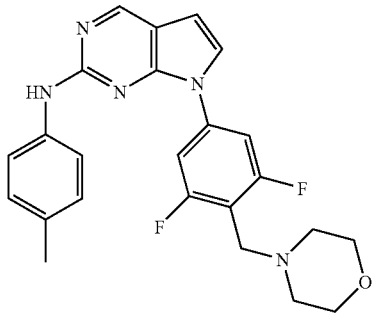 [SMILES: Cc1ccc(Nc2ncc3ccn(-c4cc(F)c(CN5CCOCC5)c(F)c4)c3n2)cc1]

The compound is prepared analogous to Example 3. HPLC: $t_R$=7.60 min. (Method B); MS-ES: (M+H)$^+$=436; TLC*: $R_f$=0.77

EXAMPLE 326

(2-Fluoro-4-{2-[4-methyl-3-(4-methyl-piperazin-1-ylmethyl)-phenylamino]-pyrrolo[2,3-d]pyrimidin-7-yl}-phenyl)-morpholin-4-yl-methanone

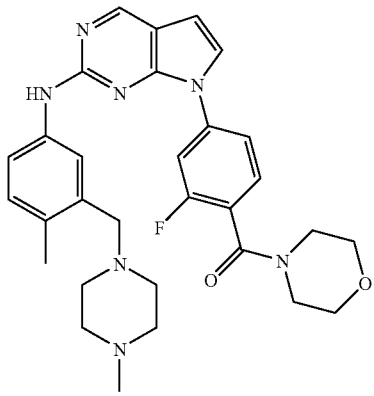

The compound is prepared analogous to Example 2. HPLC: $t_R$=7.30 min. (Method B); MS-ES: (M+H)$^+$=544; TLC*: $R_f$=0.35

EXAMPLE 327

{2-Fluoro-4-[2-(4-methyl-3-morpholin-4-ylmethyl-phenylamino)-pyrrolo[2,3-d]pyrimidin-7-yl]-phenyl}-morpholin-4-yl-methanone

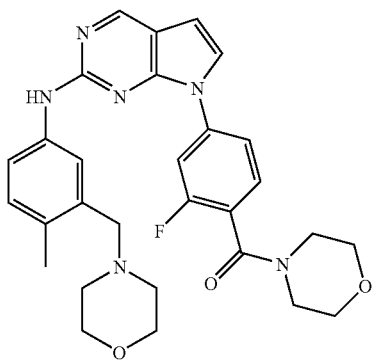 [SMILES: Cc1ccc(Nc2ncc3ccn(-c4ccc(C(=O)N5CCOCC5)c(F)c4)c3n2)cc1CN1CCOCC1]

The compound is prepared analogous to Example 2. HPLC: $t_R$=7.44 min. (Method B); MS-ES: (M+H)$^+$=531; TLC*: $R_f$=0.48

EXAMPLE 328

[7-(4-Methanesulfonyl-phenyl)-7H-pyrrolo[2,3-d]pyrimidin-2-yl]-(4-methyl-3-morpholin-4-ylmethyl-phenyl)-amine

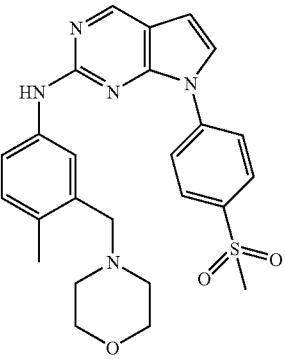 [SMILES: Cc1ccc(Nc2ncc3ccn(-c4ccc(S(C)(=O)=O)cc4)c3n2)cc1CN1CCOCC1]

The compound is prepared analogous to Example 2. HPLC: $t_R$=7.32 min. (Method B); MS-ES: (M+H)$^+$=478; TLC*: $R_f$=0.56

EXAMPLE 329

[4-(4-Cyclopropyl-piperazin-1-ylmethyl)-phenyl]-[7-(3,5-difluoro-4-morpholin-4-ylmethyl-phenyl)-7H-pyrrolo[2,3-d]pyrimidin-2-yl]-amine

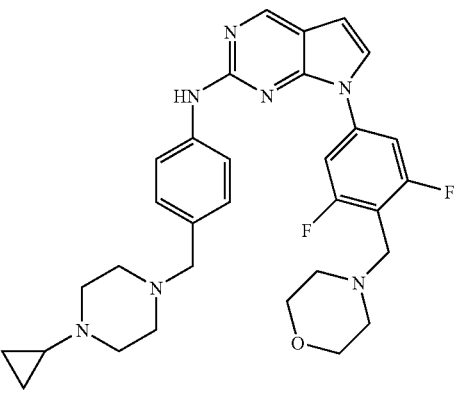 [SMILES: Fc1cc(-n2ccc3cnc(Nc4ccc(CN5CCN(C6CC6)CC5)cc4)nc32)cc(F)c1CN1CCOCC1]

The compound is prepared analogous to Example 2. HPLC: $t_R$=6.75 min. (Method B); MS-ES: (M+H)$^+$=560; TLC*: $R_f$=0.23

EXAMPLE 330

(4-{2-[4-(4-Cyclopropyl-piperazin-1-ylmethyl)-phenylamino]-pyrrolo[2,3-d]pyrimidin-7-yl}-2-fluorophenyl)-morpholin-4-yl-methanone

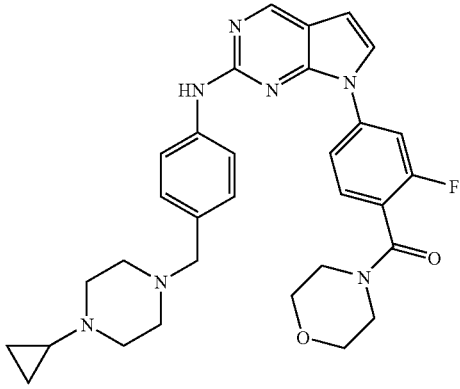 [SMILES: O=C(c1ccc(-n2ccc3cnc(Nc4ccc(CN5CCN(C6CC6)CC5)cc4)nc32)cc1F)N1CCOCC1]

The compound is prepared analogous to Example 2. HPLC: $t_R$=7.16 min. (Method B); MS-ES: (M+H)$^+$=556; TLC*: $R_f$=0.30

EXAMPLE 331

[7-(3,5-Difluoro-4-morpholin-4-ylmethyl-phenyl)-7H-pyrrolo[2,3-d]pyrimidin-2-yl]-[4-methyl-3-(4-methyl-piperazin-1-ylmethyl)-phenyl]-amine

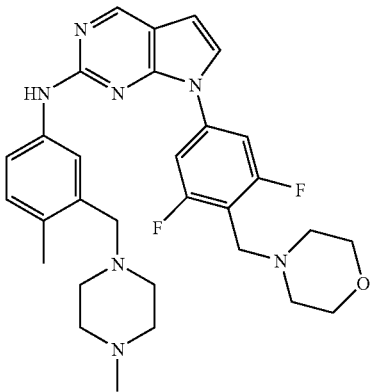 [SMILES: Cc1ccc(Nc2ncc3ccn(-c4cc(F)c(CN5CCOCC5)c(F)c4)c3n2)cc1CN1CCN(C)CC1]

The compound is prepared analogous to Example 2. HPLC: $t_R$=6.72 min. (Method B); MS-ES: (M+H)$^+$=548; TLC*: $R_f$=0.35

EXAMPLE 332

[7-(3,5-Difluoro-4-morpholin-4-ylmethyl-phenyl)-7H-pyrrolo[2,3-d]pyrimidin-2-yl]-(4-methyl-3-piperazin-1-ylmethyl-phenyl)-amine

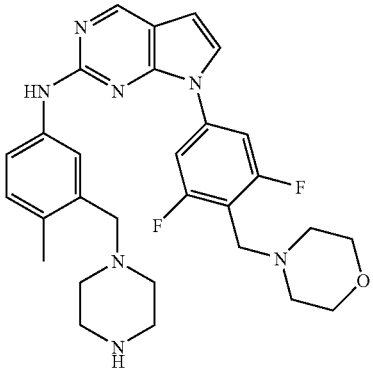 [SMILES: Cc1ccc(Nc2ncc3ccn(-c4cc(F)c(CN5CCOCC5)c(F)c4)c3n2)cc1CN1CCNCC1]

The compound is prepared analogous to Example 2, using a Boc-protected piperazine derivative in Step 2.2, Final deprotection is achieved with 4 M HCl in dioxane at rt. HPLC: $t_R$=6.45 min. (Method B); MS-ES: (M+H)$^+$=534

EXAMPLE 333

[7-(4-Methanesulfonyl-phenyl)-7H-pyrrolo[2,3-d]pyrimidin-2-yl]-(4-methyl-3-piperazin-1-ylmethyl-phenyl)-amine

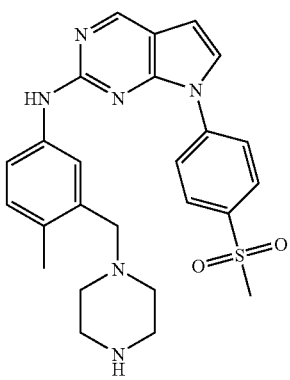 [SMILES: Cc1ccc(Nc2ncc3ccn(-c4ccc(S(C)(=O)=O)cc4)c3n2)cc1CN1CCNCC1]

The compound is prepared analogous to Example 2, using a Boc-protected piperazine derivative in Step 2.2, Final deprotection is achieved with 4 M HCl in dioxane at rt. HPLC: $t_R$=6.90 min. (Method B); MS-ES: (M+H)$^+$=477

EXAMPLE 334

4-{5-[7-(3,5-Difluoro-4-morpholin-4-ylmethyl-phenyl)-7H-pyrrolo[2,3-d]pyrimidin-2-ylamino]-2-methyl-benzyl}-piperazin-2-one

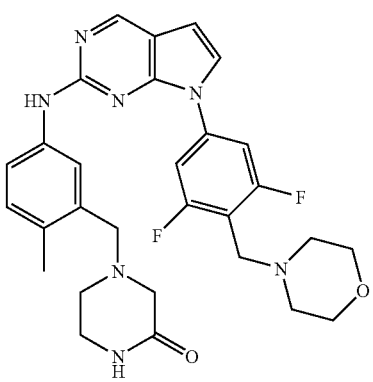 [SMILES: Cc1ccc(Nc2ncc3ccn(-c4cc(F)c(CN5CCOCC5)c(F)c4)c3n2)cc1CN1CCNC(=O)C1]

The compound is prepared analogous to Example 2. HPLC: $t_R$=6.55 min. (Method B); MS-ES: (M+H)$^+$=548; TLC*: $R_f$=0.39

EXAMPLE 335

4-{4-[7-(4-Methanesulfonyl-phenyl)-7H-pyrrolo[2,3-d]pyrimidin-2-ylamino]-benzyl}-1-methyl-piperazin-2-one

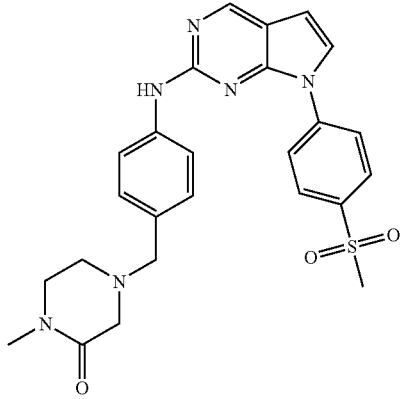 [SMILES: CN1CCN(Cc2ccc(Nc3ncc4ccn(-c5ccc(S(C)(=O)=O)cc5)c4n3)cc2)CC1=O]

The compound is prepared analogous to Example 2. HPLC: $t_R$=7.04 min. (Method B); MS-ES: (M+H)$^+$=491; TLC**: $R_f$=0.10

EXAMPLE 336

{2-Fluoro-4-[2-(4-methyl-3-piperazin-1-ylmethyl-phenylamino)-pyrrolo[2,3-d]pyrimidin-7-yl]-phenyl}-morpholin-4-yl-methanone

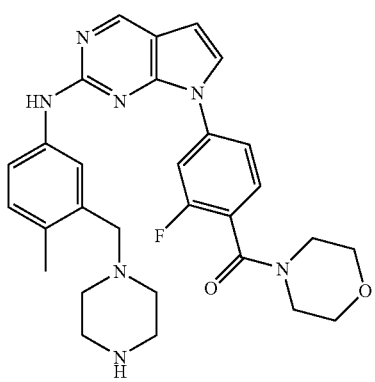 [SMILES: Cc1ccc(Nc2ncc3ccn(-c4ccc(C(=O)N5CCOCC5)c(F)c4)c3n2)cc1CN1CCNCC1]

The compound is prepared analogous to Example 2, using a Boc-protected piperazine derivative in Step 2.2, Final deprotection is achieved with 4 M HCl in dioxane at rt. HPLC: $t_R$=7.10 min. (Method B); MS-ES: (M+H)$^+$=530

EXAMPLE 337

4-(4-{7-[3-Fluoro-4-(morpholine-4-carbonyl)-phenyl]-7H-pyrrolo[2,3-d]pyrimidin-2-ylamino}-benzyl)-1-methyl-piperazin-2-one

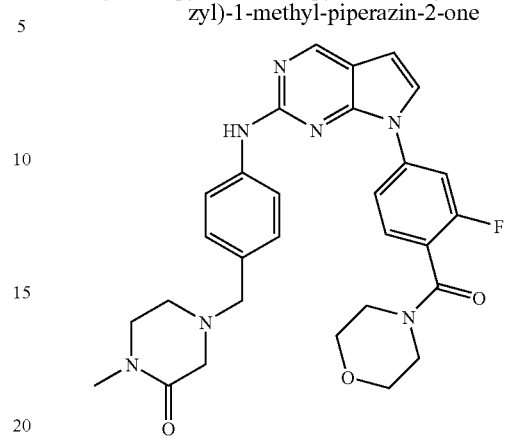

The compound is prepared analogous to Example 2. HPLC: $t_R$=7.19 min. (Method B); MS-ES: (M+H)$^+$=544; TLC*: $R_f$=0.27

EXAMPLE 338

1-[4-(4-{7-[4-(Morpholine-4-carbonyl)-phenyl]-7H-pyrrolo[2,3-d]pyrimidin-2-ylamino}-benzyl)-piperazin-1-yl]-ethanone

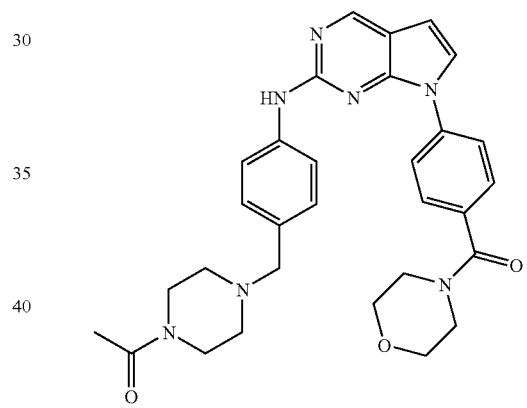

The compound is prepared analogous to Example 2. HPLC: $t_R$=7.02 min. (Method B); MS-ES: (M+H)$^+$=540; TLC*: $R_f$=0.24

EXAMPLE 339

4-(4-{2-[4-(4-Acetyl-piperazin-1-ylmethyl)-phenylamino]-pyrrolo[2 3-d]pyrimidin-7-yl}-2,6-difluoro-benzyl)-piperazin-2-one

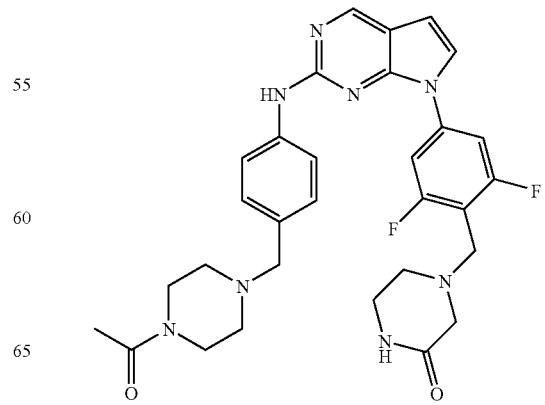

The compound is prepared analogous to Example 2.
HPLC: $t_R$=6.70 min. (Method B); MS-ES: (M+H)$^+$=575;
TLC*: $R_f$=0.15

EXAMPLE 340

4-(4-{2-[4-(4-Cyclopropyl-piperazin-1-ylmethyl)-phenylamino]-pyrrolo[2,3-d]pyrimidin-7-yl}-2,6-difluoro-benzyl)-piperazin-2-one

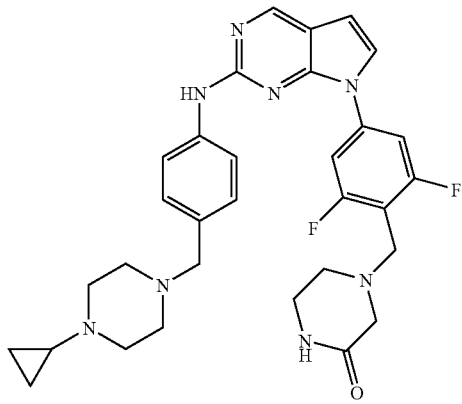 [SMILES: O=C1CN(Cc2c(F)cc(-n3ccc4cnc(Nc5ccc(CN6CCN(C7CC7)CC6)cc5)nc43)cc2F)CCN1]

The compound is prepared analogous to Example 2.
HPLC: $t_R$=6.76 min. (Method B); MS-ES: (M+H)$^+$=573;
TLC*: $R_f$=0.15

EXAMPLE 341

4-(2,6-Difluoro-4-{2-[4-(4-methyl-piperazin-1-yl)-phenylamino]-pyrrolo[2,3-d]pyrimidin-7-yl}-benzyl)-piperazin-2-one

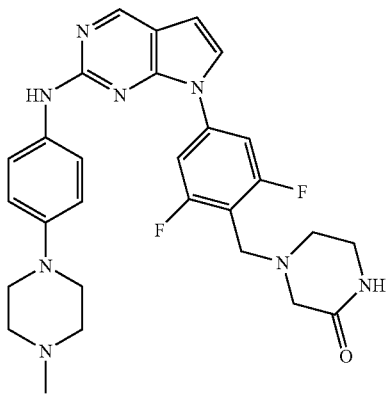 [SMILES: CN1CCN(c2ccc(Nc3ncc4ccn(-c5cc(F)c(CN6CCNC(=O)C6)c(F)c5)c4n3)cc2)CC1]

The compound is prepared analogous to Example 2.
HPLC: $t_R$=6.47 min. (Method B); MS-ES: (M+H)$^+$=533

EXAMPLE 342

4-(4-{2-[6-(cis-3,5-Dimethyl-piperazin-1-yl)-pyridin-3-ylamino]-pyrrolo[2,3-d]pyrimidin-7-yl}-2,6-difluoro-benzyl)-piperazin-2-one

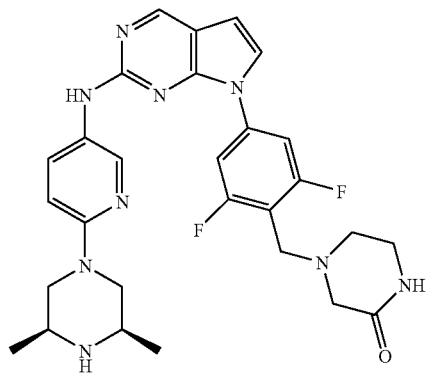 [SMILES: C[C@@H]1CN(c2ccc(Nc3ncc4ccn(-c5cc(F)c(CN6CCNC(=O)C6)c(F)c5)c4n3)cn2)C[C@H](C)N1]

The compound is prepared analogous to Example 2.
HPLC: $t_R$=6.42 min. (Method B); MS-ES: (M+H)$^+$=548

EXAMPLE 343

4-(2,6-Difluoro-4-{2-[4-methyl-3-(4-methyl-piperazin-1-ylmethyl)-phenylamino]-pyrrolo[2,3-d]pyrimidin-7-yl}-benzyl)-piperazin-2-one

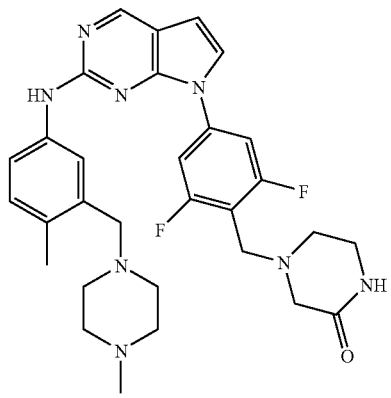 [SMILES: Cc1ccc(Nc2ncc3ccn(-c4cc(F)c(CN5CCNC(=O)C5)c(F)c4)c3n2)cc1CN1CCN(C)CC1]

The compound is prepared analogous to Example 2.
HPLC: $t_R$=6.77 min. (Method B); MS-ES: (M+H)$^+$=561;
TLC*: $R_f$=0.18

The compound is prepared analogous to Example 2.
HPLC: $t_R$=8.02 min. (Method B); MS-ES: (M+H)$^+$=560;
TLC*: $R_f$=0.18

EXAMPLE 344

4-{2,6-Difluoro-4-[2-(4-methyl-3-morpholin-4-ylm-ethyl-phenylamino)-pyrrolo[2,3-d]pyrimidin-7-yl]-benzyl}-piperazin-2-one

EXAMPLE 346

[7-(3,5-Difluoro-4-morpholin-4-ylmethyl-phenyl)-7H-pyrrolo[2,3-d]pyrimidin-2-yl]-((R)-3-methyl-4-pyrrolidin-2-yl-phenyl)-amine

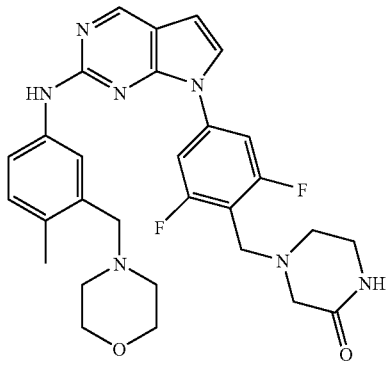 [SMILES: Cc1ccc(Nc2ncc3ccn(-c4cc(F)c(CN5CCNC(=O)C5)c(F)c4)c3n2)cc1CN1CCOCC1]

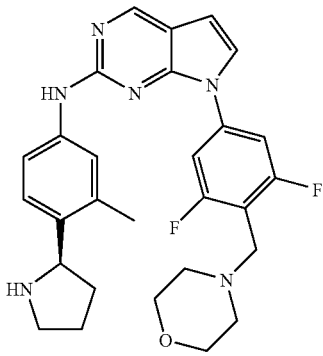

The compound is prepared analogous to Example 2.
HPLC: $t_R$=6.88 min. (Method B); MS-ES: (M+H)$^+$=548;
TLC*: $R_f$=0.35

The compound is prepared analogous to Example 2. The corresponding Boc-protected aniline is obtained from the procedure described in the *J. Am. Chem. Soc.* 2006, 128, 3538-3539 starting from 4-bromo-3-methyl-phenylamine.
HPLC: $t_R$=0.58 min (Method G); MS-ES: (M+H)$^+$=505

EXAMPLE 345

N-tert-Butyl-4-{2-[4-(4-cyclopropyl-piperazin-1-yl methyl)-phenylamino]-pyrrolo[2,3-d]pyrimidin-7-yl}-benzenesulfonamide

EXAMPLE 347

1-{5-[7-(3,5-Difluoro-4-morpholin-4-ylmethyl-phe-nyl)-7H-pyrrolo[2,3-d]pyrimidin-2-ylamino]-pyri-din-2-yl}-pyrrolidin-3-ol (racemic)

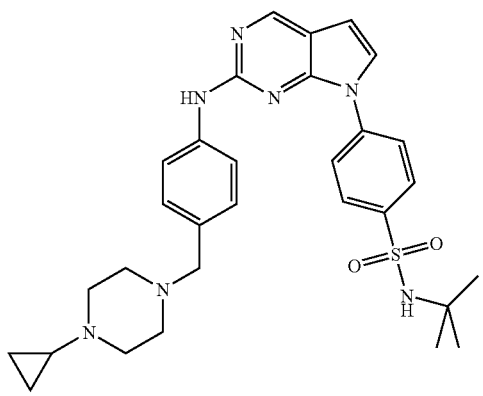 [SMILES: CC(C)(C)NS(=O)(=O)c1ccc(-n2ccc3cnc(Nc4ccc(CN5CCN(C6CC6)CC5)cc4)nc32)cc1]

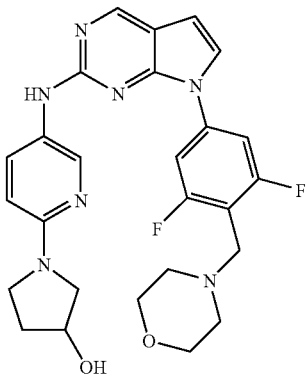 [SMILES: OC1CCN(c2ccc(Nc3ncc4ccn(-c5cc(F)c(CN6CCOCC6)c(F)c5)c4n3)cn2)C1]

The compound is prepared analogous to Example 2, using a TBDPS-protected alcohol derivative in Step 2.2, Final deprotection is achieved with 1 M TBAF in THF at rt. HPLC: $t_R$=0.57 min (Method G); MS-ES: (M+H)$^+$=508

EXAMPLE 348

N-tert-Butyl-4-{2-[4-(4-methyl-piperazin-1-yl)-phenylamino]-pyrrolo[2,3-d]pyrimidin-7-yl}-benzenesulfonamide

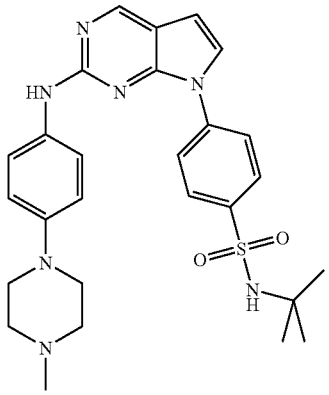 [SMILES: CN1CCN(c2ccc(Nc3ncc4ccn(-c5ccc(S(=O)(=O)NC(C)(C)C)cc5)c4n3)cc2)CC1]

The compound is prepared analogous to Example 2. HPLC: $t_R$=7.82 min. (Method B); MS-ES: (M+H)$^+$=520; TLC*: $R_f$=0.12

EXAMPLE 349

4-{2-[4-(4-Methyl-piperazin-1-yl)-phenylamino]-pyrrolo[2,3-d]pyrimidin-7-yl}-benzenesulfonamide

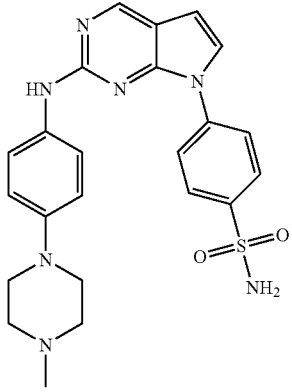 [SMILES: CN1CCN(c2ccc(Nc3ncc4ccn(-c5ccc(S(N)(=O)=O)cc5)c4n3)cc2)CC1]

The compound is prepared analogous to Example 2. HPLC: $t_R$=6.71 min. (Method B); MS-ES: (M+H)$^+$=464; TLC*: $R_f$=0.03

EXAMPLE 350

[7-(3,5-Difluoro-4-morpholin-4-ylmethyl-phenyl)-7H-pyrrolo[2,3-d]pyrimidin-2-yl]-[2-(tetrahydropyran-4-yloxy)-pyridin-4-yl]-amine

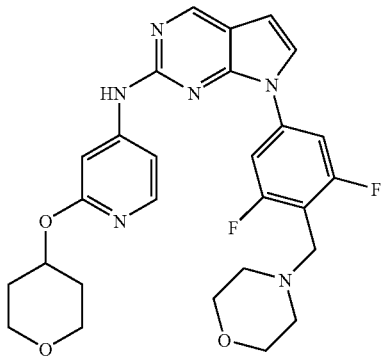 [SMILES: Fc1cc(-n2ccc3cnc(Nc4ccnc(OC5CCOCC5)c4)nc32)cc(F)c1CN1CCOCC1]

The compound is prepared analogous to 2, HPLC: $t_R$=0.67 min (Method G); MS-ES: (M+H)$^+$=523

EXAMPLE 351

N-tert-Butyl-4-{2-[6-(cis-3,5-dimethyl-piperazin-1-yl)-pyridin-3-ylamino]-pyrrolo[2,3-d]pyrimidin-7-yl}-benzenesulfonamide

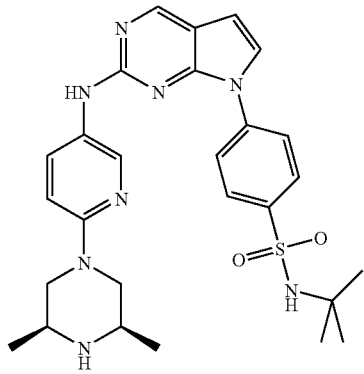

The compound is prepared analogous to Example 2. HPLC: $t_R$=7.77 min. (Method B); MS-ES: (M+H)$^+$=535; TLC*: $R_f$=0.05

EXAMPLE 352

[7-(3,5-Difluoro-4-morpholin-4-yl methyl-phenyl)-7H-pyrrolo[2,3-d]pyrimidin-2-yl]-[2-(2-morpholin-4-yl-ethoxy)-pyridin-4-yl]-amine

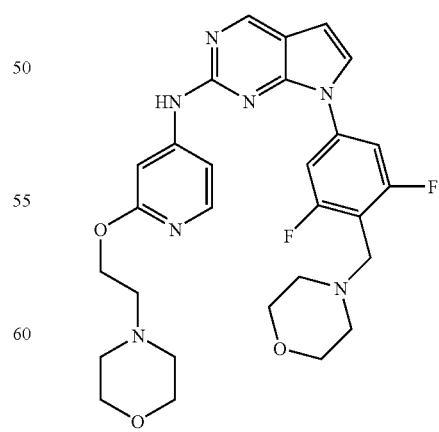

The compound is prepared analogous to Example 2. HPLC: $t_R$=0.58 min (Method G); MS-ES: (M+H)$^+$=552

EXAMPLE 353

N-tert-Butyl-4-{2-[4-methyl-3-(4-methyl-piperazin-1-ylmethyl)-phenylamino]-pyrrolo[2,3-d]pyrimidin-7-yl}-benzenesulfonamide

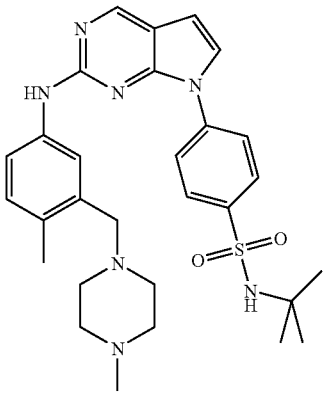 [SMILES: Cc1ccc(Nc2ncc3ccn(-c4ccc(S(=O)(=O)NC(C)(C)C)cc4)c3n2)cc1CN1CCN(C)CC1]

The compound is prepared analogous to Example 2. HPLC: $t_R$=8.07 min. (Method B); MS-ES: (M+H)$^+$=548; TLC*: $R_f$=0.22

EXAMPLE 354

[7-(3,5-Difluoro-4-morpholin-4-ylmethyl-phenyl)-7H-pyrrolo[2,3-d]pyrimidin-2-yl]-(4-morpholin-2-yl-phenyl)-amine (racemic)

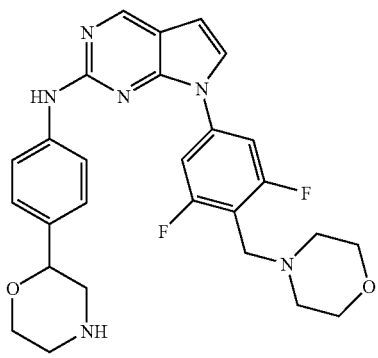 [SMILES: Fc1cc(-n2ccc3cnc(Nc4ccc(C5CNCCO5)cc4)nc32)cc(F)c1CN1CCOCC1]

The compound is prepared analogous to Example 2, using a Boc-protected morpholine derivative in Step 2.2, Final deprotection is achieved with 1 M HCl in EtOH at 60° C. HPLC: $t_R$=0.59 min (Method G); MS-ES: (M+H)$^+$=507

EXAMPLE 355

[7-(3,5-Difluoro-4-morpholin-4-yl methyl-phenyl)-7H-pyrrolo[2,3-d]pyrimidin-2-yl]-[3-(cis-3,5-dimethyl-piperazin-1-ylmethyl)-4-methyl-phenyl]-amine

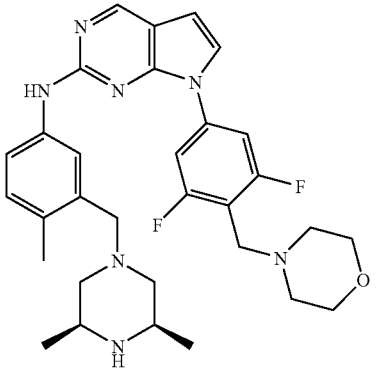 [SMILES: Cc1ccc(Nc2ncc3ccn(-c4cc(F)c(CN5CCOCC5)c(F)c4)c3n2)cc1CN1C[C@@H](C)N[C@@H](C)C1]

The compound is prepared analogous to Example 2. HPLC: $t_R$=6.73 min. (Method B); MS-ES: (M+H)$^+$=562; TLC*: $R_f$=0.22

EXAMPLE 356

N-tert-Butyl-4-{2-[6-((2R,5S)-2,5-dimethyl-piperazin-1-yl)-pyridin-3-ylamino]-pyrrolo[2,3-d]pyrimidin-7-yl}-benzenesulfonamide (racemic)

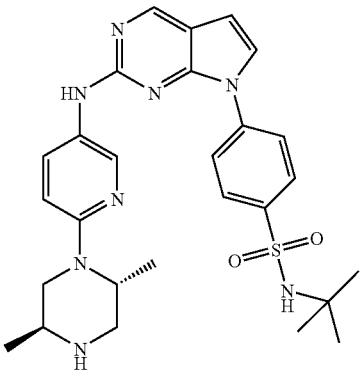 [SMILES: C[C@@H]1CN[C@@H](C)CN1c1ccc(Nc2ncc3ccn(-c4ccc(S(=O)(=O)NC(C)(C)C)cc4)c3n2)cn1]

The compound is prepared analogous to Example 2. HPLC: $t_R$=7.77 min. (Method B); MS-ES: (M+H)$^+$=535; TLC*: $R_f$=0.04

EXAMPLE 357

4-{2-[6-((2R,5S)-2,5-Dimethyl-piperazin-1-yl)-pyridin-3-ylamino]-pyrrolo[2,3-d]pyrimidin-7-yl}-benzenesulfonamide (racemic)

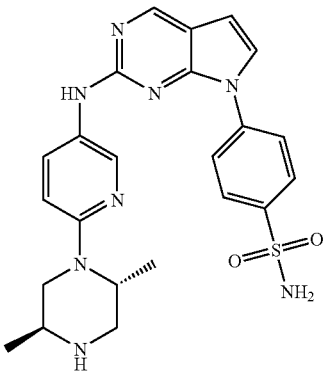 [SMILES: C[C@@H]1CN[C@@H](C)CN1c1ccc(Nc2ncc3ccn(-c4ccc(S(N)(=O)=O)cc4)c3n2)cn1]

The compound is prepared analogous to Example 2. HPLC: $t_R$=6.64 min. (Method B); MS-ES: (M+H)$^+$=479; TLC*: $R_f$=0.14

EXAMPLE 358

[7-(3,5-Difluoro-4-morpholin-4-ylmethyl-phenyl)-7H-pyrrolo[2,3-d]pyrimidin-2-yl]-[3-(2,5-dioxa-8-aza-spiro[3.5]non-8-ylmethyl)-4-methyl-phenyl]-amine

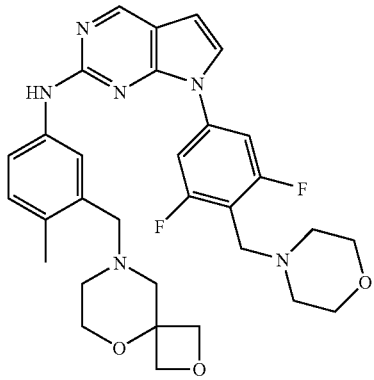 [SMILES: Cc1ccc(Nc2ncc3ccn(-c4cc(F)c(CN5CCOCC5)c(F)c4)c3n2)cc1CN1CCOC2(COC2)C1]

The compound is prepared analogous to Example 2. HPLC: $t_R$=6.93 min. (Method B); MS-ES: (M+H)$^+$=577; TLC*: $R_f$=0.58

EXAMPLE 359

(4-{2-[3-(2,5-Dioxa-8-aza-spiro[3.5]non-8-ylmethyl)-4-methyl-phenylamino]-pyrrolo[2,3-d]pyrimidin-7-yl}-2-fluoro-phenyl)-morpholin-4-yl-methanone

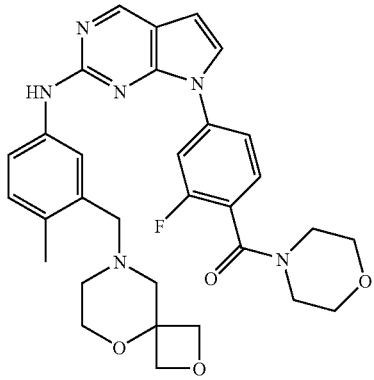 [SMILES: Cc1ccc(Nc2ncc3ccn(-c4ccc(C(=O)N5CCOCC5)c(F)c4)c3n2)cc1CN1CCOC2(COC2)C1]

The compound is prepared analogous to Example 2. HPLC: $t_R$=7.60 min. (Method B); MS-ES: (M+H)$^+$=573; TLC*: $R_f$=0.51

EXAMPLE 360

[6-(cis-3,5-Dimethyl-piperazin-1-yl)-pyridin-3-yl]-{7-[4-(2,5-dioxa-8-aza-spiro[3.5]non-8-ylmethyl)-3,5-difluoro-phenyl]-7H-pyrrolo[2,3-d]pyrimidin-2-yl}-amine

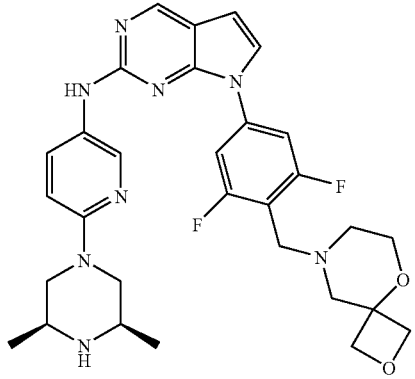 [SMILES: C[C@@H]1CN(c2ccc(Nc3ncc4ccn(-c5cc(F)c(CN6CCOC7(COC7)C6)c(F)c5)c4n3)cn2)C[C@H](C)N1]

The compound is prepared analogous to Example 2. HPLC: $t_R$=6.65 min. (Method B); MS-ES: (M+H)$^+$=577; TLC (15% methanol/85% methylene chloride): $R_f$=0.16

EXAMPLE 361

{4-[7-(3,5-Difluoro-4-morpholin-4-ylmethyl-phenyl)-7H-pyrrolo[2,3-d]pyrimidin-2-ylamino]-pyridin-2-yl}-(4-methyl-piperazin-1-yl)-methanone

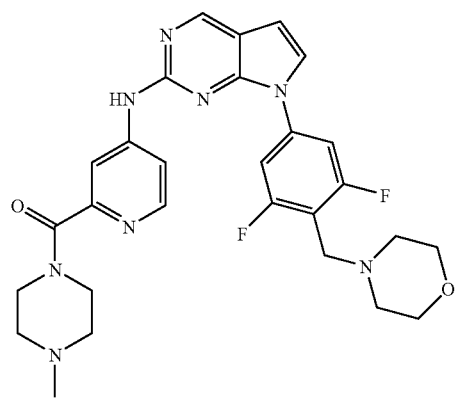 [SMILES: CN1CCN(C(=O)c2cc(Nc3ncc4ccn(-c5cc(F)c(CN6CCOCC6)c(F)c5)c4n3)ccn2)CC1]

The compound is prepared analogous to Example 2. HPLC: $t_R$=6.47 min. (Method B); MS-ES: (M+H)$^+$=549; TLC (15% methanol/85% methylene chloride): $R_f$=0.15

EXAMPLE 362

{4-[7-(3,5-Difluoro-4-morpholin-4-ylmethyl-phenyl)-7H-pyrrolo[2,3-d]pyrimidin-2-ylamino]-pyridin-2-yl}-(2,5-dioxa-8-aza-spiro[3.5]non-8-yl)-methanone

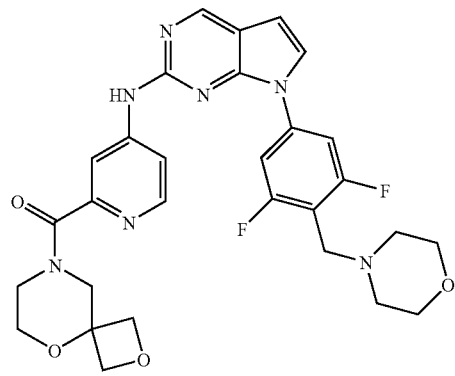 [SMILES: O=C(c1cc(Nc2ncc3ccn(-c4cc(F)c(CN5CCOCC5)c(F)c4)c3n2)ccn1)N1CCOC2(COC2)C1]

The compound is prepared analogous to Example 2. HPLC: $t_R$=6.95 min. (Method B); MS-ES: (M+H)$^+$=578; TLC (15% methanol/85% methylene chloride): $R_f$=0.47

EXAMPLE 363

N-tert-Butyl-4-{2-[4-(2-pyrrolidin-1-yl-ethoxy)-phenylamino]-pyrrolo[2,3-d]pyrimidin-7-yl}-benzenesulfonamide

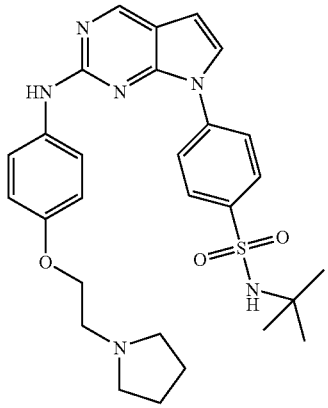 [SMILES: CC(C)(C)NS(=O)(=O)c1ccc(-n2ccc3cnc(Nc4ccc(OCCN5CCCC5)cc4)nc32)cc1]

The compound is prepared analogous to Example 2. HPLC: $t_R$=8.03 min. (Method B); MS-ES: (M+H)$^+$=535; TLC*: $R_f$=0.10

EXAMPLE 364

[7-(3,5-Difluoro-4-morpholin-4-ylmethyl-phenyl)-7H-pyrrolo[2,3-d]pyrimidin-2-yl]-[2-(3-trifluoromethyl-piperazin-1-yl)-pyridin-4-yl]-amine (racemic)

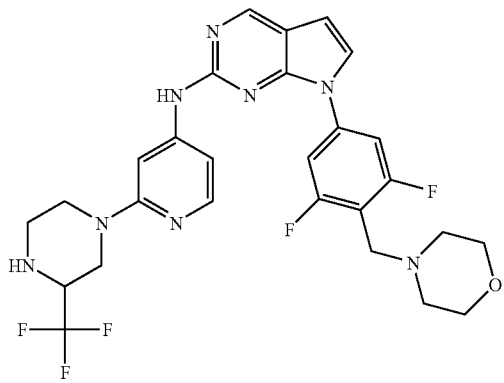 [SMILES: Fc1cc(-n2ccc3cnc(Nc4ccnc(N5CCNC(C(F)(F)F)C5)c4)nc32)cc(F)c1CN1CCOCC1]

The compound is prepared analogous to Example 2. HPLC (racemic mixture): $t_R$=3.62 min and 4.37 min (Method C); MS-ES: (M+H)$^+$=575

EXAMPLE 365

[3-(4-Cyclopropyl-piperazin-1-ylmethyl)-4-methyl-phenyl]-[7-(3,5-difluoro-4-morpholin-4-ylmethyl-phenyl)-7H-pyrrolo[2,3-d]pyrimidin-2-yl]-amine

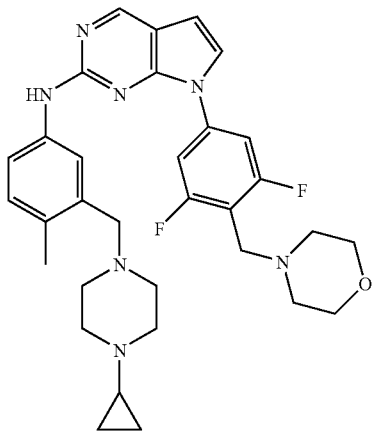 [SMILES: Cc1ccc(Nc2ncc3ccn(-c4cc(F)c(CN5CCOCC5)c(F)c4)c3n2)cc1CN1CCN(C2CC2)CC1]

The compound is prepared analogous to Example 2. HPLC: $t_R$=6.94 min. (Method B); MS-ES: (M+H)$^+$=574; TLC*: $R_f$=0.38

EXAMPLE 366

(4-{2-[3-(4-Cyclopropyl-piperazin-1-ylmethyl)-4-methyl-phenylamino]-pyrrolo[2,3-d]pyrimidin-7-yl}-2-fluoro-phenyl)-morpholin-4-yl-methanone

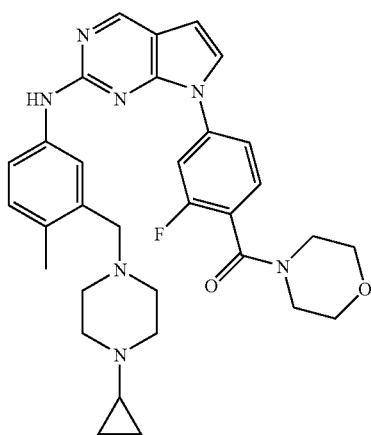 [SMILES: Cc1ccc(Nc2ncc3ccn(-c4ccc(C(=O)N5CCOCC5)c(F)c4)c3n2)cc1CN1CCN(C2CC2)CC1]

The compound is prepared analogous to Example 2. HPLC: $t_R$=7.62 min. (Method B); MS-ES: (M+H)$^+$=570; TLC*: $R_f$=0.55

EXAMPLE 367

(4-{2-[3-(cis-3,5-Dimethyl-piperazin-1-ylmethyl)-4-methyl-phenylamino]-pyrrolo[2,3-d]pyrimidin-7-yl}-2-fluoro-phenyl)-morpholin-4-yl-methanone

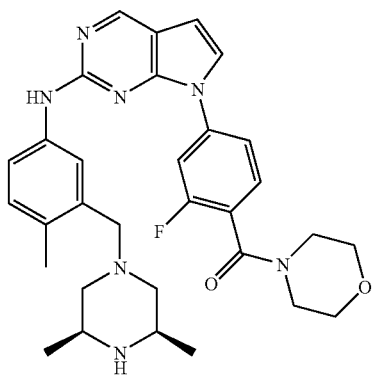 [SMILES: Cc1ccc(Nc2ncc3ccn(-c4ccc(C(=O)N5CCOCC5)c(F)c4)c3n2)cc1CN1C[C@@H](C)N[C@@H](C)C1]

The compound is prepared analogous to Example 2. HPLC: $t_R$=7.41 min (Method B); MS-ES: (M+H)$^+$=558

EXAMPLE 368

4-{2-[4-Methyl-3-(4-methyl-piperazin-1-ylmethyl)-phenylamino]-pyrrolo[2,3-d]pyrimidin-7-yl}-benzenesulfonamide

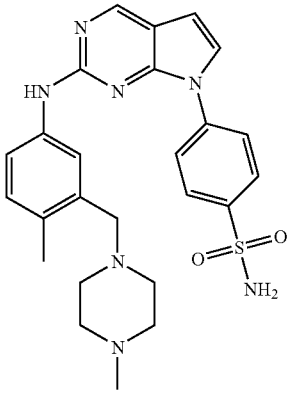 [SMILES: Cc1ccc(Nc2ncc3ccn(-c4ccc(S(N)(=O)=O)cc4)c3n2)cc1CN1CCN(C)CC1]

The compound is prepared analogous to Example 2. HPLC: $t_R$=6.84 min (Method B); MS-ES: (M+H)$^+$=492; TLC*: $R_f$=0.03

EXAMPLE 369

4-{2-[6-(cis-3,5-Dimethyl-piperazin-1-yl)-pyridin-3-ylamino]-pyrrolo[2,3-d]pyrimidin-7-yl}-benzenesulfonamide

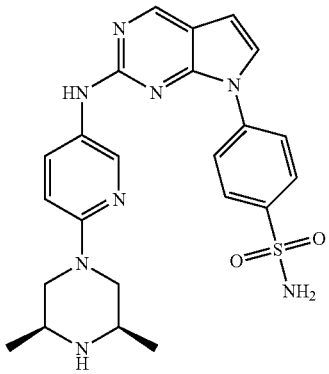 [SMILES: C[C@@H]1CN(c2ccc(Nc3ncc4ccn(-c5ccc(S(N)(=O)=O)cc5)c4n3)cn2)C[C@H](C)N1]

The compound is prepared analogous to Example 2. HPLC: $t_R$=6.67 min (Method B); MS-ES: (M+H)$^+$=479; TLC (50% methanol/50% methylene chloride): $R_f$=0.26

EXAMPLE 370

4-{5-[7-(3,5-Difluoro-4-morpholin-4-ylmethyl-phenyl)-7H-pyrrolo[2,3-d]pyrimidin-2-ylamino]-2-methyl-benzyl}-piperazine-1-carbaldehyde

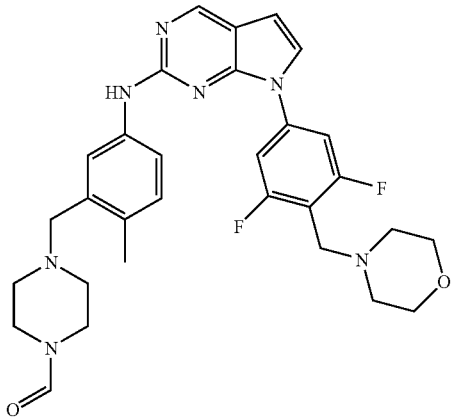 [SMILES: Cc1ccc(Nc2ncc3ccn(-c4cc(F)c(CN5CCOCC5)c(F)c4)c3n2)cc1CN1CCN(C=O)CC1]

The compound is obtained by treating [7-(3,5-difluoro-4-morpholin-4-ylmethyl-phenyl)-7H-pyrrolo[2,3-d]pyrimidin-2-yl]-(4-methyl-3-piperazin-1-ylmethyl-phenyl)-amine (Example 332) with formic acid 4-nitro-phenyl ester in presence of triethylamine in THF. HPLC: $t_R$=6.84 min (Method B); MS-ES: (M+H)$^+$=562

EXAMPLE 371

{4-[7-(3,5-Difluoro-4-morpholin-4-ylmethyl-phenyl)-7H-pyrrolo[2,3-d]pyrimidin-2-ylamino]-pyridin-2-yl}-(cis-3,5-dimethyl-piperazin-1-yl)-methanone

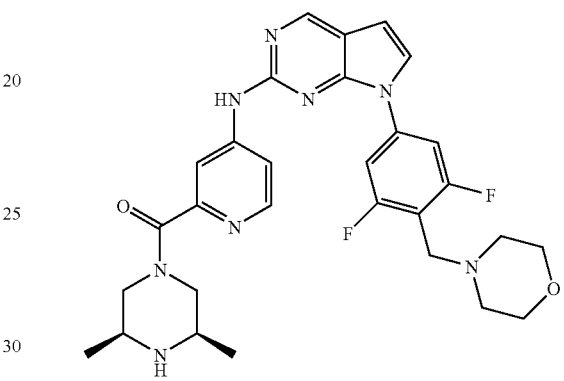

The compound is prepared analogous to Example 2. HPLC: $t_R$=6.53 min (Method B); MS-ES: (M+H)$^+$=563; TLC (15% methanol/85% methylene chloride): $R_f$=0.28

EXAMPLE 372

[7-(3,5-Difluoro-4-morpholin-4-ylmethyl-phenyl)-7H-pyrrolo[2,3-d]pyrimidin-2-yl]-(2-piperazin-1-ylmethyl-pyridin-4-yl)-amine

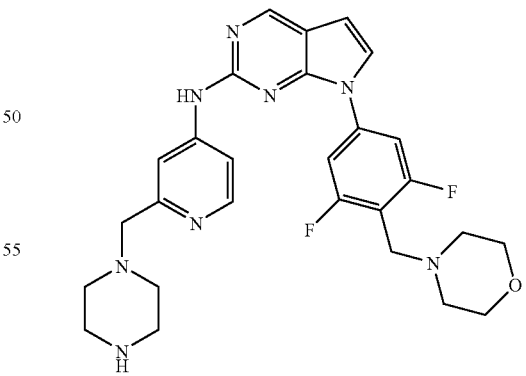

The compound is prepared analogous to Example 2, using a Boc-protected piperazine derivative in Step 2.2. Final deprotection is achieved with 4 M HCl in dioxane at rt. HPLC: $t_R$=6.52 min (Method B); MS-ES: (M+H)$^+$=521; TLC (64% methanol/32% methylene chloride/4% aq. ammonia 24%): $R_f$=0.49

EXAMPLE 373

[3-(4,7-Diaza-spiro[2.5]oct-7-ylmethyl)-4-methyl-phenyl]-[7-(3,5-difluoro-4-morpholin-4-ylmethyl-phenyl)-7H-pyrrolo[2,3-d]pyrimidin-2-yl]-amine

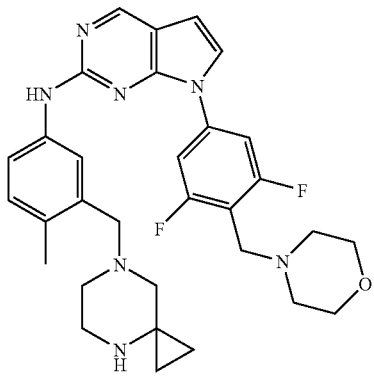 [SMILES: Cc1ccc(Nc2ncc3ccn(-c4cc(F)c(CN5CCOCC5)c(F)c4)c3n2)cc1CN1CCNC2(CC2)C1]

The compound is prepared analogous to Example 2. HPLC: $t_R$=6.62 min (Method B); MS-ES: (M+H)$^+$=560

EXAMPLE 374

(4-{2-[3-(4,7-Diaza-spiro[2.5]oct-7-ylmethyl)-4-methyl-phenylamino]-pyrrolo[2,3-d]pyrimidin-7-yl}-2-fluoro-phenyl)-morpholin-4-yl-methanone

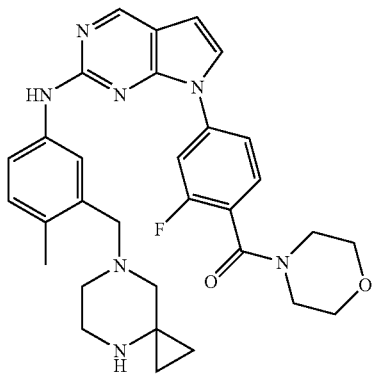 [SMILES: Cc1ccc(Nc2ncc3ccn(-c4ccc(C(=O)N5CCOCC5)c(F)c4)c3n2)cc1CN1CCNC2(CC2)C1]

The compound is prepared analogous to Example 2. HPLC: $t_R$=7.33 min (Method B); MS-ES: (M+H)$^+$=556

EXAMPLE 375

Propane-2-sulfonic acid (4-{2-[6-(cis-3,5-dimethyl-piperazin-1-yl)-pyridin-3-ylamino]-pyrrolo[2,3-d]pyrimidin-7-yl}-phenyl)-amide

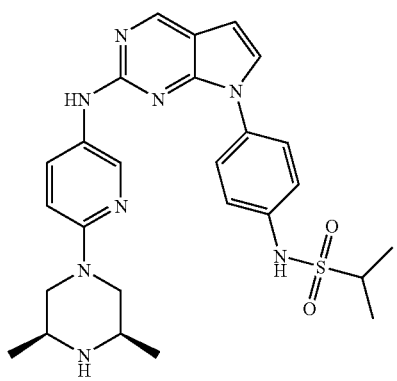 [SMILES: CC(C)S(=O)(=O)Nc1ccc(-n2ccc3cnc(Nc4ccc(N5C[C@@H](C)N[C@@H](C)C5)nc4)nc32)cc1]

The compound is prepared analogous to Example 2. HPLC: $t_R$=7.26 min (Method B); MS-ES: (M+H)$^+$=521; TLC (50% methanol/50% methylene chloride): $R_f$=0.30

EXAMPLE 376

N-tert-Butyl-4-[2-(4-methyl-3-piperazin-1-ylmethyl-phenylamino)-pyrrolo[2,3-d]pyrimidin-7-yl]-benzenesulfonamide

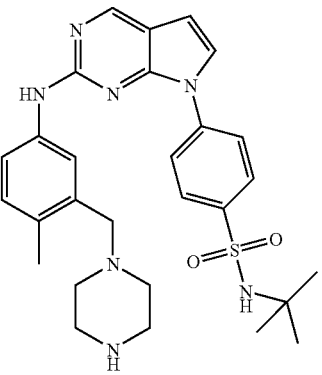 [SMILES: Cc1ccc(Nc2ncc3ccn(-c4ccc(S(=O)(=O)NC(C)(C)C)cc4)c3n2)cc1CN1CCNCC1]

The compound is prepared analogous to Example 2, using a Boc-protected piperazine derivative in Step 2.2. Final deprotection is achieved with 4 M HCl in dioxane at rt. HPLC: $t_R$=7.86 min (Method B); MS-ES: (M+H)$^+$=534; TLC (50% methanol/50% methylene chloride): $R_f$=0.09

EXAMPLE 377

[7-(3,5-Difluoro-4-morpholin-4-ylmethyl-phenyl)-7H-pyrrolo[2,3-d]pyrimidin-2-yl]-[5-(4-methyl-piperazin-1-yl)-pyridin-2-yl]-amine

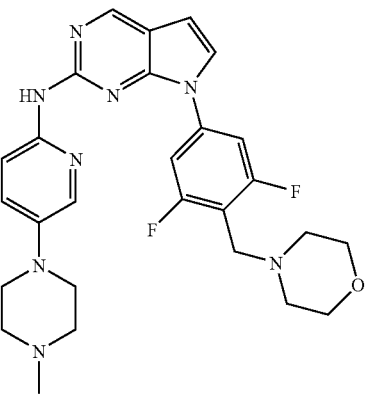 [SMILES: CN1CCN(c2ccc(Nc3ncc4ccn(-c5cc(F)c(CN6CCOCC6)c(F)c5)c4n3)nc2)CC1]

The compound is prepared analogous to Example 2. HPLC: $t_R$=3.90 min (Method C); MS-ES: (M+H)$^+$=521

EXAMPLE 378

[7-(3,5-Difluoro-4-morpholin-4-ylmethyl-phenyl)-7H-pyrrolo[2,3-d]pyrimidin-2-yl]-[3-((2R,5S)-2,5-dimethyl-piperazin-1-ylmethyl)-4-methyl-phenyl]-amine (racemic)

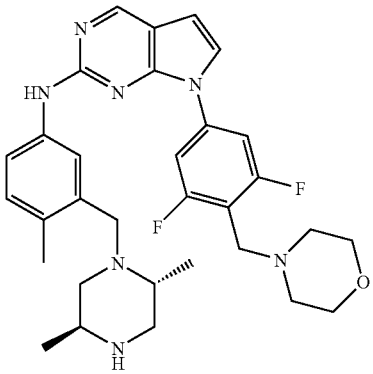 [SMILES: Cc1ccc(Nc2ncc3ccn(-c4cc(F)c(CN5CCOCC5)c(F)c4)c3n2)cc1CN1C[C@H](C)NC[C@H]1C]

The compound is prepared analogous to Example 2. HPLC: $t_R$=6.73 min (Method B); MS-ES: (M+H)$^+$=562; TLC (100% methanol): $R_f$=0.11

EXAMPLE 379

(4-{2-[3-((2R,5S)-2,5-Dimethyl-piperazin-1-ylmethyl)-4-methyl-phenylamino]-pyrrolo[2,3-d]pyrimidin-7-yl}-2-fluoro-phenyl)-morpholin-4-yl-methanone (racemic)

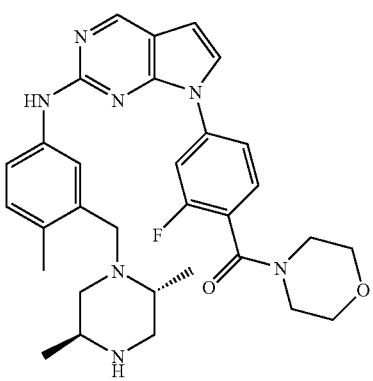 [SMILES: Cc1ccc(Nc2ncc3ccn(-c4ccc(C(=O)N5CCOCC5)c(F)c4)c3n2)cc1CN1C[C@H](C)NC[C@H]1C]

The compound is prepared analogous to Example 2. HPLC: $t_R$=7.38 min (Method B); MS-ES: (M+H)$^+$=558; TLC (100% methanol): $R_f$=0.12

EXAMPLE 380

N-(4-{2-[6-(cis-3,5-Dimethyl-piperazin-1-yl)-pyridin-3-ylamino]-pyrrolo[2,3-d]pyrimidin-7-yl}-phenyl)-methanesulfonamide

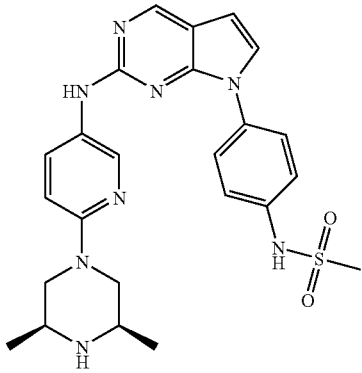

The compound is prepared analogous to Example 2. HPLC: $t_R$=6.89 min (Method B); MS-ES: (M+H)$^+$=493; TLC (50% methanol/50% methylene chloride): $R_f$=0.25

EXAMPLE 381

{2-Fluoro-4-[2-(4-piperidin-4-ylmethyl-phenylamino)-pyrrolo[2,3-d]pyrimidin-7-yl]-phenyl}-morpholin-4-yl-methanone

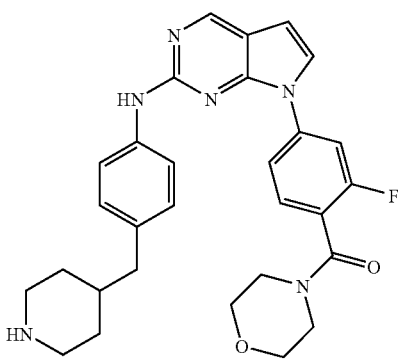 [SMILES: O=C(c1ccc(-n2ccc3cnc(Nc4ccc(CC5CCNCC5)cc4)nc32)cc1F)N1CCOCC1]

The compound is prepared analogous to Example 2, using a trifluoroacetyl-protected piperidine derivative in Step 2.2. Final deprotection is achieved with $K_2CO_3$ in methanol/water at rt. The corresponding aniline is obtained by the procedure described in patent WO98/05292 p. 104-105 compound (111), followed by nitro reduction. HPLC: $t_R$=7.52 min (Method B); MS-ES: (M+H)⁺=515; TLC (50% methanol/50% methylene chloride): $R_f$=0.06

EXAMPLE 382

4-{2,6-Difluoro-4-[2-(4-methyl-3-piperazin-1-ylmethyl-phenylamino)-pyrrolo[2,3-d]pyrimidin-7-yl]-benzyl}-piperazin-2-one

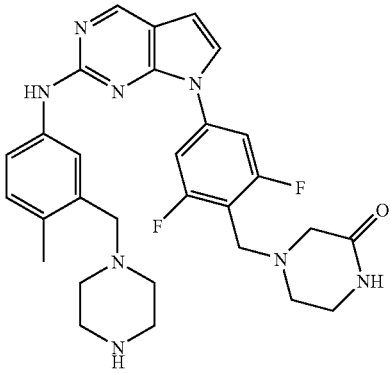 [SMILES: Cc1ccc(Nc2ncc3ccn(-c4cc(F)c(CN5CCNC(=O)C5)c(F)c4)c3n2)cc1CN1CCNCC1]

The compound is prepared analogous to Example 2, using a Boc-protected piperazine derivative in Step 2.2. Final deprotection is achieved with 4 M HCl in dioxane at rt. HPLC: $t_R$=6.64 min (Method B); MS-ES: (M+H)⁺=547

EXAMPLE 383

[7-(3,5-Difluoro-4-morpholin-4-ylmethyl-phenyl)-7H-pyrrolo[2,3-d]pyrimidin-2-yl]-(4-piperidin-4-ylmethyl-phenyl)-amine

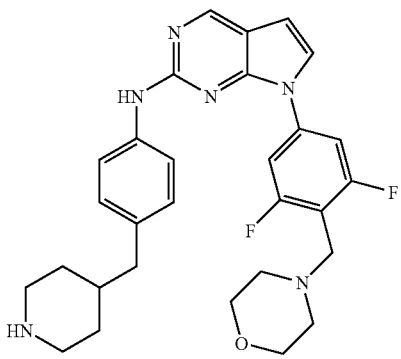

The compound is prepared analogous to Example 2, using a trifluoroacetyl-protected piperidine derivative in Step 2.2. Final deprotection is achieved with $K_2CO_3$ in methanol/water at rt. The corresponding aniline is obtained by the procedure described in patent WO98/05292 p. 104-105 compound (111), followed by nitro reduction. HPLC: $t_R$=6.93 min (Method B); MS-ES: (M+H)⁺=519; TLC (49% methanol/49% methylene chloride/2% 7N ammonia in methanol): $R_f$=0.06

EXAMPLE 384

[7-(3,5-Difluoro-4-morpholin-4-ylmethyl-phenyl)-7H-pyrrolo[2,3-d]pyrimidin-2-yl]-[2-(4-methyl-piperazin-1-ylmethyl)-pyridin-4-yl]-amine

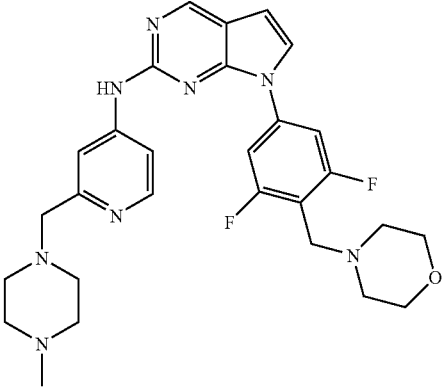 [SMILES: CN1CCN(Cc2cc(Nc3ncc4ccn(-c5cc(F)c(CN6CCOCC6)c(F)c5)c4n3)ccn2)CC1]

The compound is prepared analogous to Example 2. HPLC: $t_R$=6.57 min (Method B); MS-ES: (M+H)⁺=535

EXAMPLE 385

[7-(3,5-Difluoro-4-morpholin-4-ylmethyl-phenyl)-7H-pyrrolo[2,3-d]pyrimidin-2-yl]-[3-(3,3-dimethyl-piperazin-1-ylmethyl)-4-methyl-phenyl]-amine

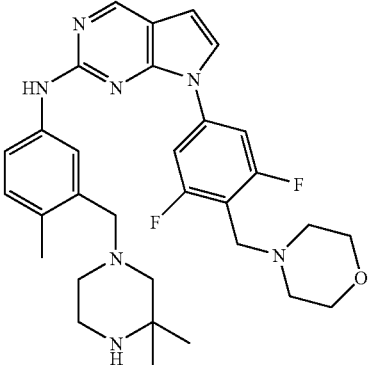 [SMILES: Cc1ccc(Nc2ncc3ccn(-c4cc(F)c(CN5CCOCC5)c(F)c4)c3n2)cc1CN1CCNC(C)(C)C1]

The compound is prepared analogous to Example 2. HPLC: $t_R$=7.03 min (Method B); MS-ES: (M+H)⁺=562

EXAMPLE 386

(4-{2-[3-(3,3-Dimethyl-piperazin-1-ylmethyl)-4-methyl-phenylamino]-pyrrolo[2,3-d]pyrimidin-7-yl}-2-fluoro-phenyl)-morpholin-4-yl-methanone

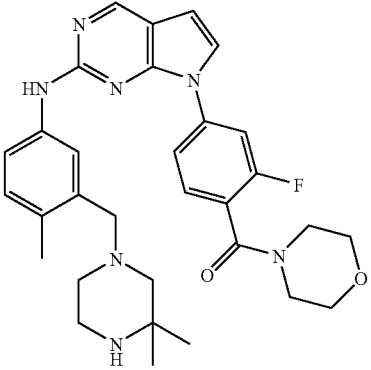 [SMILES: Cc1ccc(Nc2ncc3ccn(-c4ccc(C(=O)N5CCOCC5)c(F)c4)c3n2)cc1CN1CCNC(C)(C)C1]

The compound is prepared analogous to Example 2. HPLC: $t_R$=7.82 min (Method B); MS-ES: (M+H)$^+$=558

EXAMPLE 387

N-tert-Butyl-4-{2-[3-(cis-3,5-dimethyl-piperazin-1-ylmethyl)-4-methyl-phenylamino]-pyrrolo[2,3-d]pyrimidin-7-yl}-benzenesulfonamide

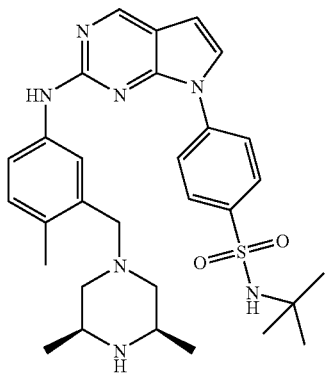 [SMILES: Cc1ccc(Nc2ncc3ccn(-c4ccc(S(=O)(=O)NC(C)(C)C)cc4)c3n2)cc1CN1C[C@@H](C)N[C@@H](C)C1]

The compound is prepared analogous to Example 2. HPLC: $t_R$=8.06 min (Method B); MS-ES: (M+H)$^+$=562; TLC (33% methanol/67% methylene chloride): $R_f$=0.23

EXAMPLE 388

1-{5-[7-(3,5-Difluoro-4-morpholin-4-ylmethyl-phenyl)-7H-pyrrolo[2,3-d]pyrimidin-2-ylamino]-pyridin-2-ylmethyl}-pyrrolidin-3-ol (racemic)

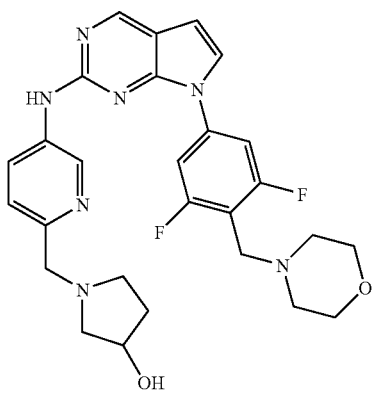 [SMILES: OC1CCN(Cc2ccc(Nc3ncc4ccn(-c5cc(F)c(CN6CCOCC6)c(F)c5)c4n3)cn2)C1]

The compound is prepared analogous to Example 2. HPLC: $t_R$=4.00 min (Method C); MS-ES: (M)$^+$=521

EXAMPLE 389

3-{4-[7-(3,5-Difluoro-4-morpholin-4-ylmethyl-phenyl)-7H-pyrrolo[2,3-d]pyrimidin-2-ylamino]-phenyl}-hexahydro-pyrido[1,2-a]pyrazin-1-one

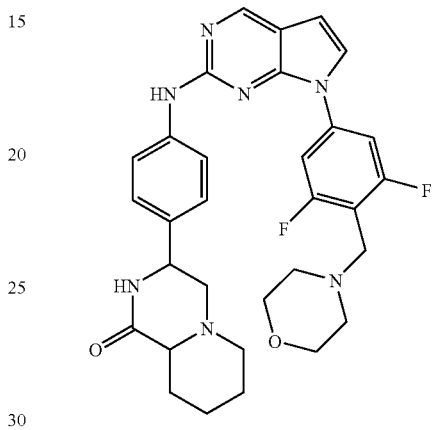

The compound is prepared analogous to Example 2. HPLC: $t_R$=0.60 min (Method G); MS-ES: (M+H)$^+$=574

EXAMPLE 390

{4-[7-(3,5-Difluoro-4-morpholin-4-ylmethyl-phenyl)-7H-pyrrolo[2,3-d]pyrimidin-2-ylamino]-pyridin-2-yl}-piperazin-1-yl-methanone

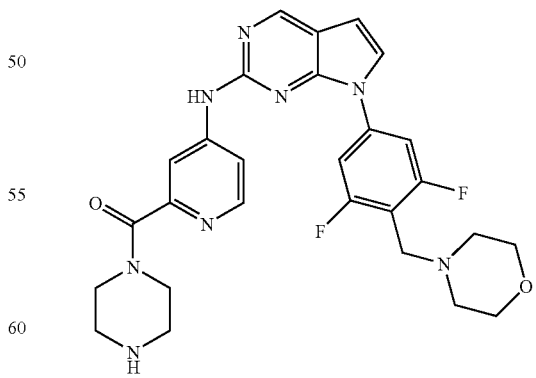

The compound is prepared analogous to Example 2, using a Boc-protected piperazine derivative in Step 2.2. Final deprotection is achieved with 4 M HCl in dioxane at rt. HPLC: $t_R$=6.37 min (Method B); MS-ES: (M+H)$^+$=535

EXAMPLE 391

[7-(3,5-Difluoro-4-morpholin-4-ylmethyl-phenyl)-7H-pyrrolo[2,3-d]pyrimidin-2-yl]-[2-(cis-3,5-dimethyl-piperazin-1-ylmethyl)-pyridin-4-yl]-amine

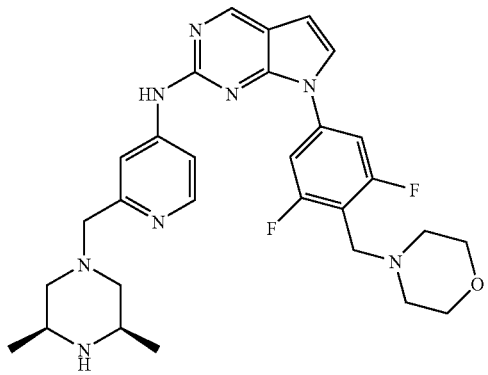 [SMILES: C[C@@H]1CN(Cc2cc(Nc3ncc4ccn(-c5cc(F)c(CN6CCOCC6)c(F)c5)c4n3)ccn2)C[C@H](C)N1]

The compound is prepared analogous to Example 2. HPLC: $t_R$=6.75 min (Method B); MS-ES: (M+H)$^+$=549

EXAMPLE 392

[7-(3,5-Difluoro-4-morpholin-4-ylmethyl-phenyl)-7H-pyrrolo[2,3-d]pyrimidin-2-yl]-[2-(piperidin-4-ylmethoxy)-pyridin-4-yl]-amine

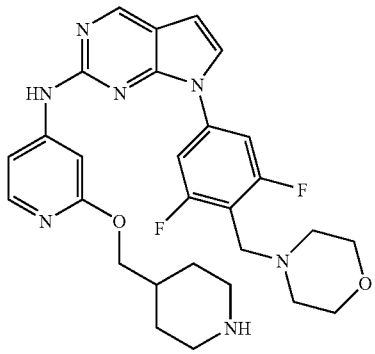 [SMILES: Fc1cc(-n2ccc3cnc(Nc4ccnc(OCC5CCNCC5)c4)nc32)cc(F)c1CN1CCOCC1]

The compound is prepared analogous to Example 2, using a Boc-protected piperazine derivative in Step 2.2. Final deprotection is achieved with 4 M HCl in dioxane at rt. HPLC: $t_R$=6.67 min (Method B); MS-ES: (M+H)$^+$=536; TLC (33% methanol/66% methylene chloride/1% aq. ammonia 24%): $R_f$=0.28

EXAMPLE 393

[7-(3,5-Difluoro-4-morpholin-4-ylmethyl-phenyl)-7H-pyrrolo[2,3-d]pyrimidin-2-yl]-[3-(3,3-difluoro-pyrrolidin-1-ylmethyl)-4-methyl-phenyl]-amine

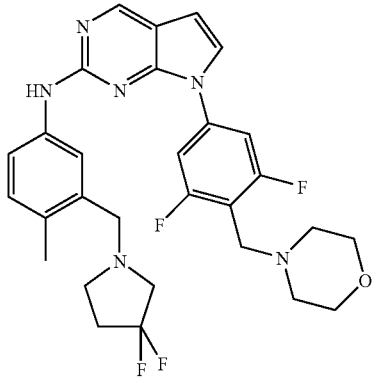 [SMILES: Cc1ccc(Nc2ncc3ccn(-c4cc(F)c(CN5CCOCC5)c(F)c4)c3n2)cc1CN1CCC(F)(F)C1]

The compound is prepared analogous to Example 2. HPLC: $t_R$=7.08 min (Method B); MS-ES: (M+H)$^+$=555; TLC*: $R_f$=0.63

EXAMPLE 394

1-{5-[7-(3,5-Difluoro-4-morpholin-4-ylmethyl-phenyl)-7H-pyrrolo[2,3-d]pyrimidin-2-ylamino]-2-methyl-benzyl}-azetidin-3-ol

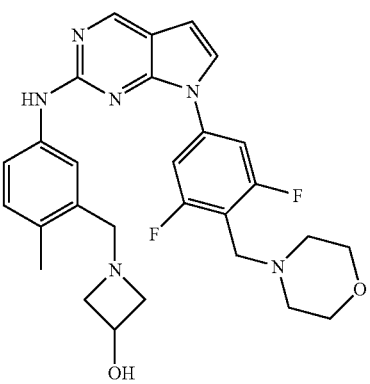 [SMILES: Cc1ccc(Nc2ncc3ccn(-c4cc(F)c(CN5CCOCC5)c(F)c4)c3n2)cc1CN1CC(O)C1]

The compound is prepared analogous to Example 2. HPLC: $t_R$=6.67 min (Method B); MS-ES: (M+H)$^+$=521; TLC (20% methanol/80% methylene chloride): $R_f$=0.36

EXAMPLE 395

4-{5-[7-(3,5-Difluoro-4-morpholin-4-ylmethyl-phenyl)-7H-pyrrolo[2,3-d]pyrimidin-2-ylamino]-2-methyl-benzyl}-1-methyl-piperazin-2-one

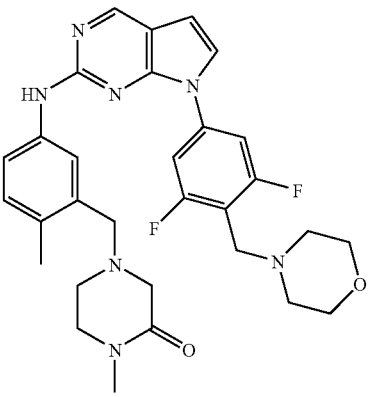 [SMILES: Cc1ccc(Nc2ncc3ccn(-c4cc(F)c(CN5CCOCC5)c(F)c4)c3n2)cc1CN1CCN(C)C(=O)C1]

The compound is prepared analogous to Example 2. HPLC: $t_R$=6.83 min (Method B); MS-ES: (M+H)$^+$=562

EXAMPLE 396

[7-(3,5-Difluoro-4-morpholin-4-ylmethyl-phenyl)-7H-pyrrolo[2,3-d]pyrimidin-2-yl]-{2-[4-(2-dimethylamino-ethyl)-piperazin-1-ylmethyl]-pyridin-4-yl}-amine

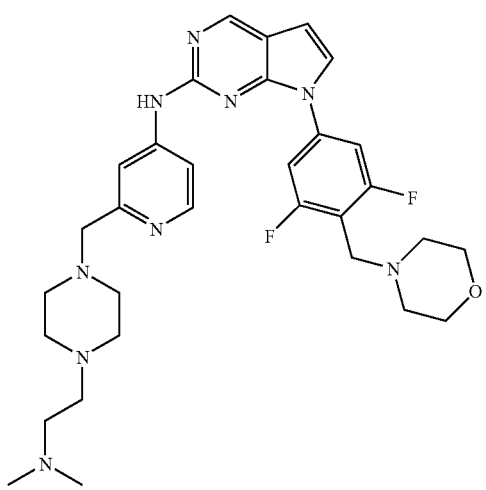 [SMILES: CN(C)CCN1CCN(Cc2cc(Nc3ncc4ccn(-c5cc(F)c(CN6CCOCC6)c(F)c5)c4n3)ccn2)CC1]

The compound is prepared analogous to Example 2. HPLC: $t_R$=6.51 min (Method B); MS-ES: (M+H)$^+$=592

EXAMPLE 397

4-{4-[7-(3,5-Difluoro-4-morpholin-4-ylmethyl-phenyl)-7H-pyrrolo[2,3-d]pyrimidin-2-ylamino]-pyridin-2-ylmethyl}-1-methyl-piperazin-2-one

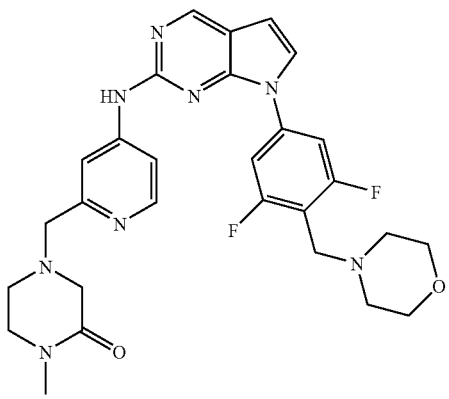 [SMILES: CN1CCN(Cc2cc(Nc3ncc4ccn(-c5cc(F)c(CN6CCOCC6)c(F)c5)c4n3)ccn2)CC1=O]

The compound is prepared analogous to Example 2. HPLC: $t_R$=7.00 min (Method B); MS-ES: (M+H)$^+$=579

EXAMPLE 398

[7-(3,5-Difluoro-4-morpholin-4-ylmethyl-phenyl)-7H-pyrrolo[2,3-d]pyrimidin-2-yl]-{3-[4-(2-dimethylamino-ethyl)-piperazin-1-ylmethyl]-4-methyl-phenyl}-amine

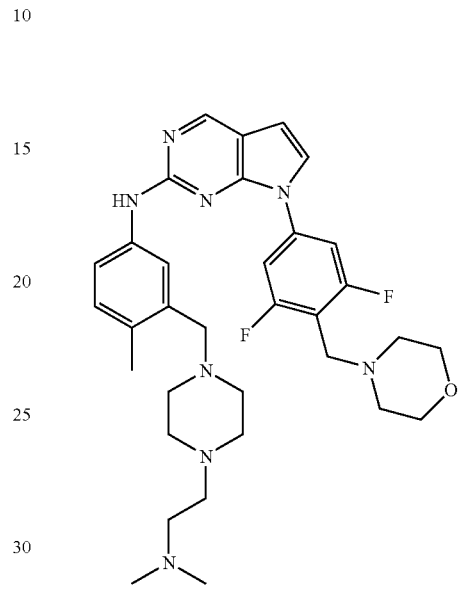

The compound is prepared analogous to Example 2. HPLC: $t_R$=6.81 min (Method B); MS-ES: (M+H)$^+$=605

EXAMPLE 399

1-{5-[7-(3,5-Difluoro-4-morpholin-4-ylmethyl-phenyl)-7H-pyrrolo[2,3-d]pyrimidin-2-ylamino]-2-methyl-benzyl}-piperazin-2-one

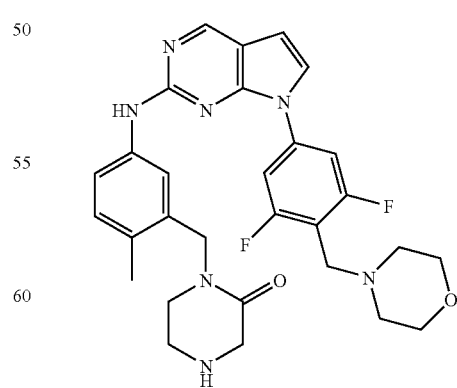

The compound is prepared analogous to Example 2, using a Boc-protected piperazine derivative in Step 2.2. Final deprotection is achieved with 4 M HCl in dioxane at rt. HPLC: $t_R$=6.76 min (Method B); MS-ES: (M+H)$^+$=548; TLC*: $R_f$=0.27

EXAMPLE 400

1-{2-Chloro-5-[7-(3,5-difluoro-4-morpholin-4-ylmethyl-phenyl)-7H-pyrrolo[2,3-d]pyrimidin-2-ylamino]-benzyl}-azetidin-3-ol

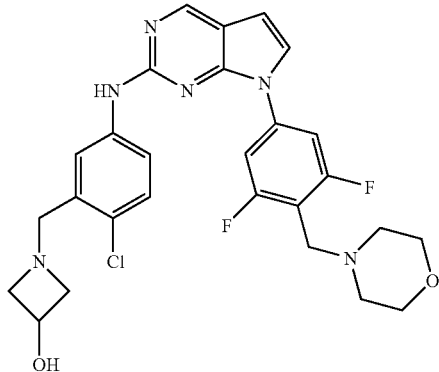 [SMILES: OC1CN(Cc2cc(Nc3ncc4ccn(-c5cc(F)c(CN6CCOCC6)c(F)c5)c4n3)ccc2Cl)C1]

The compound is prepared analogous to Example 2. HPLC: $t_R$=7.04 min (Method B); MS-ES: (M+H)$^+$=541

EXAMPLE 401

(4-Chloro-3-piperazin-1-ylmethyl-phenyl)-[7-(3,5-difluoro-4-morpholin-4-ylmethyl-phenyl)-7H-pyrrolo[2,3-d]pyrimidin-2-yl]-amine

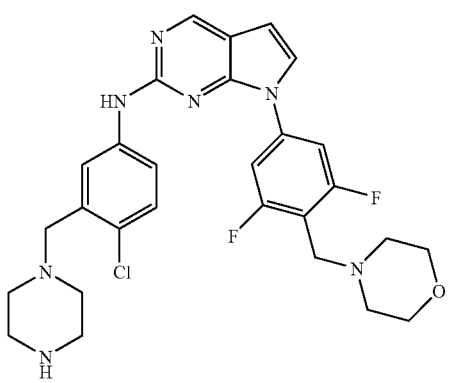 [SMILES: Fc1cc(-n2ccc3cnc(Nc4ccc(Cl)c(CN5CCNCC5)c4)nc32)cc(F)c1CN1CCOCC1]

The compound is prepared analogous to Example 2, using a Boc-protected piperazine derivative in Step 2.2. Final deprotection is achieved with 4 M HCl in dioxane at rt. HPLC: $t_R$=6.93 min (Method B); MS-ES: (M+H)$^+$=554

EXAMPLE 402

[7-(3,5-Difluoro-4-morpholin-4-ylmethyl-phenyl)-7H-pyrrolo[2,3-d]pyrimidin-2-yl]-[2-(3,3-difluoro-pyrrolidin-1-ylmethyl)-pyridin-4-yl]-amine

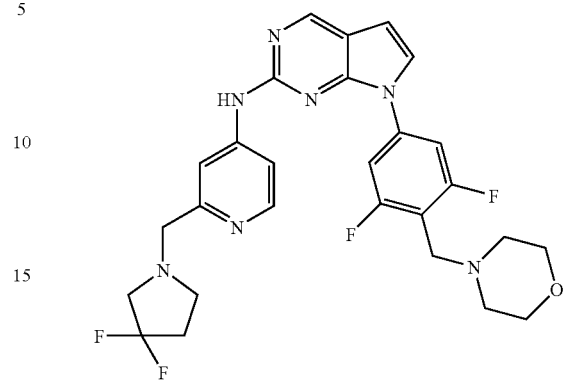

The compound is prepared analogous to Example 2. HPLC: $t_R$=7.71 min (Method B); MS-ES: (M+H)$^+$=542

EXAMPLE 403

(1,1-Dioxido-thiomorpholin-4-yl)-(2-fluoro-4-{2-[4-methyl-3-(3-trifluoromethyl-piperazin-1-ylmethyl-phenylamino]-pyrrolo[2,3-d]pyrimidin-7-yl}-phenyl)-methanone (racemic)

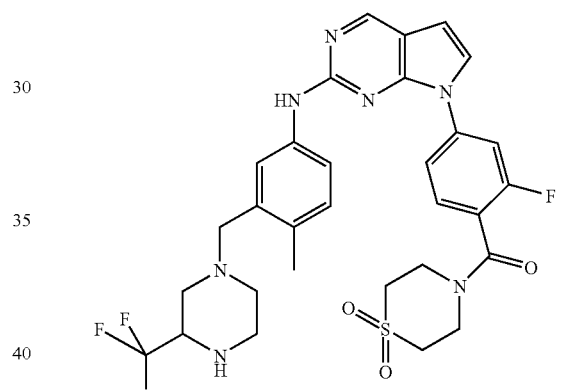

The compound is prepared analogous to Example 2. HPLC: $t_R$=7.74 min (Method B); MS-ES: (M+H)$^+$=646; TLC*: $R_f$=0.41

EXAMPLE 404

[7-(3,5-Difluoro-4-morpholin-4-ylmethyl-phenyl)-7H-pyrrolo[2,3-d]pyrimidin-2-yl]-[4-methyl-3-(3-trifluoromethyl-piperazin-1-ylmethyl)-phenyl]-amine (racemic)

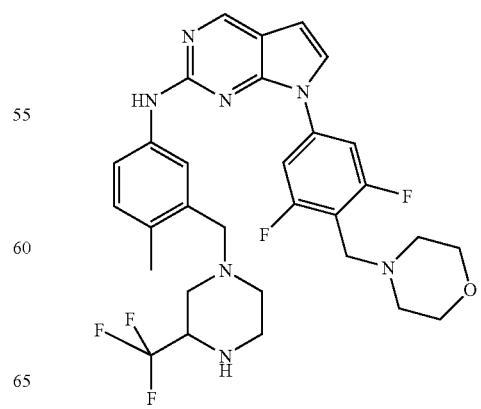

The compound is prepared analogous to Example 2. HPLC: $t_R$=7.25 min (Method B); MS-ES: (M+H)$^+$=602; TLC*: $R_f$=0.31

EXAMPLE 405

[7-(3,5-Difluoro-4-morpholin-4-ylmethyl-phenyl)-7H-pyrrolo[2,3-d]pyrimidin-2-yl]-[3-(3-methoxy-azetidin-1-ylmethyl)-4-methyl-phenyl]-amine

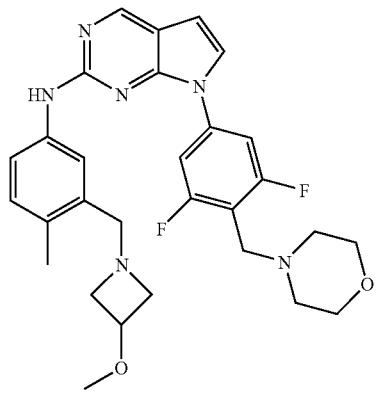 [SMILES: COC1CN(Cc2cc(Nc3ncc4ccn(-c5cc(F)c(CN6CCOCC6)c(F)c5)c4n3)ccc2C)C1]

The compound is prepared analogous to Example 2. HPLC: $t_R$=7.02 min (Method B); MS-ES: (M+H)$^+$=535; TLC*: $R_f$=0.19

EXAMPLE 406

(1,1-Dioxido-thiomorpholin-4-yl)-(2-fluoro-4-{2-[2-(4-methyl-piperazin-1-ylmethyl)-pyridin-4-ylamino]-pyrrolo[2,3-d]pyrimidin-7-yl}-phenyl)-methanone

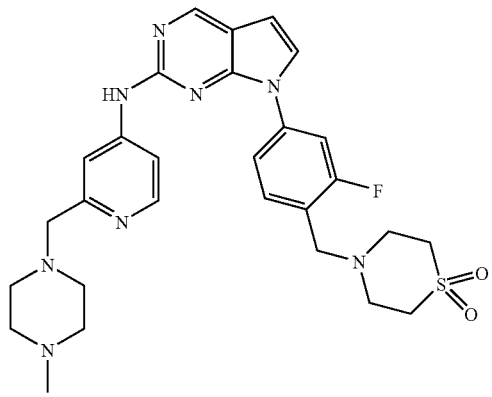 [SMILES: CN1CCN(Cc2cc(Nc3ncc4ccn(-c5ccc(CN6CCS(=O)(=O)CC6)c(F)c5)c4n3)ccn2)CC1]

The compound is prepared analogous to Example 2. HPLC: $t_R$=7.18 min (Method B); MS-ES: (M+H)$^+$=579

EXAMPLE 407

[2-(4-Cyclopropyl-piperazin-1-ylmethyl)-pyridin-4-yl]-[7-(3,5-difluoro-4-morpholin-4-ylmethyl-phenyl)-7H-pyrrolo[2,3-d]pyrimidin-2-yl]-amine

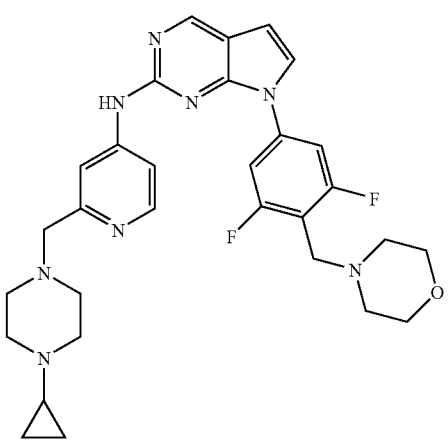 [SMILES: Fc1cc(-n2ccc3cnc(Nc4ccnc(CN5CCN(C6CC6)CC5)c4)nc32)cc(F)c1CN1CCOCC1]

The compound is prepared analogous to Example 2. HPLC: $t_R$=6.81 min (Method B); MS-ES: (M+H)$^+$=561

EXAMPLE 408

[7-(3,5-Difluoro-4-morpholin-4-ylmethyl-phenyl)-7H-pyrrolo[2,3-d]pyrimidin-2-yl]-[2-(3-trifluoromethyl-piperazin-1-ylmethyl)-pyridin-4-yl]-amine (racemic)

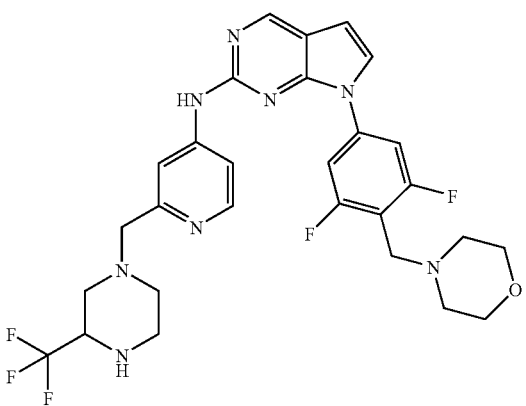 [SMILES: Fc1cc(-n2ccc3cnc(Nc4ccnc(CN5CCNC(C(F)(F)F)C5)c4)nc32)cc(F)c1CN1CCOCC1]

The compound is prepared analogous to Example 2.
HPLC: $t_R$=6.85 min (Method B); MS-ES: (M+H)$^+$=589

EXAMPLE 409

1-{4-[7-(3,5-Difluoro-4-morpholin-4-ylmethyl-phenyl)-7H-pyrrolo[2,3-d]pyrimidin-2-ylamino]-pyridin-2-ylmethyl}-piperazin-2-one

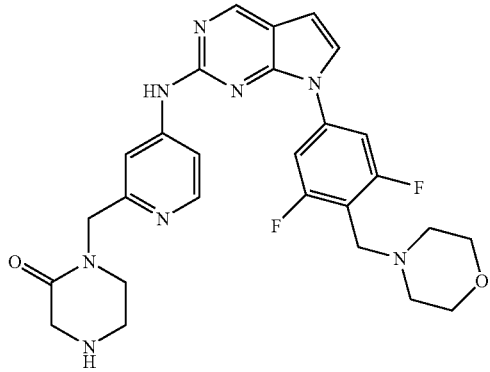 [SMILES: O=C1CNCCN1Cc1cc(Nc2ncc3ccn(-c4cc(F)c(CN5CCOCC5)c(F)c4)c3n2)ccn1]

The compound is prepared analogous to Example 2, using a Boc-protected piperazine derivative in Step 2.2. Final deprotection is achieved with 4 M HCl in dioxane at rt. HPLC: $t_R$=6.38 min (Method B); MS-ES: (M+H)$^+$=535

EXAMPLE 410

4-{5-[7-(3,5-Difluoro-4-morpholin-4-ylmethyl-phenyl)-7H-pyrrolo[2,3-d]pyrimidin-2-ylamino]-2-methyl-benzyl}-1-(2-dimethylamino-ethyl)-piperazin-2-one

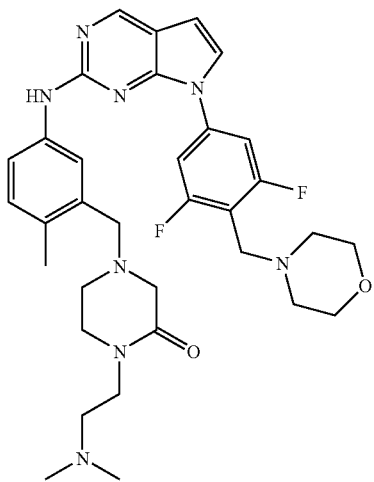 [SMILES: Cc1ccc(Nc2ncc3ccn(-c4cc(F)c(CN5CCOCC5)c(F)c4)c3n2)cc1CN1CCN(CCN(C)C)C(=O)C1]

The compound is prepared analogous to Example 2.
HPLC: $t_R$=6.86 min (Method B); MS-ES: (M+H)$^+$=619; TLC*: $R_f$=0.14

EXAMPLE 411

1-{5-[7-(3,5-Difluoro-4-morpholin-4-ylmethyl-phenyl)-7H-pyrrolo[2,3-d]pyrimidin-2-ylamino]-2-methyl-benzyl}-pyrrolidin-3-ol (racemic)

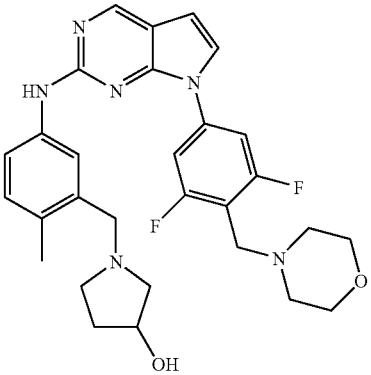 [SMILES: Cc1ccc(Nc2ncc3ccn(-c4cc(F)c(CN5CCOCC5)c(F)c4)c3n2)cc1CN1CCC(O)C1]

The compound is prepared analogous to Example 2.
HPLC: $t_R$=6.81 min (Method B); MS-ES: (M+H)$^+$=535; TLC* with 1% aq. ammonia 24%: $R_f$=0.66

EXAMPLE 412

[7-(3,5-Difluoro-4-morpholin-4-ylmethyl-phenyl)-7H-pyrrolo[2,3-d]pyrimidin-2-yl]-(3-imidazol-1-ylmethyl-4-methyl-phenyl)-amine

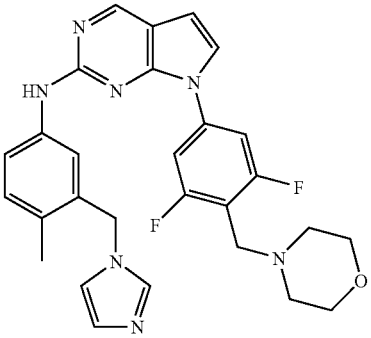 [SMILES: Cc1ccc(Nc2ncc3ccn(-c4cc(F)c(CN5CCOCC5)c(F)c4)c3n2)cc1Cn1ccnc1]

The compound is prepared analogous to Example 2.
HPLC: $t_R$=6.90 min (Method B); MS-ES: (M+H)$^+$=516; TLC*: $R_f$=0.52

EXAMPLE 413

[7-(3,5-Difluoro-4-morpholin-4-ylmethyl-phenyl)-7H-pyrrolo[2,3-d]pyrimidin-2-yl]-(4-methyl-3-pyrazol-1-ylmethyl-phenyl)-amine

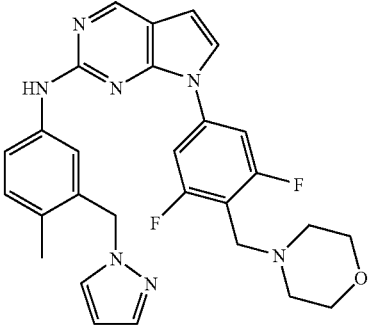 [SMILES: Cc1ccc(Nc2ncc3ccn(-c4cc(F)c(CN5CCOCC5)c(F)c4)c3n2)cc1Cn1cccn1]

The compound is prepared analogous to Example 2.
HPLC: $t_R$=7.81 min (Method B); MS-ES: (M+H)$^+$=516; TLC*: $R_f$=0.77

EXAMPLE 414

[7-(3,5-Difluoro-4-morpholin-4-ylmethyl-phenyl)-7H-pyrrolo[2,3-d]pyrimidin-2-yl]-(4-methyl-3-[1,2,4]triazol-4-ylmethyl-phenyl)-amine

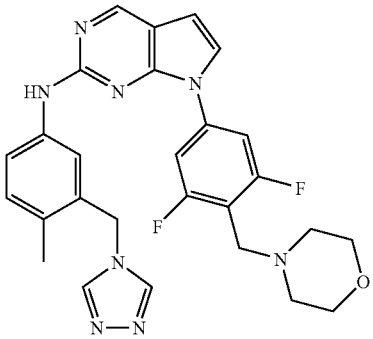 [SMILES: Cc1ccc(Nc2ncc3ccn(-c4cc(F)c(CN5CCOCC5)c(F)c4)c3n2)cc1Cn1cnnc1]

The compound is prepared analogous to Example 2. HPLC: $t_R$=7.30 min (Method B); MS-ES: (M+H)$^+$=517; TLC*: $R_f$=0.40

EXAMPLE 415

1-{5-[7-(3,5-Difluoro-4-morpholin-4-ylmethyl-phenyl)-7H-pyrrolo[2,3-d]pyrimidin-2-ylamino]-2-methyl-benzyl}-4-methyl-piperazin-2-one

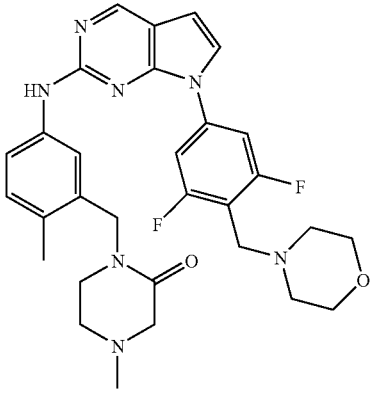 [SMILES: Cc1ccc(Nc2ncc3ccn(-c4cc(F)c(CN5CCOCC5)c(F)c4)c3n2)cc1CN1CCN(C)CC1=O]

The compound is obtained from the reaction of 1-{5-[7-(3,5-Difluoro-4-morpholin-4-ylmethyl-phenyl)-7H-pyrrolo[2,3-d]pyrimidin-2-ylamino]-2-methyl-benzyl}-piperazin-2-one (Example 399) with formaldehyde and sodium cyanoborohydride in methanol and DCM 2:1 at rt. HPLC: $t_R$=6.91 min (Method B); MS-ES: (M+H)$^+$=562; TLC*: $R_f$=0.28

EXAMPLE 416

1-{4-[7-(3,5-Difluoro-4-morpholin-4-ylmethyl-phenyl)-7H-pyrrolo[2,3-d]pyrimidin-2-ylamino]-pyridin-2-ylmethyl}-pyrrolidin-3-ol (racemic)

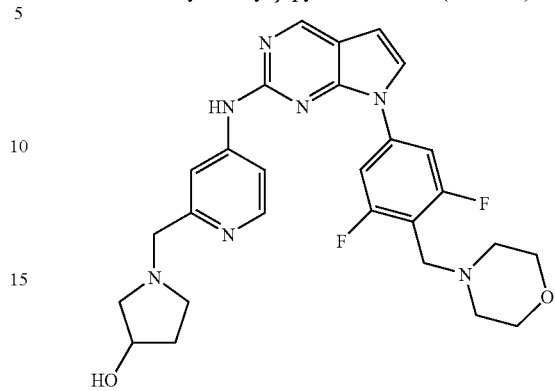

The compound is prepared analogous to Example 2. HPLC: $t_R$=6.45 min (Method B); MS-ES: (M+H)$^+$=522

EXAMPLE 417

[7-(3,5-Difluoro-4-morpholin-4-ylmethyl-phenyl)-7H-pyrrolo[2,3-d]pyrimidin-2-l]-[3-(3-methoxy-pyrrolidin-1-ylmethyl)-4-methyl-phenyl]-amine (racemic)

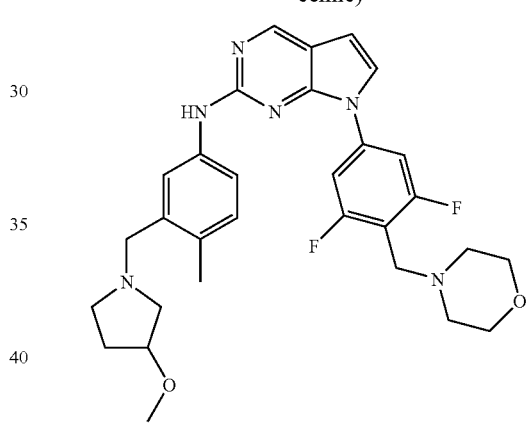

The compound is prepared analogous to Example 2. HPLC: $t_R$=7.22 min (Method B); MS-ES: (M+H)$^+$=549

EXAMPLE 418

[7-(3,5-Difluoro-4-morpholin-4-ylmethyl-phenyl)-7H-pyrrolo[2,3-d]pyrimidin-2-yl]-[3-(4-dimethylaminomethyl-[1,2,3]triazol-1-ylmethyl)-4-methyl-phenyl]-amine

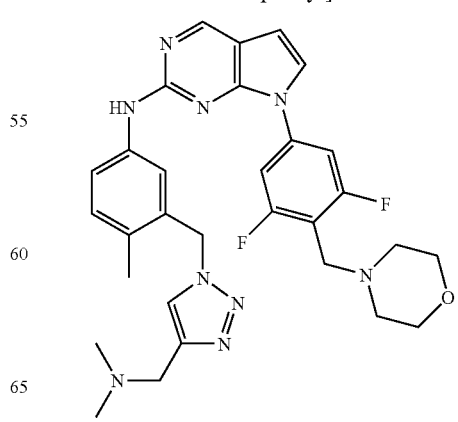

The compound is prepared analogous to Example 2. HPLC: $t_R$=7.11 min (Method B); MS-ES: (M+H)⁺=574; TLC*: $R_f$=0.19

EXAMPLE 419

(1-{5-[7-(3,5-Difluoro-4-morpholin-4-ylmethyl-phenyl)-7H-pyrrolo[2,3-d]pyrimidin-2-ylamino]-2-methyl-benzyl}-1H-[1,2,3]triazol-4-yl)-methanol

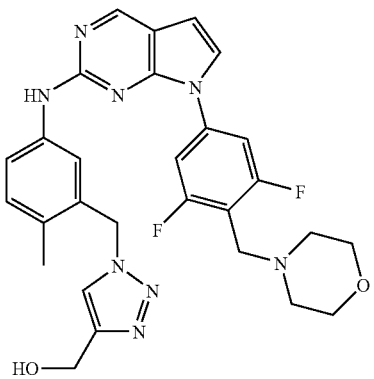 [SMILES: Cc1ccc(Nc2ncc3ccn(-c4cc(F)c(CN5CCOCC5)c(F)c4)c3n2)cc1Cn1cc(CO)nn1]

The compound is prepared analogous to Example 2. HPLC: $t_R$=7.19 min (Method B); MS-ES: (M+H)⁺=547; TLC*: $R_f$=0.31

EXAMPLE 420

[3-(Azetidin-3-yloxymethyl)-4-methyl-phenyl]-[7-(3,5-difluoro-4-morpholin-4-ylmethyl-phenyl)-7H-pyrrolo[2,3-d]pyrimidin-2-yl]-amine

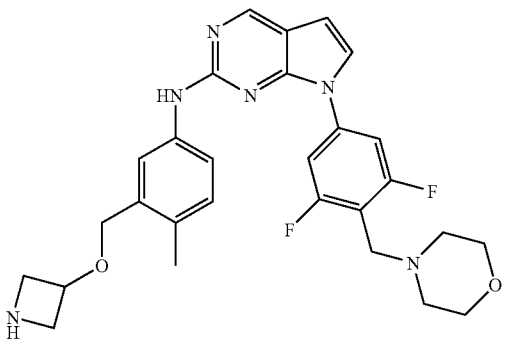 [SMILES: Cc1ccc(Nc2ncc3ccn(-c4cc(F)c(CN5CCOCC5)c(F)c4)c3n2)cc1COC1CNC1]

The compound is prepared analogous to Example 2, using a Boc-protected piperazine derivative in Step 2.2. Final deprotection is achieved with 4 M HCl in dioxane at rt. HPLC: $t_R$=6.98 min (Method B); MS-ES: (M+H)⁺=521

EXAMPLE 421

{7-[4-(1,1-Dioxido-thiomorpholin-4-ylmethyl)-3,5-difluoro-phenyl]-7H-pyrrolo[2,3-d]pyrimidin-2-yl}-[4-methyl-3-(4-methyl-piperazin-1-ylmethyl)-phenyl]-amine

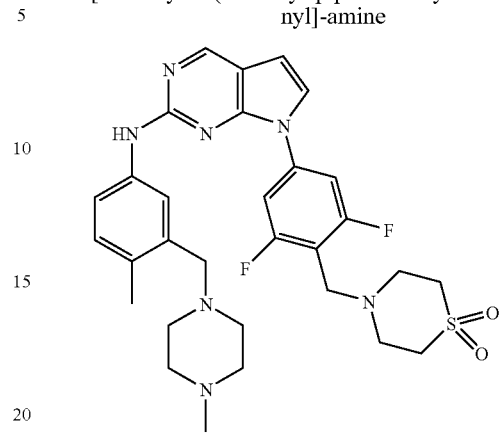

The compound is prepared analogous to Example 2. HPLC: $t_R$=7.63 min (Method B); MS-ES: (M+H)⁺=596; TLC*: $R_f$=0.17

EXAMPLE 422

4-(5-{7-[4-(1,1-Dioxido-thiomorpholin-4-ylmethyl)-3,5-difluoro-phenyl]-7H-pyrrolo[2,3-d]pyrimidin-2-ylamino}-2-methyl-benzyl)-1-methyl-piperazin-2-one

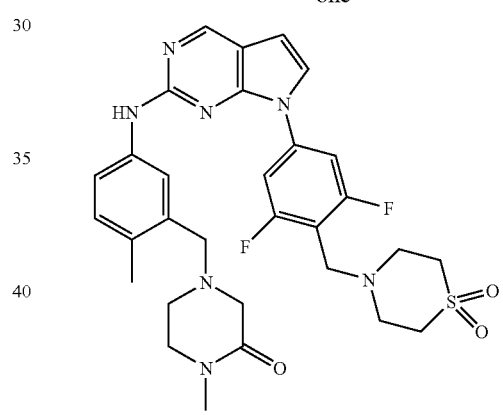

The compound is prepared analogous to Example 2. HPLC: $t_R$=7.71 min (Method B); MS-ES: (M+H)⁺=610; TLC*: $R_f$=0.23

EXAMPLE 423

1-(5-{7-[4-(1,1-Dioxido-thiomorpholin-4-ylmethyl)-3,5-difluoro-phenyl]-7H-pyrrolo[2,3-d]pyrimidin-2-ylamino}-2-methyl-benzyl)-azetidin-3-ol

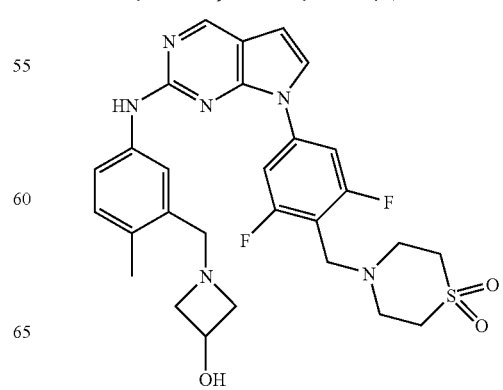

The compound is prepared analogous to Example 2. HPLC: $t_R$=7.55 min (Method B); MS-ES: (M+H)$^+$=569; TLC*: $R_f$=0.14

EXAMPLE 424

[7-(3,5-Difluoro-4-morpholin-4-ylmethyl-phenyl)-7H-pyrrolo[2,3-d]pyrimidin-2-yl]-(1,2,3 4-tetrahydro-1,4-epiazano-naphthalen-6-yl)-amine

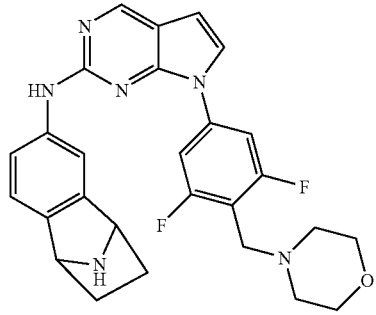 [SMILES: Fc1cc(-n2ccc3cnc(Nc4ccc5c(c4)C4CCC5N4)nc32)cc(F)c1CN1CCOCC1]

The compound is prepared analogous to Example 2, using a Boc-protected derivative in Step 2.2. Final deprotection is achieved with 4 M HCl in dioxane and then TFA at rt. The aniline building block is obtained from patent WO 2007/072158 p. 45 Scheme 4. HPLC: $t_R$=6.78 min (Method B); MS-ES: (M+H)$^+$=489; TLC (33% methanol/67% methylene chloride): $R_f$=0.52

EXAMPLE 425

1-(5-{7-[4-(1,1-Dioxido-thiomorpholin-4-ylmethyl)-3,5-difluoro-phenyl]-7H-pyrrolo[2,3-d]pyrimidin-2-ylamino}-2-methyl-benzyl)-pyrrolidin-3-ol (racemic)

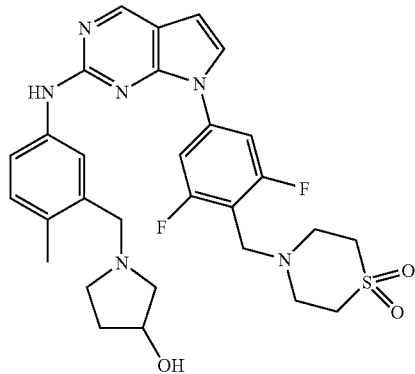 [SMILES: Cc1ccc(Nc2ncc3ccn(-c4cc(F)c(CN5CCS(=O)(=O)CC5)c(F)c4)c3n2)cc1CN1CCC(O)C1]

The compound is prepared analogous to Example 2. HPLC: $t_R$=7.68 min (Method B); MS-ES: (M+H)$^+$=583; TLC*: $R_f$=0.10

EXAMPLE 426

[7-(3,5-Difluoro-4-morpholin-4-ylmethyl-phenyl)-7H-pyrrolo[2,3-d]pyrimidin-2-yl]-[2-(3-methoxy-pyrrolidin-1-ylmethyl)-pyridin-4-yl]-amine (racemic)

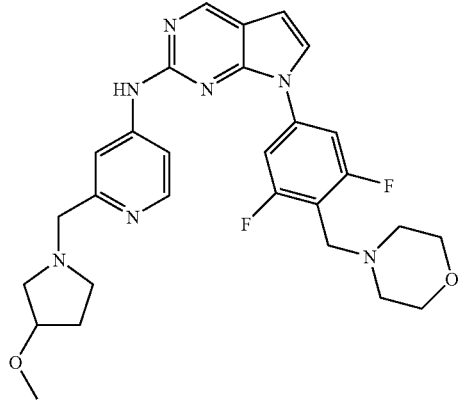 [SMILES: COC1CCN(Cc2cc(Nc3ncc4ccn(-c5cc(F)c(CN6CCOCC6)c(F)c5)c4n3)ccn2)C1]

The compound is prepared analogous to Example 2. HPLC: $t_R$=6.77 min (Method B); MS-ES: (M+H)$^+$=536

EXAMPLE 427

[7-(3,5-Difluoro-4-morpholin-4-ylmethyl-phenyl)-7H-pyrrolo[2,3-d]pyrimidin-2-yl]-[2-(3-dimethylamino-pyrrolidin-1-ylmethyl)-pyridin-4-yl]-amine (racemic)

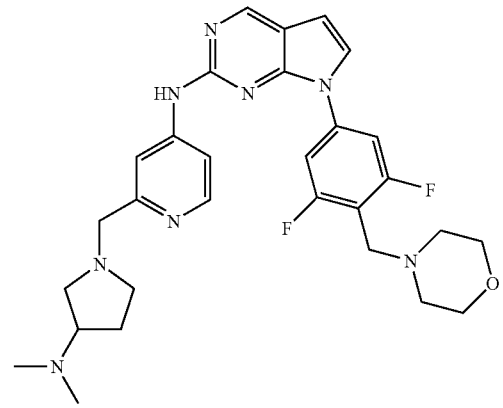 [SMILES: CN(C)C1CCN(Cc2cc(Nc3ncc4ccn(-c5cc(F)c(CN6CCOCC6)c(F)c5)c4n3)ccn2)C1]

The compound is prepared analogous to Example 2. HPLC: $t_R$=6.79 min (Method B); MS-ES: (M+H)$^+$=549

EXAMPLE 428

{7-[4-(1,1-Dioxido-thiomorpholin-4-ylmethyl)-3,5-difluoro-phenyl]-7H-pyrrolo[2,3-d]pyrimidin-2-yl}-(4-methyl-3-piperazin-1-ylmethyl-phenyl)-amine

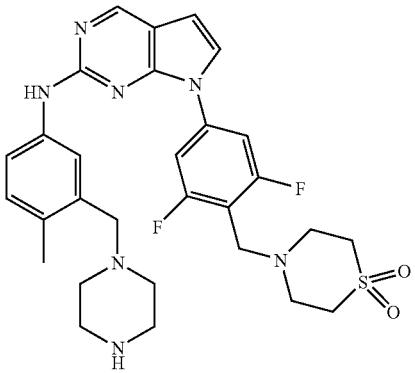 [SMILES: Cc1ccc(Nc2ncc3ccn(-c4cc(F)c(CN5CCS(=O)(=O)CC5)c(F)c4)c3n2)cc1CN1CCNCC1]

The compound is prepared analogous to Example 2, using a Boc-protected derivative in Step 2.2. Final deprotection is achieved with 4 M HCl in dioxane at rt. HPLC: $t_R$=7.43 min (Method B); MS-ES: $(M+H)^+$=582; TLC*: $R_f$=0.15

EXAMPLE 429

[6-(cis-3,5-Dimethyl-piperazin-1-yl)-5-methyl-pyridin-3-yl]-{7-[4-1,1-dioxido-thiomorpholin-4-ylmethyl)-3,5-difluoro-phenyl]-7H-pyrrolo[2,3-d]pyrimidin-2-yl}-amine

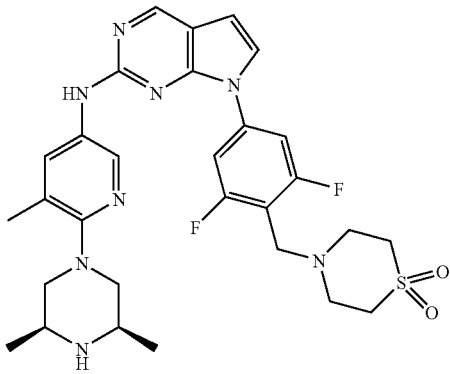 [SMILES: Cc1cc(Nc2ncc3ccn(-c4cc(F)c(CN5CCS(=O)(=O)CC5)c(F)c4)c3n2)cnc1N1C[C@@H](C)N[C@@H](C)C1]

The compound is prepared analogous to Example 2. HPLC: $t_R$=7.74 min (Method B); MS-ES: $(M+H)^+$=597; TLC*: $R_f$=0.06

EXAMPLE 430

[5-Chloro-6-(cis-3,5-dimethyl-piperazin-1-yl)-pyridin-3-yl]-{7-[4-(1,1-dioxido-thiomorpholin-4-ylmethyl)-3,5-difluoro-phenyl]-7H-pyrrolo[2,3-d]pyrimidin-2-yl}-amine

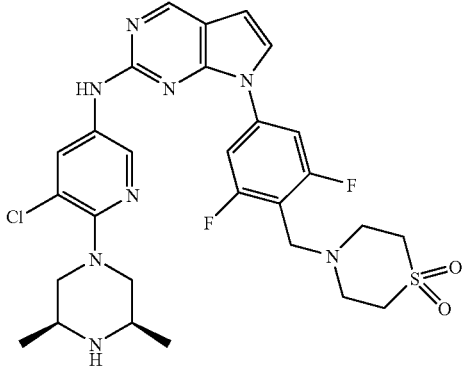 [SMILES: C[C@@H]1CN(c2ncc(Nc3ncc4ccn(-c5cc(F)c(CN6CCS(=O)(=O)CC6)c(F)c5)c4n3)cc2Cl)C[C@H](C)N1]

The compound is prepared analogous to Example 2. HPLC: $t_R$=8.33 min (Method B); MS-ES: $(M+H)^+$=617; TLC*: $R_f$=0.15

EXAMPLE 431

[7-(3,5-Difluoro-4-morpholin-4-ylmethyl-phenyl)-7H-pyrrolo[2,3-d]pyrimidin-2-yl]-(2,3-dihydro-1H-indol-6-yl)-amine

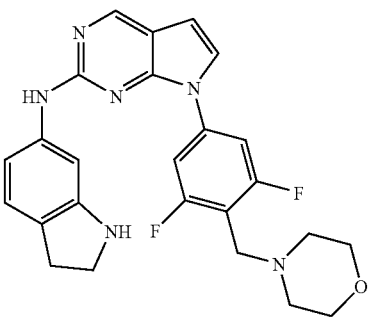 [SMILES: Fc1cc(-n2ccc3cnc(Nc4ccc5c(c4)NCC5)nc32)cc(F)c1CN1CCOCC1]

The compound is prepared analogous to Example 2 with the aniline derivative obtained from the hydrogenation of 6-nitro-2,3-dihydro-1H-indole. HPLC: $t_R$=6.71 min (Method B); MS-ES: $(M+H)^+$=463; TLC**: $R_f$=0.24

EXAMPLE 432

[3,5-Dimethyl-4-(2-morpholin-4-yl-ethoxy)-phenyl]-{7-[4-(1,1-dioxido-thiomorpholin-4-ylmethyl)-3,5-difluoro-phenyl]-7H-pyrrolo[2,3-d]pyrimidin-2-yl}-amine

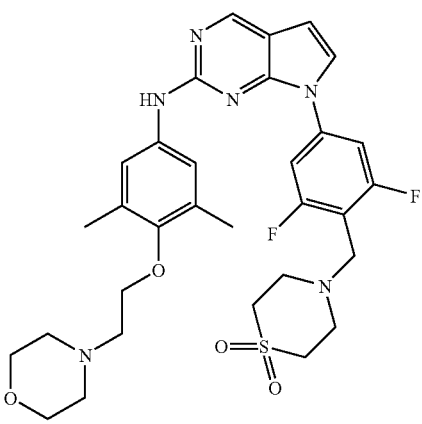 [SMILES: Cc1cc(Nc2ncc3ccn(-c4cc(F)c(CN5CCS(=O)(=O)CC5)c(F)c4)c3n2)cc(C)c1OCCN1CCOCC1]

The compound is prepared analogous to Example 2. HPLC: $t_R$=7.86 min (Method B); MS-ES: $(M+H)^+$=627

EXAMPLE 433

[7-(3,5-Difluoro-4-morpholin-4-ylmethyl-phenyl)-7H-pyrrolo[2,3-d]pyrimidin-2-yl]-[3,5-dimethyl-4-(2-morpholin-4-yl-ethoxy)-phenyl]-amine

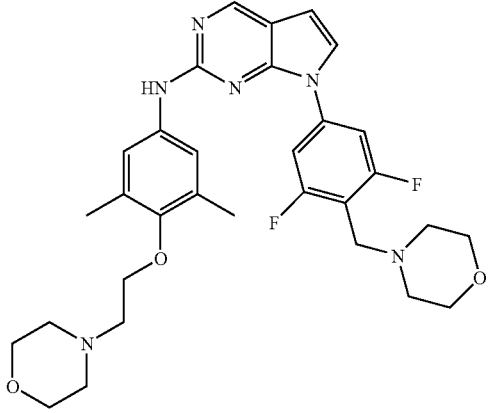 [SMILES: Cc1cc(Nc2ncc3ccn(-c4cc(F)c(CN5CCOCC5)c(F)c4)c3n2)cc(C)c1OCCN1CCOCC1]

The compound is prepared analogous to Example 2.
HPLC: $t_R$=7.04 min (Method B); MS-ES: (M+H)$^+$=579

EXAMPLE 434

[7-(3,5-Difluoro-4-morpholin-4-ylmethyl-phenyl)-7H-pyrrolo[2,3-d]pyrimidin-2-yl]-[3-(3-dimethylamino-pyrrolidin-1-ylmethyl)-4-methyl-phenyl]-amine (racemic)

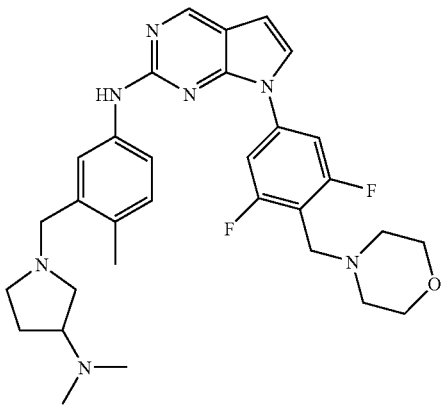

The compound is prepared analogous to Example 2.
HPLC: $t_R$=6.78 min (Method B); MS-ES: (M+H)$^+$=562

EXAMPLE 435

[3-(3-Dimethylamino-pyrrolidin-1-ylmethyl)-4-methyl-phenyl]-{7-[4-(1,1-dioxido-thiomorpholin-4-ylmethyl)-3,5-difluoro-phenyl]-7H-pyrrolo[2,3-d]pyrimidin-2-yl}-amine (racemic)

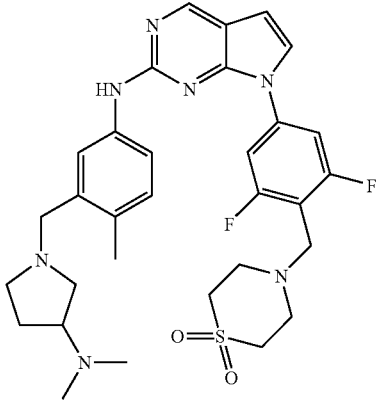 [SMILES: Cc1ccc(Nc2ncc3ccn(-c4cc(F)c(CN5CCS(=O)(=O)CC5)c(F)c4)c3n2)cc1CN1CCC(N(C)C)C1]

The compound is prepared analogous to Example 2.
HPLC: $t_R$=7.57 min (Method B); MS-ES: (M+H)$^+$=610

EXAMPLE 436

[3-(7-Aza-bicyclo[2.2.1]hept-7-ylmethyl)-4-methyl-phenyl]-[7-(3,5-difluoro-4-morpholin-4-ylmethyl-phenyl)-7H-pyrrolo[2,3-d]pyrimidin-2-yl]-amine

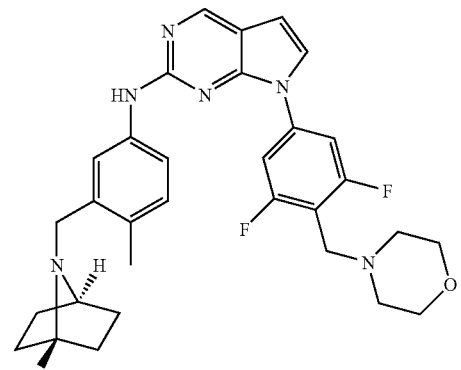

The compound is prepared analogous to Example 2.
HPLC: $t_R$=7.37 min (Method B); MS-ES: (M+H)$^+$=545

EXAMPLE 437

(4-{2-[4-Methyl-3-(4-methyl-piperazin-1-ylmethyl)-phenylamino]-pyrrolo[2,3-d]pyrimidin-7-yl}-phenyl)-morpholin-4-yl-methanone

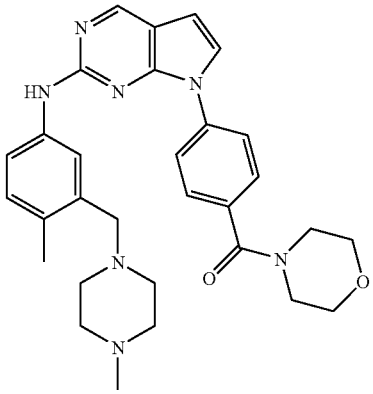 [SMILES: Cc1ccc(Nc2ncc3ccn(-c4ccc(C(=O)N5CCOCC5)cc4)c3n2)cc1CN1CCN(C)CC1]

The compound is prepared analogous to Example 2.
HPLC: $t_R$=7.10 min (Method B); MS-ES: (M+H)$^+$=526;
TLC*: $R_f$=0.23

EXAMPLE 438

[7-(4-Ethyl-phenyl)-7H-pyrrolo[2,3-d]pyrimidin-2-yl]-[6-(4-methyl-piperazin-1-yl)-pyridin-3-yl]-amine

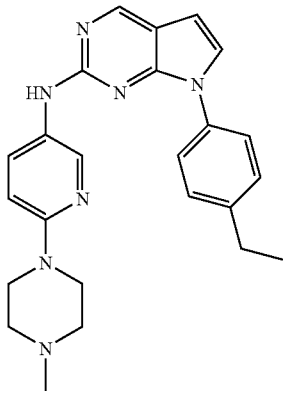 [SMILES: CCc1ccc(-n2ccc3cnc(Nc4ccc(N5CCN(C)CC5)nc4)nc32)cc1]

The compound is prepared analogous to Example 3. HPLC: $t_R$=4.79 min (Method F); MS-ES: (M+H)$^+$=414

EXAMPLE 439

3-Methyl-4-{2-[6-(4-methyl-piperazin-1-yl)-pyridin-3-ylamino]-pyrrolo[2,3-d]pyrimidin-7-yl}-benzonitrile

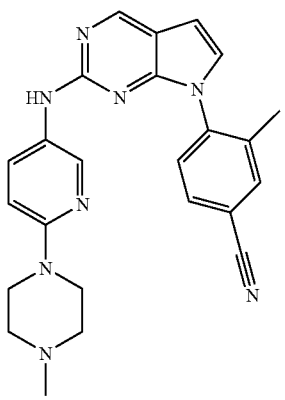 [SMILES: Cc1cc(C#N)ccc1-n1ccc2cnc(Nc3ccc(N4CCN(C)CC4)nc3)nc21]

The compound is prepared analogous to Example 3. HPLC: $t_R$=4.45 min (Method F); MS-ES: (M+H)$^+$=425

EXAMPLE 440

{7-[4-(1,1-Dioxido-thiomorpholin-4-ylmethyl)-3,5-difluoro-phenyl]-7H-pyrrolo[2,3-d]pyrimidin-2-yl}-[5-(4-methyl-piperazin-1-yl)-pyridin-2-yl]-amine

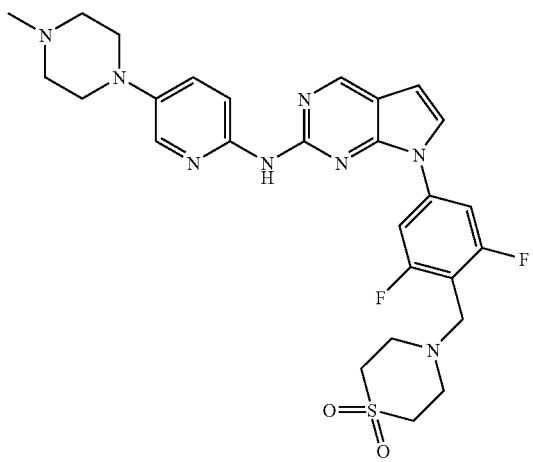 [SMILES: CN1CCN(c2ccc(Nc3ncc4ccn(-c5cc(F)c(CN6CCS(=O)(=O)CC6)c(F)c5)c4n3)nc2)CC1]

The compound is prepared analogous to Example 2. HPLC: $t_R$=4.29 min (Method F); MS-ES: (M+H)$^+$=569

EXAMPLE 441

[6-(cis-3,5-Dimethyl-piperazin-1-yl)-pyridin-3-yl]-{7-[4-(1,1-dioxido-thiomorpholin-4-ylmethyl)-3,5-difluoro-phenyl]-7H-pyrrolo[2,3-d]pyrimidin-2-yl}-amine

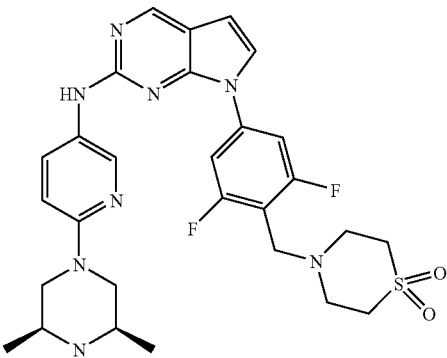

The compound is prepared analogous to Example 2. HPLC: $t_R$=4.40 min (Method F); MS-ES: (M+H)$^+$=583; TLC (20% methanol/80% methylene chloride): $R_f$=0.32

EXAMPLE 442

[2-(4,7-Diaza-spiro[2.5]oct-7-yl)-pyridin-4-yl]-{7-[4-(1,1-dioxido-thiomorpholin-4-ylmethyl)-3,4-difluoro-phenyl]-7H-pyrrolo[2,3-d]pyrimidin-2-yl}-amine

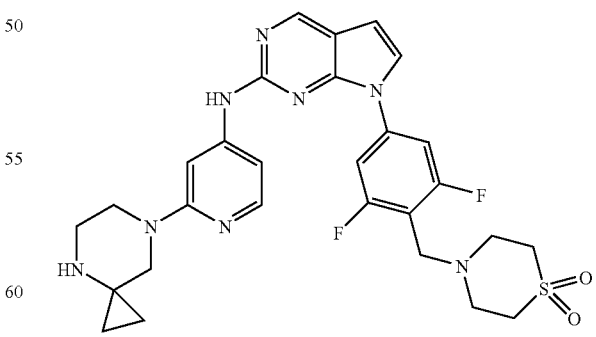

The compound is prepared analogous to Example 2. HPLC: $t_R$=4.48 min (Method F); MS-ES: (M+H)$^+$=581; TLC (20% methanol/80% methylene chloride): $R_f$=0.38

EXAMPLE 443

{7-[4-(1,1-Dioxido-thiomorpholin-4-ylmethyl)-3,5-difluoro-phenyl]-7H-pyrrolo[2,3-d]pyrimidin-2-yl}-[6-(4-methyl-piperazin-1-yl)-pyridin-3-yl]-amine

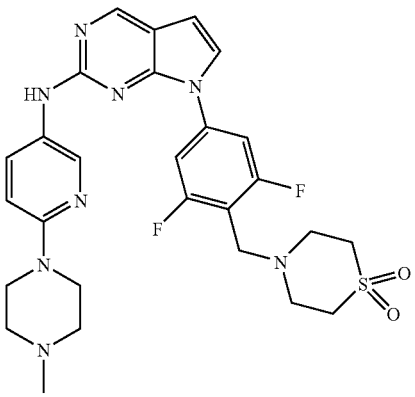 [SMILES: CN1CCN(c2ccc(Nc3ncc4ccn(-c5cc(F)c(CN6CCS(=O)(=O)CC6)c(F)c5)c4n3)cn2)CC1]

The compound is prepared analogous to Example 2. HPLC: $t_R$=4.36 min (Method F); MS-ES: (M+H)$^+$=569

EXAMPLE 444

{7-[4-(1,1-Dioxido-thiomorpholin-4-ylmethyl)-3,5-difluoro-phenyl]-7H-pyrrolo[2,3-d]pyrimidin-2-yl}-(6-piperazin-1-yl-pyridin-3-yl)-amine

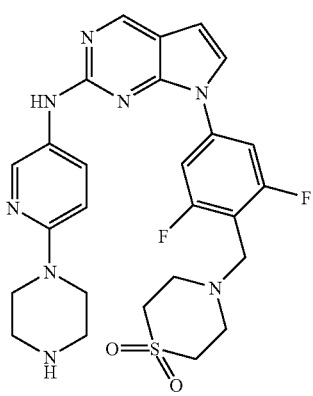 [SMILES: O=S1(=O)CCN(Cc2c(F)cc(-n3ccc4cnc(Nc5ccc(N6CCNCC6)nc5)nc43)cc2F)CC1]

The compound is prepared analogous to Example 2, using a Boc-protected piperazine derivative in Step 2.2. Final deprotection is achieved with TFA in CH$_2$Cl$_2$ at rt. HPLC: $t_R$=4.29 min (Method F); MS-ES: (M+H)$^+$=555

EXAMPLE 445

2,6-Difluoro-4-{2-[6-(4-methyl-piperazin-1-yl)-pyridin-3-ylamino]-pyrrolo[2,3-d]pyrimidin-7-yl}-benzonitrile

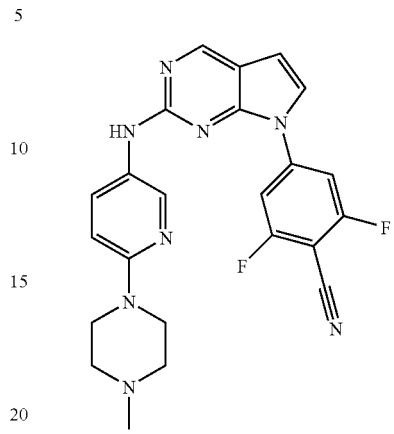

The compound is prepared analogous to Example 3. HPLC: $t_R$=4.74 min (Method F); MS-ES: (M+H)$^+$=447

EXAMPLE 446

[7-(3,5-Difluoro-4-methoxymethyl-phenyl)-7H-pyrrolo[2,3-d]pyrimidin-2-yl]-[6-(4-methyl-piperazin-1-yl)-pyridin-3-yl]-amine

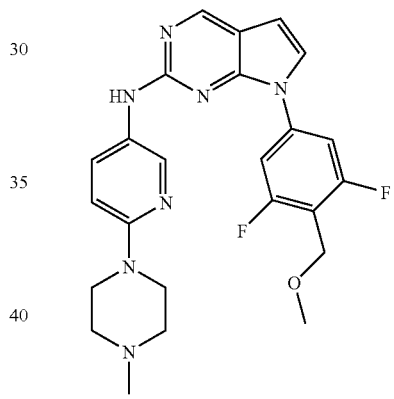

The compound is prepared analogous to Example 3. The corresponding aryle bromide is obtained from the reaction of (4-bromo-2,6-difluoro-phenyl)-methanol withiodomethane in presence of sodium hydride in THF. HPLC: $t_R$=4.69 min (Method F); MS-ES: (M+H)$^+$=466

EXAMPLE 447

{7-[4-(cis-2,6-dimethyl-morpholin-4-ylmethyl)-3,5-difluoro-phenyl]-7H-pyrrolo[2,3-d]pyrimidin-2-yl}-[6-(4-methyl-piperazin-1-yl)-pyridin-3-yl]-amine

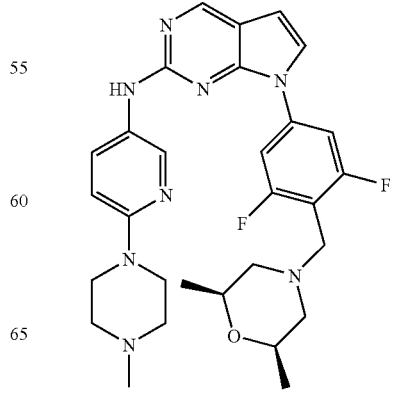

The compound is prepared analogous to Example 2.
HPLC: $t_R$=4.14 min (Method F); MS-ES: (M+H)$^+$=549

EXAMPLE 448

1-Methyl-5-{2-[6-(4-methyl-piperazin-1-yl)-pyridin-3-ylamino]-pyrrolo[2,3-d]pyrimidin-7-yl}-1,3-dihydro-indol-2-one

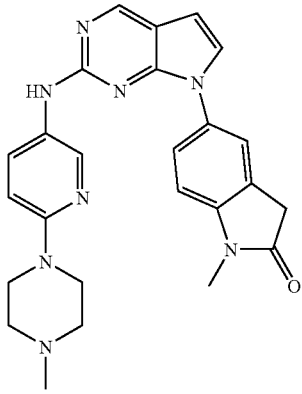 [SMILES: CN1CCN(c2ccc(Nc3ncc4ccn(-c5ccc6c(c5)CC(=O)N6C)c4n3)cn2)CC1]

The compound is prepared analogous to Example 3.
HPLC: $t_R$=4.25 min (Method F); MS-ES: (M+H)$^+$=455

EXAMPLE 449

{7-[4-(1-Methoxy-ethyl)-phenyl]-7H-pyrrolo[2,3-d]pyrimidin-2-yl}-[6-(4-methyl-piperazin-1-yl)-pyridin-3-yl]-amine (racemic)

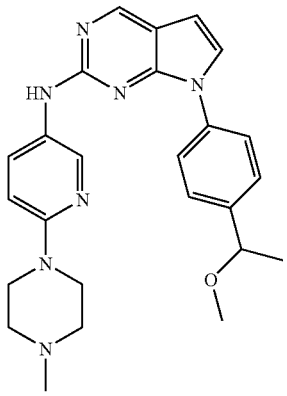 [SMILES: COC(C)c1ccc(-n2ccc3cnc(Nc4ccc(N5CCN(C)CC5)nc4)nc32)cc1]

The compound is prepared analogous to Example 3. The corresponding aryle bromide is obtained from the reaction of 1-(4-bromo-phenyl)-ethanol on iodomethane under Ar in presence of sodium hydride in THF. HPLC: $t_R$=4.54 min (Method F); MS-ES: (M+H)$^+$=444

EXAMPLE 450

[7-(3,5-Difluoro-4-morpholin-4-ylmethyl-phenyl)-7H-pyrrolo[2,3-d]pyrimidin-2-yl]-[4-methyl-3-(7-methyl-2,7-diaza-spiro[4.4]non-2-ylmethyl)-phenyl]-amine

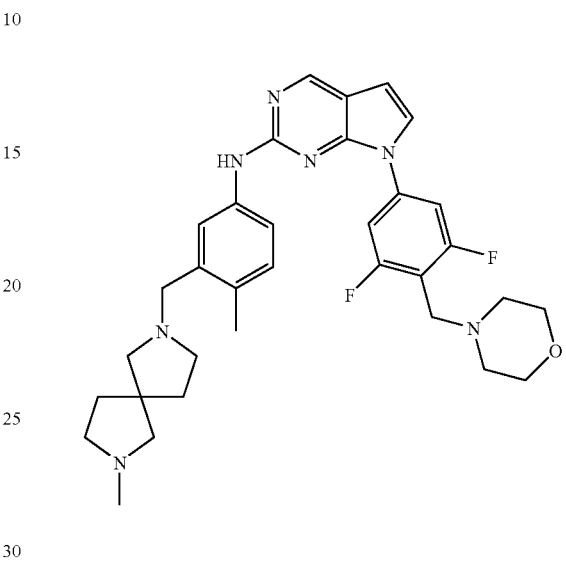

The compound is prepared analogous to Example 2.
HPLC: $t_R$=6.71 min (Method B); MS-ES: (M+H)$^+$=588; TLC (53% chloroform, 36% methanol, 10% water, 0.5% acetic acid): $R_f$=0.25

EXAMPLE 451

{5-[7-(3,5-Difluoro-4-morpholin-4-ylmethyl-phenyl)-7H-pyrrolo[2,3-d]pyrimidin-2-ylamino]-2-methyl-phenyl}-(4-methyl-piperazin-1-yl)-methanone

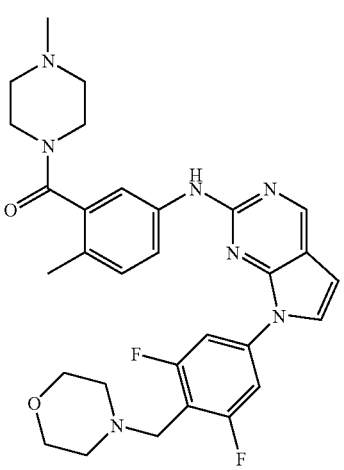 [SMILES: Cc1ccc(Nc2ncc3ccn(-c4cc(F)c(CN5CCOCC5)c(F)c4)c3n2)cc1C(=O)N1CCN(C)CC1]

The compound is prepared analogous to Example 2.
HPLC: $t_R$=3.94 min (Method C); MS-ES: (M+H)$^+$=562

EXAMPLE 452

{5-[7-(3,5-Difluoro-4-morpholin-4-ylmethyl-phenyl)-7H-pyrrolo[2,3-d]pyrimidin-2-ylamino]-2-methyl-phenyl}-(cis-3,5-dimethyl-piperazin-1-yl)-methanone

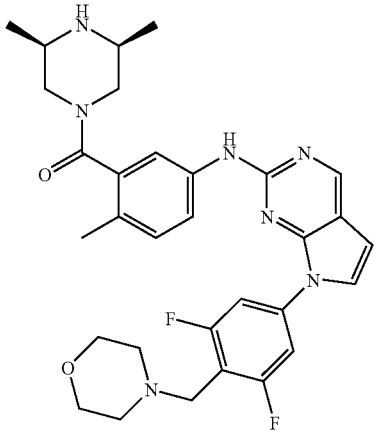 [SMILES: Cc1ccc(Nc2ncc3ccn(-c4cc(F)c(CN5CCOCC5)c(F)c4)c3n2)cc1C(=O)N1C[C@@H](C)N[C@@H](C)C1]

The compound is prepared analogous to Example 2.
HPLC: $t_R$=4.00 min (Method C); MS-ES: (M+H)$^+$=576

EXAMPLE 453

[7-(3,5-Difluoro-phenyl)-7H-pyrrolo[2,3-d]pyrimidin-2-yl]-[6-(cis-3,5-dimethyl-piperazin-1-yl)-pyridin-3-yl]-amine

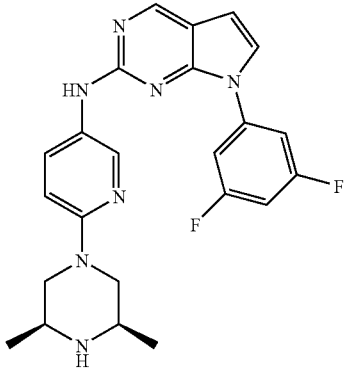 [SMILES: C[C@@H]1CN(c2ccc(Nc3ncc4ccn(-c5cc(F)cc(F)c5)c4n3)cn2)C[C@H](C)N1]

The compound is prepared analogous to Example 2.
HPLC: $t_R$=0.74 min (Method E1); MS-ES: (M+H)$^+$=436

EXAMPLE 454

{7-[4-(cis-2,6-dimethyl-morpholin-4-ylmethyl)-3,5-difluoro-phenyl]-7H-pyrrolo[2,3-d]pyrimidin-2-yl}-(6-piperazin-1-yl-pyridin-3-yl)-amine

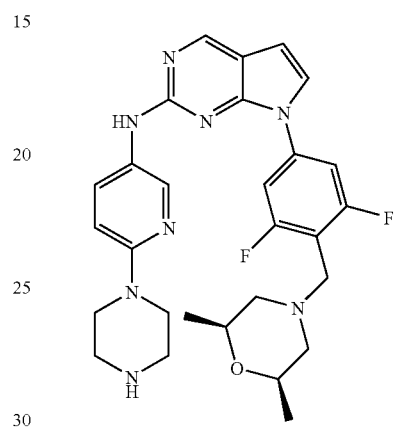

The compound is prepared analogous to Example 2, using a Boc-protected piperazine derivative in Step 2.2. Final deprotection is achieved with TFA in CH$_2$Cl$_2$ at rt. HPLC: $t_R$=1.14 min (Method E2); MS-ES: (M+H)$^+$=535

EXAMPLE 455

{3-[7-(3,5-Difluoro-4-morpholin-4-ylmethyl-phenyl)-7H-pyrrolo[2,3-d]pyrimidin-2-ylamino]-phenyl}-(cis-3,5-dimethyl-piperazin-1-yl)-methanone

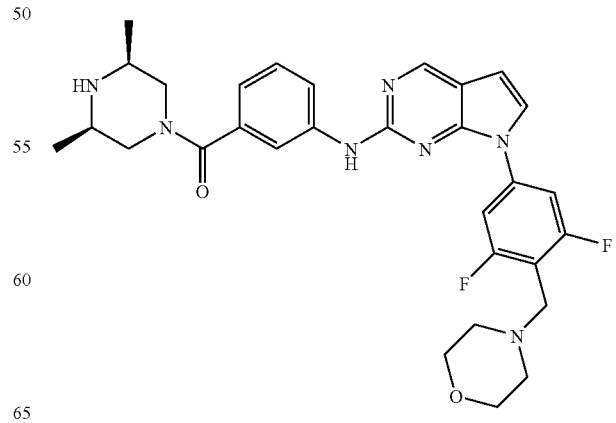

The compound is prepared analogous to Example 2.
HPLC: $t_R$=3.97 min (Method C); MS-ES: (M+H)$^+$=562

EXAMPLE 456

[2-(4-Cyclopropyl-piperazin-1-yl)-pyridin-4-yl]-[7-(3,5-difluoro-4-morpholin-4-ylmethyl-phenyl)-7H-pyrrolo[2,3-d]pyrimidin-2-yl]-amine

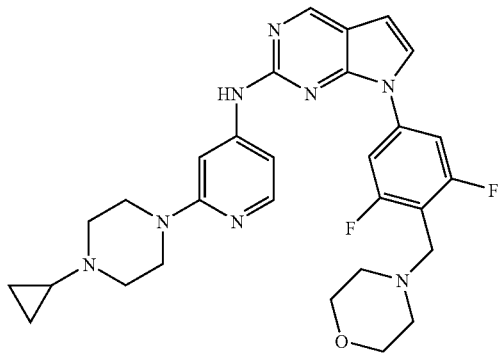 [SMILES: Fc1cc(-n2ccc3cnc(Nc4ccnc(N5CCN(C6CC6)CC5)c4)nc32)cc(F)c1CN1CCOCC1]

The compound is prepared analogous to Example 2.
HPLC: $t_R$=3.96 min (Method C); MS-ES: (M+H)$^+$=547

EXAMPLE 457

[6-(4-Cyclopropyl-piperazin-1-yl)-pyridin-3-yl]-[7-(3,5-difluoro-4-morpholin-4-ylmethyl-phenyl)-7H-pyrrolo[2,3-d]pyrimidin-2-yl]-amine

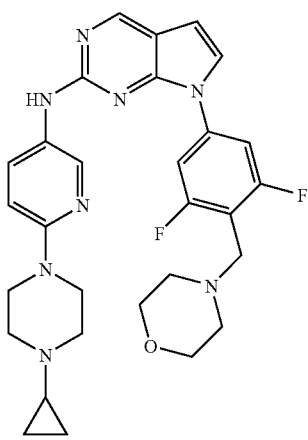 [SMILES: Fc1cc(-n2ccc3cnc(Nc4ccc(N5CCN(C6CC6)CC5)nc4)nc32)cc(F)c1CN1CCOCC1]

The compound is prepared analogous to Example 2.
HPLC: $t_R$=3.89 min (Method C); MS-ES: (M+H)$^+$=547

EXAMPLE 458

1-(4-{2-[6-(cis-3,5-Dimethyl-piperazin-1-yl)-pyridin-3-ylamino]-pyrrolo[2,3-d]pyrimidin-7-yl}-2,6-difluoro-benzyl)-pyrrolidin-2-one

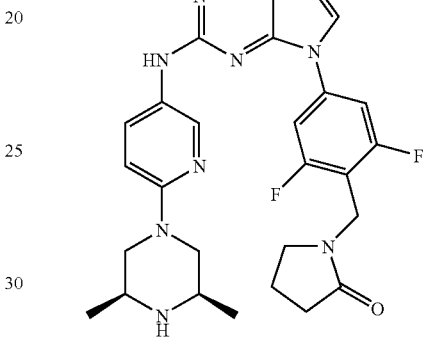

The compound is prepared analogous to Example 2.
HPLC: $t_R$=0.81 min (Method E1); MS-ES: (M+H)$^+$=533

EXAMPLE 459

(4-Cyclopropyl-piperazin-1-yl)-{3-[7-(3,5-difluoro-4-morpholin-4-ylmethyl-phenyl)-7H-pyrrolo[2,3-d]pyrimidin-2-ylamino]-phenyl}-methanone

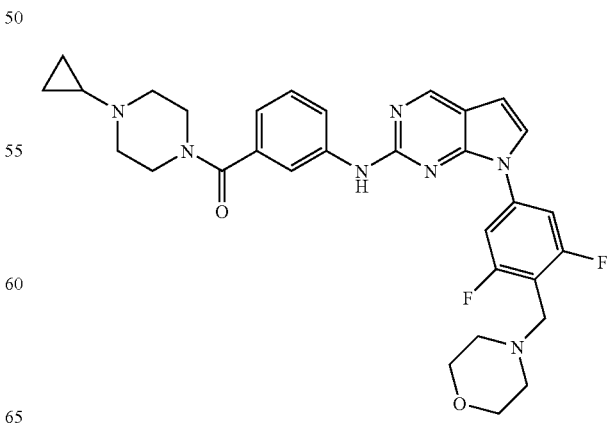

The compound is prepared analogous to Example 2. HPLC: $t_R$=4.02 min (Method C); MS-ES: (M+H)$^+$=574

EXAMPLE 460

[7-(3,5-Difluoro-4-morpholin-4-ylmethyl-phenyl)-7H-pyrrolo[2,3-d]pyrimidin-2-yl]-(3-methyl-4-piperazin-1-ylmethyl-phenyl)-amine

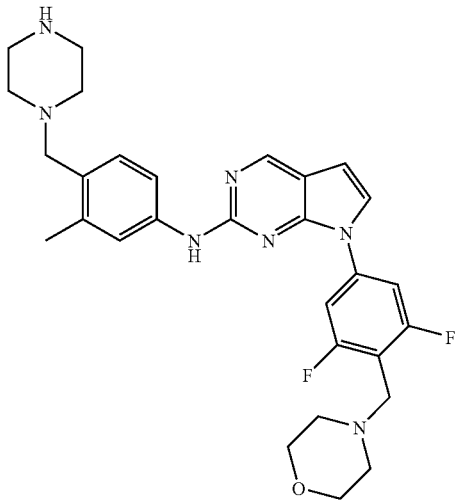 [SMILES: Cc1cc(Nc2ncc3ccn(-c4cc(F)c(CN5CCOCC5)c(F)c4)c3n2)ccc1CN1CCNCC1]

The compound is prepared analogous to Example 2, using a Boc-protected piperazine derivative in Step 2.2. Final deprotection is achieved with TFA in CH$_2$Cl$_2$ at rt. HPLC: $t_R$=3.96 min (Method C); MS-ES: (M+H)$^+$=534

EXAMPLE 461

[7-(3,5-Difluoro-4-morpholin-4-ylmethyl-phenyl)-7H-pyrrolo[2,3-d]pyrimidin-2-yl]-[4-(cis-3,5-dimethyl-piperazin-1-ylmethyl)-3-methyl-phenyl]-amine

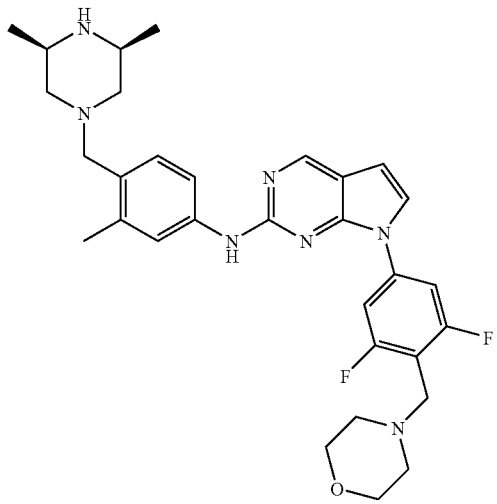 [SMILES: Cc1cc(Nc2ncc3ccn(-c4cc(F)c(CN5CCOCC5)c(F)c4)c3n2)ccc1CN1C[C@@H](C)N[C@@H](C)C1]

The compound is prepared analogous to Example 2. HPLC: $t_R$=4.01 min (Method C); MS-ES: (M+H)$^+$=562

EXAMPLE 462

1-(4-{2-[4-(cis-3,5-Dimethyl-piperazin-1-ylmethyl)-phenylamino]-pyrrolo[2,3-d]pyrimidin-7-yl}-2,6-difluoro-benzyl)-pyrrolidin-2-one

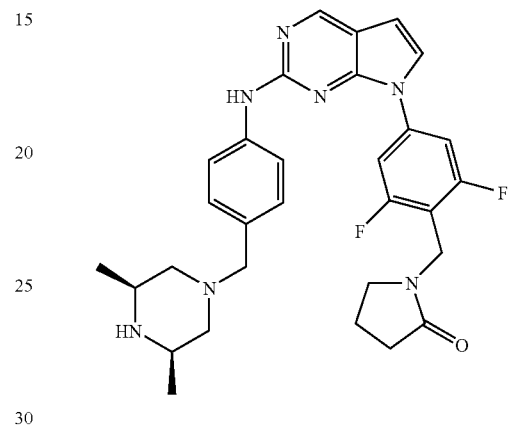

The compound is prepared analogous to Example 2. HPLC: $t_R$=0.70 min (Method E1); MS-ES: (M+H)$^+$=546

EXAMPLE 463

1-{2,6-Difluoro-4-[2-(4-methyl-3-piperazin-1-ylmethyl-phenylamino)-pyrrolo[2,3-d]pyrimidin-7-yl]-benzyl}-pyrrolidin-2-one

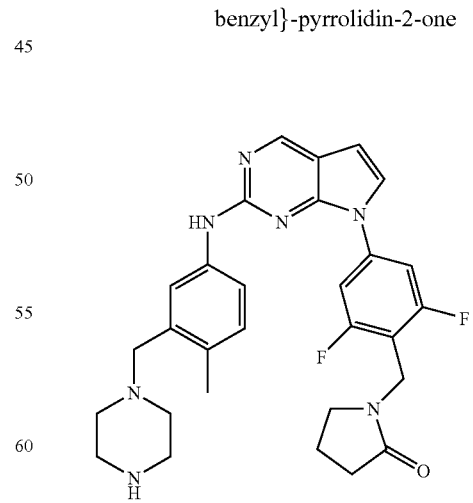

The compound is prepared analogous to Example 2, using a Boc-protected piperazine derivative in Step 2.2. Final deprotection is achieved with TFA in CH$_2$Cl$_2$ at rt. HPLC: t$_R$=0.72 min (Method E1); MS-ES: (M+H)$^+$=532

EXAMPLE 464

N-tert-Butyl-4-{2-[4-(cis-3,5-dimethyl-piperazin-1-ylmethyl)-phenylamino]-pyrrolo[2,3-d]pyrimidin-7-yl}-benzenesulfonamide

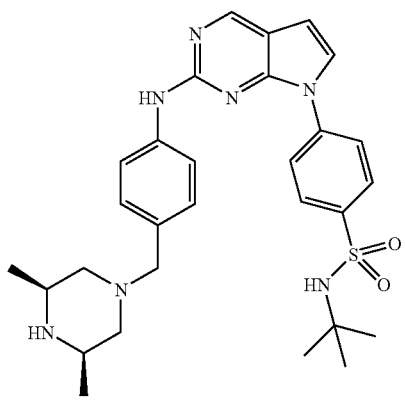 [SMILES: C[C@@H]1CN(Cc2ccc(Nc3ncc4ccn(-c5ccc(S(=O)(=O)NC(C)(C)C)cc5)c4n3)cc2)C[C@H](C)N1]

The compound is prepared analogous to Example 2. HPLC: t$_R$=0.76 min (Method E1); MS-ES: (M+H)$^+$=548

EXAMPLE 465

[7-(3,5-Difluoro-4-morpholin-4-ylmethyl-phenyl)-7H-pyrrolo[2,3-d]pyrimidin-2-yl]-{6-[4-(2-dimethylamino-ethyl)-piperazin-1-yl]-pyridin-3-yl}-amine

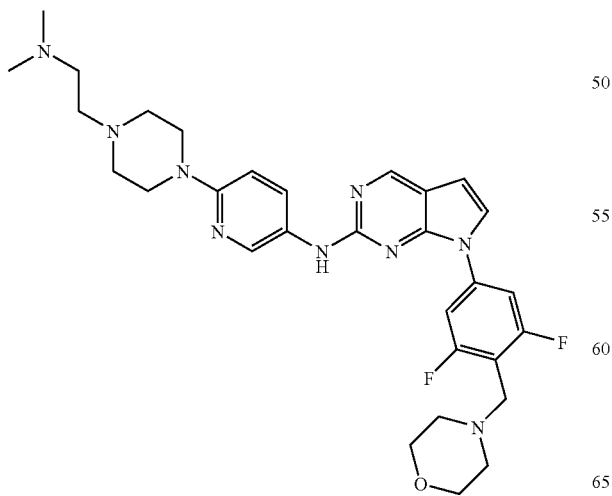

The compound is prepared analogous to Example 2. HPLC: t$_R$=3.84 min (Method C); MS-ES: (M+H)$^+$=578

EXAMPLE 466

{5-[7-(3,5-Difluoro-4-morpholin-4-ylmethyl-phenyl)-7H-pyrrolo[2,3-d]pyrimidin-2-ylamino]-pyridin-2-yl}-(4-methyl-piperazin-1-yl)-methanone

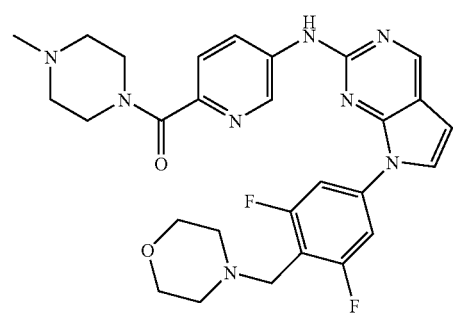 [SMILES: CN1CCN(C(=O)c2ccc(Nc3ncc4ccn(-c5cc(F)c(CN6CCOCC6)c(F)c5)c4n3)cn2)CC1]

The compound is prepared analogous to Example 2. HPLC: t$_R$=3.99 min (Method F); MS-ES: (M+H)$^+$=549

EXAMPLE 467

2-(1-{5-[7-(3,5-Difluoro-4-morpholin-4-ylmethyl-phenyl)-7H-pyrrolo[2,3-d]pyrimidin-2-ylamino]-2-methyl-benzyl}-1H-pyrazol-4-yl)-ethanol

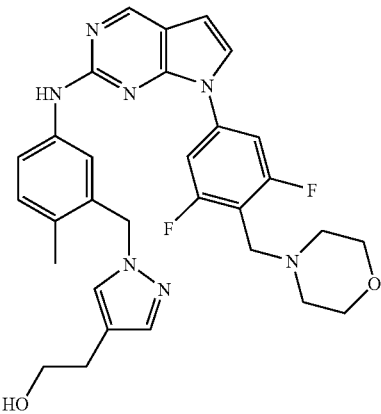 [SMILES: Cc1ccc(Nc2ncc3ccn(-c4cc(F)c(CN5CCOCC5)c(F)c4)c3n2)cc1Cn1cc(CCO)cn1]

The compound is prepared analogous to Example 2. HPLC: $t_R$=7.34 min (Method B); MS-ES: (M+H)$^+$=560; TLC*: $R_f$=0.36

EXAMPLE 468

6-{2-[4-(cis-3,5-Dimethyl-piperazin-1-ylmethyl)-phenylamino]-pyrrolo[2,3-d]pyrimidin-7-yl}-3,4-dihydro-1H-quinolin-2-one

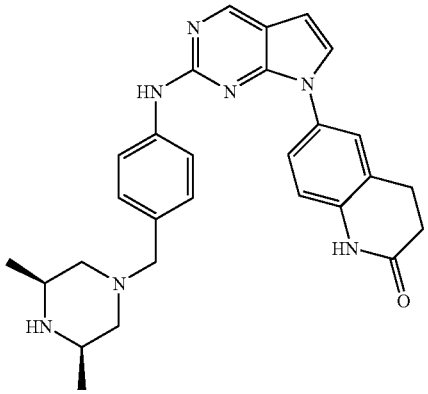 [SMILES: C[C@@H]1CN(Cc2ccc(Nc3ncc4ccn(-c5ccc6c(c5)CCC(=O)N6)c4n3)cc2)C[C@H](C)N1]

The compound is prepared analogous to Example 2. HPLC: $t_R$=0.49 min (Method E1); MS-ES: (M+H)$^+$=482

EXAMPLE 469

[7-(3,5-Difluoro-4-morpholin-4-ylmethyl-phenyl)-7H-pyrrolo[2,3-d]pyrimidin-2-yl]-[6-(3-trifluoromethyl-piperazin-1-yl)-pyridin-3-yl]-amine (racemic)

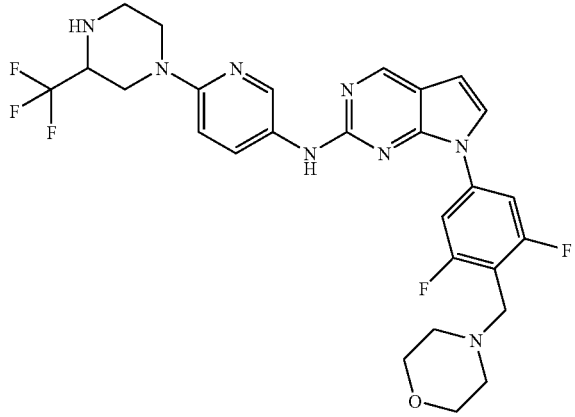 [SMILES: Fc1cc(-n2ccc3cnc(Nc4ccc(N5CCNC(C(F)(F)F)C5)nc4)nc32)cc(F)c1CN1CCOCC1]

The compound is prepared analogous to Example 2. HPLC: $t_R$=4.06 min (Method C); MS-ES: (M+H)$^+$=575

EXAMPLE 470

1-{5-[7-(3,5-Difluoro-4-morpholin-4-ylmethyl-phenyl)-7H-pyrrolo[2,3-d]pyrimidin-2-ylamino]-pyridin-2-yl}-piperazin-2-one

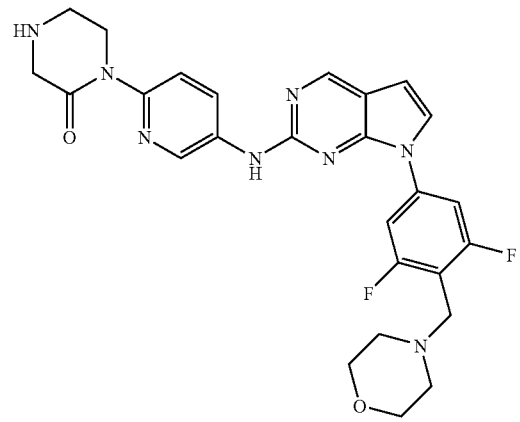 [SMILES: O=C1CNCCN1c1ccc(Nc2ncc3ccn(-c4cc(F)c(CN5CCOCC5)c(F)c4)c3n2)cn1]

The compound is prepared analogous to Example 2, using a Boc-protected piperazine derivative in Step 2.2. Final deprotection is achieved with TFA in CH$_2$Cl$_2$ at rt. HPLC: $t_R$=3.91 min (Method C); MS-ES: (M+H)$^+$=521

EXAMPLE 471

[7-(3,5-Difluoro-4-morpholin-4-ylmethyl-phenyl)-7H-pyrrolo[2,3-d]pyrimidin-2-yl]-[4-(3,3-difluoro-pyrrolidin-1-ylmethyl)-phenyl]-amine

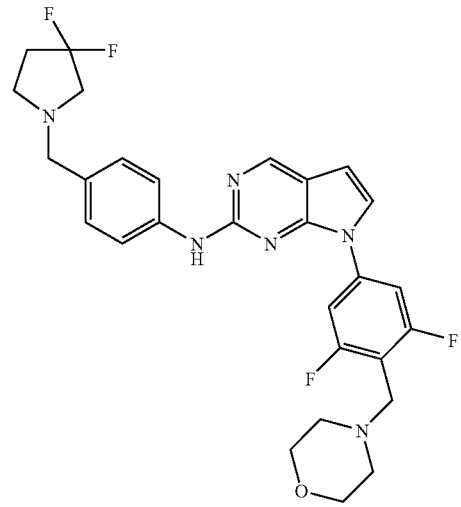 [SMILES: Fc1cc(-n2ccc3cnc(Nc4ccc(CN5CCC(F)(F)C5)cc4)nc32)cc(F)c1CN1CCOCC1]

The compound is prepared analogous to Example 2.
HPLC: $t_R$=4.19 min (Method F); MS-ES: (M+H)$^+$=541

EXAMPLE 472

[7-(3,5-Difluoro-4-morpholin-4-yl methyl-phenyl)-7H-pyrrolo[2,3-d]pyrimidin-2-yl]-[6-(4-methyl-piperazin-1-ylmethyl)-pyridin-3-yl]-amine

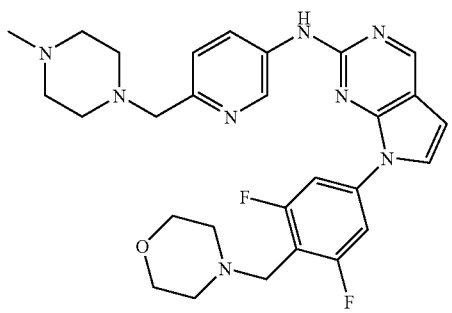 [SMILES: CN1CCN(Cc2ccc(Nc3ncc4ccn(-c5cc(F)c(CN6CCOCC6)c(F)c5)c4n3)cn2)CC1]

The compound is prepared analogous to Example 2.
HPLC: $t_R$=1.12 min (Method E2); MS-ES: (M+H)$^+$=535

EXAMPLE 473

[7-(3,5-Difluoro-4-morpholin-4-ylmethyl-phenyl)-7H-pyrrolo[2,3-d]pyrimidin-2-yl]-[4-(3,3-dimethyl-piperazin-1-ylmethyl)-phenyl]-amine

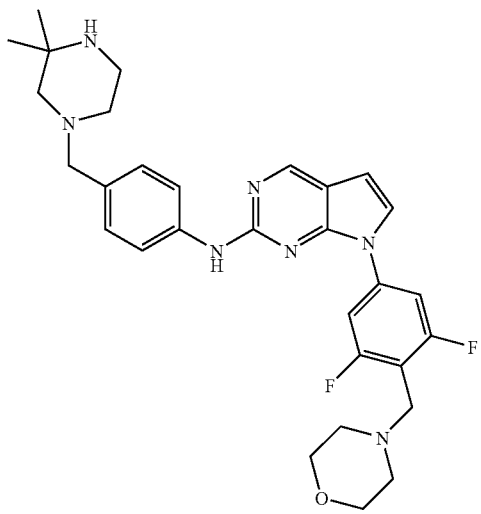 [SMILES: CC1(C)CN(Cc2ccc(Nc3ncc4ccn(-c5cc(F)c(CN6CCOCC6)c(F)c5)c4n3)cc2)CCN1]

The compound is prepared analogous to Example 2.
HPLC: $t_R$=0.01 min (Method C); MS-ES: (M+H)$^+$=548

EXAMPLE 474

[7-(3,5-Difluoro-4-morpholin-4-ylmethyl-phenyl)-7H-pyrrolo[2,3-d]pyrimidin-2-yl]-((S)-4-piperazin-2-yl-phenyl)-amine

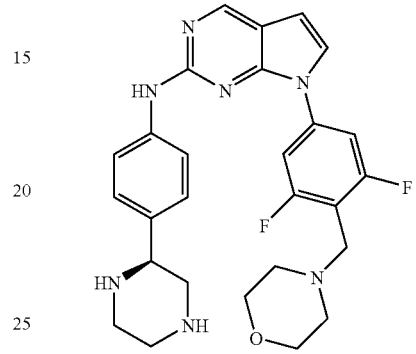

The compound is prepared analogous to Example 2, using a Boc-protected piperazine derivative in Step 2.2. Final deprotection is achieved with TFA in CH$_2$Cl$_2$ at rt. The aniline used for this synthesis is prepared from 2-(4-nitro-phenyl)-piperazine (racemic) via Boc-protection, nitro reduction and chiral separation (other enantiomer used for Example 475).
HPLC: $t_R$=0.68 min (Method E2); MS-ES: (M+H)$^+$=506

EXAMPLE 475

[7-(3,5-Difluoro-4-morpholin-4-ylmethyl-phenyl)-7H-pyrrolo[2,3-d]pyrimidin-2-yl]-((R)-4-piperazin-2-yl-phenyl)-amine

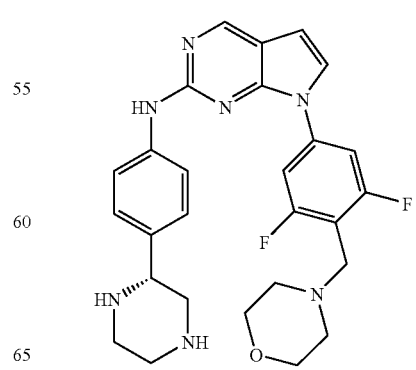

The compound is prepared analogous to Example 2 and represents the enantiomer of Example 474. HPLC: $t_R$=0.68 min (Method E2); MS-ES: (M+H)⁺=506

EXAMPLE 476

[7-(3,5-Difluoro-4-morpholin-4-ylmethyl-phenyl)-7H-pyrrolo[2,3-d]pyrimidin-2-yl]-[4-(3-trifluoromethyl-piperazin-1-ylmethyl)-phenyl]-amine (racemic)

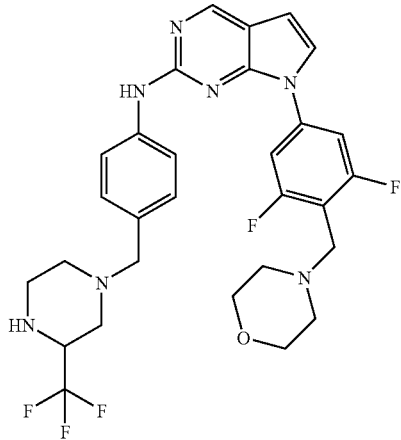 [SMILES: Fc1cc(-n2ccc3cnc(Nc4ccc(CN5CCNC(C(F)(F)F)C5)cc4)nc32)cc(F)c1CN1CCOCC1]

The compound is prepared analogous to Example 2. HPLC: $t_R$=4.24 min (Method C); MS-ES: (M+H)⁺=588

EXAMPLE 477

[7-(3,5-Difluoro-4-morpholin-4-ylmethyl-phenyl)-7H-pyrrolo[2,3-d]pyrimidin-2-yl]-[4-(cis-3,5-dimethyl-piperazin-1-ylmethyl)-2-fluoro-phenyl]-amine

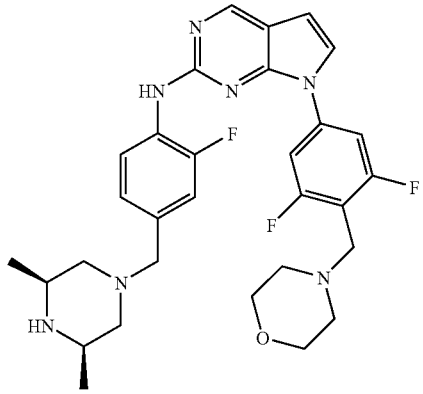 [SMILES: C[C@@H]1CN(Cc2ccc(Nc3ncc4ccn(-c5cc(F)c(CN6CCOCC6)c(F)c5)c4n3)c(F)c2)C[C@H](C)N1]

The compound is prepared analogous to Example 2. HPLC: $t_R$=4.06 min (Method C); MS-ES: (M+H)⁺=566

EXAMPLE 478

1-{5-[7-(3,5-Difluoro-4-morpholin-4-ylmethyl-phenyl)-7H-pyrrolo[2,3-d]pyrimidin-2-ylamino]-pyridin-2-yl}-4-methyl-piperazin-2-one

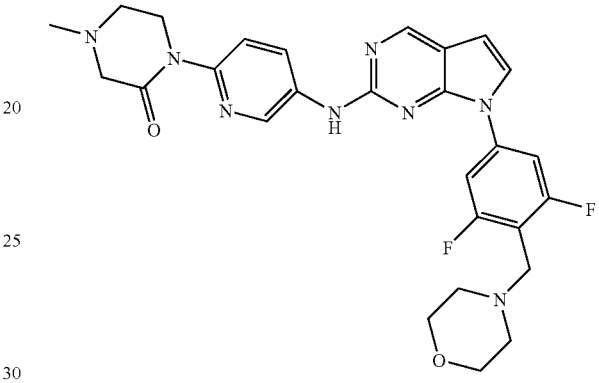

The compound is obtained from the reaction of 1-{5-[7-(3,5-Difluoro-4-morpholin-4-ylmethyl-phenyl)-7H-pyrrolo[2,3-d]pyrimidin-2-ylamino]-pyridin-2-yl}-piperazin-2-one (Example 470) with formaldehyde and sodium cyanoborohydride in methanol and DCM 2:1 at rt. HPLC: $t_R$=3.94 min (Method C); MS-ES: (M+H)⁺=535

EXAMPLE 479

1-{4-[7-(3,5-Difluoro-4-morpholin-4-ylmethyl-phenyl)-7H-pyrrolo[2,3-d]pyrimidin-2-ylamino]-benzyl}-azetidin-3-ol

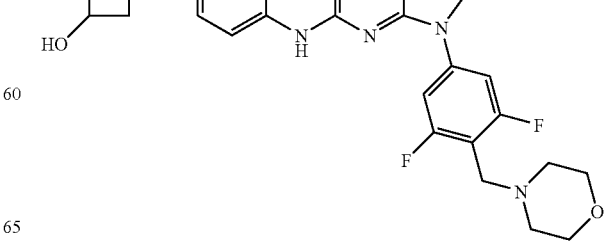

The compound is prepared analogous to Example 2. HPLC: $t_R$=3.97 min (Method C); MS-ES: (M+H)$^+$=507

EXAMPLE 480

[7-(3,5-Difluoro-4-morpholin-4-ylmethyl-phenyl)-7H-pyrrolo[2,3-d]pyrimidin-2-yl]-(6-morpholin-4-ylmethyl-pyridin-3-yl)-amine

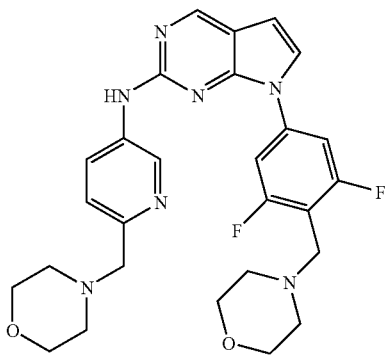 [SMILES: Fc1cc(-n2ccc3cnc(Nc4ccc(CN5CCOCC5)nc4)nc32)cc(F)c1CN1CCOCC1]

The compound is prepared analogous to Example 2. HPLC: $t_R$=1.20 min (Method E2); MS-ES: (M+H)$^+$=522

EXAMPLE 481

[7-(3,5-Difluoro-4-morpholin-4-ylmethyl-phenyl)-7H-pyrrolo[2,3-d]pyrimidin-2-yl]-[4-methyl-3-(4-methyl-pyrazol-1-ylmethyl)-phenyl]-amine

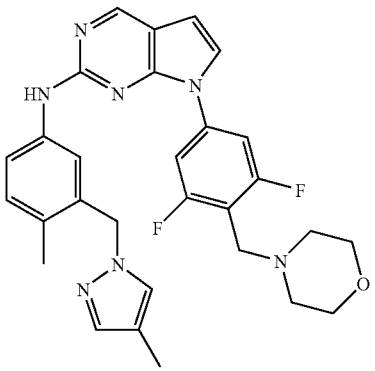 [SMILES: Cc1cnn(Cc2cc(Nc3ncc4ccn(-c5cc(F)c(CN6CCOCC6)c(F)c5)c4n3)ccc2C)c1]

The compound is prepared analogous to Example 2. HPLC: $t_R$=8.11 min (Method B); MS-ES: (M+H)$^+$=530; TLC*: $R_f$=0.67

EXAMPLE 482

{7-[3,5-Difluoro-4-(3-methoxy-azetidin-1-ylmethyl)-phenyl]-7H-pyrrolo[2,3-d]pyrimidin-2-yl}-(4-methyl-3-piperazin-1-ylmethyl-phenyl)-amine

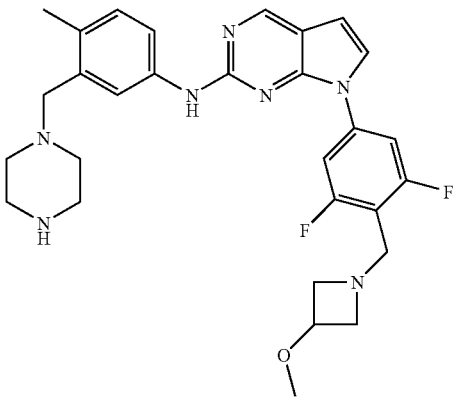 [SMILES: COC1CN(Cc2c(F)cc(-n3ccc4cnc(Nc5ccc(C)c(CN6CCNCC6)c5)nc43)cc2F)C1]

The compound is prepared analogous to Example 2, using a Boc-protected piperazine derivative in Step 2.2. Final deprotection is achieved with TFA in CH$_2$Cl$_2$ at rt. HPLC: $t_R$=4.05 min (Method F); MS-ES: (M+H)$^+$=534

EXAMPLE 483

4-(4-{2-[6-(cis-3,5-Dimethyl-piperazin-1-yl)-5-methyl-pyridin-3-ylamino]-pyrrolo[2,3-d]pyrimidin-7-yl}-2,6-difluoro-benzyl)-morpholin-3-one

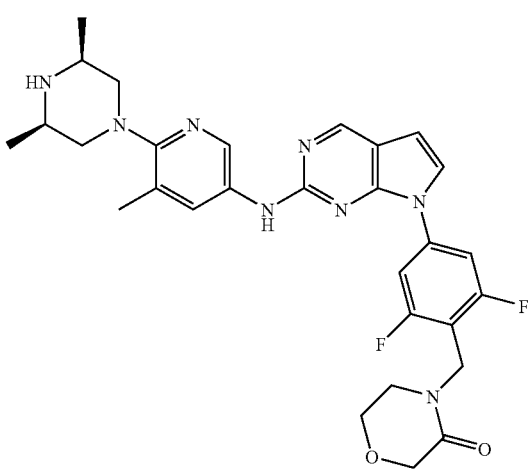 [SMILES: Cc1cc(Nc2ncc3ccn(-c4cc(F)c(CN5CCOCC5=O)c(F)c4)c3n2)cnc1N1C[C@@H](C)N[C@@H](C)C1]

The compound is prepared analogous to Example 2. HPLC: $t_R$=4.58 min (Method F); MS-ES: (M+H)$^+$=563

EXAMPLE 484

4-(4-{2-[4-(cis-3,5-Dimethyl-piperazin-1-ylmethyl)-phenylamino]-pyrrolo[2,3-d]pyrimidin-7-yl}-2,6-difluoro-benzyl)-morpholin-3-one

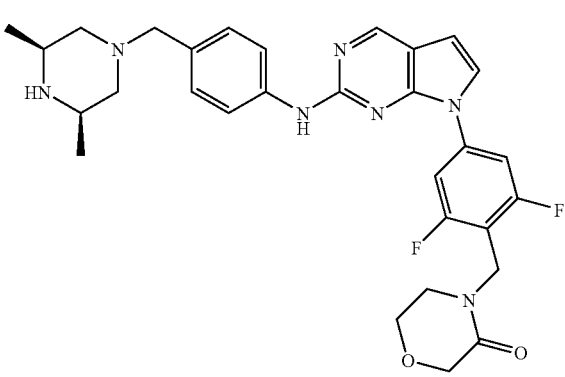 [SMILES: C[C@@H]1CN(Cc2ccc(Nc3ncc4ccn(-c5cc(F)c(CN6CCOCC6=O)c(F)c5)c4n3)cc2)C[C@H](C)N1]

The compound is prepared analogous to Example 2. HPLC: $t_R$=4.40 min (Method F); MS-ES: (M+H)$^+$=562

EXAMPLE 485

4-{2,6-Difluoro-4-[2-(4-methyl-3-piperazin-1-ylmethyl-phenylamino)-pyrrolo[2,3-d]pyrimidin-7-yl}-benzyl]-morpholin-3-one

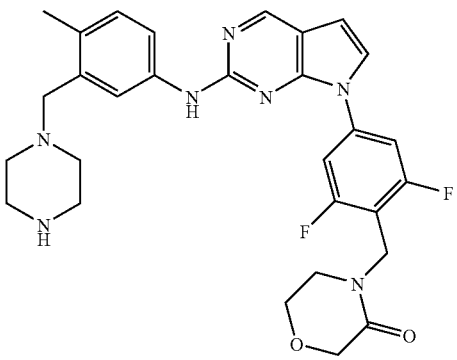 [SMILES: Cc1ccc(Nc2ncc3ccn(-c4cc(F)c(CN5CCOCC5=O)c(F)c4)c3n2)cc1CN1CCNCC1]

The compound is prepared analogous to Example 2, using a Boc-protected piperazine derivative in Step 2.2. Final deprotection is achieved with TFA in CH$_2$Cl$_2$ at rt. HPLC: t$_R$=4.44 min (Method F); MS-ES: (M+H)$^+$=548

EXAMPLE 486

[7-(3,5-Difluoro-4-morpholin-4-yl methyl-phenyl)-7H-pyrrolo[2,3-d]pyrimidin-2-yl]-(6-piperazin-1-ylmethyl-pyridin-3-yl)-amine

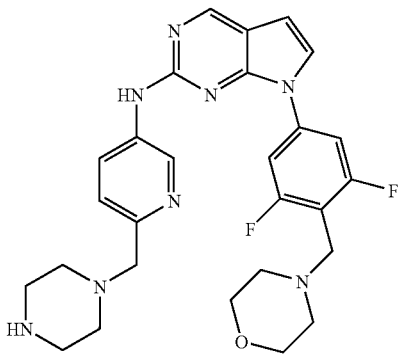 [SMILES: Fc1cc(-n2ccc3cnc(Nc4ccc(CN5CCNCC5)nc4)nc32)cc(F)c1CN1CCOCC1]

The compound is prepared analogous to Example 2. HPLC: t$_R$=1.12 min (Method E); MS-ES: (M+H)$^+$=521

EXAMPLE 487

[7-(3,5-Difluoro-4-morpholin-4-ylmethyl-phenyl)-7H-pyrrolo[2,3-d]pyrimidin-2-yl]-(5-methyl-6-piperazin-1-yl-pyridin-3-yl)-amine

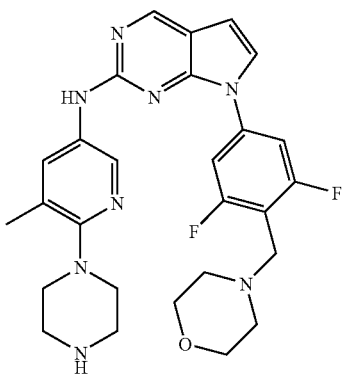 [SMILES: Cc1cc(Nc2ncc3ccn(-c4cc(F)c(CN5CCOCC5)c(F)c4)c3n2)cnc1N1CCNCC1]

The compound is prepared analogous to Example 2, using a Boc-protected piperazine derivative in Step 2.2. Final deprotection is achieved with TFA in CH$_2$Cl$_2$ at rt. HPLC: t$_R$=3.99 min (Method C); MS-ES: (M+H)$^+$=521

EXAMPLE 488

[7-(3,5-Difluoro-4-morpholin-4-ylmethyl-phenyl)-7H-pyrrolo[2,3-d]pyrimidin-2-yl]-[6-(dimethyl-piperazin-1-yl)-5-methyl-pyridin-3-yl]-amine

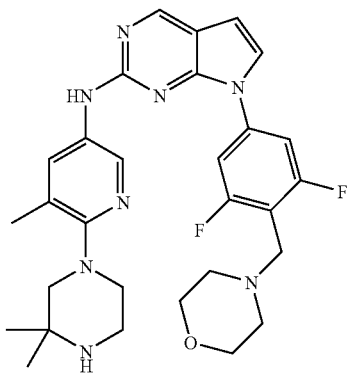 [SMILES: Cc1cc(Nc2ncc3ccn(-c4cc(F)c(CN5CCOCC5)c(F)c4)c3n2)cnc1N1CCNC(C)(C)C1]

The compound is prepared analogous to Example 2. HPLC: t$_R$=4.16 min (Method C); MS-ES: (M+H)$^+$=549

EXAMPLE 489

[5-Chloro-6-(cis-3,5-dimethyl-piperazin-1-yl)-pyridin-3-yl]-[7-(3,5-difluoro-4-morpholin-4-ylmethyl-phenyl)-7H-pyrrolo[2,3-d]pyrimidin-2-yl]-amine

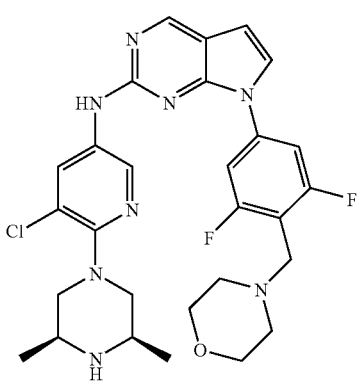 [SMILES: C[C@@H]1CN(c2ncc(Nc3ncc4ccn(-c5cc(F)c(CN6CCOCC6)c(F)c5)c4n3)cc2Cl)C[C@H](C)N1]

The compound is prepared analogous to Example 2. HPLC: t$_R$=4.42 min (Method F); MS-ES: (M+H)$^+$=569

EXAMPLE 490

5-[7-(3,5-Difluoro-4-morpholin-4-ylmethyl-phenyl)-7H-pyrrolo[2,3-d]pyrimidin-2-ylamino]-2-(cis-3,5-dimethyl-piperazin-1-yl)-nicotinonitrile

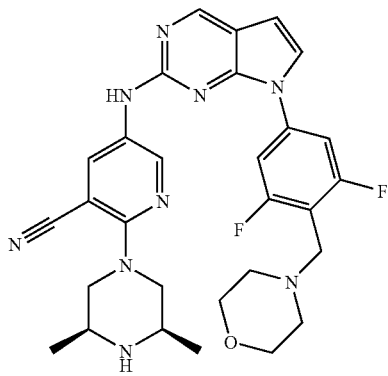 [SMILES: C[C@@H]1CN(c2ncc(Nc3ncc4ccn(-c5cc(F)c(CN6CCOCC6)c(F)c5)c4n3)cc2C#N)C[C@H](C)N1]

The compound is prepared analogous to Example 2.
HPLC: $t_R$=4.34 min (Method C); MS-ES: (M+H)$^+$=560

EXAMPLE 491

4-{3-Chloro-5-[7-(3,5-difluoro-4-morpholin-4-ylmethyl-phenyl)-7H-pyrrolo[2,3-d]pyrimidin-2-ylamino]-pyridin-2-yl}-piperazin-2-one

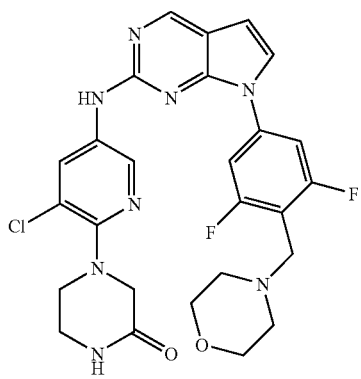 [SMILES: O=C1CN(c2ncc(Nc3ncc4ccn(-c5cc(F)c(CN6CCOCC6)c(F)c5)c4n3)cc2Cl)CCN1]

The compound is prepared analogous to Example 2.
HPLC: $t_R$=4.56 min (Method C); MS-ES: (M+H)$^+$=555

EXAMPLE 492

1-{5-[7-(3,5-Difluoro-4-morpholin-4-ylmethyl-phenyl)-7H-pyrrolo[2,3-d]pyrimidin-2-ylamino]-pyridin-2-yl}-3,3-dimethyl-piperazin-2-one

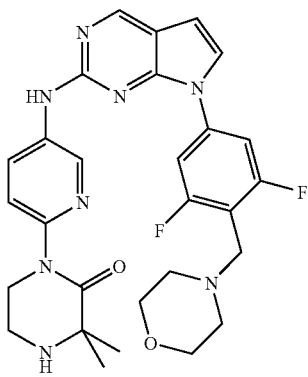 [SMILES: CC1(C)NCCN(c2ccc(Nc3ncc4ccn(-c5cc(F)c(CN6CCOCC6)c(F)c5)c4n3)cn2)C1=O]

The compound is prepared analogous to Example 2.
HPLC: $t_R$=4.04 min (Method C); MS-ES: (M+H)$^+$=549

EXAMPLE 493

1-{5-[7-(3,5-Difluoro-4-morpholin-4-ylmethyl-phenyl)-7H-pyrrolo[2,3-d]pyrimidin-2-ylamino]-3-methyl-pyridin-2-yl}-3,3-dimethyl-piperazin-2-one

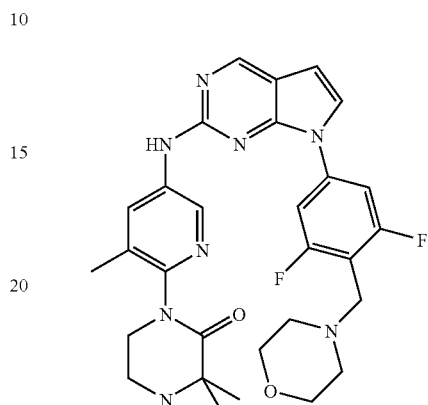

The compound is prepared analogous to Example 2.
HPLC: $t_R$=3,54 min (Method C); MS-ES: (M+H)$^+$=563

EXAMPLE 494

[4-Chloro-3-(4-methyl-piperazin-1-yl methyl)-phenyl]-[7-(3,5-difluoro-4-morpholin-4-ylmethyl-phenyl)-7H-pyrrolo[2,3-d]pyrimidin-2-yl]-amine

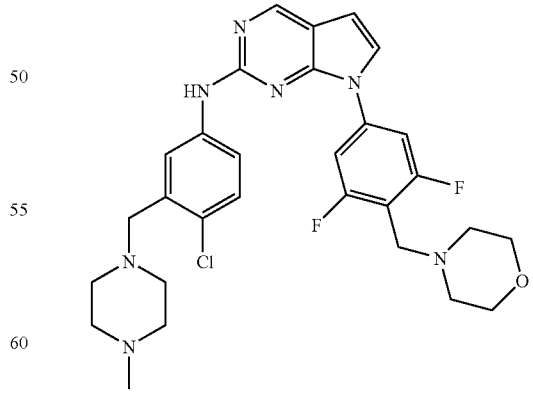

The compound is prepared analogous to Example 2.
HPLC: $t_R$=7.25 min (Method B); MS-ES: (M+H)$^+$=568

EXAMPLE 495

1-{5-[7-(3,5-Difluoro-4-morpholin-4-ylmethyl-phenyl)-7H-pyrrolo[2,3-d]pyrimidin-2-ylamino]-3-methyl-pyridin-2-yl}-piperazin-2-one

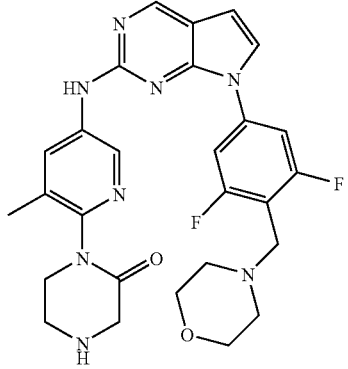 [SMILES: Cc1cc(Nc2ncc3ccn(-c4cc(F)c(CN5CCOCC5)c(F)c4)c3n2)cnc1N1CCNCC1=O]

The compound is prepared analogous to Example 2, using a Boc-protected piperazine derivative in Step 2.2. Final deprotection is achieved with TFA in $CH_2Cl_2$ at rt. HPLC: $t_R$=3.98 min (Method C); MS-ES: $(M+H)^+$=535

EXAMPLE 496

[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-5-trifluoromethyl-pyridin-3-yl]-amine

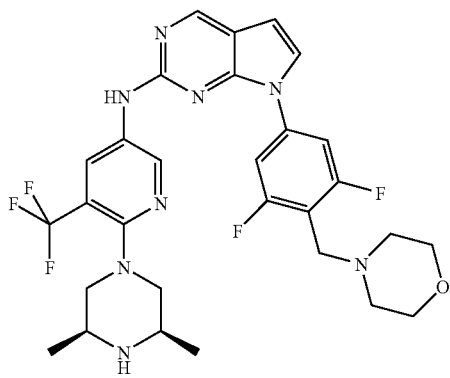 [SMILES: C[C@@H]1CN(c2ncc(Nc3ncc4ccn(-c5cc(F)c(CN6CCOCC6)c(F)c5)c4n3)cc2C(F)(F)F)C[C@H](C)N1]

The compound is prepared analogous to Example 2. HPLC: $t_R$=4.67 min (Method C); MS-ES: $(M+H)^+$=603

EXAMPLE 497

[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-5-methoxy-pyridin-3-yl]-amine

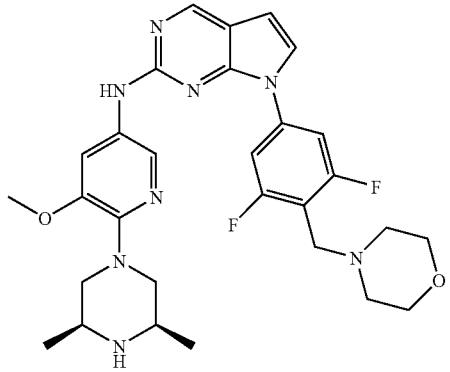 [SMILES: COc1cc(Nc2ncc3ccn(-c4cc(F)c(CN5CCOCC5)c(F)c4)c3n2)cnc1N1C[C@@H](C)N[C@@H](C)C1]

The compound is prepared analogous to Example 2. HPLC: $t_R$=4.07 min (Method C); MS-ES: $(M+H)^+$=565

EXAMPLE 498

1-{4-[7-(3,5-Difluoro-4-morpholin-4-ylmethyl-phenyl)-7H-pyrrolo[2,3-d]pyrimidin-2-ylamino]-benzyl}-piperazin-2-one

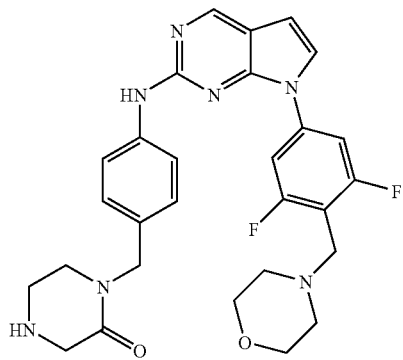 [SMILES: O=C1CNCCN1Cc1ccc(Nc2ncc3ccn(-c4cc(F)c(CN5CCOCC5)c(F)c4)c3n2)cc1]

The compound is prepared analogous to Example 2, using a Boc-protected piperazine derivative in Step 2.2. Final deprotection is achieved with TFA in $CH_2Cl_2$ at rt. HPLC: $t_R$=3.96 min (Method C); MS-ES: $(M+H)^+$=534

EXAMPLE 499

(4-{2-[6-(cis-3,5-Dimethyl-piperazin-1-yl)-pyridin-3-ylamino]-pyrrolo[2,3-d]pyrimidin-7-yl}-2-fluoro-phenyl)-morpholin-4-yl-methanone

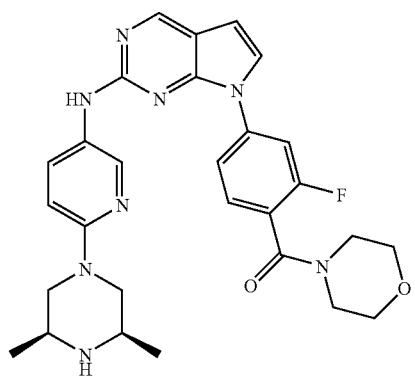 [SMILES: C[C@@H]1CN(c2ccc(Nc3ncc4ccn(-c5ccc(C(=O)N6CCOCC6)c(F)c5)c4n3)cn2)C[C@H](C)N1]

The compound is prepared analogous to Example 2. HPLC: $t_R$=4.27 min (Method C); MS-ES: $(M+H)^+$=531

EXAMPLE 500

4-{4-[7-(3,5-Difluoro-4-morpholin-4-ylmethyl-phenyl)-7H-pyrrolo[2,3-d]pyrimidin-2-ylamino]-pyridin-2-yl}-piperazin-2-one

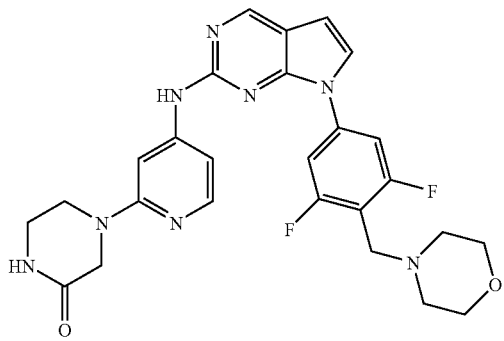 [SMILES: O=C1CN(c2cc(Nc3ncc4ccn(-c5cc(F)c(CN6CCOCC6)c(F)c5)c4n3)ccn2)CCN1]

The compound is prepared analogous to Example 2. HPLC: $t_R$=4.20 min (Method C); MS-ES: (M+H)$^+$=521

EXAMPLE 501

[7-(3,5-Difluoro-4-morpholin-4-ylmethyl-phenyl)-7H-pyrrolo[2,3-d]pyrimidin-2-yl]-(1,2',3',4',5',6'-hexahydro-[2,4']bipyridinyl-5-yl)-amine

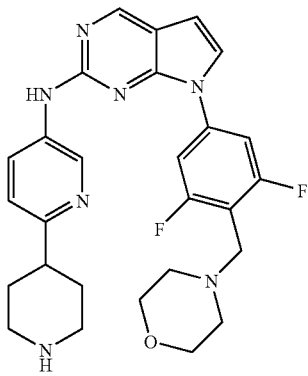 [SMILES: Fc1cc(-n2ccc3cnc(Nc4ccc(C5CCNCC5)nc4)nc32)cc(F)c1CN1CCOCC1]

The compound is prepared analogous to Example 2, using a Boc-protected piperazine derivative in Step 2.2. Final deprotection is achieved with TFA in CH$_2$Cl$_2$ at rt. HPLC: $t_R$=3.92 min (Method C); MS-ES: (M+H)$^+$=506

EXAMPLE 502

(5-Chloro-6-piperazin-1-yl-pyridin-3-yl)-[7-(3,5-difluoro-4-morpholin-4-ylmethyl-phenyl)-7H-pyrrolo[2,3-d]pyrimidin-2-yl]-amine

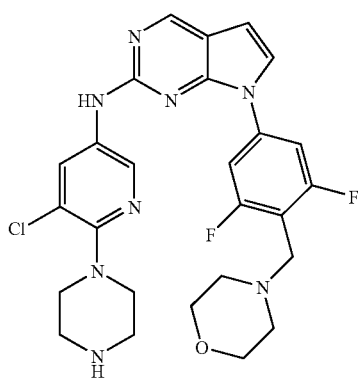 [SMILES: Fc1cc(-n2ccc3cnc(Nc4cnc(N5CCNCC5)c(Cl)c4)nc32)cc(F)c1CN1CCOCC1]

The compound is prepared analogous to Example 2, using a Boc-protected piperazine derivative in Step 2.2. Final deprotection is achieved with TFA in CH$_2$Cl$_2$ at rt. HPLC: $t_R$=4.27 min (Method C); MS-ES: (M+H)$^+$=541

EXAMPLE 503

1-{4-[7-(3,5-Difluoro-4-morpholin-4-ylmethyl-phenyl)-7H-pyrrolo[2,3-d]pyrimidin-2-ylamino]-pyridin-2-yl}-3,3-dimethyl-piperazin-2-one

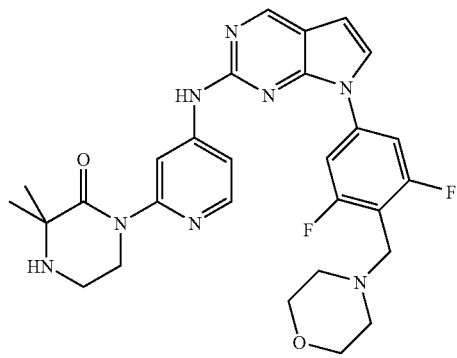 [SMILES: CC1(C)NCCN(c2cc(Nc3ncc4ccn(-c5cc(F)c(CN6CCOCC6)c(F)c5)c4n3)ccn2)C1=O]

The compound is prepared analogous to Example 2. HPLC: $t_R$=4.00 min (Method C); MS-ES: (M+H)$^+$=549

EXAMPLE 504

4-{4-[7-(3,5-Difluoro-4-morpholin-4-ylmethyl-phenyl)-7H-pyrrolo[2,3-d]pyrimidin-2-ylamino]-pyridin-2-yl}-1-methyl-piperazin-2-one

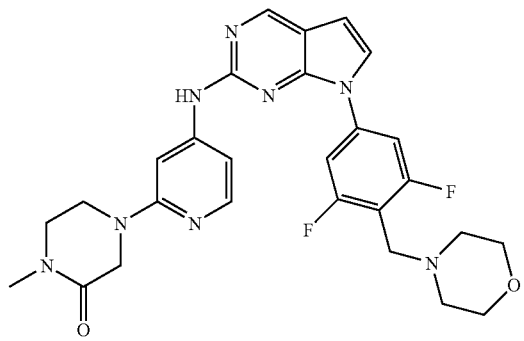 [SMILES: CN1CCN(c2cc(Nc3ncc4ccn(-c5cc(F)c(CN6CCOCC6)c(F)c5)c4n3)ccn2)CC1=O]

The compound is prepared analogous to Example 2. HPLC: $t_R$=4.23 min (Method C); MS-ES: (M+H)$^+$=535

EXAMPLE 505

4-{5-[7-(3,5-Difluoro-4-morpholin-4-methyl-phenyl)-7H-pyrrolo[2,3-d]pyrimidin-2-ylamino]-pyridin-2-ylmethyl}-1-methyl-piperazin-2-one

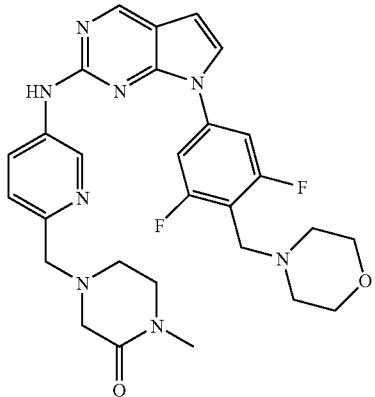 [SMILES: CN1CCN(Cc2ccc(Nc3ncc4ccn(-c5cc(F)c(CN6CCOCC6)c(F)c5)c4n3)cn2)CC1=O]

The compound is prepared analogous to Example 2. HPLC: $t_R$=4.06 min (Method C); MS-ES: $(M+H)^+$=549

EXAMPLE 506

[7-(3,5-Difluoro-4-morpholin-4-ylmethyl-phenyl)-7H-pyrrolo[2,3-d]pyrimidin-2-yl]-[4-(3-methoxy-pyrrolidin-1-ylmethyl)-phenyl]-amine (racemic)

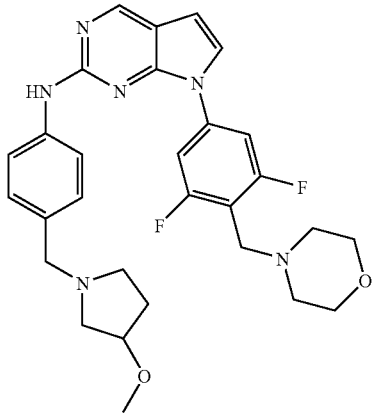 [SMILES: COC1CCN(Cc2ccc(Nc3ncc4ccn(-c5cc(F)c(CN6CCOCC6)c(F)c5)c4n3)cc2)C1]

The compound is prepared analogous to Example 2. HPLC: $t_R$=4.17 min (Method C); MS-ES: $(M+H)^+$=535

EXAMPLE 507

[7-(3,5-Difluoro-4-morpholin-4-ylmethyl-phenyl)-7H-pyrrolo[2,3-d]pyrimidin-2-yl]-((S)-3-morpholin-3-yl-phenyl)-amine

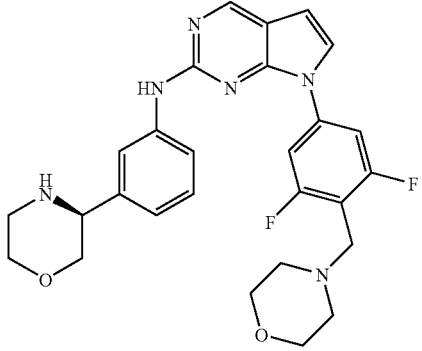 [SMILES: Fc1cc(-n2ccc3cnc(Nc4cccc([C@H]5COCCN5)c4)nc32)cc(F)c1CN1CCOCC1]

The compound is prepared analogous to Example 2, using a Boc-protected morpholine derivative in Step 2.2. Final deprotection is achieved with HCl in EtOH at 60° C. HPLC: $t_R$=0.60 min (Method G); MS-ES: $(M+H)^+$=507

EXAMPLE 508

[7-(3,5-Difluoro-4-morpholin-4-ylmethyl-phenyl)-7H-pyrrolo[2,3-d]pyrimidin-2-yl]-[4-((S)-4-ethyl-morpholin-3-yl)-phenyl]-amine

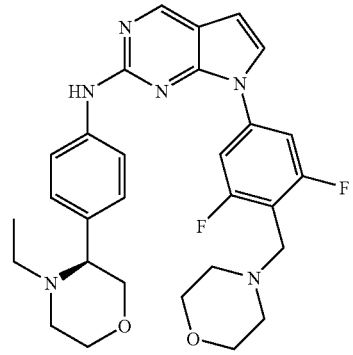 [SMILES: CCN1CCOC[C@@H]1c1ccc(Nc2ncc3ccn(-c4cc(F)c(CN5CCOCC5)c(F)c4)c3n2)cc1]

The compound is obtained by treating [7-(3,5-difluoro-4-morpholin-4-ylmethyl-phenyl)-7H-pyrrolo[2,3-d]pyrimidin-2-yl]-((S)-3-morpholin-3-yl-phenyl)-amine (Example 507) with acetaldehyde in methanol and sodium cyanoborohydride at rt to 60° C. HPLC: $t_R$=0.63 min (Method G); MS-ES: $(M+H)^+$=535

EXAMPLE 509

[7-(3,5-Difluoro-4-morpholin-4-ylmethyl-phenyl)-7H-pyrrolo[2,3-d]pyrimidin-2-yl]-[4-((S)-4-methyl-morpholin-3-yl)-phenyl]-amine

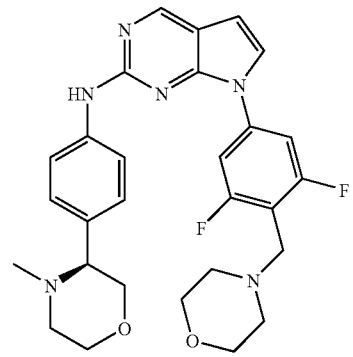 [SMILES: CN1CCOC[C@@H]1c1ccc(Nc2ncc3ccn(-c4cc(F)c(CN5CCOCC5)c(F)c4)c3n2)cc1]

The compound is obtained by treating [7-(3,5-difluoro-4-morpholin-4-ylmethyl-phenyl)-7H-pyrrolo[2,3-d]pyrimidin-2-yl]-((S)-3-morpholin-3-yl-phenyl)-amine (Example 507) with formaldehyde in methanol and sodium cyanoborohydride at rt to 60° C. HPLC: $t_R$=0.61 min (Method G); MS-ES: $(M+H)^+$=521

EXAMPLE 510

[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-5-methyl-pyridin-3-yl]-amine

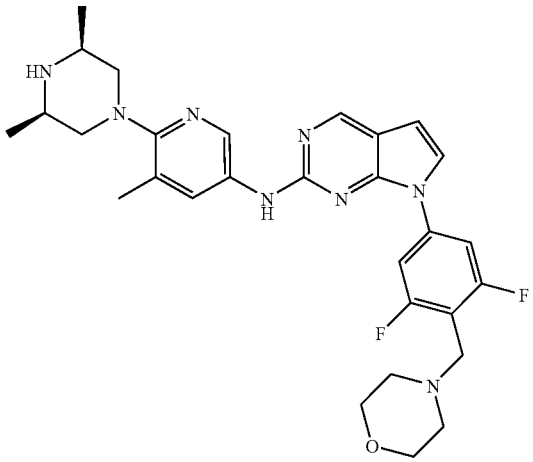 [SMILES: Cc1cc(Nc2ncc3ccn(-c4cc(F)c(CN5CCOCC5)c(F)c4)c3n2)cnc1N1C[C@@H](C)N[C@@H](C)C1]

The compound is prepared analogous to Example 2. HPLC: $t_R$=0.61 min (Method G); MS-ES: (M+H)$^+$=549; TLC (10% methanol/90% methylene chloride/1% ammonia): $R_f$=0.18

EXAMPLE 511

[7-(3,5-Difluoro-4-morpholin-4-ylmethyl-phenyl)-7H-pyrrolo[2,3-d]pyrimidin-2-yl]-((S)-4-morpholin-3-yl-phenyl)-amine

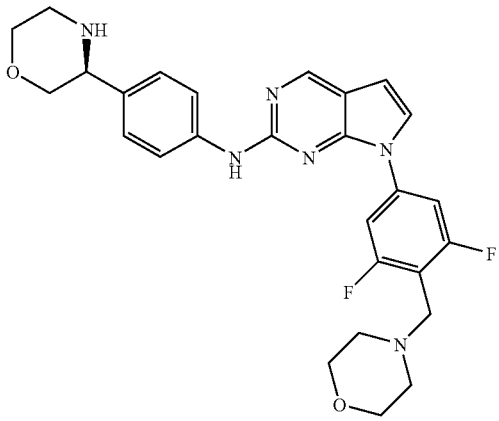 [SMILES: Fc1cc(-n2ccc3cnc(Nc4ccc([C@H]5COCCN5)cc4)nc32)cc(F)c1CN1CCOCC1]

The compound is prepared analogous to Example 2, using a Boc-protected morpholine derivative in Step 2.2. Final deprotection is achieved with 1.25 M HCl in EtOH at 60° C. HPLC: $t_R$=0.61 min (Method G); MS-ES: (M+H)$^+$=507; TLC (10% methanol/90% methylene chloride/1% ammonia): $R_f$=0.50

EXAMPLE 512

[6-(6,6-Difluoro-[1,4]diazepan-1-yl)-5-methyl-pyridin-3-yl]-[7-(3,5-difluoro-4-morpholin-4-ylmethyl-phenyl)-7H-pyrrolo[2,3-d]pyrimidin-2-yl]-amine

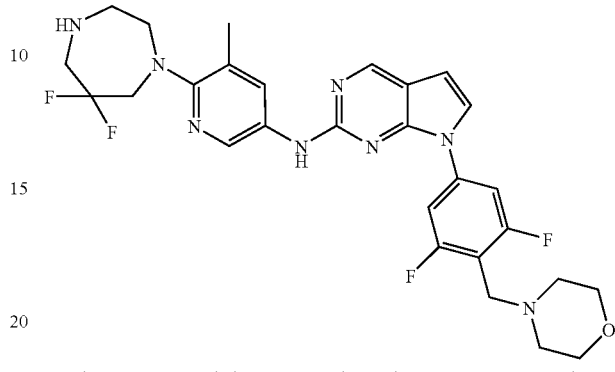

The compound is prepared analogous to Example 2. HPLC: $t_R$=0.65 min (Method G); MS-ES: (M+H)$^+$=571

EXAMPLE 513

[7-(3,5-Difluoro-4-morpholin-4-ylmethyl-phenyl)-7H-pyrrolo[2,3-d]pyrimidin-2-yl]-[6-(2-morpholin-4-yl-ethoxy)-pyridin-3-yl]-amine

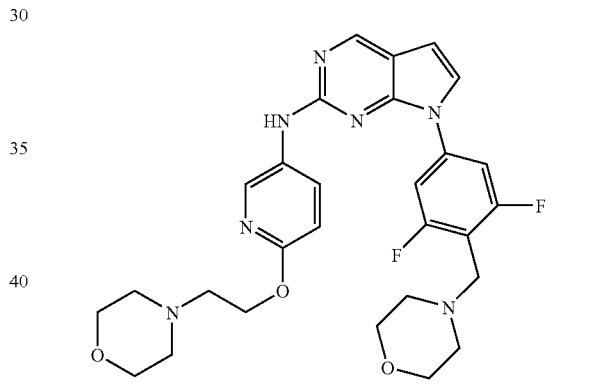

The compound is prepared analogous to Example 2. HPLC: $t_R$=0.59 min (Method G); MS-ES: (M+H)$^+$=552

EXAMPLE 514

[6-Azetidin-3-yloxy)-pyridin-3-yl]-[7-(3,5-difluoro-4-morpholin-4-ylmethyl-phenyl)-7H-pyrrolo[2,3-d]pyrimidin-2-yl]-amine

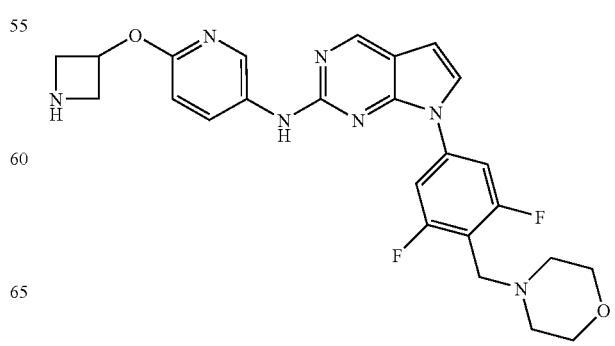

The compound is prepared analogous to Example 2, using a Boc-protected azetidine derivative in Step 2.2. Final deprotection is achieved with 1.25 M HCl in EtOH at 60° C. HPLC: $t_R$=0.55 min (Method G); MS-ES: (M+H)$^+$=538

EXAMPLE 515

[7-(3,5-Difluoro-4-morpholin-4-ylmethyl-phenyl)-7H-pyrrolo[2,3-d]pyrimidin-2-yl]-[6-(tetrahydro-pyran-4-yloxy)-pyridin-3-yl]-amine

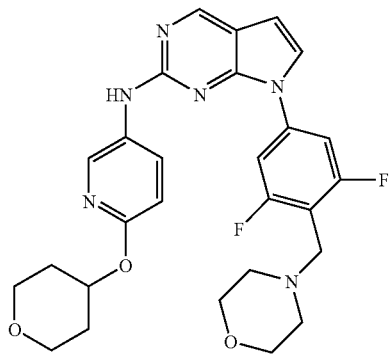 [SMILES: Fc1cc(-n2ccc3cnc(Nc4ccc(OC5CCOCC5)nc4)nc32)cc(F)c1CN1CCOCC1]

The compound is prepared analogous to Example 2. HPLC: $t_R$=0.71 min (Method G); MS-ES: (M+H)$^+$=523

EXAMPLE 516

[7-(3,5-Difluoro-4-morpholin-4-ylmethyl-phenyl)-7H-pyrrolo[2,3-d]pyrimidin-2-yl]-[6-(2-methoxy-ethoxy)-pyridin-3-yl]-amine

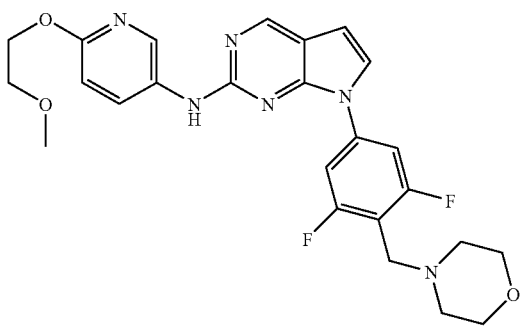 [SMILES: COCCOc1ccc(Nc2ncc3ccn(-c4cc(F)c(CN5CCOCC5)c(F)c4)c3n2)cn1]

The compound is prepared analogous to Example 2. HPLC: $t_R$=0.67 min (Method G); MS-ES: (M+H)$^+$=497

EXAMPLE 517

[7-(3,5-Difluoro-4-morpholin-4-ylmethyl-phenyl)-7H-pyrrolo[2,3-d]pyrimidin-2-yl]-[6-(tetrahydro-pyran-4-ylmethoxy)-pyridin-3-yl]-amine

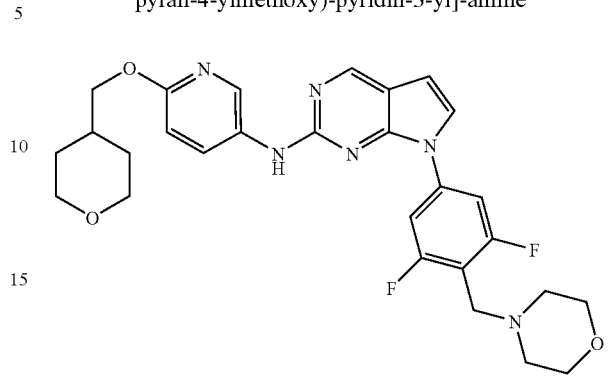

The compound is prepared analogous to Example 2. HPLC: $t_R$=0.74 min (Method G); MS-ES: (M+H)$^+$=537

EXAMPLE 518

2-{5-[7-(3,5-Difluoro-4-morpholin-4-ylmethyl-phenyl)-7H-pyrrolo[2,3-d]pyrimidin-2-ylamino]-pyridin-2-yloxy}-ethanol

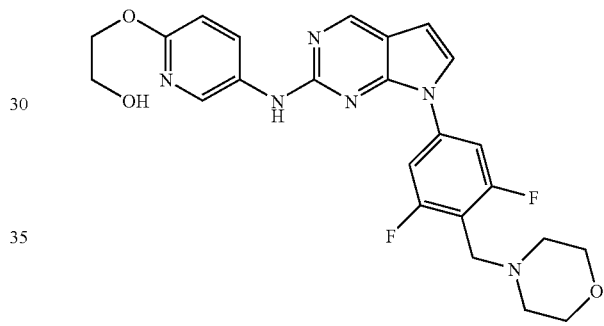

The compound is prepared analogous to Example 2, using a TBDPS-protected alcohol derivative in Step 2.2. Final deprotection is achieved with 1 M TBAF in THF at rt. HPLC: $t_R$=0.60 min (Method G) and MS-ES: (M+H)$^+$=483.

EXAMPLE 519

[7-(3,5-Difluoro-4-morpholin-4-ylmethyl-phenyl)-7H-pyrrolo[2,3-d]pyrimidin-2-yl]-[6-(pyrrolidin-3-yloxy)-pyridin-3-yl]-amine (racemic)

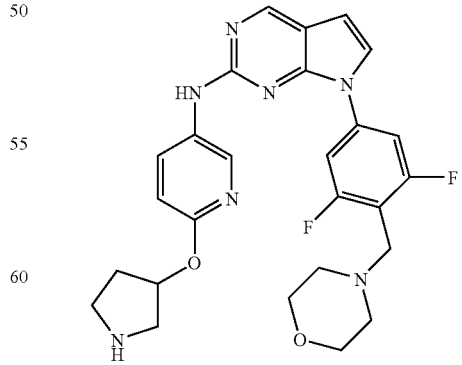

The compound is prepared analogous to Example 2, using a Boc-protected pyrrolidine derivative in Step 2.2. Final deprotection is achieved with 1.25 M HCl in EtOH at 50° C. HPLC: $t_R$=0.58 min (Method G); MS-ES: (M+H)$^+$=508

EXAMPLE 520

{4-[(S)-4-(2-Benzyloxy-ethyl)-morpholin-3-yl]-phenyl}-[7-(3,5-difluoro-4-morpholin-4-ylmethyl-phenyl)-7H-pyrrolo[2,3-d]pyrimidin-2-yl]-amine

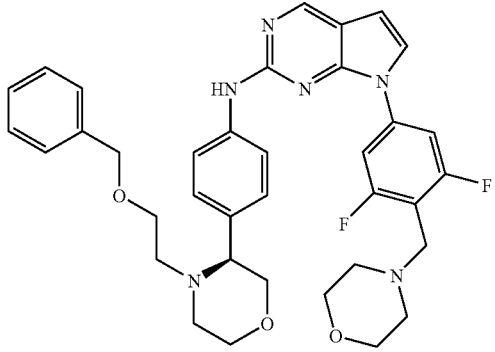 [SMILES: Fc1cc(-n2ccc3cnc(Nc4ccc([C@H]5COCCN5CCOCc5ccccc5)cc4)nc32)cc(F)c1CN1CCOCC1]

The compound is obtained by treating [7-(3,5-difluoro-4-morpholin-4-ylmethyl-phenyl)-7H-pyrrolo[2,3-d]pyrimidin-2-yl]-((S)-4-morpholin-3-yl-phenyl)-amine (Example 511) with benzyloxyacetaldehyde in methanol and sodium cyanoborohydride at 60° C. HPLC: $t_R$=0.78 min (Method G); MS-ES: $(M+H)^+$=641

EXAMPLE 521

2-((S)-3-{4-[7-(3,5-difluoro-4-morpholin-4-ylmethyl-phenyl)-7H-pyrrolo[2,3-d]pyrimidin-2-ylamino]-phenyl}-morpholin-4-yl)-ethanol

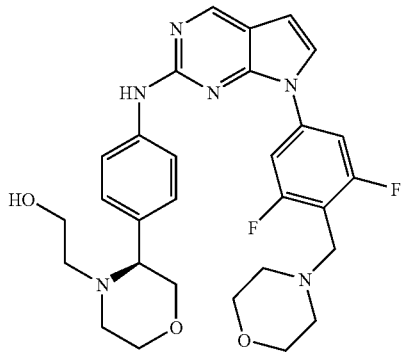 [SMILES: OCCN1CCOC[C@@H]1c1ccc(Nc2ncc3ccn(-c4cc(F)c(CN5CCOCC5)c(F)c4)c3n2)cc1]

The compound is obtained by treating [7-(3,5-Difluoro-4-morpholin-4-ylmethyl-phenyl)-7H-pyrrolo[2,3-d]pyrimidin-2-yl]-((S)-4-morpholin-3-yl-phenyl)-amine (Example 511) with (tert-butyldimethylsilyloxy)-acetaldehyde in methanol and sodium cyanoborohydride at 60° C., followed by a deprotection with TBAF in THF. HPLC: $t_R$=0.60 min (Method G); MS-ES: $(M+H)^+$=551

EXAMPLE 522

{3-Fluoro-4-[2-(4-isopropoxy-phenylamino)-pyrrolo[2,3-d]pyrimidin-7-yl]-phenyl}-morpholin-4-yl-methanone

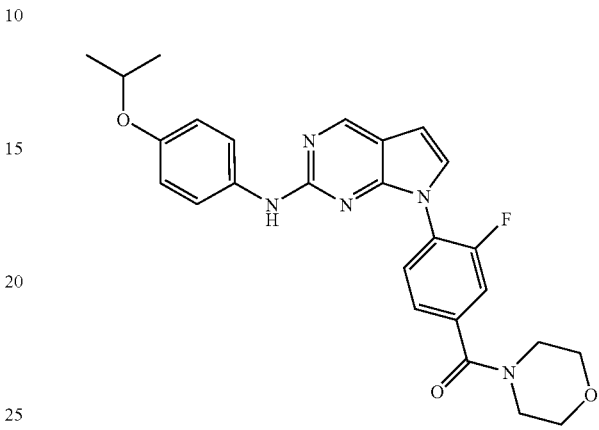

The compound is prepared analogous to Example 3. HPLC: $t_R$=1.60 min (Method A); MS-ES: $(M+H)^+$=476.

EXAMPLE 523

Soft Capsules 5000 soft gelatin capsules, each comprising as active ingredient 0.05 g of one of the compounds of formula I mentioned in the preceding Examples, are prepared as follows: 250 g pulverized active ingredient is suspended in 2 L Lauroglykol® (propylene glycol laurate, Gattefossé S.A., Saint Priest, France) and ground in a wet pulverizer. 0.419 g portions of the mixture are then introduced into soft gelatin capsules using a capsule-filling machine.

Assays

Compounds of the present invention are assayed to measure their capacity to inhibit JAK2 and either STAT1 or STAT5 translocation pathway as described above. Results are provided in the Table 2:

TABLE 2

Inhibition of JAK2 and the STAT1/STAT5 translocation pathway

| ex.# | JAK2/IC50 [µmol l-1] | STAT1/IC50 [µmol l-1] | STAT5/IC50 [µmol l-1] |
|---|---|---|---|
| 1 | <0.003 | 0.0435 | n.d. |
| 2 | 0.0032 | 0.19 | n.d. |
| 3 | 0.0094 | 0.0985 | n.d. |
| 4 | 0.0022 | 0.0367 | n.d. |
| 5 | <0.003 | n.d. | n.d. |
| 6 | <0.003 | n.d. | n.d. |
| 7 | 0.0062 | 0.2545 | n.d. |
| 8 | <0.003 | 0.032 | n.d. |
| 9 | <0.003 | n.d. | n.d. |
| 10 | <0.003 | n.d. | n.d. |
| 11 | 0.19 | n.d. | n.d. |
| 12 | <0.003 | n.d. | n.d. |
| 13 | 0.0038 | 0.032 | n.d. |
| 14 | 2.1 | n.d. | n.d. |
| 15 | 0.0085 | n.d. | n.d. |
| 16 | <0.003 | 0.025 | n.d. |

TABLE 2-continued

Inhibition of JAK2 and the STAT1/STAT5 translocation pathway

| ex.# | JAK2/IC50 [µmol I-1] | STAT1/IC50 [µmol I-1] | STAT5/IC50 [µmol I-1] |
|---|---|---|---|
| 17 | <0.003 | 0.0205 | n.d. |
| 18 | <0.003 | n.d. | n.d. |
| 19 | 0.0069 | n.d. | n.d. |
| 20 | 0.0039 | n.d. | n.d. |
| 21 | 0.023 | n.d. | n.d. |
| 22 | 0.17 | n.d. | n.d. |
| 23 | 0.0036 | n.d. | n.d. |
| 24 | 0.0035 | n.d. | n.d. |
| 25 | <0.003 | n.d. | n.d. |
| 26 | <0.003 | n.d. | n.d. |
| 27 | <0.003 | 0.085 | n.d. |
| 28 | 0.004 | n.d. | n.d. |
| 29 | <0.003 | 0.091 | n.d. |
| 30 | <0.003 | 0.2045 | n.d. |
| 31 | <0.003 | 0.046 | n.d. |
| 32 | 0.0054 | n.d. | n.d. |
| 33 | <0.003 | n.d. | n.d. |
| 34 | <0.003 | 0.0695 | n.d. |
| 35 | 0.0049 | n.d. | n.d. |
| 36 | <0.003 | 0.0109 | n.d. |
| 37 | <0.003 | n.d. | n.d. |
| 38 | 0.0045 | n.d. | n.d. |
| 39 | 0.014 | 1.3695 | n.d. |
| 40 | <0.003 | 0.155 | n.d. |
| 41 | <0.003 | 0.075 | n.d. |
| 42 | 0.0031 | 0.17 | n.d. |
| 43 | <0.003 | 0.35 | n.d. |
| 44 | <0.003 | 0.1425 | n.d. |
| 45 | 0.0061 | n.d. | n.d. |
| 46 | 0.038 | n.d. | n.d. |
| 47 | <0.003 | 0.073 | n.d. |
| 48 | 0.027 | 4.213 | n.d. |
| 49 | 0.014 | 0.878 | n.d. |
| 50 | <0.003 | 0.184 | n.d. |
| 51 | <0.003 | n.d. | n.d. |
| 52 | <0.003 | n.d. | n.d. |
| 53 | <0.003 | 0.0905 | n.d. |
| 54 | 0.0044 | 3.1085 | n.d. |
| 55 | 0.02 | n.d. | n.d. |
| 56 | 0.032 | 4.675 | n.d. |
| 57 | <0.003 | 0.7725 | n.d. |
| 58 | 0.012 | 5.295 | n.d. |
| 59 | 0.0065 | 0.92 | n.d. |
| 60 | 0.0081 | 4.0785 | n.d. |
| 61 | 0.0071 | 0.835 | n.d. |
| 62 | 0.18 | 5.39 | n.d. |
| 63 | 0.073 | n.d. | n.d. |
| 64 | <0.003 | 0.04 | n.d. |
| 65 | 0.0054 | 0.0995 | n.d. |
| 66 | 0.0035 | 0.0755 | n.d. |
| 67 | <0.003 | 0.039 | n.d. |
| 68 | <0.003 | 0.105 | n.d. |
| 69 | 0.0048 | n.d. | n.d. |
| 70 | 0.0056 | 0.275 | n.d. |
| 71 | 0.0068 | 0.362 | n.d. |
| 72 | 0.0037 | 0.75 | n.d. |
| 73 | <0.003 | 0.0805 | n.d. |
| 74 | <0.003 | 0.0755 | n.d. |
| 75 | <0.003 | 0.0825 | n.d. |
| 76 | 0.038 | 0.9345 | n.d. |
| 77 | 0.038 | 2.62 | n.d. |
| 78 | 0.029 | 0.545 | n.d. |
| 79 | 0.0048 | 0.257 | n.d. |
| 80 | 0.43 | 10 | n.d. |
| 81 | 0.018 | 2.7 | n.d. |
| 82 | 0.0041 | 0.86 | n.d. |
| 83 | <0.003 | 0.46 | n.d. |
| 84 | <0.003 | 0.275 | n.d. |
| 85 | 0.0038 | 3.505 | n.d. |
| 86 | 0.008 | 12.975 | n.d. |
| 87 | 0.0038 | 18.3 | n.d. |
| 88 | 0.0089 | 3.27 | n.d. |
| 89 | <0.003 | 0.41 | n.d. |
| 90 | 0.0034 | 0.715 | n.d. |
| 91 | <0.003 | 0.435 | n.d. |
| 92 | 0.0042 | 0.26 | n.d. |
| 93 | <0.003 | 0.191 | n.d. |
| 94 | 0.0038 | 0.259 | n.d. |
| 95 | 0.0165 | 2.365 | n.d. |
| 96 | 0.0485 | 26.2 | n.d. |
| 97 | 0.0094 | 1.455 | n.d. |
| 98 | 0.0056 | 0.575 | n.d. |
| 99 | 0.0039 | 0.555 | n.d. |
| 100 | <0.003 | 0.51 | n.d. |
| 101 | <0.003 | 0.18 | n.d. |
| 102 | <0.003 | 0.275 | n.d. |
| 103 | <0.003 | 0.22 | n.d. |
| 104 | 0.0036 | 0.865 | n.d. |
| 105 | 0.0115 | 5.845 | n.d. |
| 106 | 0.033 | 8.385 | n.d. |
| 107 | 0.0081 | 1.835 | n.d. |
| 108 | 0.0066 | 1.685 | n.d. |
| 109 | 0.0083 | 0.3105 | n.d. |
| 110 | 0.0135 | 1.1125 | n.d. |
| 111 | 0.0145 | 0.8465 | n.d. |
| 112 | <0.003 | 0.073 | n.d. |
| 113 | 0.0042 | 0.108 | n.d. |
| 114 | 0.0059 | 0.2015 | n.d. |
| 115 | 0.016 | 0.7145 | n.d. |
| 116 | 0.0125 | 0.563 | n.d. |
| 117 | 0.0094 | 0.384 | n.d. |
| 118 | 0.075 | 1.515 | n.d. |
| 119 | 0.088 | 1.757 | n.d. |
| 120 | 0.155 | 7.851 | n.d. |
| 121 | 0.0155 | 0.152 | n.d. |
| 122 | 0.0033 | 0.1645 | n.d. |
| 123 | 0.028 | 0.8025 | n.d. |
| 124 | 0.085 | 2.155 | n.d. |
| 125 | <0.003 | 0.12 | n.d. |
| 126 | 0.011 | 1.6225 | n.d. |
| 127 | 0.0105 | 0.7205 | n.d. |
| 128 | 0.12 | 3.6775 | n.d. |
| 129 | 0.009 | 0.471 | n.d. |
| 130 | 0.115 | 8.412 | n.d. |
| 131 | 0.016 | 1.502 | n.d. |
| 132 | 0.0405 | 6.2805 | n.d. |
| 133 | 0.0071 | 0.573 | n.d. |
| 134 | 0.0205 | 1.875 | n.d. |
| 135 | 0.0049 | 0.42 | n.d. |
| 136 | 0.011 | 0.775 | n.d. |
| 137 | 0.0033 | 0.15 | n.d. |
| 138 | <0.003 | 0.165 | n.d. |
| 139 | 0.011 | 0.63 | n.d. |
| 140 | 0.0045 | 0.31 | n.d. |
| 141 | <0.003 | 0.13 | n.d. |
| 142 | <0.003 | 0.101 | n.d. |
| 143 | <0.003 | 0.195 | n.d. |
| 144 | 0.0047 | 0.475 | n.d. |
| 145 | 0.007 | 0.365 | n.d. |
| 146 | 0.03 | 2.51 | n.d. |
| 147 | <0.003 | 0.033 | n.d. |
| 148 | 0.0079 | 0.047 | n.d. |
| 149 | 0.13 | 1.509 | n.d. |
| 150 | 0.0045 | 0.0645 | n.d. |
| 151 | 0.0057 | 0.2285 | n.d. |
| 152 | 0.0035 | 0.168 | n.d. |
| 153 | <0.003 | 0.0175 | n.d. |
| 154 | 0.25 | 6.435 | n.d. |
| 155 | 0.2 | 3.275 | n.d. |
| 156 | 0.013 | 0.06 | n.d. |
| 157 | 0.0061 | 0.13 | n.d. |
| 158 | 0.0094 | 0.265 | n.d. |
| 159 | 0.0465 | 1.123 | n.d. |
| 160 | 0.0418 | 0.973 | n.d. |
| 161 | 0.87 | 9.348 | n.d. |
| 162 | 0.305 | 9.695 | n.d. |
| 163 | 0.295 | 23.495 | n.d. |
| 164 | 0.23 | 10.725 | n.d. |
| 165 | <0.003 | 0.125 | n.d. |
| 166 | 0.0034 | 0.145 | n.d. |

TABLE 2-continued

Inhibition of JAK2 and the STAT1/STAT5 translocation pathway

| ex.# | JAK2/IC50 [μmol l-1] | STAT1/IC50 [μmol l-1] | STAT5/IC50 [μmol l-1] |
|---|---|---|---|
| 167 | 0.039 | 2.07 | n.d. |
| 168 | 0.0305 | 3.905 | n.d. |
| 169 | 0.0043 | 0.093 | n.d. |
| 170 | 0.017 | 0.3745 | n.d. |
| 171 | <0.003 | 0.26 | n.d. |
| 172 | <0.003 | 0.22 | n.d. |
| 173 | 0.0055 | 0.235 | n.d. |
| 174 | <0.003 | 0.15 | n.d. |
| 175 | <0.003 | 0.275 | n.d. |
| 176 | 0.0073 | 1.55 | n.d. |
| 177 | 0.0053 | 1.035 | n.d. |
| 178 | 0.0091 | 0.79 | n.d. |
| 179 | 0.0104 | 1.515 | n.d. |
| 180 | <0.003 | 0.12 | n.d. |
| 181 | 0.0155 | 16.6 | n.d. |
| 182 | <0.003 | 0.125 | n.d. |
| 183 | 0.0033 | 0.095 | n.d. |
| 184 | <0.003 | 0.035 | n.d. |
| 185 | <0.003 | 0.29 | n.d. |
| 186 | <0.003 | 0.095 | n.d. |
| 187 | <0.003 | 0.055 | n.d. |
| 188 | <0.003 | 0.06 | n.d. |
| 189 | 0.0095 | 0.846 | n.d. |
| 190 | 0.0052 | 0.439 | n.d. |
| 191 | 0.0285 | 3.9175 | n.d. |
| 192 | 0.0115 | 1.488 | n.d. |
| 193 | 0.0084 | 0.351 | n.d. |
| 194 | <0.003 | 0.2015 | n.d. |
| 195 | 0.0053 | 0.3525 | n.d. |
| 196 | <0.003 | 0.176 | n.d. |
| 197 | <0.003 | 0.09 | n.d. |
| 198 | <0.003 | n.d. | n.d. |
| 199 | <0.003 | 0.222 | n.d. |
| 200 | 0.0037 | n.d. | n.d. |
| 201 | <0.003 | 0.199 | n.d. |
| 202 | 0.0045 | 0.198 | n.d. |
| 203 | 0.0074 | 0.4125 | n.d. |
| 204 | <0.003 | n.d. | n.d. |
| 205 | 0.005 | n.d. | n.d. |
| 206 | <0.003 | n.d. | n.d. |
| 207 | <0.003 | n.d. | n.d. |
| 208 | 0.0048 | 0.442 | n.d. |
| 209 | 0.125 | n.d. | n.d. |
| 210 | 0.0058 | 0.634 | n.d. |
| 211 | 0.0059 | n.d. | n.d. |
| 212 | <0.003 | 0.1055 | n.d. |
| 213 | 0.0059 | 0.7275 | n.d. |
| 214 | 0.0051 | 0.643 | n.d. |
| 215 | 0.42 | 10 | n.d. |
| 216 | 0.0033 | 0.579 | n.d. |
| 217 | 0.0073 | 0.993 | n.d. |
| 218 | 1.05 | 10 | n.d. |
| 219 | 0.0077 | 0.518 | n.d. |
| 220 | 0.011 | 0.88 | n.d. |
| 221 | 0.0047 | 0.36 | n.d. |
| 222 | 0.29 | n.d. | n.d. |
| 223 | 0.0092 | 0.455 | n.d. |
| 224 | 0.0085 | 1.075 | n.d. |
| 225 | 0.0074 | 0.4335 | n.d. |
| 226 | 0.0105 | 0.666 | n.d. |
| 227 | 0.0415 | n.d. | n.d. |
| 228 | 0.0565 | n.d. | n.d. |
| 229 | 0.021 | 1.5765 | n.d. |
| 230 | 0.0205 | 2.475 | n.d. |
| 231 | 0.0032 | 0.2575 | n.d. |
| 232 | 0.019 | 1.16 | n.d. |
| 233 | 0.0064 | 1.182 | n.d. |
| 234 | 0.0081 | 0.91 | n.d. |
| 235 | 0.056 | n.d. | n.d. |
| 236 | 0.046 | n.d. | n.d. |
| 237 | 0.007 | 2.555 | n.d. |
| 238 | 0.0111 | 0.785 | n.d. |
| 239 | 0.0039 | 0.66 | n.d. |
| 240 | 0.0052 | 0.73 | n.d. |
| 241 | 0.0054 | 0.37 | n.d. |
| 242 | 0.0043 | 0.355 | n.d. |
| 243 | <0.003 | 0.225 | n.d. |
| 244 | <0.003 | 0.43 | n.d. |
| 245 | <0.003 | 0.43 | n.d. |
| 246 | 0.028 | 3.995 | n.d. |
| 247 | 0.0037 | 0.255 | n.d. |
| 248 | 0.024 | 4.27 | n.d. |
| 249 | 0.0043 | 0.815 | n.d. |
| 250 | 0.0091 | 0.94 | n.d. |
| 251 | 0.0061 | 0.45 | n.d. |
| 252 | 0.0033 | 0.34 | n.d. |
| 253 | 0.0071 | 0.13 | n.d. |
| 254 | <0.003 | n.d. | n.d. |
| 255 | 0.0069 | 0.115 | n.d. |
| 256 | <0.003 | 0.115 | n.d. |
| 257 | 0.01 | 0.15 | n.d. |
| 258 | <0.003 | 0.08 | n.d. |
| 259 | <0.003 | 0.08 | n.d. |
| 260 | 0.005 | 0.28 | n.d. |
| 261 | 0.012 | 0.18 | n.d. |
| 262 | 0.0042 | 0.285 | n.d. |
| 263 | <0.003 | 0.055 | n.d. |
| 264 | <0.003 | 0.165 | n.d. |
| 265 | <0.003 | 0.04 | n.d. |
| 266 | 0.0084 | 0.15 | n.d. |
| 267 | <0.003 | 0.05 | n.d. |
| 268 | 0.0078 | 0.21 | n.d. |
| 269 | 0.01 | 0.465 | n.d. |
| 270 | 0.0043 | 0.035 | n.d. |
| 271 | 0.0031 | 0.065 | n.d. |
| 272 | 0.011 | 0.175 | n.d. |
| 273 | 0.006 | 0.19 | n.d. |
| 274 | 0.0072 | 0.52 | n.d. |
| 275 | 0.007 | n.d. | n.d. |
| 276 | 0.12 | n.d. | n.d. |
| 277 | 0.0083 | n.d. | n.d. |
| 278 | 0.011 | n.d. | n.d. |
| 279 | 0.004 | n.d. | n.d. |
| 280 | 0.0035 | n.d. | n.d. |
| 281 | 0.024 | n.d. | n.d. |
| 282 | 0.082 | n.d. | n.d. |
| 283 | 0.023 | n.d. | n.d. |
| 284 | 0.0037 | n.d. | n.d. |
| 285 | <0.003 | n.d. | n.d. |
| 286 | 0.0106 | 0.285 | n.d. |
| 287 | 0.0465 | 0.441 | n.d. |
| 288 | <0.003 | 0.0675 | n.d. |
| 289 | <0.017 | 0.2315 | n.d. |
| 290 | <0.003 | 0.037 | n.d. |
| 291 | <0.003 | 0.054 | n.d. |
| 292 | <0.003 | 0.0125 | n.d. |
| 293 | <0.003 | 0.008 | n.d. |
| 294 | <0.003 | 0.415 | n.d. |
| 295 | 0.0145 | 0.795 | n.d. |
| 296 | <0.003 | 1.105 | n.d. |
| 297 | 0.03 | 2.145 | n.d. |
| 298 | 0.023 | 2.21 | n.d. |
| 299 | 0.0185 | 0.145 | n.d. |
| 300 | 0.0175 | 2.03 | n.d. |
| 301 | <0.003 | 0.05 | n.d. |
| 302 | 0.0061 | 0.085 | n.d. |
| 303 | 0.0049 | 0.295 | n.d. |
| 304 | 0.0135 | 1.485 | n.d. |
| 305 | 0.026 | 2.675 | n.d. |
| 306 | 0.0395 | 0.55 | n.d. |
| 307 | 0.014 | 0.12 | n.d. |
| 308 | <0.003 | 0.015 | n.d. |
| 309 | 0.78 | 4.155 | n.d. |
| 310 | 0.0064 | 0.57 | n.d. |
| 311 | 0.031 | 1.4 | n.d. |
| 312 | 0.013 | 0.565 | n.d. |
| 313 | 0.0037 | n.d. | n.d. |
| 314 | <0.003 | n.d. | n.d. |
| 315 | <0.003 | n.d. | n.d. |
| 316 | 0.073 | n.d. | n.d. |

TABLE 2-continued

Inhibition of JAK2 and the STAT1/STAT5 translocation pathway

| ex.# | JAK2/IC50 [μmol I-1] | STAT1/IC50 [μmol I-1] | STAT5/IC50 [μmol I-1] |
|---|---|---|---|
| 317 | 0.94 | n.d. | n.d. |
| 318 | <0.003 | n.d. | n.d. |
| 319 | <0.003 | n.d. | n.d. |
| 320 | 0.0095 | n.d. | n.d. |
| 321 | <0.003 | n.d. | n.d. |
| 322 | <0.003 | n.d. | n.d. |
| 323 | 0.0032 | n.d. | n.d. |
| 324 | 0.026 | n.d. | n.d. |
| 325 | 0.025 | n.d. | n.d. |
| 326 | <0.003 | n.d. | n.d. |
| 327 | <0.003 | n.d. | n.d. |
| 328 | 0.016 | n.d. | n.d. |
| 329 | 0.004 | n.d. | n.d. |
| 330 | 0.014 | n.d. | n.d. |
| 331 | 0.003 | n.d. | 0.0028 |
| 332 | 0.003 | 0.375 | 0.073 |
| 333 | 0.0039 | 0.53 | n.d. |
| 334 | 0.003 | 0.26 | n.d. |
| 335 | 0.0093 | 0.36 | n.d. |
| 336 | 0.0036 | 0.205 | n.d. |
| 337 | 0.0061 | 0.185 | n.d. |
| 338 | 0.0039 | 0.135 | n.d. |
| 339 | 0.0037 | 0.285 | n.d. |
| 340 | 0.0072 | 0.27 | n.d. |
| 341 | 0.003 | n.d. | n.d. |
| 342 | 0.003 | 0.4788 | n.d. |
| 343 | 0.003 | 0.1512 | n.d. |
| 344 | 0.003 | n.d. | n.d. |
| 345 | 0.0033 | n.d. | n.d. |
| 346 | 0.003 | n.d. | 0.0028 |
| 347 | 0.003 | n.d. | 0.0133 |
| 348 | 0.0062 | n.d. | n.d. |
| 349 | 0.016 | n.d. | n.d. |
| 350 | 0.003 | n.d. | 0.0218 |
| 351 | 0.0043 | n.d. | 0.0013 |
| 352 | 0.003 | n.d. | 0.0221 |
| 353 | 0.0049 | n.d. | 0.017 |
| 354 | 0.003 | n.d. | 0.0013 |
| 355 | 0.0037 | n.d. | 0.0053 |
| 356 | 0.0032 | n.d. | 0.0059 |
| 357 | 0.0069 | n.d. | n.d. |
| 358 | 0.0072 | n.d. | 0.059 |
| 359 | 0.0074 | n.d. | 0.135 |
| 360 | 0.0033 | n.d. | 0.0072 |
| 361 | 0.023 | n.d. | 0.2595 |
| 362 | 0.024 | n.d. | 0.152 |
| 363 | 0.0032 | n.d. | 0.011 |
| 364 | 0.003 | n.d. | 0.0028 |
| 365 | 0.0046 | n.d. | 0.043 |
| 366 | 0.0086 | n.d. | 0.065 |
| 367 | 0.0084 | n.d. | 0.144 |
| 368 | 0.0032 | n.d. | n.d. |
| 369 | 0.003 | n.d. | 0.057 |
| 370 | 0.003 | n.d. | 0.0313 |
| 371 | 0.013 | n.d. | 0.135 |
| 372 | 0.0047 | n.d. | 0.057 |
| 373 | 0.0043 | n.d. | n.d. |
| 374 | 0.0099 | n.d. | n.d. |
| 375 | 0.0065 | n.d. | 0.0077 |
| 376 | 0.003 | n.d. | 0.067 |
| 377 | 0.049 | n.d. | >2.6 |
| 378 | 0.013 | n.d. | 0.045 |
| 379 | 0.011 | n.d. | n.d. |
| 380 | 0.0032 | n.d. | 0.046 |
| 381 | 0.003 | n.d. | 0.043 |
| 382 | 0.0035 | n.d. | 0.121 |
| 383 | 0.0051 | n.d. | 0.0061 |
| 384 | 0.003 | n.d. | 0.012 |
| 385 | 0.003 | n.d. | 0.0655 |
| 386 | 0.11 | n.d. | 0.101 |
| 387 | 0.0096 | n.d. | 0.0455 |
| 388 | 0.003 | n.d. | n.d. |
| 389 | 0.003 | n.d. | n.d. |
| 390 | 0.015 | n.d. | 0.104 |
| 391 | 0.0049 | n.d. | 0.15 |
| 392 | 0.003 | n.d. | 0.068 |
| 393 | 0.013 | n.d. | 0.052 |
| 394 | 0.003 | n.d. | 0.0016 |
| 395 | 0.003 | n.d. | 0.017 |
| 396 | 0.003 | n.d. | 0.147 |
| 397 | 0.003 | n.d. | 0.013 |
| 398 | 0.003 | n.d. | 0.245 |
| 399 | 0.003 | n.d. | 0.0066 |
| 400 | 0.007 | n.d. | 0.0017 |
| 401 | 0.007 | n.d. | 0.1385 |
| 402 | 0.003 | n.d. | 1.372 |
| 403 | 0.003 | n.d. | 0.0225 |
| 404 | 0.0056 | n.d. | 0.141 |
| 405 | 0.003 | n.d. | 0.0032 |
| 406 | 0.004 | n.d. | >4 |
| 407 | 0.003 | n.d. | 0.305 |
| 408 | 0.003 | n.d. | 0.0092 |
| 409 | 0.003 | n.d. | 0.0816 |
| 410 | 0.003 | n.d. | 0.0083 |
| 411 | 0.003 | n.d. | 0.0026 |
| 412 | 0.003 | n.d. | 0.0265 |
| 413 | 0.003 | n.d. | 0.0285 |
| 414 | 0.003 | n.d. | 0.0042 |
| 415 | 0.003 | n.d. | 0.0069 |
| 416 | 0.003 | n.d. | n.d. |
| 417 | 0.003 | n.d. | 0.005 |
| 418 | 0.0046 | n.d. | 0.016 |
| 419 | 0.0043 | n.d. | 0.0385 |
| 420 | 0.003 | n.d. | n.d. |
| 421 | 0.003 | n.d. | 0.0027 |
| 422 | 0.003 | n.d. | 0.0057 |
| 423 | 0.003 | n.d. | 0.0059 |
| 424 | 0.003 | n.d. | 0.009 |
| 425 | 0.003 | n.d. | 0.0036 |
| 426 | 0.003 | n.d. | 0.0183 |
| 427 | 0.003 | n.d. | 0.0332 |
| 428 | 0.003 | n.d. | 0.0107 |
| 429 | 0.003 | n.d. | 0.041 |
| 430 | 0.003 | n.d. | 0.0036 |
| 431 | 0.0032 | n.d. | 0.0235 |
| 432 | 0.003 | n.d. | 0.0004 |
| 433 | 0.003 | n.d. | 0.0063 |
| 434 | 0.003 | n.d. | 0.0315 |
| 435 | 0.003 | n.d. | 0.0034 |
| 436 | 0.003 | n.d. | 0.0061 |
| 437 | 0.0033 | n.d. | n.d. |
| 438 | 0.003 | n.d. | n.d. |
| 439 | 0.019 | n.d. | n.d. |
| 440 | 0.0032 | n.d. | 0.061 |
| 441 | 0.003 | 0.045 | n.d. |
| 442 | 0.003 | n.d. | n.d. |
| 443 | 0.003 | 0.0095 | n.d. |
| 444 | 0.003 | 0.09 | n.d. |
| 445 | 0.043 | n.d. | n.d. |
| 446 | 0.0043 | 0.05 | 0.0013 |
| 447 | 0.0096 | 0.105 | 0.0118 |
| 448 | 0.005 | n.d. | 0.0074 |
| 449 | 0.003 | n.d. | n.d. |
| 450 | 0.003 | n.d. | n.d. |
| 451 | 0.0038 | n.d. | 0.024 |
| 452 | 0.0062 | n.d. | 0.0795 |
| 453 | 0.0041 | n.d. | 0.036 |
| 454 | 0.0045 | n.d. | 0.0535 |
| 455 | 0.0043 | n.d. | 0.038 |
| 456 | 0.003 | n.d. | 0.0019 |

TABLE 2-continued

Inhibition of JAK2 and the STAT1/STAT5 translocation pathway

| ex.# | JAK2/IC50 [μmol l-1] | STAT1/IC50 [μmol l-1] | STAT5/IC50 [μmol l-1] |
|---|---|---|---|
| 457 | 0.003 | n.d. | 0.021 |
| 458 | 0.003 | n.d. | 0.0014 |
| 459 | 0.0051 | n.d. | 0.1045 |
| 460 | 0.003 | n.d. | n.d. |
| 461 | 0.003 | n.d. | n.d. |
| 462 | 0.003 | n.d. | 0.051 |
| 463 | 0.003 | n.d. | 0.048 |
| 464 | 0.003 | n.d. | 0.059 |
| 465 | 0.003 | n.d. | 0.0032 |
| 466 | 0.0079 | n.d. | 0.056 |
| 467 | 0.0046 | n.d. | n.d. |
| 468 | 0.003 | n.d. | 0.014 |
| 469 | 0.003 | n.d. | 0.025 |
| 470 | 0.061 | n.d. | 0.017 |
| 471 | 0.0035 | n.d. | 0.0315 |
| 472 | 0.0036 | n.d. | 0.092 |
| 473 | 0.003 | n.d. | 0.0123 |
| 474 | 0.003 | n.d. | 0.0086 |
| 475 | 0.003 | n.d. | 0.0053 |
| 476 | 0.003 | n.d. | 0.0345 |
| 477 | 0.017 | n.d. | 0.718 |
| 478 | 0.0055 | n.d. | 0.051 |
| 479 | 0.0035 | n.d. | 0.015 |
| 480 | 0.003 | n.d. | 0.071 |
| 481 | 0.0051 | n.d. | n.d. |
| 482 | 0.003 | n.d. | 0.15 |
| 483 | 0.003 | n.d. | 0.0123 |
| 484 | 0.003 | n.d. | 0.067 |
| 485 | 0.003 | n.d. | 0.11 |
| 486 | 0.003 | n.d. | 0.487 |
| 487 | 0.003 | n.d. | 0.0058 |
| 488 | 0.003 | n.d. | 0.0405 |
| 489 | 0.0007 | n.d. | 0.012 |
| 490 | 0.0034 | n.d. | 0.014 |
| 491 | 0.003 | n.d. | 0.015 |
| 492 | 0.0022 | n.d. | 0.0555 |
| 493 | 0.003 | n.d. | 0.1045 |
| 494 | 0.003 | n.d. | 0.394 |
| 495 | 0.003 | n.d. | 0.051 |
| 496 | 0.003 | n.d. | 0.0972 |
| 497 | 0.003 | n.d. | 0.0077 |
| 498 | 0.003 | n.d. | 0.083 |
| 499 | 0.0048 | n.d. | 0.22 |
| 500 | 0.003 | n.d. | 0.016 |
| 501 | 0.003 | n.d. | 0.038 |
| 502 | 0.003 | n.d. | 0.017 |
| 503 | 0.003 | n.d. | 0.0275 |
| 504 | 0.003 | n.d. | 0.0815 |
| 505 | 0.0041 | n.d. | 0.06 |
| 506 | 0.003 | n.d. | 0.038 |
| 507 | <0.003 | n.d. | 0.0002 |
| 508 | 0.0041 | n.d. | 0.0148 |
| 509 | <0.003 | n.d. | 0.0431 |
| 510 | 0.003 | n.d. | 0.001 |
| 511 | 0.003 | n.d. | 0.0039 |
| 512 | 0.003 | n.d. | 0.014 |
| 513 | 0.0046 | n.d. | 0.116 |
| 514 | 0.025 | n.d. | 1.323 |
| 515 | 0.003 | n.d. | 0.054 |
| 516 | 0.0064 | n.d. | 0.119 |
| 517 | 0.003 | n.d. | 0.0695 |
| 518 | 0.003 | n.d. | 0.0395 |
| 519 | 0.0036 | n.d. | 0.0605 |
| 520 | 0.057 | n.d. | 0.543 |
| 521 | 0.003 | n.d. | n.d. |
| 522 | 0.008 | 2.89 | n.d. | n.d. = not determined

As shown in Table 2, the compounds of ex. 1-522 show JAK2 inhibition IC50-values in the range <0.003-2.1 μmol l-1, in particular in the range <0.003-0.05 μmol l-1.

Compounds of the invention selectively inhibit JAK2 when compared to other kinases, for example cMet, cKit, ALK and PDGFRa as shown by the results of Table 3.

The compounds are assayed in an antibody based kinase phosphorylation assay using the recombinant domains of cMet, cKit, ALK and PDGFRalpha kinases and a generic phospho-tyrosine peptide substrate. LanthaScreen™ is the detection of Time-Resolved Fluorescence Resonance Energy Transfer (TR-FRET) using lanthanide chelates to measure interactions between various binding partners. In a TR-FRET kinase assay, a long-lifetime lanthanide donor species is conjugated to an antibody that specifically binds to a phosphorylated product of a kinase reaction that is labeled with a suitable acceptor fluorophore. This antibody-mediated interaction brings the lanthanide donor and the acceptor into proximity such that resonance energy transfer can take place, resulting in a detectible increase in FRET. The LanthaScreen is run at ambient temperature and terminated by the addition of stop solution, followed by Tb-labeled P-20 antibody. After incubating in the dark, the plates are transferred to a fluorescence reader for counting. The effect of compound on the enzymatic activity is in all assays obtained from the linear progress curves and determined from one reading (end point measurement).

TABLE 3

| ex.# | JAK2/IC50 [μmol l-1] | cMet/IC50 [μmol l-1] | cKit/IC50 [μmol l-1] | ALK/IC50 [μmol l-1] | PDGFRa/IC50 [μmol l-1] |
|---|---|---|---|---|---|
| 96 | 0.0485 | >10 | >10 | >10 | >10 |
| 151 | 0.0057 | >10 | >10 | >10 | >10 |
| 184 | <0.003 | >10 | >10 | >10 | >10 |
| 203 | 0.0064 | 6.9 | 4.7 | >10 | >10 |
| 235 | 0.056 | >10 | >10 | >10 | >10 |
| 238 | 0.0111 | 8.2 | >10 | >10 | 6.6 |
| 278 | 0.011 | 1.4 | 1.35 | >10 | 2.65 |
| 300 | 0.0175 | >10 | 3.4 | >10 | 7.7 |
| 301 | <0.003 | 3.6 | 4.75 | >10 | 5.6 |
| 311 | 0.031 | >10 | >10 | >10 | >10 |
| 332 | 0.001 | 7.567 | 1.552 | 9.05 | 6.7 |
| 372 | 0.0047 | >10 | 5.7 | >10 | >10 |
| 380 | 0.0032 | 5.4 | 1.7 | >10 | 5.3 |
| 382 | 0.0035 | 2.4 | 1.1 | >10 | 7.7 |
| 440 | 0.0032 | >10 | >10 | >10 | >10 |
| 446 | 0.0043 | 6 | 2.65 | >10 | 7.45 |
| 503 | <0.003 | 6.1 | 9.5 | >10 | >10 |
| 521 | <0.003 | 3.5 | 2.9 | >10 | 2.8 |

Compounds of the present invention are further assayed to measure their capacity to inhibit JAK1, as described above. Compounds of ex. 1-522 show in this assay IC50-values in the range of <0.003->10 μmol l-1.

Compounds of the present invention are further assayed to measure their capacity to inhibit JAK3 as described above. Compounds of ex. 1-522 show in this assay IC50-values in the range of <0.003->10 μmol l-1.

Compounds of the present invention are further assayed to measure their capacity to inhibit TYK2 as described above. Compounds of ex. 1-522 show in this assay IC50-values in the range of <0.003->10 μmol l-1.

The invention claimed is:
1. A compound selected from the group consisting of:
{4-[7-(3,5-Difluoro-4-morpholin-4-ylmethyl-phenyl)-7H-pyrrolo[2,3-d]pyrimidin-2-ylamino]-phenyl}-(4-methyl-piperazin-1-yl)-methanone;
{2-Fluoro-4-[2-(4-fluoro-phenylamino)-pyrrolo[2,3-d]pyrimidin-7-yl]-phenyl}-morpholin-4-yl-methanone;
{4-[2-(4-Fluoro-phenylamino)-pyrrolo[2,3-d]pyrimidin-7-yl]-phenyl}-morpholin-4-yl-methanone
4-[2-(4-Fluoro-phenylamino)-pyrrolo[2,3-d]pyrimidin-7-yl]-N-(2-morpholin-4-yl-ethyl)-benzamide;
{2,6-Difluoro-4-[2-(4-isopropoxy-phenylamino)-pyrrolo[2,3-d]pyrimidin-7-yl]-phenyl}-morpholin-4-yl-methanone;
2-{4-[2-(4-Isopropoxy-phenylamino)-pyrrolo[2,3-d]pyrimidin-7-yl]-phenyl}-2-methyl-1-morpholin-4-yl-propan-1-one;
(1-{4-[2-(4-Isopropoxy-phenylamino)-pyrrolo[2,3-d]pyrimidin-7-yl]-phenyl}-cyclopropyl)-morpholin-4-yl-methanone;
{2,6-Difluoro-4-[2-(4-fluoro-3-methyl-phenylamino)-pyrrolo[2,3-d]pyrimidin-7-yl]-phenyl}-morpholin-4-yl-methanone;
{2-Chloro-4-[2-(4-fluoro-3-methyl-phenylamino)-pyrrolo[2,3-d]pyrimidin-7-yl]-phenyl}-morpholin-4-yl-methanone;
{4-[2-(4-Fluoro-3-methyl-phenylamino)-pyrrolo[2,3-d]pyrimidin-7-yl]-2-methyl-phenyl}-morpholin-4-yl-methanone;
{2-Fluoro-4-[2-(4-fluoro-3-methyl-phenylamino)-pyrrolo[2,3-c]pyrimidin-7-yl]-phenyl}-morpholin-4-yl-methanone;
[7-(3-Fluoro-4-morpholin-4-ylmethyl-phenyl)-7H-pyrrolo[2,3-d]pyrimidin-2-yl]-(4-isopropoxy-phenyl)-amine;
{2-Fluoro-4-[2-(4-isopropoxy-phenylamino)-pyrrolo[2,3-d]pyrimidin-7-yl]-phenyl}-morpholin-4-yl-methanone;
{2-Chloro-4-[2-(4-isopropoxy-phenylamino)-pyrrolo[2,3-d]pyrimidin-7-yl]-phenyl}-morpholin-4-yl-methanone;
{4-[2-(4-Isopropoxy-phenylamino)-pyrrolo[2,3-d]pyrimidin-7-yl]-2-methyl-phenyl}-morpholin-4-yl-methanone;
2-{4-[2-(4-Isopropoxy-phenylamino)-pyrrolo[2,3-d]pyrimidin-7-yl]-phenyl}-1-morpholin-4-yl-ethanone;

(4-Isopropoxy-phenyl)-[7-(4-morpholin-4-ylmethyl-phenyl)-7H-pyrrolo[2,3-d]pyrimidin-2-yl]-amine;
[7-(3-Chloro-4-morpholin-4-ylmethyl-phenyl)-7H-pyrrolo[2,3-d]pyrimidin-2-yl]-(4-isopropoxy-phenyl)-amine;
(4-Isopropoxy-phenyl)-[7-(3-methyl-4-morpholin-4-ylmethyl-phenyl)-7H-pyrrolo[2,3-d]pyrimidin-2-yl]-amine;
(4-Isopropoxy-phenyl)-{7-[4-(2-morpholin-4-yl-ethyl)-phenyl]-7H-pyrrolo[2,3-d]pyrimidin-2-yl}-amine;
{4-[2-(3-Chloro-4-methyl-phenylamino)-pyrrolo[2,3-d]pyrimidin-7-yl]-2,6-difluoro-phenyl}-morpholin-4-yl-methanone;
(3-Chloro-4-methyl-phenyl)-[7-(3-fluoro-4-morpholin-4-ylmethyl-phenyl)-7H-pyrrolo[2,3-d]pyrimidin-2-yl]-amine;
(3-Chloro-4-methyl-phenyl)-[7-(4-morpholin-4-ylmethyl-phenyl)-7H-pyrrolo[2,3-d]pyrimidin-2-yl]-amine;
(4-Fluoro-3-methyl-phenyl)-[7-(4-morpholin-4-ylmethyl-phenyl)-7H-pyrrolo[2,3-d]pyrimidin-2-yl]-amine;
[7-(3,5-Difluoro-4-morpholin-4-ylmethyl-phenyl)-7H-pyrrolo[2,3-d]pyrimidin-2-yl]-(4-isopropoxy-phenyl)-amine;
(4-Fluoro-3-methyl-phenyl)-[7-(3-fluoro-4-morpholin-4-ylmethyl-phenyl)-7H-pyrrolo[2,3-d]pyrimidin-2-yl]-amine;
(3-Chloro-4-methyl-phenyl)-[7-(3,5-difluoro-4-morpholin-4-ylmethyl-phenyl)-7H-pyrrolo[2,3-d]pyrimidin-2-yl]-amine;
[7-(3,5-Difluoro-4-morpholin-4-ylmethyl-phenyl)-7H-pyrrolo[2,3-d]pyrimidin-2-yl]-(4-fluoro-3-methyl-phenyl)-amine;
[7-(3,5-Difluoro-4-morpholin-4-ylmethyl-phenyl)-7H-pyrrolo[2,3-d]pyrimidin-2-yl]-(4-methoxymethyl-phenyl)-amine;
1-Morpholin-4-yl-2-[4-(2-p-tolylamino-pyrrolo[2,3-d]pyrimidin-7-yl)-phenyl]-ethanone;
2-{4-[2-(4-Fluoro-3-methoxy-phenylamino)-pyrrolo[2,3-d]pyrimidin-7-yl]-phenyl}-1-morpholin-4-yl-ethanone;
1-Morpholin-4-yl-2-[4-(2-phenylamino-pyrrolo[2,3-d]pyrimidin-7-yl)-phenyl]-ethanone;
[7-(4-Morpholin-4-ylmethyl-phenyl)-7H-pyrrolo[2,3-d]pyrimidin-2-yl]-p-tolyl-amine;
(3,4-Diethoxy-phenyl)-[7-(4-morpholin-4-ylmethyl-phenyl)-7H-pyrrolo[2,3-d]pyrimidin-2-yl]-amine;
{2-Fluoro-4-[2-(4-fluoro-3-methoxy-phenylamino)-pyrrolo[2,3-d]pyrimidin-7-yl]-phenyl}-morpholin-4-yl-methanone;
{4-[2-(3,4-Dimethyl-phenylamino)-pyrrolo[2,3-d]pyrimidin-7-yl]-2-fluoro-phenyl}-morpholin-4-yl-methanone;
{2-Fluoro-4-[7-(3-fluoro-4-morpholin-4-ylmethyl-phenyl)-7H-pyrrolo[2,3-d]pyrimidin-2-ylamino]-phenyl}-(4-methyl-piperazin-1-yl)-methanone;
(3,4-Dimethyl-phenyl)-[7-(4-morpholin-4-ylmethyl-phenyl)-7H-pyrrolo[2,3-d]pyrimidin-2-yl]-amine;
(3,4-Dimethyl-phenyl)-[7-(3-fluoro-4-morpholin-4-ylmethyl-phenyl)-6-methyl-7H-pyrrolo[2,3-d]pyrimidin-2-yl]-amine;
(4-Fluoro-3-methoxy-phenyl)-[7-(3-fluoro-4-morpholin-4-ylmethyl-phenyl)-6-methyl-7H-pyrrolo[2,3-d]pyrimidin-2-yl]-amine;
2-{4-[2-(3,4-Dimethyl-phenylamino)-pyrrolo[2,3-d]pyrimidin-7-yl]-phenyl}-1-morpholin-4-yl-ethanone;
(3,4-Diethoxy-phenyl)-[7-(3-fluoro-4-morpholin-4-ylmethyl-phenyl)-6-methyl-7H-pyrrolo[2,3-d]pyrimidin-2-yl]-amine;
{4-[2-(3,4-Dimethyl-phenylamino)-pyrrolo[2,3-d]pyrimidin-7-yl]-phenyl}-morpholin-4-yl-methanone;
[7-(3,5-Difluoro-4-morpholin-4-ylmethyl-phenyl)-7H-pyrrolo[2,3-d]pyrimidin-2-yl]-[4-(4-methyl-piperazin-1-ylmethyl)-phenyl]-amine;
[7-(3-Chloro-4-morpholin-4-ylmethyl-phenyl)-7H-pyrrolo[2,3-d]pyrimidin-2-yl]-(4-methoxymethyl-phenyl)-amine;
[7-(3-Chloro-4-morpholin-4-ylmethyl-phenyl)-7H-pyrrolo[2,3-d]pyrimidin-2-yl]-(3,4-diethoxy-phenyl)-amine;
(4-Isopropoxy-phenyl)-{7-[4-(1-morpholin-4-yl-ethyl)-phenyl]-7H-pyrrolo[2,3-d]pyrimidin-2-yl}-amine (racemic);
[7-(3,5-Difluoro-4-morpholin-4-ylmethyl-phenyl)-7H-pyrrolo[2,3-d]pyrimidin-2-yl]-[3-(4-methyl-piperazin-1-ylmethyl)-phenyl]-amine;
(2,6-Difluoro-4-{2-[4-(4-methyl-piperazin-1-ylmethyl)-phenylamino]-pyrrolo[2,3-d]pyrimidin-7-yl}-phenyl)-morpholin-4-yl-methanone;
[7-(3,5-Difluoro-4-morpholin-4-ylmethyl-phenyl)-7H-pyrrolo[2,3-d]pyrimidin-2-yl]-phenyl-amine;
[7-(3,5-Difluoro-4-morpholin-4-ylmethyl-phenyl)-7H-pyrrolo[2,3-d]pyrimidin-2-yl]-pyridin-2-yl-amine;
[7-(3,5-Difluoro-4-morpholin-4-ylmethyl-phenyl)-7H-pyrrolo[2,3-d]pyrimidin-2-yl]-pyridin-3-yl-amine;
[7-(3,5-Difluoro-4-morpholin-4-ylmethyl-phenyl)-7H-pyrrolo[2,3-d]pyrimidin-2-yl]-pyridin-4-yl-amine;
[2,6-Difluoro-4-(2-phenylamino-pyrrolo[2,3-d]pyrimidin-7-yl)-phenyl]-morpholin-4-yl-methanone;
{2,6-Difluoro-4-[2-(pyridin-2-ylamino)-pyrrolo[2,3-d]pyrimidin-7-yl]-phenyl}-morpholin-4-yl-methanone;
{2,6-Difluoro-4-[2-(pyridin-3-ylamino)-pyrrolo[2,3-d]pyrimidin-7-yl]-phenyl}-morpholin-4-yl-methanone;
{2,6-Difluoro-4-[2-(pyridin-4-ylamino)-pyrrolo[2,3-d]pyrimidin-7-yl]-phenyl}-morpholin-4-yl-methanone;
{2,6-Difluoro-4-[2-(6-methyl-pyridin-3-ylamino)-pyrrolo[2,3-d]pyrimidin-7-yl]-phenyl}-morpholin-4-yl-methanone;
{2,6-Difluoro-4-[2-(4-fluoro-3-methyl-phenylamino)-pyrrolo[2,3-d]pyrimidin-7-yl]-phenyl}-morpholin-4-yl-methanone;
{2,6-Difluoro-4-[2-(4-fluoro-3-methyl-phenylamino)-pyrrolo[2,3-d]pyrimidin-7-yl]-phenyl}-morpholin-4-yl-methanone;
{4-[2-(5,6-Dimethyl-pyridin-2-ylamino)-pyrrolo[2,3-d]pyrimidin-7-yl]-2-fluoro-phenyl}-morpholin-4-yl-methanone;
{2,6-Difluoro-4-[2-(4-fluoro-3-methyl-phenylamino)-pyrrolo[2,3-d]pyrimidin-7-yl]-phenyl}-morpholin-4-yl-methanone;
{2-Fluoro-4-[2-(pyridin-3-ylamino)-pyrrolo [2,3-d]pyrimidin-7-yl]-phenyl}-morpholin-4-yl-methanone;
{2-Fluoro-4-[2-(6-methoxy-pyridin-3-ylamino)-pyrrolo[2,3-d]pyrimidin-7-yl]-phenyl}-morpholin-4-yl-methanone;
{2-Fluoro-4-[2-(6-isopropoxy-pyridin-3-ylamino)-pyrrolo[2,3-d]pyrimidin-7-yl]-phenyl}-morpholin-4-yl-methanone;
{4-[2-(4-Isopropoxy-phenylamino)-pyrrolo[2,3-d]pyrimidin-7-yl]-phenyl}-morpholin-4-yl-methanone;
{4-[2-(6-Isopropoxy-pyridin-3-ylamino)-pyrrolo[2,3-d]pyrimidin-7-yl]-phenyl}-morpholin-4-yl-methanone;

{4-[2-(3-Fluoro-4-methyl-phenylamino)-pyrrolo[2,3-d]pyrimidin-7-yl]-phenyl}-morpholin-4-yl-methanone;
{4-[2-(6-Methoxy-pyridin-3-ylamino)-pyrrolo[2,3-d]pyrimidin-7-yl]-phenyl}-morpholin-4-yl-methanone;
{4-[2-(6-Methyl-pyridin-3-ylamino)-pyrrolo[2,3-d]pyrimidin-7-yl]-phenyl}-morpholin-4-yl-methanone;
{4-[2-(4-Methoxymethyl-phenylamino)-pyrrolo[2,3-d]pyrimidin-7-yl]-phenyl}-morpholin-4-yl-methanone;
{4-[2-(3-Methoxy-4-methyl-phenylamino)-pyrrolo[2,3-d]pyrimidin-7-yl]-phenyl}-morpholin-4-yl-methanone;
{2,6-Difluoro-4-[2-(5-methyl-pyridin-3-ylamino)-pyrrolo[2,3-d]pyrimidin-7-yl]-phenyl}-morpholin-4-yl-methanone;
(2,6-Difluoro-4-{2-[3-(4-methyl-piperazin-1-ylmethyl)-phenylamino]-pyrrolo[2,3-d]pyrimidin-7-yl}-phenyl)-morpholin-4-yl-methanone;
(4-{2-[6-(cis-3,5-Dimethyl-piperazin-1-yl)-pyridin-3-ylamino]-pyrrolo[2,3-d]pyrimidin-7-yl}-2,6-difluoro-phenyl)-morpholin-4-yl-methanone;
[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-pyridin-3-yl]-amine;
(4-{2-[6-((2R,5S)-2,5-Dimethyl-piperazin-1-yl)-pyridin-3-ylamino]-pyrrolo[2,3-d]pyrimidin-7-yl}-2,6-difluoro-phenyl)-morpholin-4-yl-methanone (racemic);
[7-(3,5-Difluoro-4-morpholin-4-ylmethyl-phenyl)-7H-pyrrolo[2,3-d]pyrimidin-2-yl]-[6-((2R,5S)-2,5-dimethyl-piperazin-1-yl)-pyridin-3-yl]-amine (racemic);
{4-[2-(3,4-Diethoxy-phenylamino)-6-methyl-pyrrolo[2,3-d]pyrimidin-7-yl]-2-fluoro-phenyl}-morpholin-4-yl-methanone;
{2-Fluoro-4-[2-(4-morpholin-4-ylmethyl-phenylamino)-pyrrolo[2,3-d]pyrimidin-7-yl]-phenyl}-morpholin-4-yl-methanone;
[7-(3,5-Difluoro-4-morpholin-4-ylmethyl-phenyl)-7H-pyrrolo[2,3-d]pyrimidin-2-yl]-(3,4-dimethyl-phenyl)-amine;
{4-[2-(3,4-Dimethyl-phenylamino)-pyrrolo[2,3-d]pyrimidin-7-yl]-2-methyl-phenyl}-morpholin-4-yl-methanone;
{4-[2-(4-Chloro-3-methoxy-phenylamino)-pyrrolo[2,3-d]pyrimidin-7-yl]-2-fluoro-phenyl}-morpholin-4-yl-methanone;
{4-[2-(4-Fluoro-3-methoxy-phenylamino)-pyrrolo[2,3-d]pyrimidin-7-yl]-2-methyl-phenyl}-morpholin-4-yl-methanone;
4-[2-(3,4-Dimethyl-phenylamino)-pyrrolo[2,3-d]pyrimidin-7-yl]-2-fluoro-N-(2-morpholin-4-yl-ethyl)-benzamide;
{2-Fluoro-4-[2-(3-methoxy-4-methyl-phenylamino)-pyrrolo[2,3-d]pyrimidin-7-yl]-phenyl}-morpholin-4-yl-methanone;
[7-(3,5-Difluoro-4-morpholin-4-ylmethyl-phenyl)-7H-pyrrolo[2,3-d]pyrimidin-2-yl]-(3-methoxy-4-methyl-phenyl)-amine;
{7-[4-(3,3-Dimethyl-morpholin-4-ylmethyl)-3,5-difluoro-phenyl]-7H-pyrrolo[2,3-d]pyrimidin-2-yl}-(3,4-dimethyl-phenyl)-amine;
[2-Fluoro-4-(2-p-tolylamino-pyrrolo[2,3-d]pyrimidin-7-yl)-phenyl]-morpholin-4-yl-methanone;
[7-(3,5-Difluoro-4-morpholin-4-ylmethyl-phenyl)-7H-pyrrolo[2,3-d]pyrimidin-2-yl]-p-tolyl-amine;
(2-Fluoro-4-{2-[4-methyl-3-(4-methyl-piperazin-1-ylmethyl)-phenylamino]-pyrrolo[2,3-d]pyrimidin-7-yl}-phenyl)-morpholin-4-yl-methanone;
[7-(3,5-Difluoro-4-morpholin-4-ylmethyl-phenyl)-7H-pyrrolo[2,3-d]pyrimidin-2-yl]-[4-methyl-3-(4-methyl-piperazin-1-ylmethyl)-phenyl]-amine;
[7-(3,5-Difluoro-4-morpholin-4-ylmethyl-phenyl)-7H-pyrrolo[2,3-d]pyrimidin-2-yl]-[3-(cis-3,5-dimethyl-piperazin-1-ylmethyl)-4-methyl-phenyl]-amine;
{4-[7-(3,5-Difluoro-4-morpholin-4-ylmethyl-phenyl)-7H-pyrrolo[2,3-d]pyrimidin-2-ylamino]-pyridin-2-yl}-(4-methyl-piperazin-1-yl)-methanone;
[7-(3,5-Difluoro-4-morpholin-4-ylmethyl-phenyl)-7H-pyrrolo[2,3-d]pyrimidin-2-yl]-[2-(4-methyl-piperazin-1-ylmethyl)-pyridin-4-yl]-amine;
(4-{2-[4-Methyl-3-(4-methyl-piperazin-1-ylmethyl)-phenylamino]-pyrrolo[2,3-d]pyrimidin-7-yl}-phenyl)-morpholin-4-yl-methanone;
{5-[7-(3,5-Difluoro-4-morpholin-4-ylmethyl-phenyl)-7H-pyrrolo[2,3-d]pyrimidin-2-ylamino]-2-methyl-phenyl}-(4-methyl-piperazin-1yl)-methanone;
{5-[7-(3,5-Difluoro-4-morpholin-4-ylmethyl-phenyl)-7H-pyrrolo[2,3-d]pyrimidin-2-ylamino]-pyridin-2-yl}-(4-methyl-piperazin-1-yl)-methanone;
[7-(3,5-Difluoro-4-morpholin-4-ylmethyl-phenyl)-7H-pyrrolo[2,3-d]pyrimidin-2-yl]-[6-(4-methyl-piperazin-1-ylmethyl)-pyridin-3-yl]-amine;
4-(4-{2-[6-(cis-3,5-Dimethyl-piperazin-1-yl)-5-methyl-pyridin-3-ylamino]-pyrrolo[2,3-d]pyrimidin-7-yl}-2,6-difluoro-benzyl)-morpholin-3-one;
[5-Chloro-6-(cis-3,5-dimethyl-piperazin-1-yl)-pyridin-3-yl]-[7-(3,5-difluoro-4-morpholin-4-ylmethyl-phenyl)-7H-pyrrolo[2,3-d]pyrimidin-2-yl]-amine;
[4-Chloro-3-(4-methyl-piperazin-1-ylmethyl)-phenyl]-[7-(3,5-difluoro-4-morpholin-4-ylmethyl-phenyl)-7H-pyrrolo[2,3-d]pyrimidin-2-yl]-amine;
[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-5-methoxy-pyridin-3-yl]-amine;
(4-{2-[6-(cis -3,5-Dimethyl-piperazin-1-yl)-pyridin-3-ylamino]-pyrrolo[2,3-d]pyrimidin-7-yl}-2-fluoro-phenyl)-morpholin-4-yl-methanone;
[7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-5-methyl-pyridin-3-yl]-amine; and
{3-Fluoro-4-[2-(4-isopropoxy-phenylamino)-pyrrolo[2,3-d]pyrimidin-7-yl]-phenyl}-morpholin-4-yl-methanone; or a pharmaceutically acceptable salt thereof.

2. A pharmaceutical composition comprising a therapeutically effective amount of a compound according to claim 1 in free form or in pharmaceutically acceptable salt form as active ingredient and one or more pharmaceutically acceptable carrier material(s) or diluents.

3. A combined pharmaceutical composition, adapted for simultaneous or sequential administration, comprising a therapeutically effective amount of a compound according to claim 1 in free form or in pharmaceutically acceptable salt form; therapeutically effective amount(s) of one or more combination partners; and one or more pharmaceutically acceptable carrier material(s) or diluents.

4. A compound which is [7-(3,5-Difluoro-4-morpholin-4-ylmethyl-phenyl)-7H-pyrrolo[2,3-d]pyrimidin-2-yl]-[6-(cis-3,5-dimethyl-piperazin-1-yl)-pyridin-3-yl]-amine, and which has the following structure:

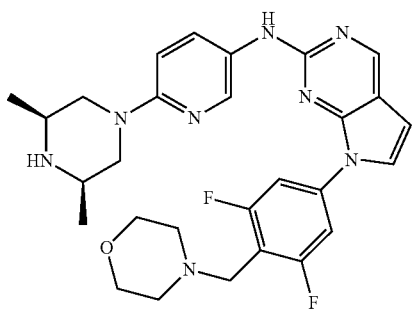 [SMILES: C[C@@H]1CN(c2ccc(Nc3ncc4ccn(-c5cc(F)c(CN6CCOCC6)c(F)c5)c4n3)cn2)C[C@H](C)N1]

or a pharmaceutically acceptable salt thereof

5. A pharmaceutical composition comprising a therapeutically effective amount of a compound according to claim 4 in free form or in pharmaceutically acceptable salt form as active ingredient and one or more pharmaceutically acceptable carrier material(s) or diluents.

6. A combined pharmaceutical composition, adapted for simultaneous or sequential administration, comprising a therapeutically effective amount of a compound according to claim 4 in free form or in pharmaceutically acceptable salt form; therapeutically effective amount(s) of one or more combination partners; and one or more pharmaceutically acceptable carrier material(s) or diluents.

7. A pharmaceutical composition comprising a compound according to claim 4, or a pharmaceutically acceptable salt thereof, and at least one pharmaceutically acceptable carrier or diluent.

8. A pharmaceutical composition comprising a compound according to claim 1, or a pharmaceutically acceptable salt thereof, and at least one pharmaceutically acceptable carrier or diluent.

* * * * *

SEQUENCE LISTING

<160> NUMBER OF SEQ ID NOS: 2

<210> SEQ ID NO 1
<211> LENGTH: 14
<212> TYPE: PRT
<213> ORGANISM: Artificial
<220> FEATURE:
<223> OTHER INFORMATION: FITC-labeled Insulin Receptor Kinase Substrate
      IRS-1 derivative (mammalian), see J. Biol. Chem. 268(33),
      125146-51 (1993)
<220> FEATURE:
<221> NAME/KEY: MOD_RES
<222> LOCATION: (1)..(1)
<223> OTHER INFORMATION: X at the C-terminus is FITC-labeled
      aminocaproic acid
<220> FEATURE:
<221> NAME/KEY: MOD_RES
<222> LOCATION: (14)..(14)
<223> OTHER INFORMATION: X at the N-terminus is glycylamide (Gly-NH2)

<400> SEQUENCE: 1

Xaa Lys Lys Ser Arg Gly Asp Tyr Met Thr Met Gln Ile Xaa
1               5                   10

<210> SEQ ID NO 2
<211> LENGTH: 15
<212> TYPE: PRT
<213> ORGANISM: Artificial
<220> FEATURE:
<223> OTHER INFORMATION: FITC-labeled peptide substrate for JAK2 and
      JAK3, Caliper Sciences, Mountain View, California, USA
<220> FEATURE:
<221> NAME/KEY: MOD_RES
<222> LOCATION: (1)..(1)
<223> OTHER INFORMATION: X at the C-terminus is FITC labeled glycine
<220> FEATURE:
<221> NAME/KEY: MOD_RES
<222> LOCATION: (15)..(15)
<223> OTHER INFORMATION: X at the N-terminus is lysylamide (Lys-NH2)

<400> SEQUENCE: 2

Xaa Gly Glu Glu Glu Glu Tyr Phe Glu Leu Val Lys Lys Lys Xaa
1               5                   10                  15